US009738723B2

(12) United States Patent
Hammond et al.

(10) Patent No.: US 9,738,723 B2
(45) Date of Patent: Aug. 22, 2017

(54) HUMANIZED ANTI-OX40 ANTIBODIES AND USES THEREOF

(71) Applicant: MEDIMMUNE, LLC, Gaithersburg, MD (US)

(72) Inventors: Scott A. Hammond, Gaithersburg, MD (US); Michael Oberst, Gaithersburg, MD (US); Qun Du, Gaithersburg, MD (US); Melissa Damschroder, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/877,547

(22) Filed: Oct. 7, 2015

(65) Prior Publication Data

US 2016/0137740 A1 May 19, 2016

Related U.S. Application Data

(60) Provisional application No. 62/062,431, filed on Oct. 10, 2014.

(51) Int. Cl.
*C07K 16/28* (2006.01)
*A61K 39/00* (2006.01)

(52) U.S. Cl.
CPC .... *C07K 16/2878* (2013.01); *A61K 2039/505* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/73* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 5,457,035 A | 10/1995 | Baum et al. | | |
| 6,312,700 B1 | 11/2001 | Weinberg | | |
| 8,283,450 B2 * | 10/2012 | Kato | C07K 16/2878 | 530/387.3 |
| 8,614,295 B2 * | 12/2013 | Lawson | C07K 16/2878 | 424/130.1 |
| 8,748,585 B2 * | 6/2014 | Attinger | C07K 16/2878 | 424/133.1 |
| 2002/0068319 A1 | 6/2002 | Ni et al. | | |

FOREIGN PATENT DOCUMENTS

| | | |
|---|---|---|
| WO | WO95/21915 | 8/1995 |
| WO | WO2006/121810 A2 | 11/2006 |
| WO | WO2008/106116 A2 | 9/2008 |
| WO | WO2012/097313 A2 | 7/2012 |
| WO | WO2013/028231 A1 | 2/2013 |
| WO | WO2014/148895 A1 | 9/2014 |

OTHER PUBLICATIONS

Al-Shamkhani, A., et al., "OX40 is differentially expressed on activated rat and mouse T cells and is the sole receptor for the OX40 ligand," European Journal of Immunology, vol. 26, Issue 8, pp. 1695-1699 (Aug. 26, 1996).
Baruah, P., et al., "Decreased levels of alternative co-stimulatory receptors OX40 and 4-1BB characterise T cells from head and neck cancer patients," Immunobiology, vol. 217, Issue 7, pp. 669-675 (Jul. 2012).
Croft, M., "Control of immunity by the TNFR-related molecule OX40 (CD134)," Annual Review of Immunology, vol. 28, pp. 57-78 (2010).
Croft, M., et al., "The significance of OX40 and OX40L to T-cell biology and immune disease," Immunological Reviews, vol. 229, Issue 1, pp. 173-191 (May 2009).
Curti, B. D., et al, "OX40 Is a Potent Immune-Stimulating Target in Late-Stage Cancer Patients," Cancer Research, vol. 73, Issue 24, pp. 7189-7198 (Dec. 15, 2013).
Dall'Acqua, W. F., et al., "Modulation of the Effector Functions of a Human IgG1 through Engineering of Its Hinge Region," The Journal of Immunology, vol. 177, Issue 2, pp. 1129-1138 (Jul. 15, 2006).
Innes, H. E., et al., "Significance of the metastasis-inducing protein AGR2 for outcome in hormonally treated breast cancer patients," British Journal of Cancer, vol. 94, Issue 7, pp. 1057-1065 (Apr. 10, 2006).
Jensen, S. M., et al., "Signaling Through OX40 Enhances Antitumor Immunity," Seminars in Oncology, vol. 37, Issue 5, pp. 524-532 (Oct. 2010).
Kjaergaard, J., et al., "Therapeutic efficacy of OX-40 receptor antibody depends on tumor immunogenicity and anatomic site of tumor growth," Cancer Research, vol. 60, Issue 19, pp. 5514-5521 (Oct. 1, 2000).
Ladanyi, A., et al., "T-cell activation marker expression on tumor-infiltrating lymphocytes as prognostic factor in cutaneous malignant melanoma," Clinical Cancer Research, vol. 10, Issue 2, pp. 521-530 (Jan. 15, 2004).
Melero, I. et al., "Clinical development of immunostimulatory monoclonal antibodies and opportunities for combination," Clinical Cancer Research, vol. 19, Issue 5, pp. 997-1008 (Mar. 1, 2013).
Ndhlovu, L. C., et al., "Critical involvement of OX40 ligand signals in the T cell priming events during experimental autoimmune encephalomyelitis," The Journal of Immunology, vol. 167, Issue 5, pp. 2991-2999 (Sep. 1, 2001).
Petty, J. K., et al., "Survival in human colorectal cancer correlates with expression of the T-cell costimulatory molecule OX-40 (CD134)," The American Journal of Surgery, vol. 183, Issue 5, pp. 512-518 (May 2002).
Piconese, S., et al., "OX40 triggering blocks suppression by regulatory T cells and facilitates tumor rejection," The Journal of Experimental Medicine, vol. 205, Issue 4, pp. 825-839 (Apr. 14, 2008).

(Continued)

*Primary Examiner* — Elly-Gerald Stoica

(57) ABSTRACT

The disclosure provides humanized anti-OX40 antibodies. Also provided are methods of making such antibodies, and methods of use, e.g., treatment of cancer.

24 Claims, 59 Drawing Sheets

(56) References Cited

OTHER PUBLICATIONS

Figure 6:
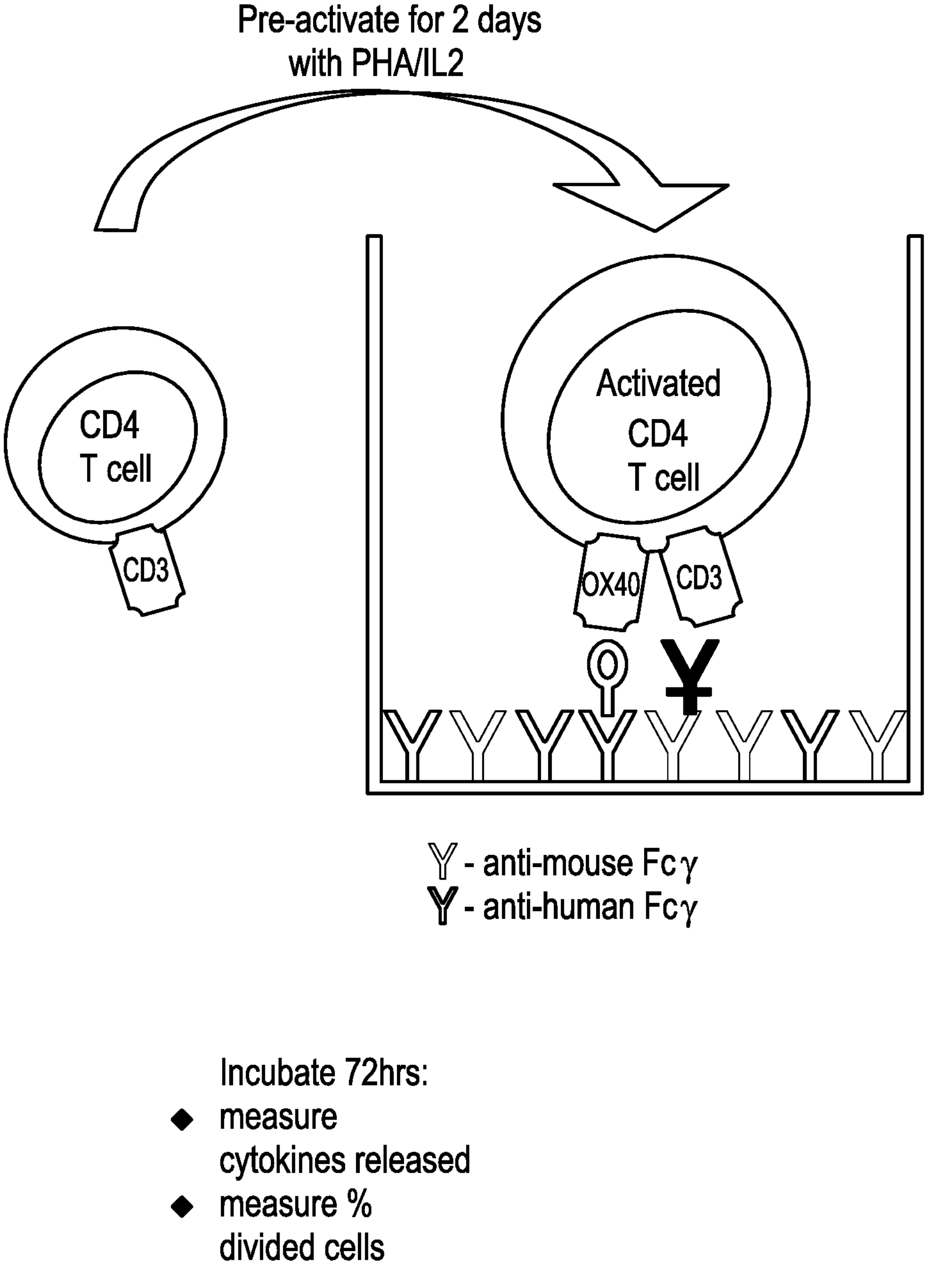

Ramstad, T., et al., "Immunohistochemical analysis of primary breast tumors and tumor-draining lymph nodes by means of the T-cell costimulatory molecule OX-40," The American Journal of Surgery, vol. 179, Issue 5, pp. 400-406 (May 200).

Sarff, M., et al., "OX40 (CD134) expression in sentinel lymph nodes correlates with prognostic features of primary melanomas," The American Journal of Surgery, vol. 195, Issue 5, pp. 621-625 (2008).

Vetto, J. T., et al., "Presence of the T-cell activation marker OX-40 on tumor infiltrating lymphocytes and draining lymph node cells from patients with melanoma and head and neck cancers," The American Journal of Surgery, vol. 174, Issue 3, pp. 258-265 (Sep. 1997).

Voo, K. S., et al., "Antibodies Targeting Human OX40 Expand Effector T Cells and Block Inducible and Natural Regulatory T Cell Function," The Journal of Immunology, vol. 191, Issue 7, pp. 3641-3650 (Oct. 1, 2013).

Vu, M. D. et al., "OX40 costimulation turns off Foxp3+ Tregs," Blood, vol. 110, Issue 7, pp. 2501-2510 (Oct. 1, 2007).

Weinberg, A. D., et al., "Engagement of the OX-40 receptor in vivo enhances antitumor immunity," The Journal of Immunology, vol. 164, Issue 4, pp. 2160-2169 (Feb. 15, 2000).

International search report for PCT Application No. PCT/US2015/054490, mailed on Jan. 19, 2016.

Written opinion for PCT Application No. PCT/US2015/054490, mailed on Jan. 19, 2016.

* cited by examiner

FIGURE 1

| 9B12VH mutant variants pairing with humanized VL | | | | | | | | | | |
|---|---|---|---|---|---|---|---|---|---|---|
| | | VH mutation position | | | | | | | Removing Sequence liabilities | |
| Clone ID | VH mutant (nick name) | 27D | 39K | 47Y | 48M | 71R | 78Y | 91F | NG (CDR2H) | RYDYDG (CDR3H) |
| OX40mAb1 | 9B12 chimera | D | K | Y | M | R | Y | F | | |
| OX40mAb2 | 9B12 mouse VH | D | K | Y | M | R | Y | F | | |
| OX40mAb5 | hu | G | Q | W | I | P | F | Y | NG | RYDYDG |
| OX40mAb8 | huKR | G | K | W | I | R | F | Y | | |
| OX40mAb10 | m1 | D | Q | W | I | P | F | Y | | |
| OX40mAb11 | m2 | G | K | Y | M | P | F | Y | | |
| OX40mAb12 | m3 | G | Q | W | I | R | Y | F | | |
| OX40mAb13 | KR-DYMYF | D | K | Y | M | R | Y | F | | |
| OX40mAb14 | KR-DYIYF | D | K | Y | I | R | Y | F | | |
| OX40mAb15 | KR-DYIFF | D | K | Y | I | R | F | F | | |
| OX40mAb16 | KR-DYIYY | D | K | Y | I | R | Y | Y | | |
| OX40mAb17 | KR-DYIFY | D | K | Y | I | R | F | Y | | |
| OX40mAb18 | KYYF | G | K | Y | I | R | Y | F | | |
| OX40mAb19 | KYRYF | G | K | Y | I | R | Y | F | | |
| OX40mAb20 | KYRY | G | K | Y | I | R | Y | Y | NG | RYDYDG |
| OX40mAb21 | KYY | G | K | Y | I | R | Y | Y | | |
| OX40mAb22 | 55A,96K-A | G | K | Y | I | R | Y | Y | NA | KYDYDG |
| OX40mAb23 | 55A | G | K | Y | I | R | Y | Y | NA | RYDYDG |
| OX40mAb24 | 96K | G | K | Y | I | R | Y | Y | NG | KYDYDG |
| OX40mAb25 | 54S | G | K | Y | I | R | Y | Y | SG | RYDYDG |
| OX40mAb25a | 54S,96K | G | K | Y | I | R | Y | Y | SG | KYDYDG |
| OX40mAb26 | mouseVH-55A | D | K | Y | M | R | Y | F | NA | RYDYDG |
| OX40mAb27 | 55A,96K | G | K | Y | I | R | Y | Y | NA | KYDYDG |
| OX40mAb28 | huIgG4P | G | K | Y | I | R | Y | Y | NG | KYDYDG |
| OX40mAb29 | huIgG1TM | G | K | Y | I | R | Y | Y | NG | KYDYDG |
| OX40mAb30 | mIgG1 | G | K | Y | I | R | Y | Y | NG | KYDYDG |
| OX40mAb31 | huIgG4P | G | K | Y | I | R | Y | Y | NA | KYDYDG |
| OX40mAb32 | huIgG1TM | G | K | Y | I | R | Y | Y | NA | KYDYDG |
| OX40mAb37 | mIgG1 | G | K | Y | I | R | Y | Y | NA | KYDYDG |

FIGURE 2A-D
A
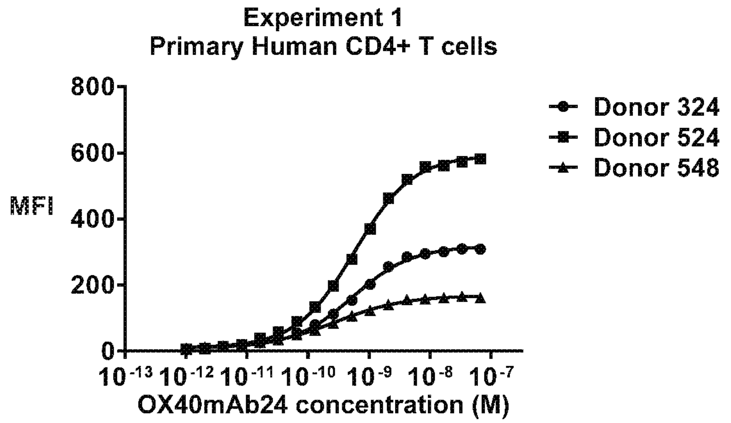
B
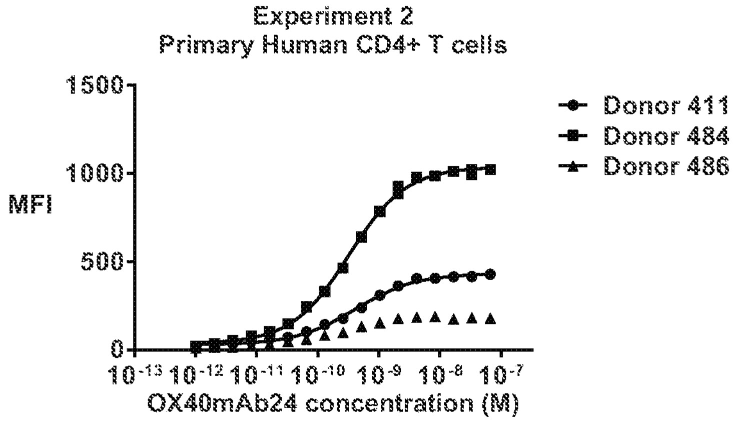

(FIGURE 2A-D, con't.)
C
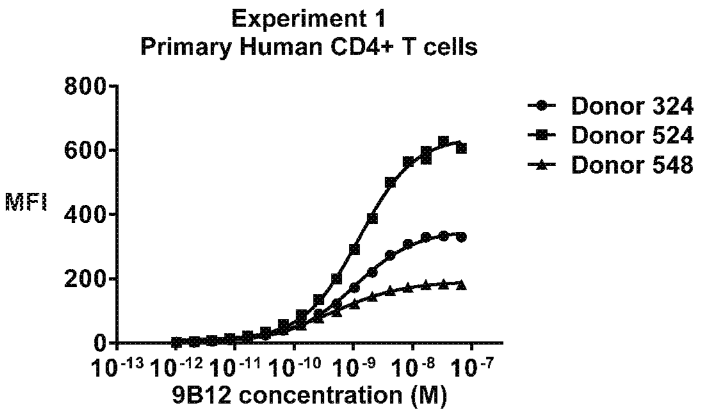
D
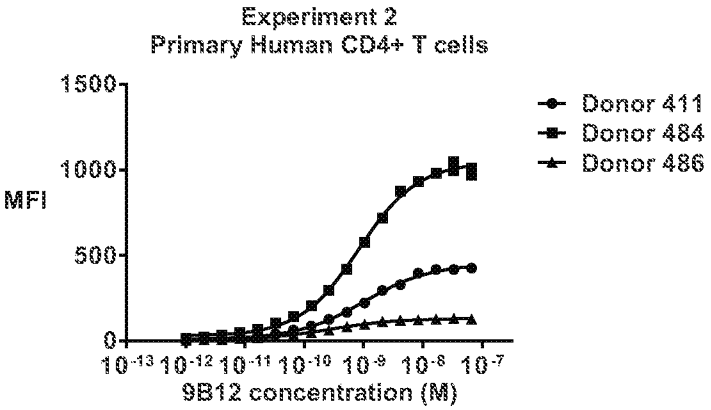

FIGURE 3A-F
A
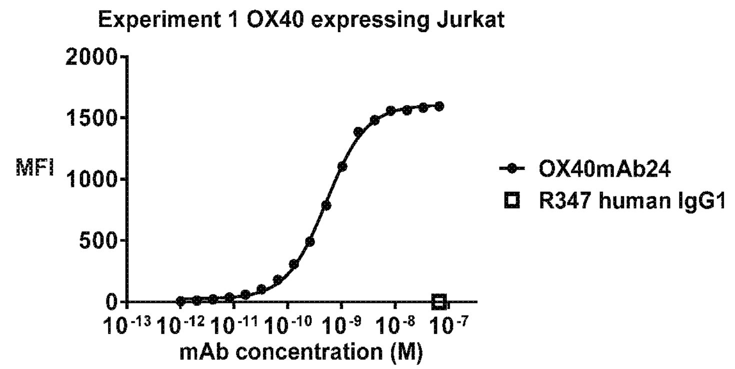
B
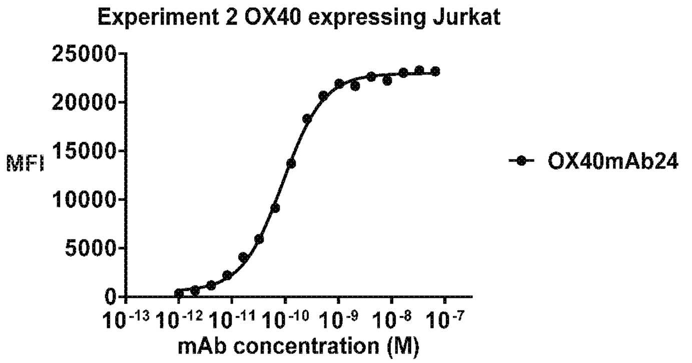
C
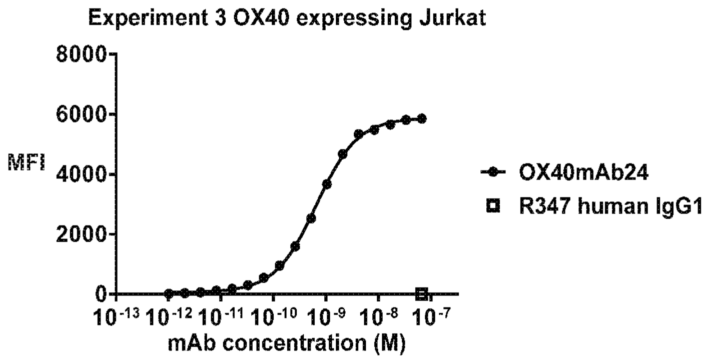

(FIGURE 3A-F, con't)
D
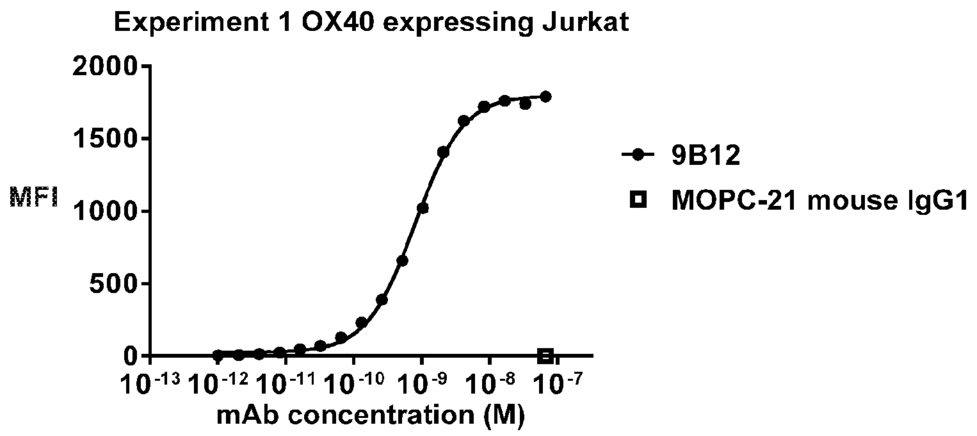
E
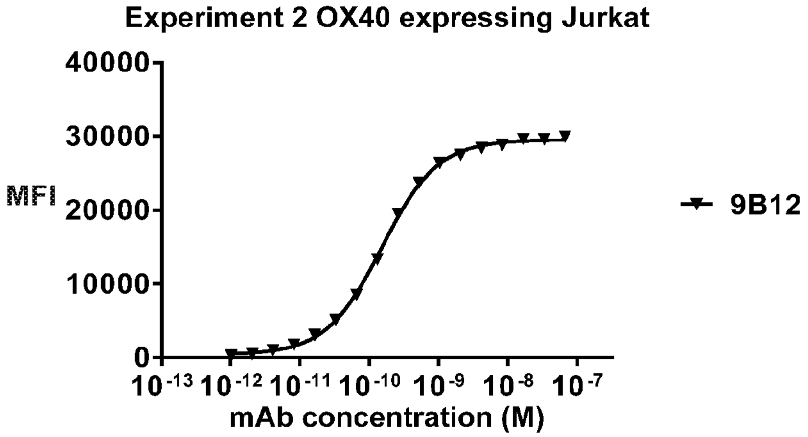
F
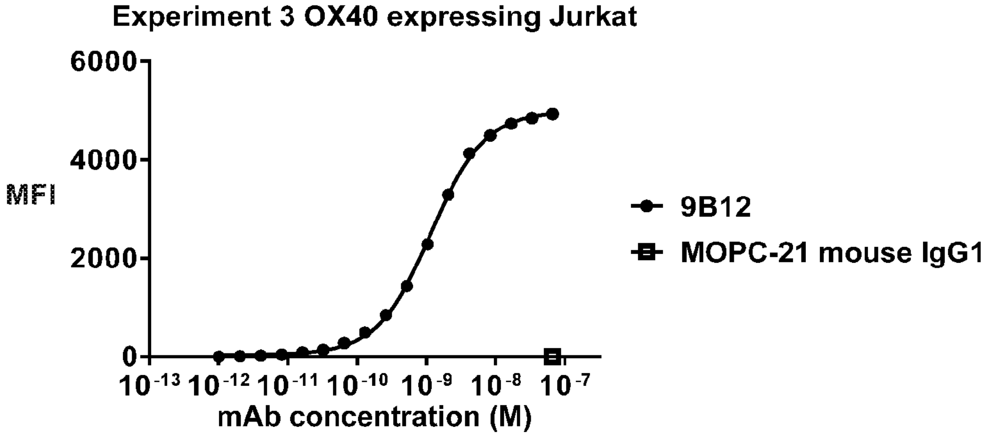

FIGURE 4A-B
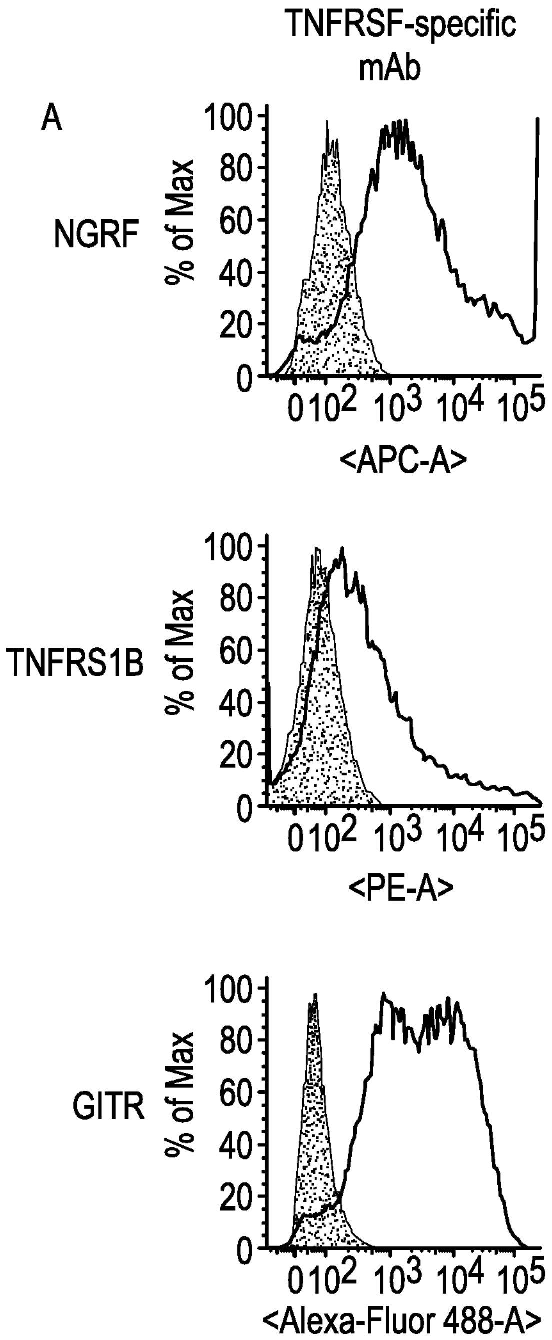

(FIGURE 4A-B, con't)
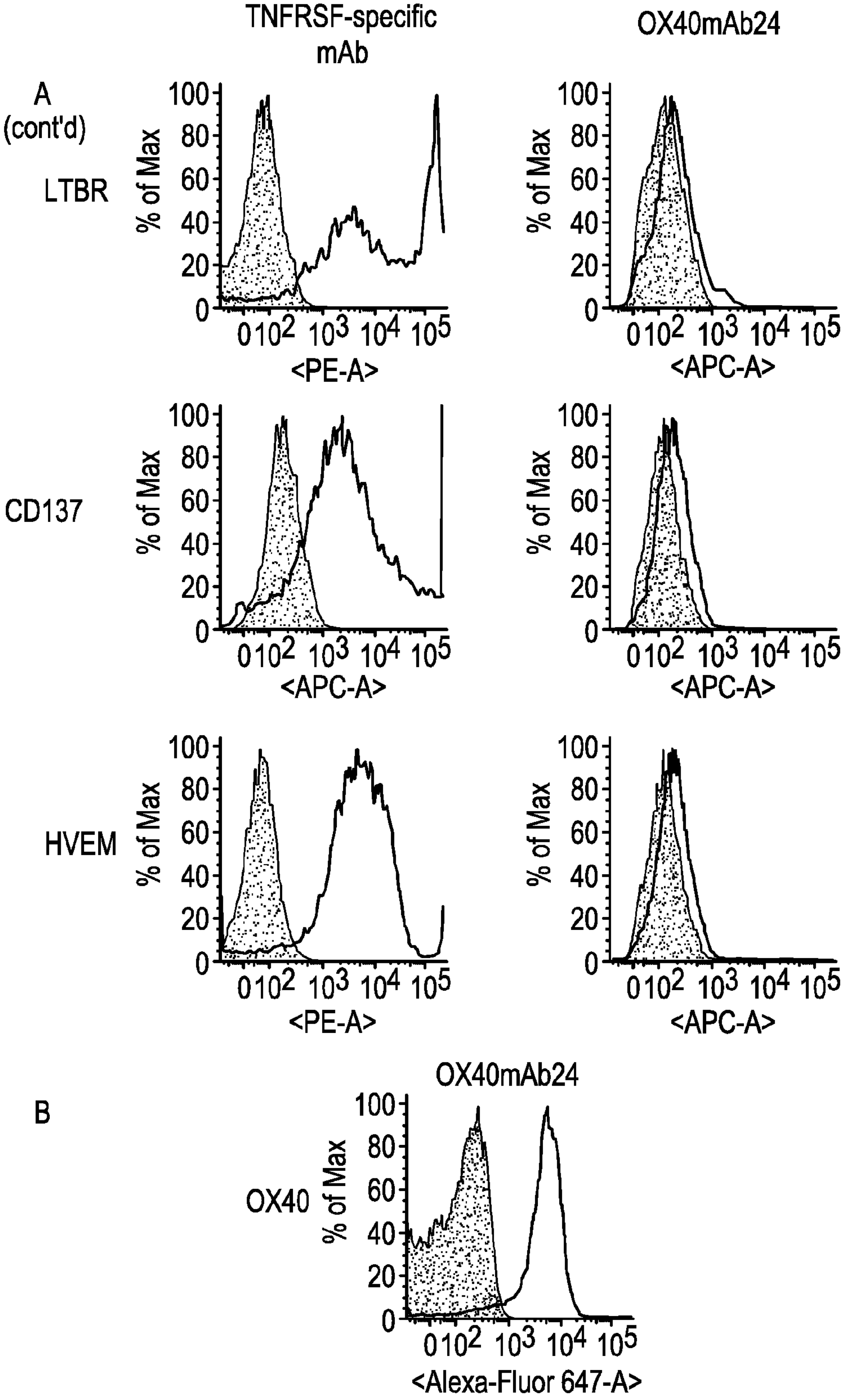

FIGURE 5A-B
A
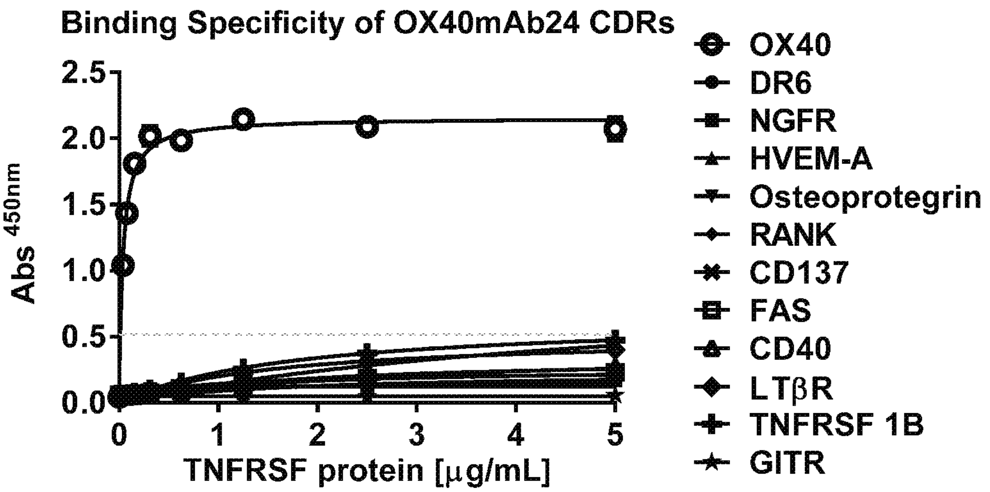
B
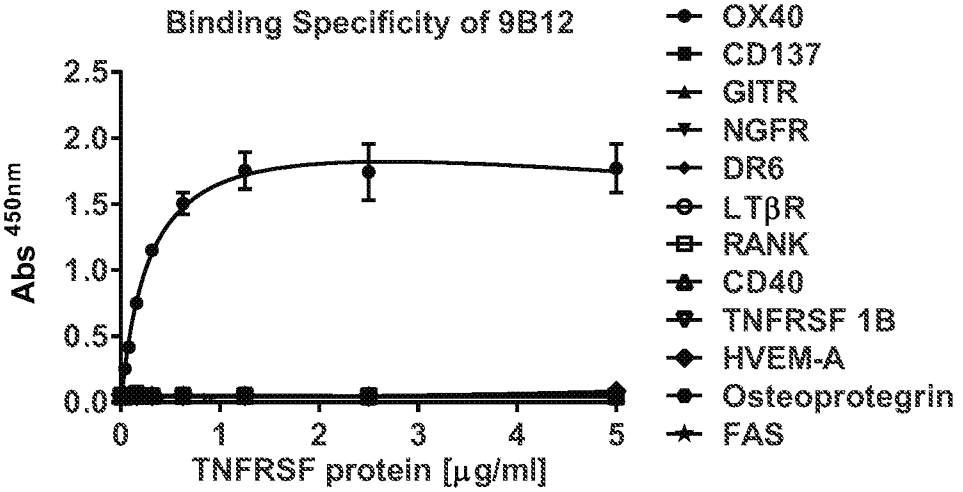

FIGURE 7A-C
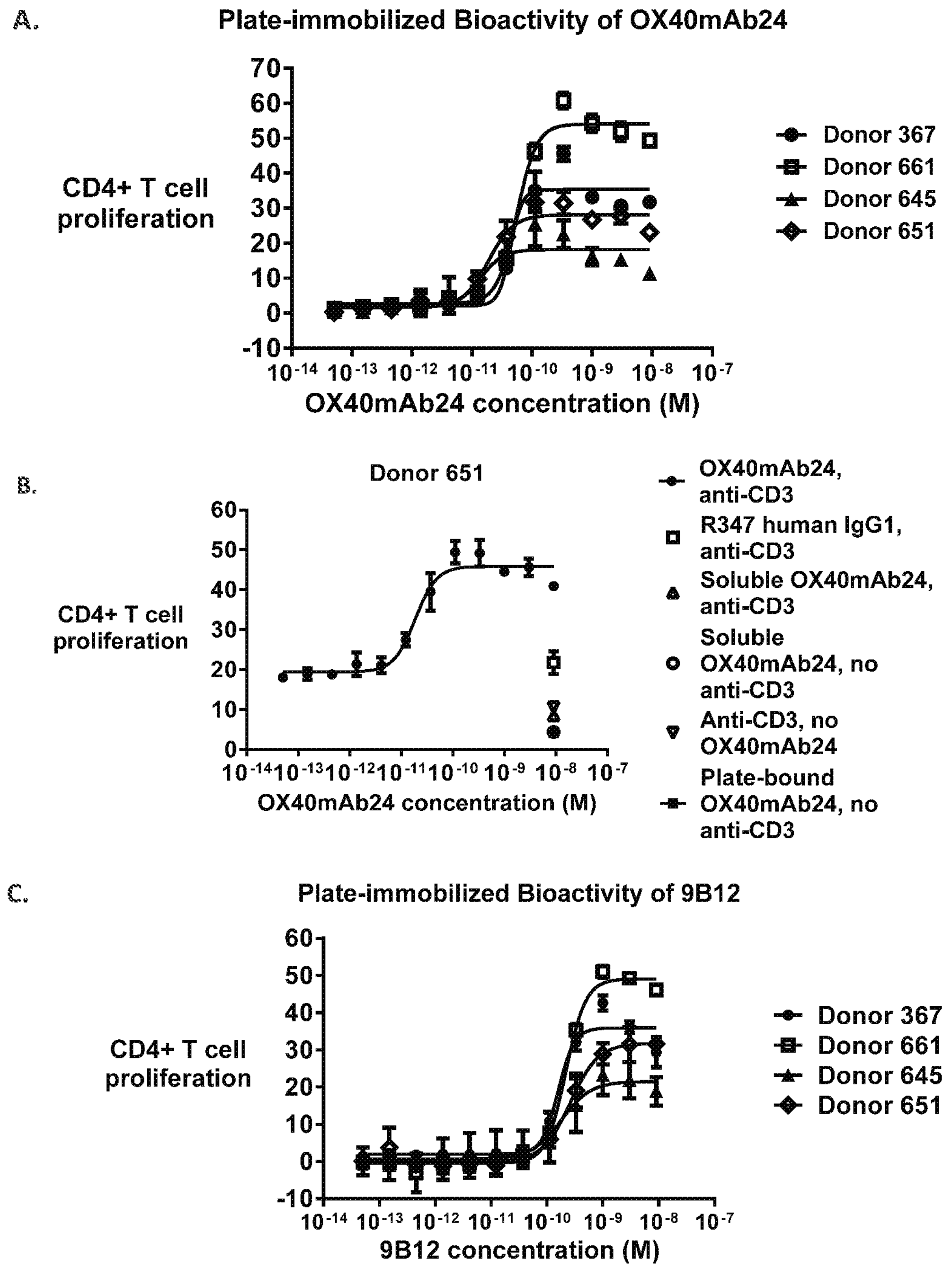

FIGURE 8A-E
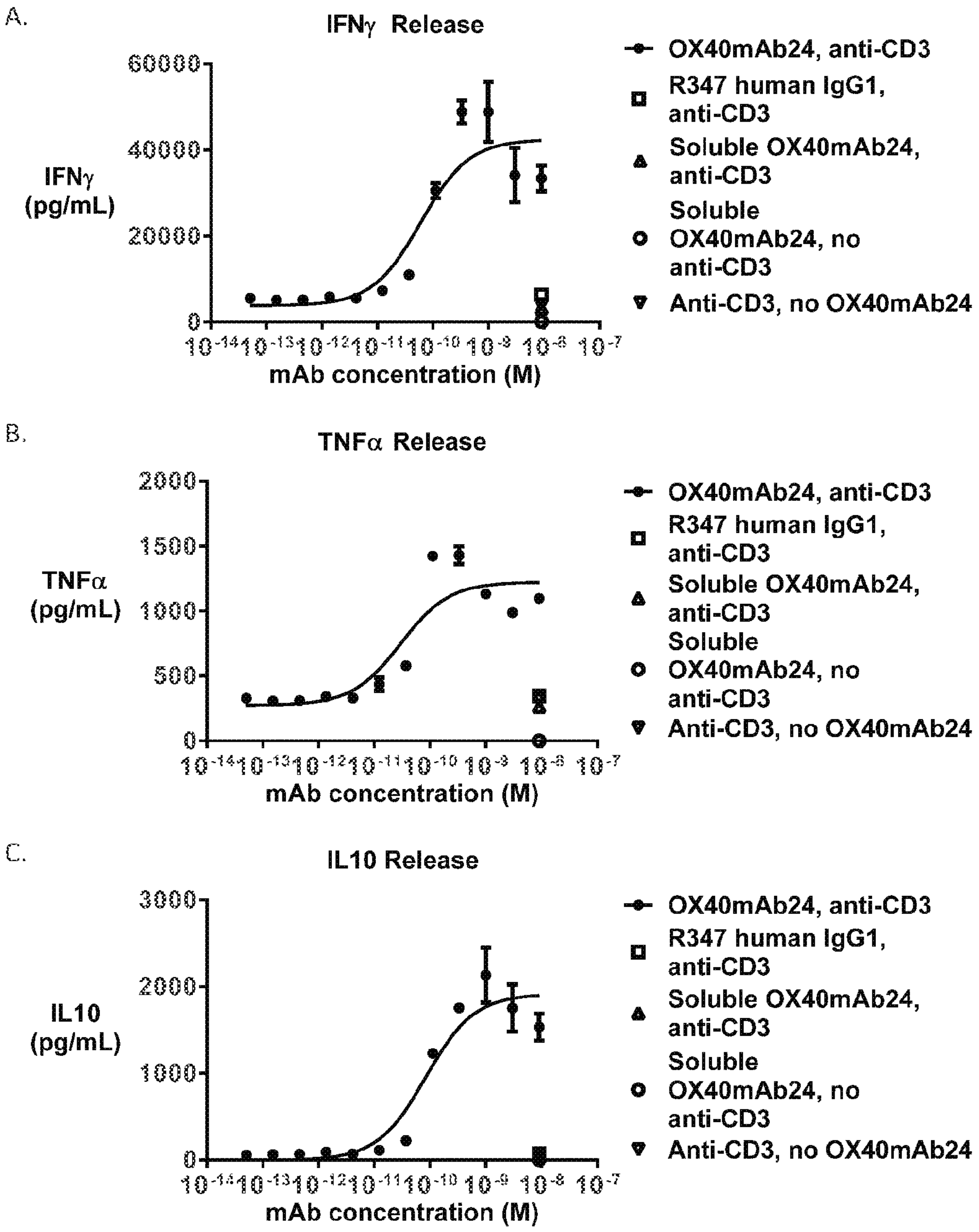

(FIGURE 8A-E, con't)
D.
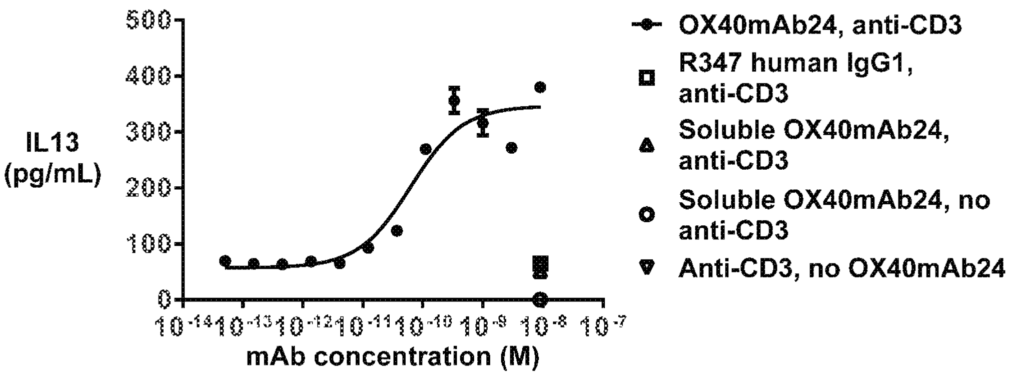
E.
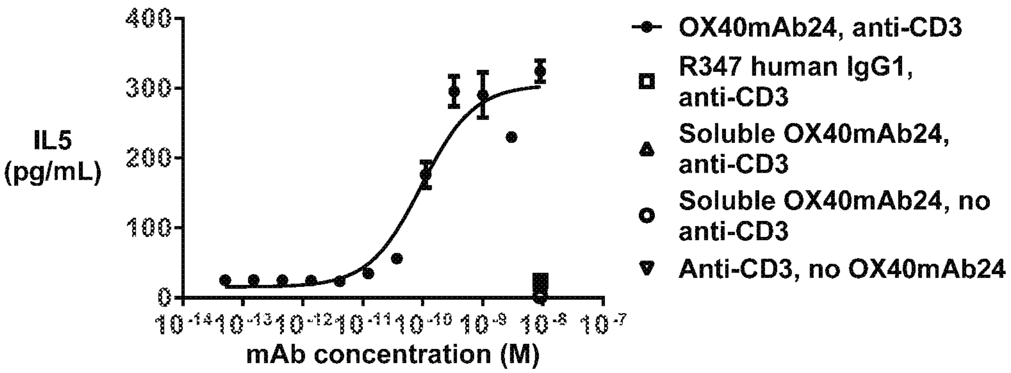

FIGURE 9A-E
A.
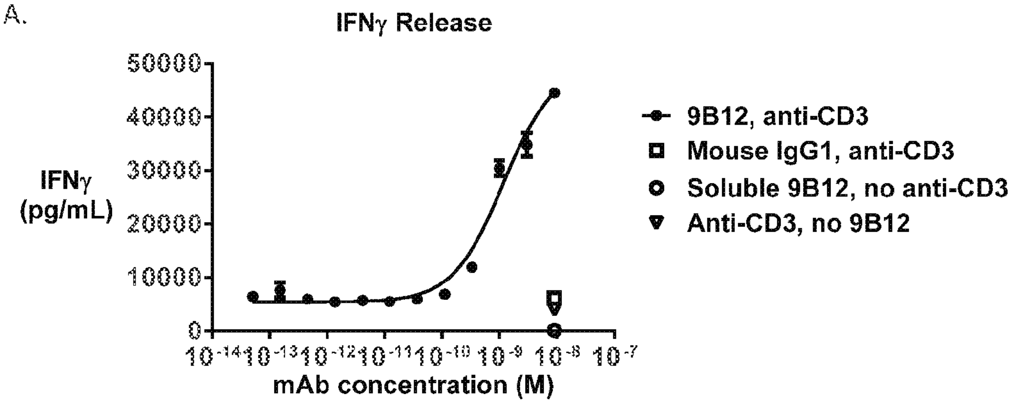
B.
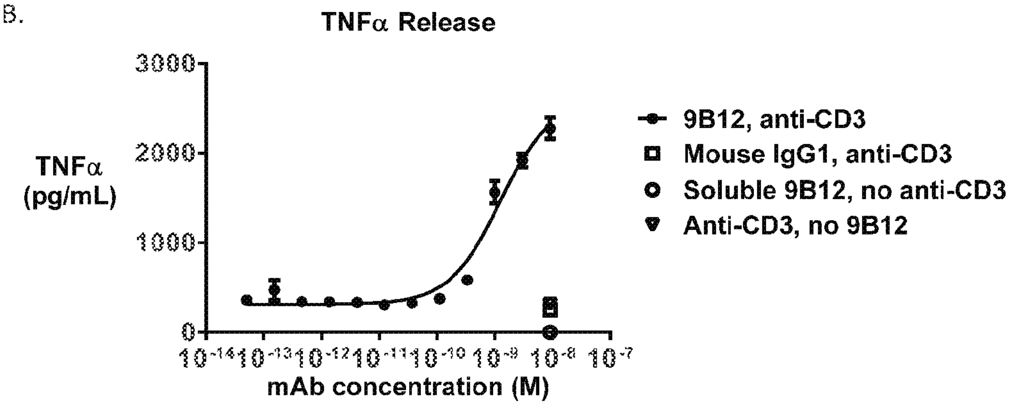
C.
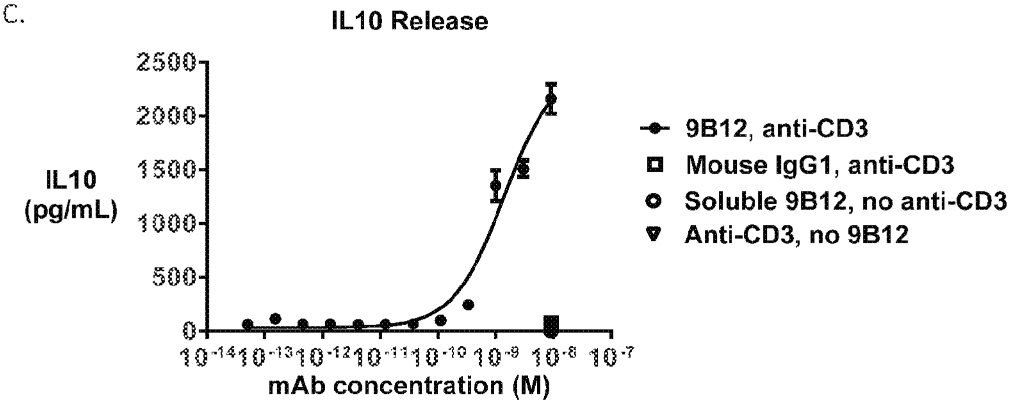

(FIGURE 9A-E, con't)
D.
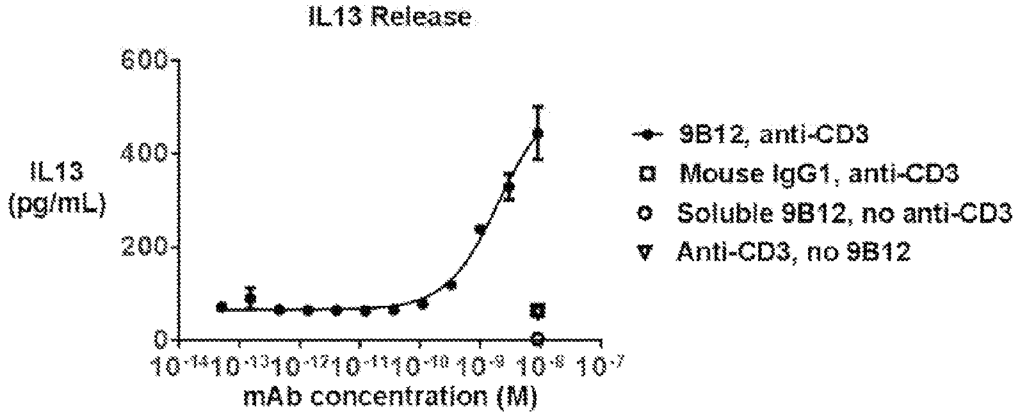
E.
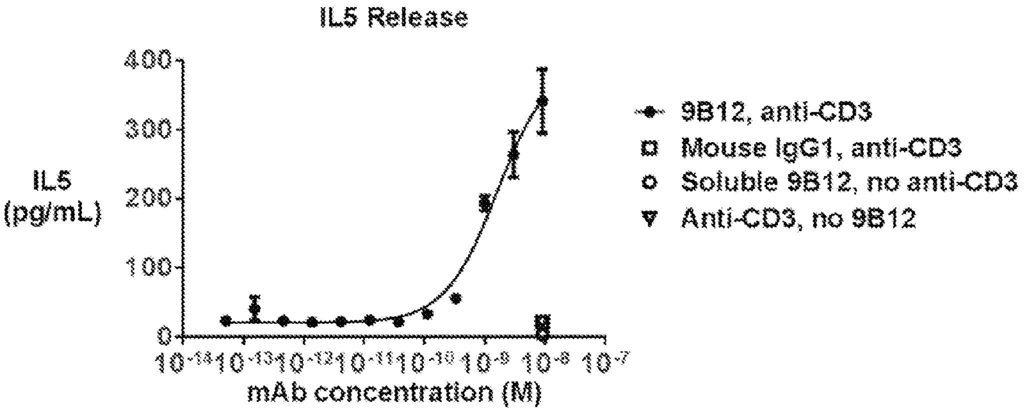

FIGURE 11A-D
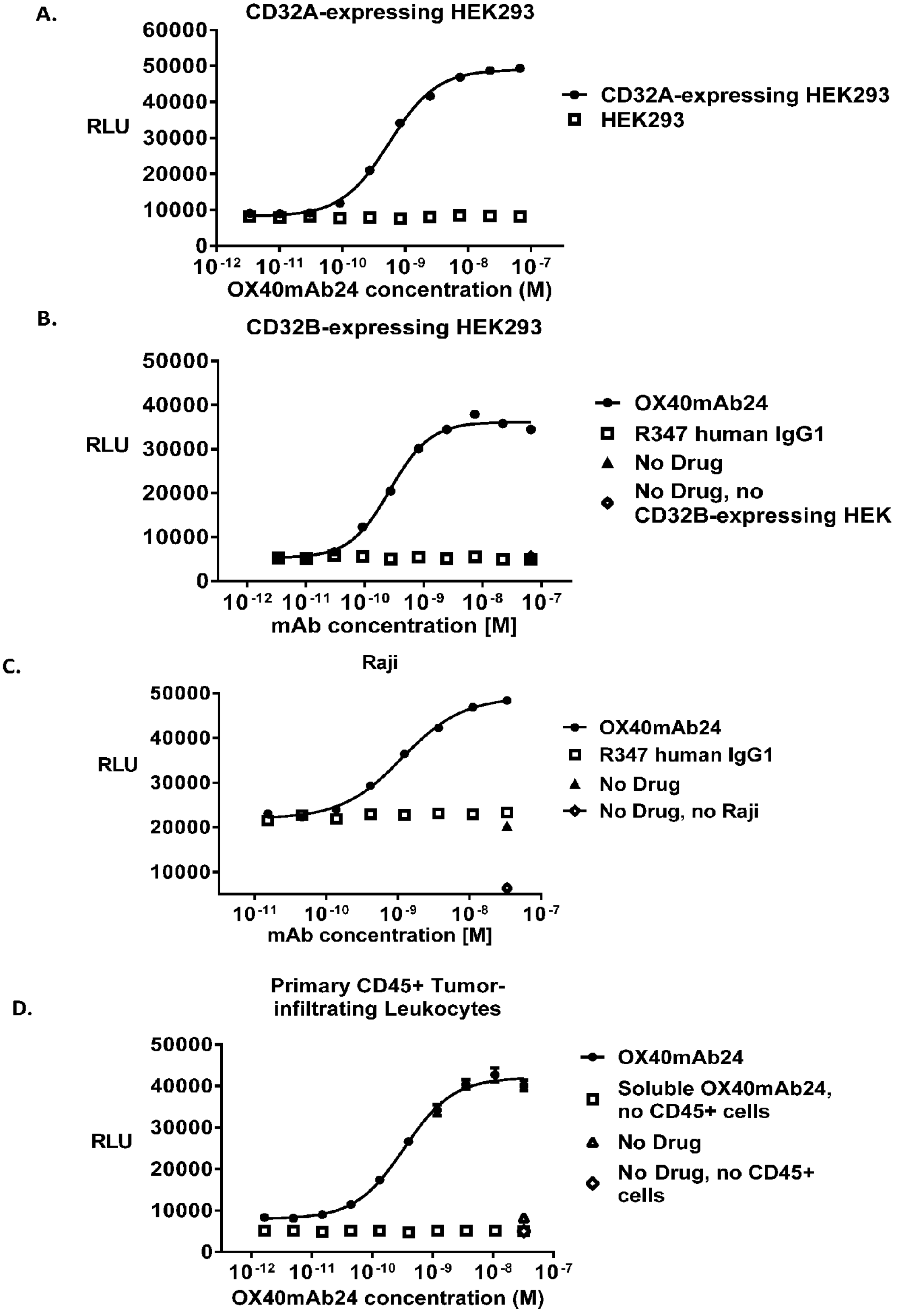

FIGURE 12A-B
A.
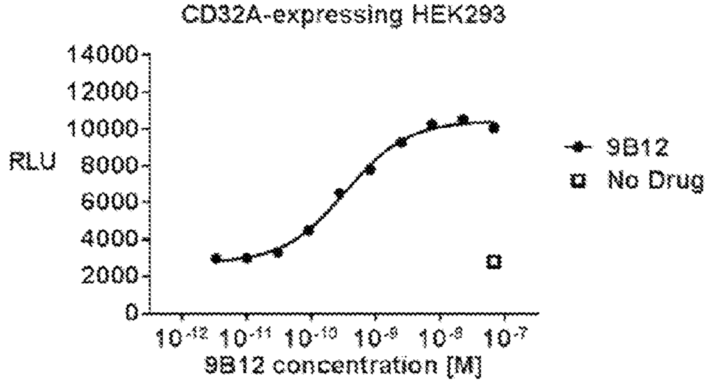
B.
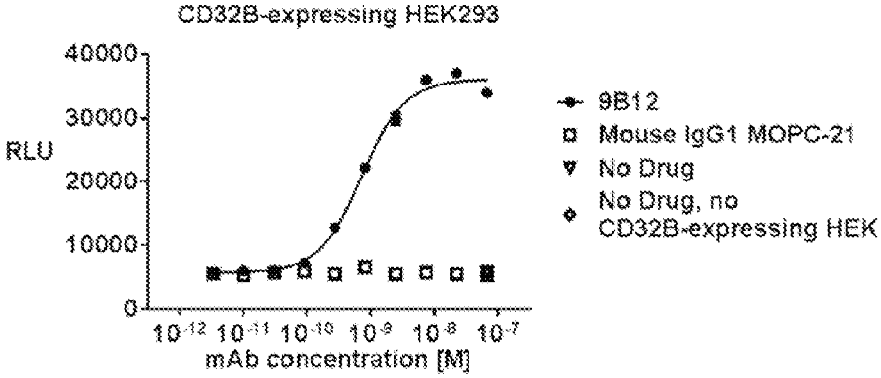

FIGURE 12C-D
C.
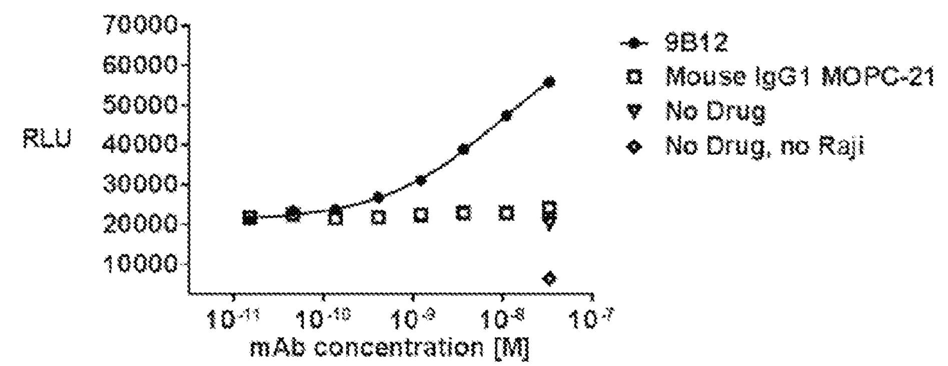
D.
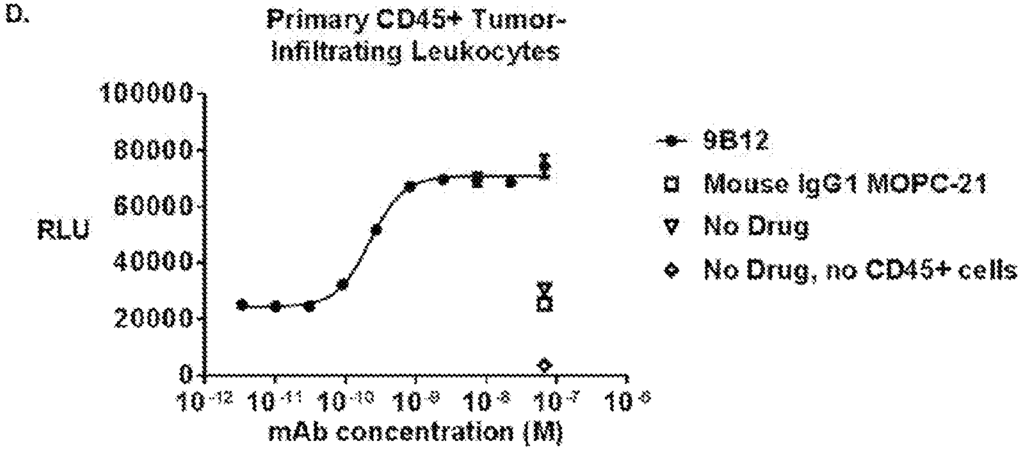

FIGURE 13A-B
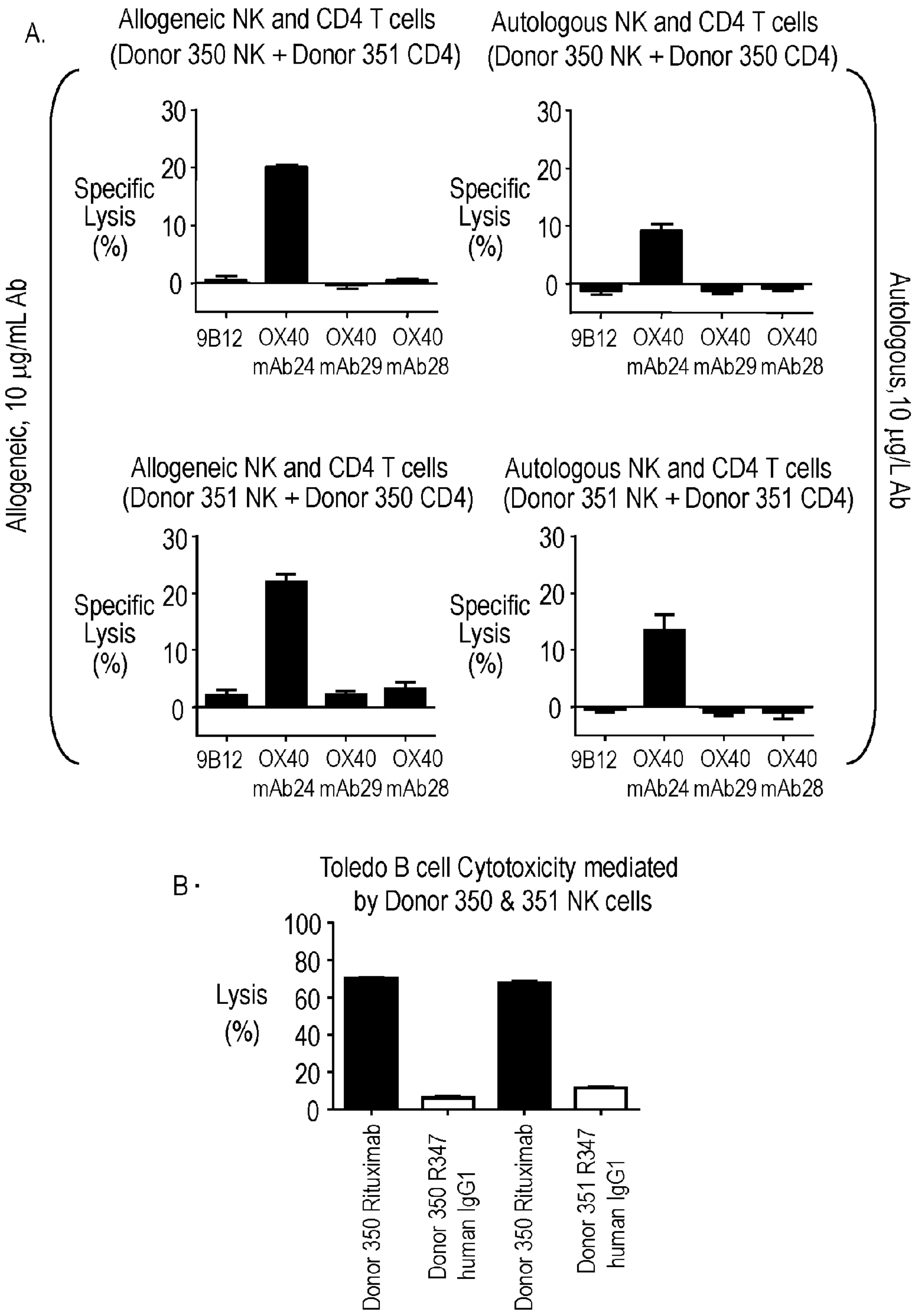

FIGURE 14A-B
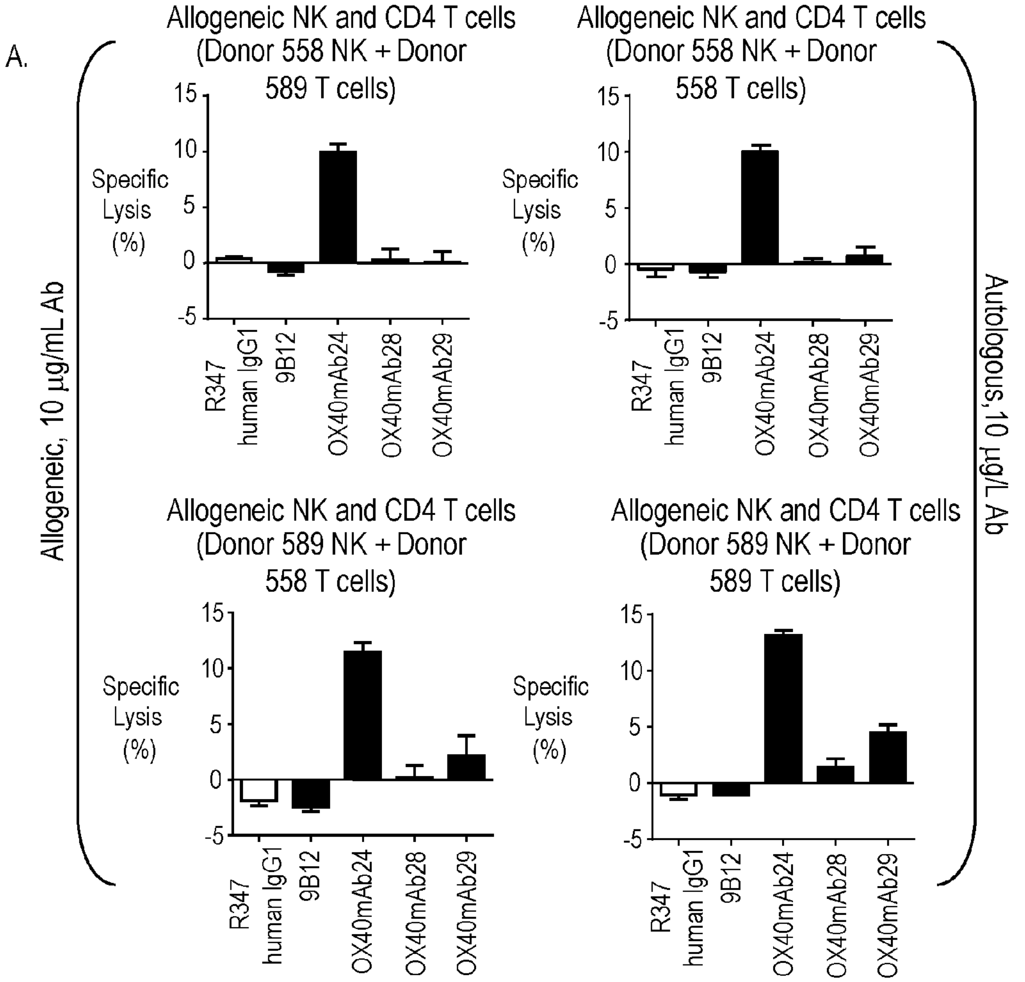
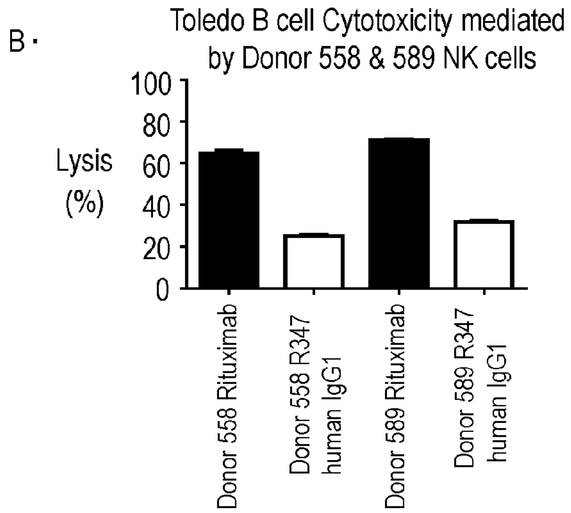

FIGURE 15A-D
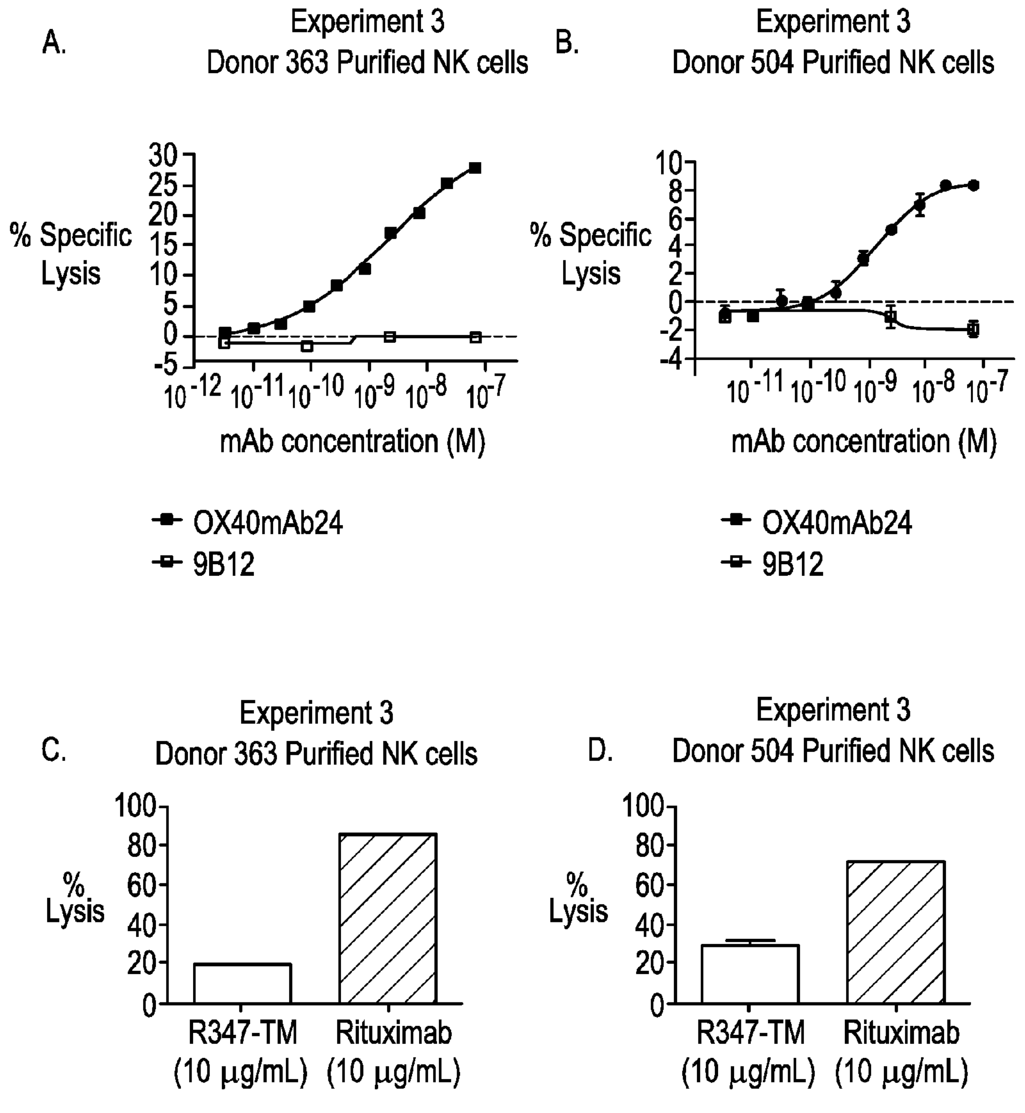

FIGURE 16A-D
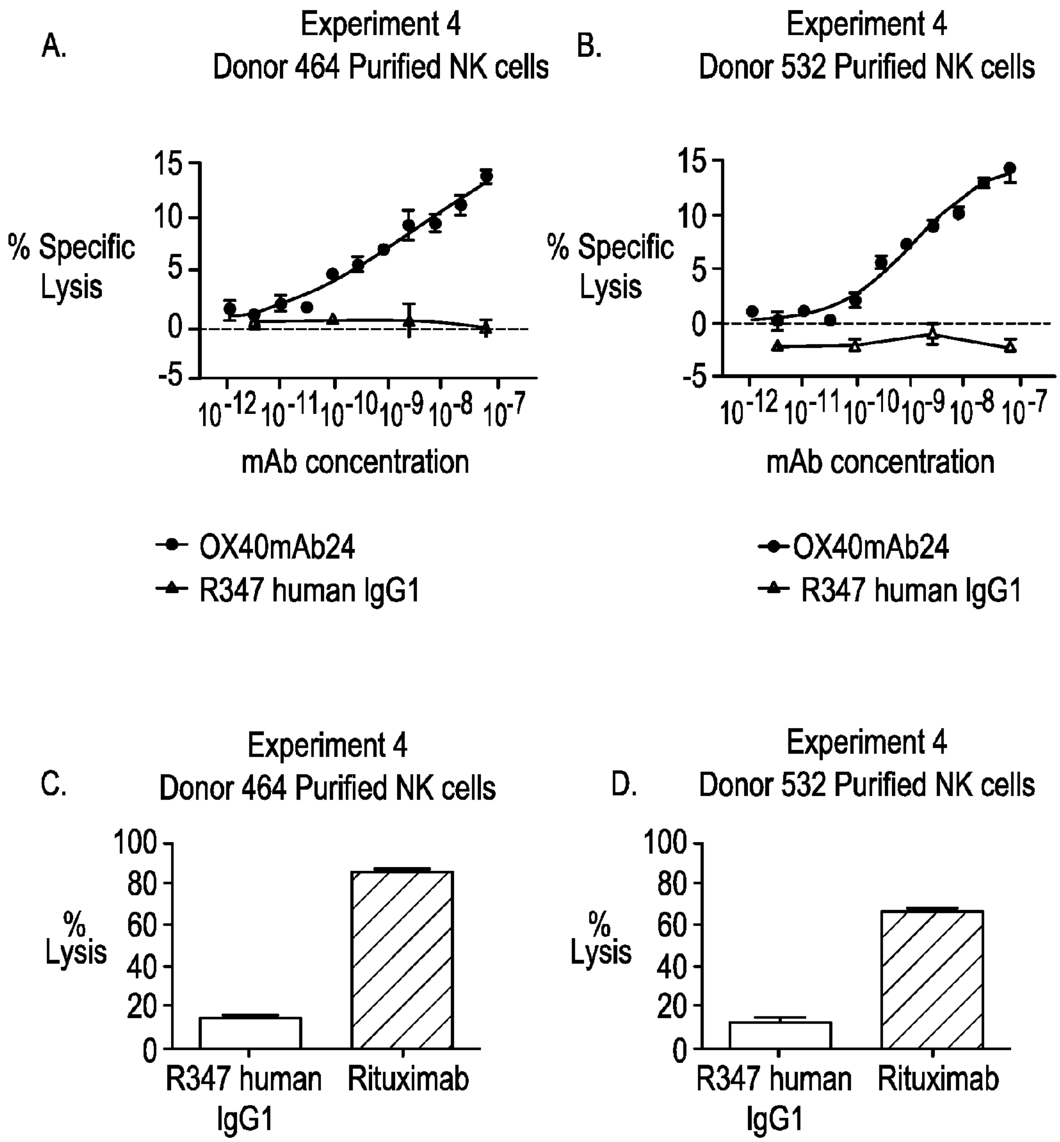

FIGURE 17A-B
A
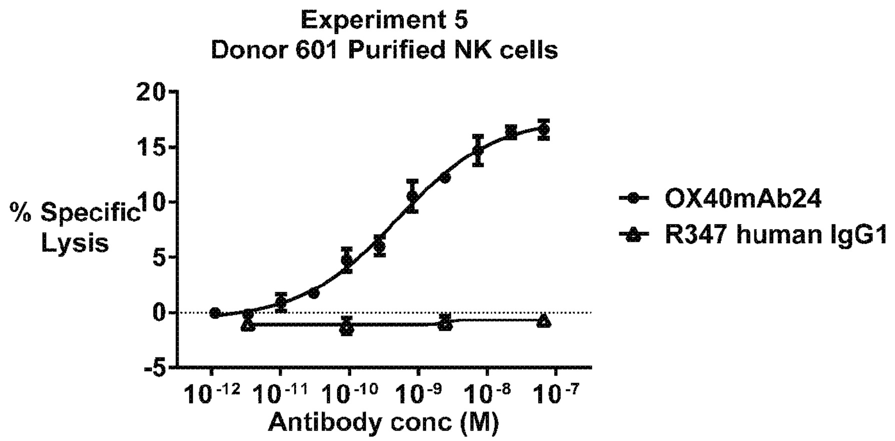
B
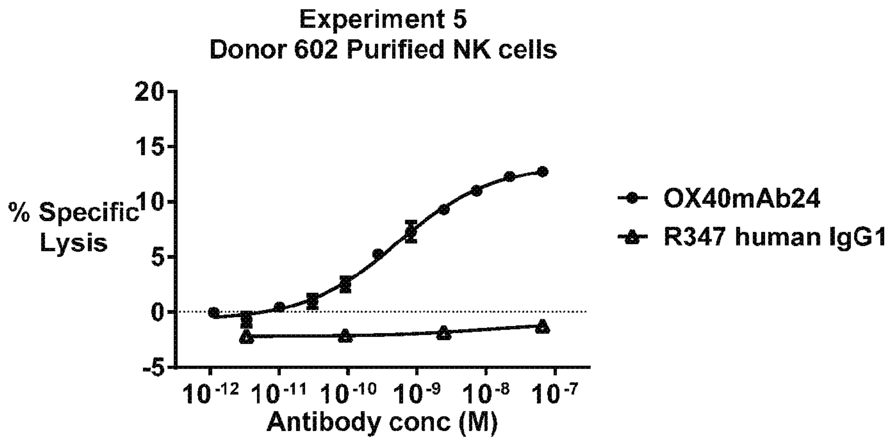

FIGURE 18A-B
A.
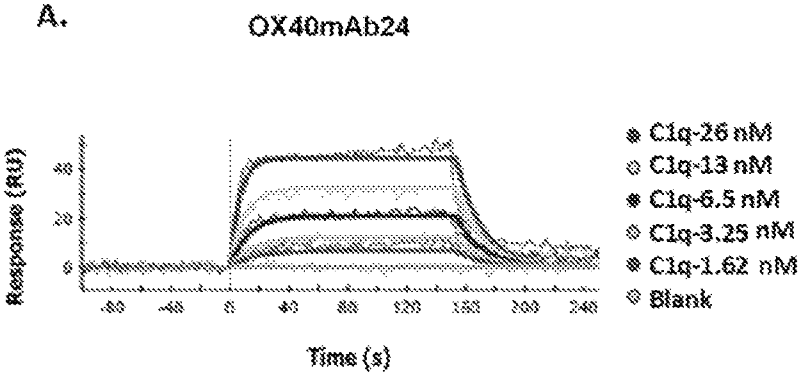
B.
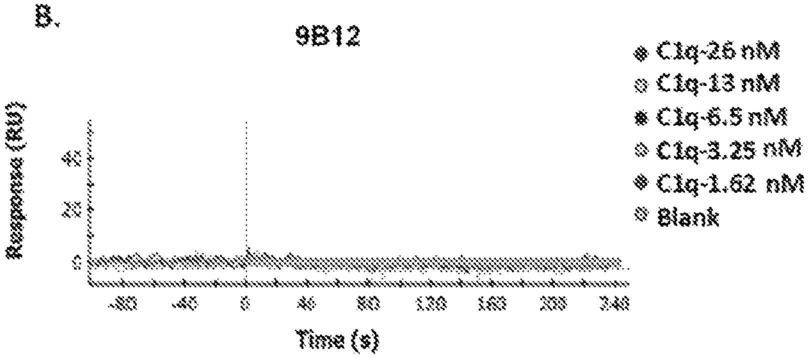

FIGURE 19A-B
A
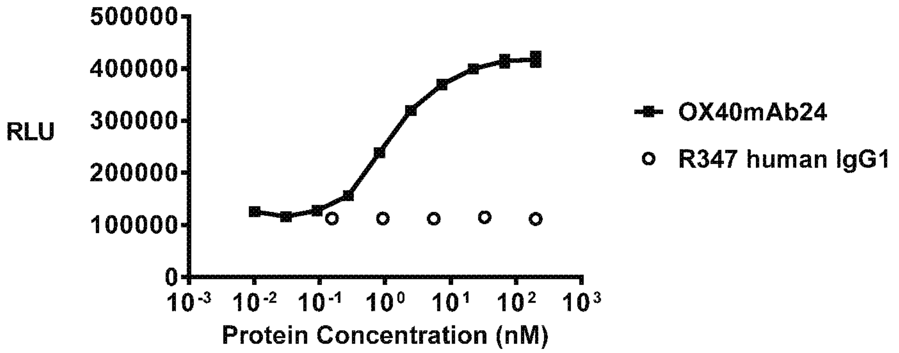
B
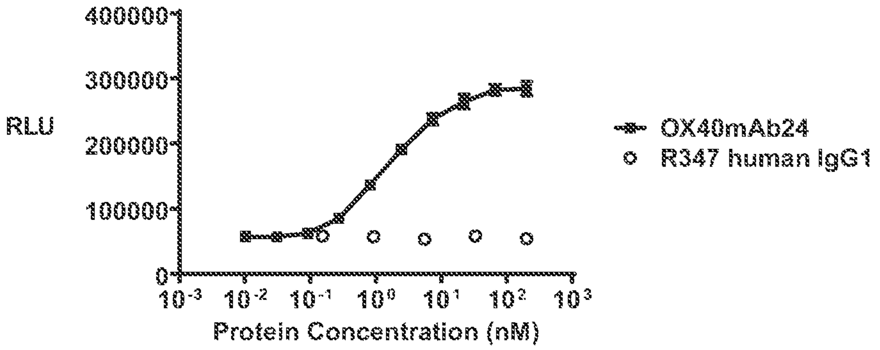

FIGURE 20A-B
A
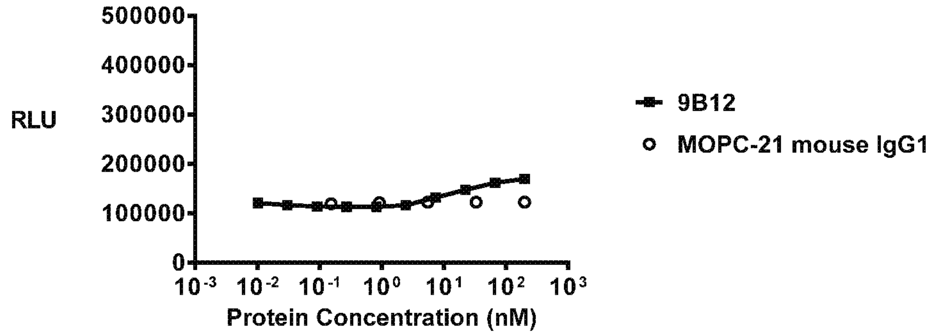
B
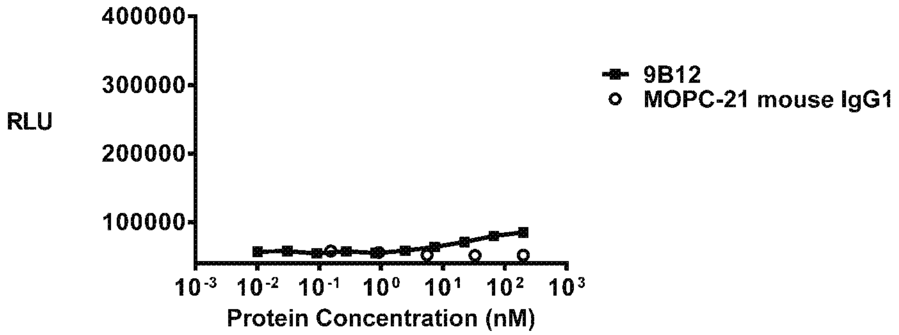

FIGURE 21A-B
A
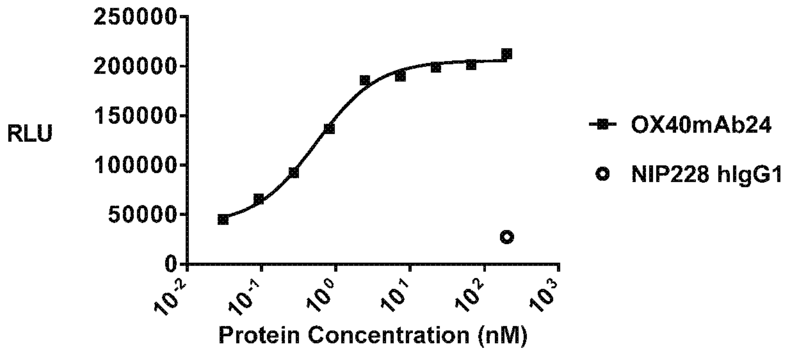
B
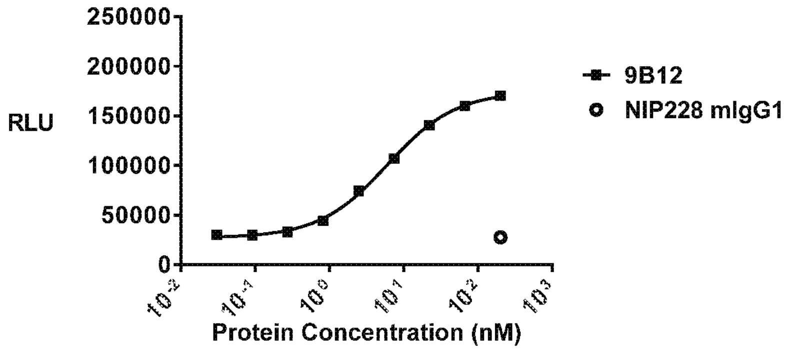

FIGURE 22A-D
A
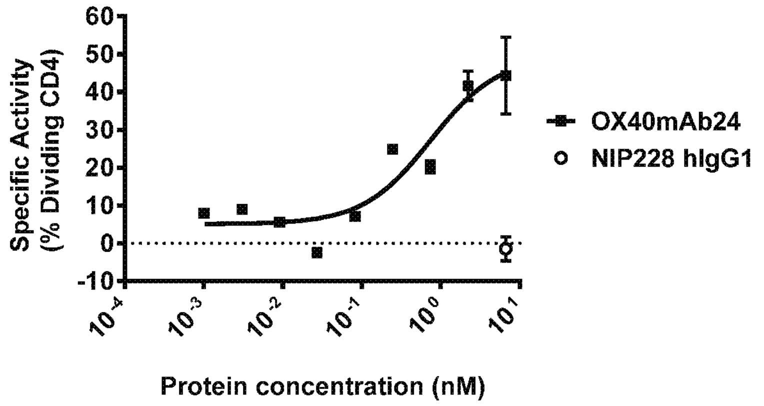
B
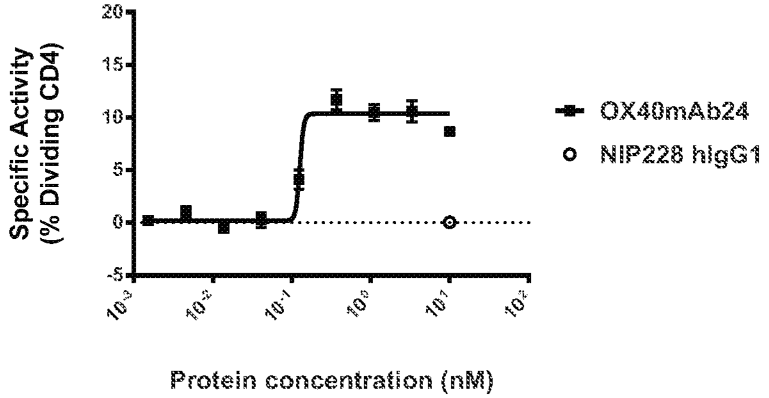

(FIGURE 22A-D, con't)
C
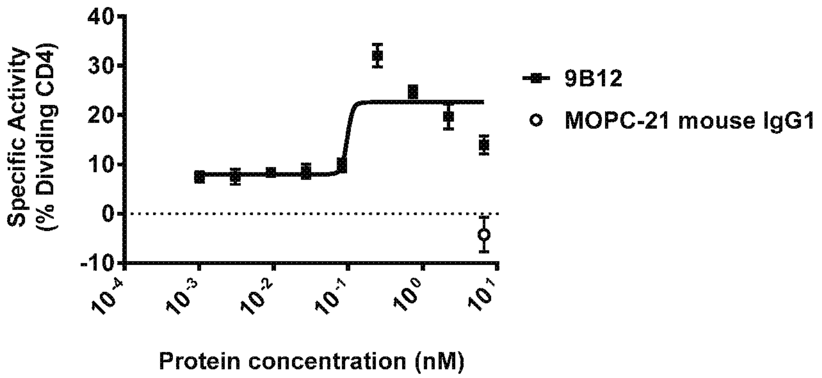
D
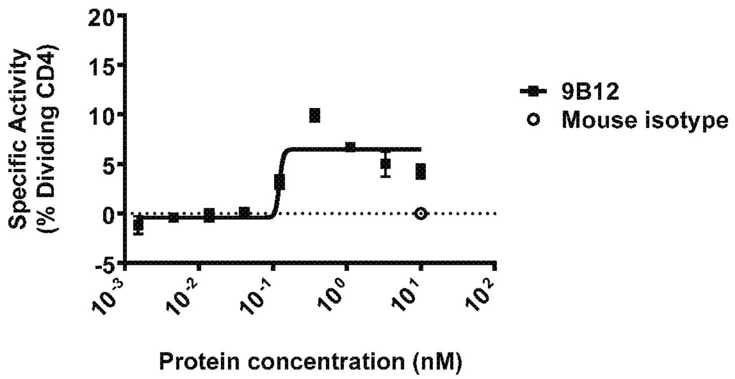

FIGURE 23A-B
A
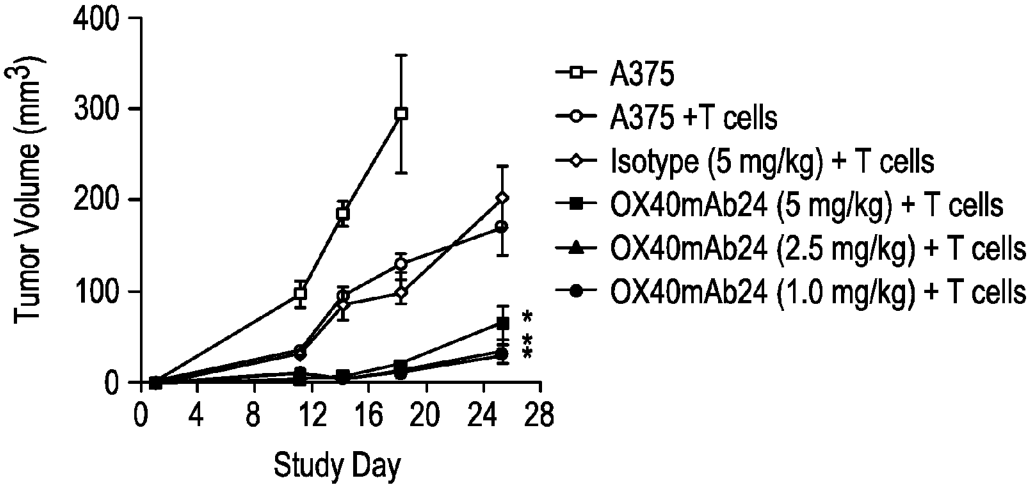
B
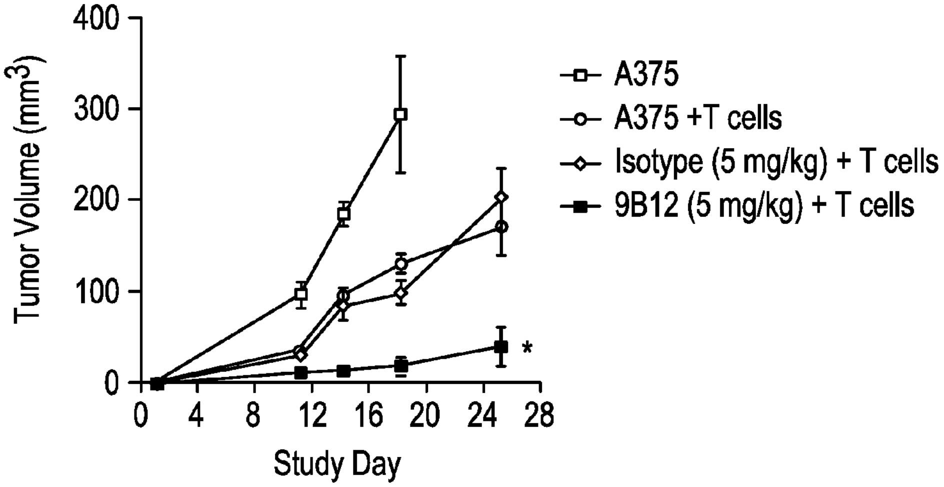

FIGURE 24A-B
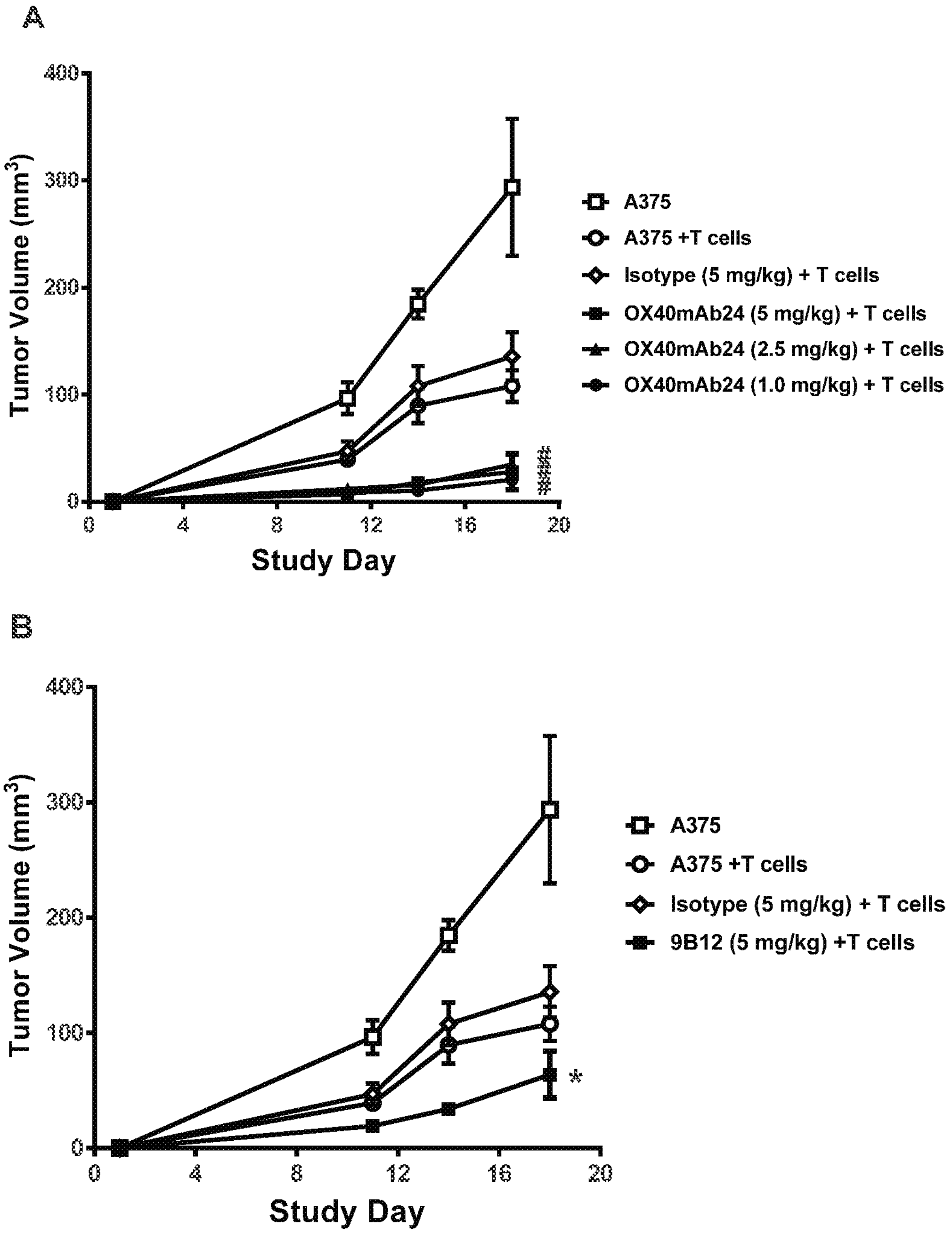

FIGURE 26A-B
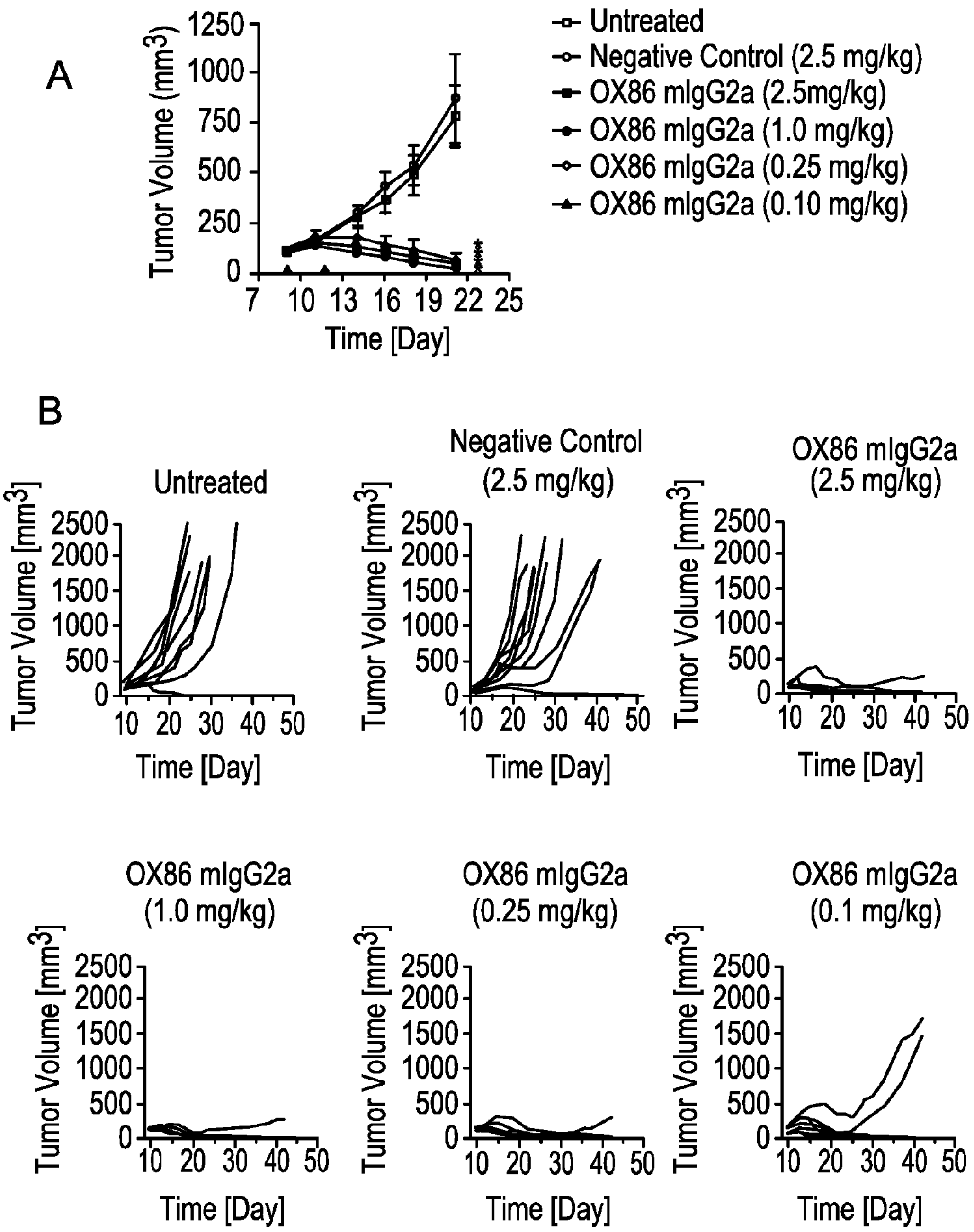

FIGURE 27A-B
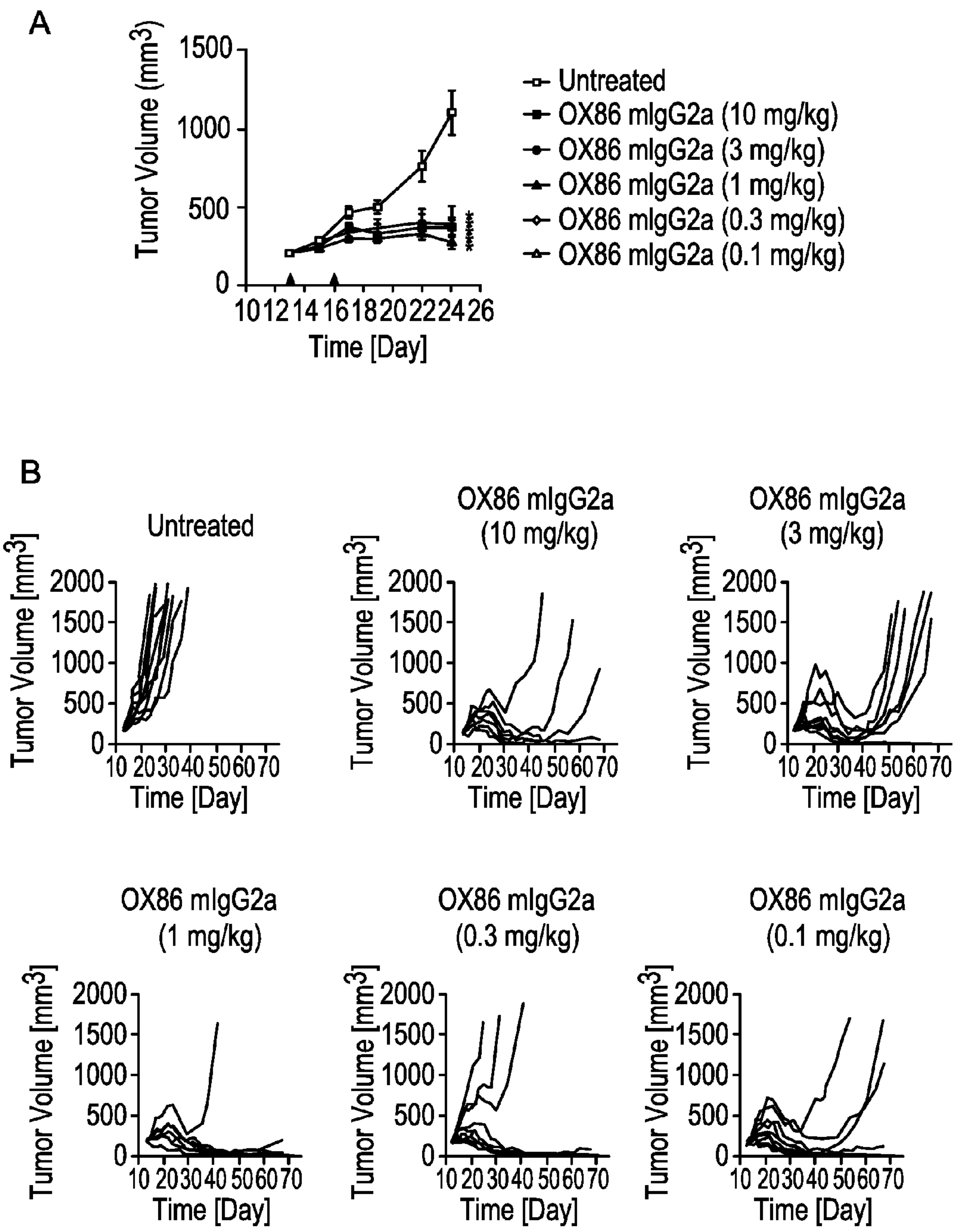

FIGURE 28A-B
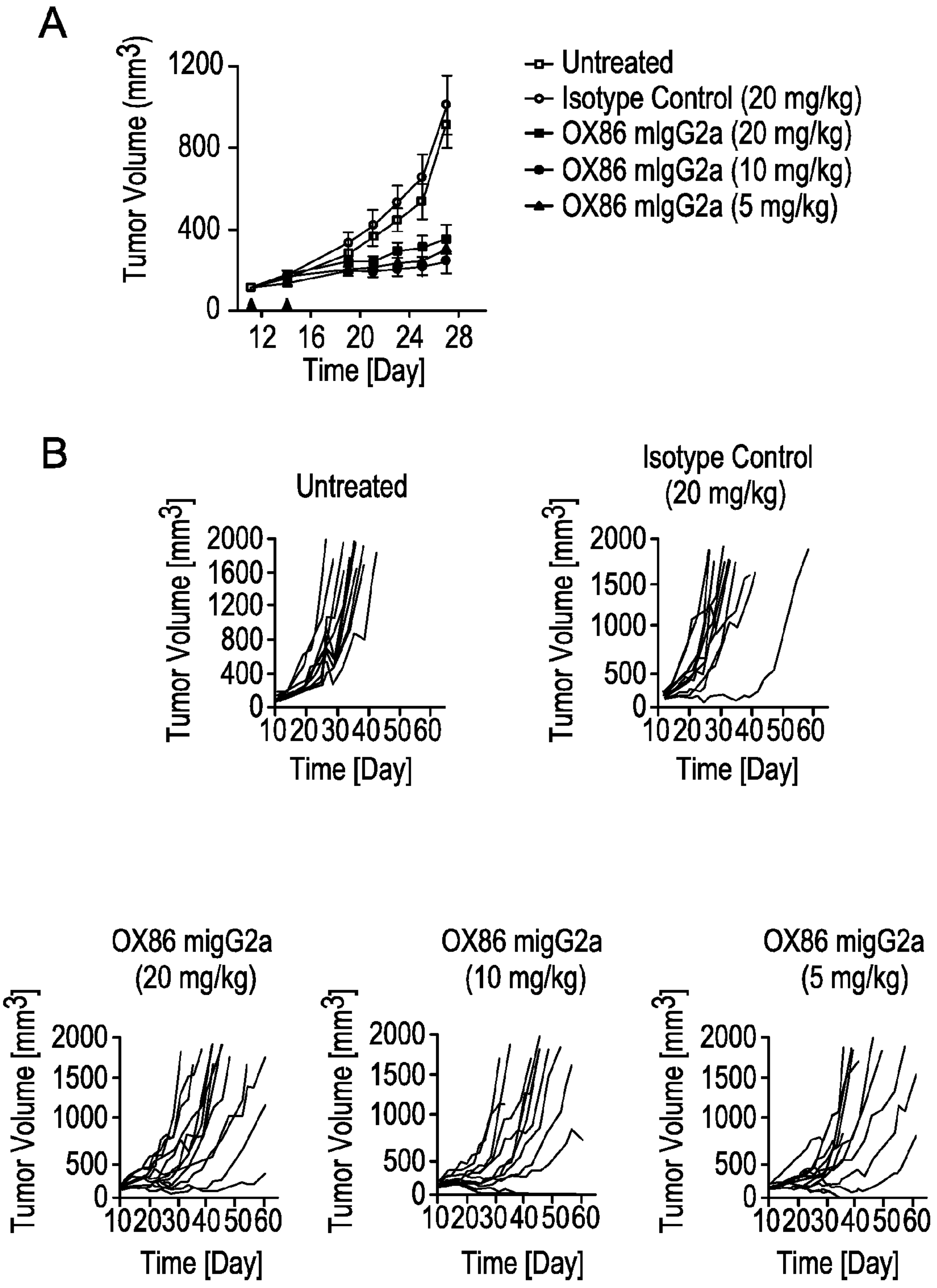

FIGURE 29A-B
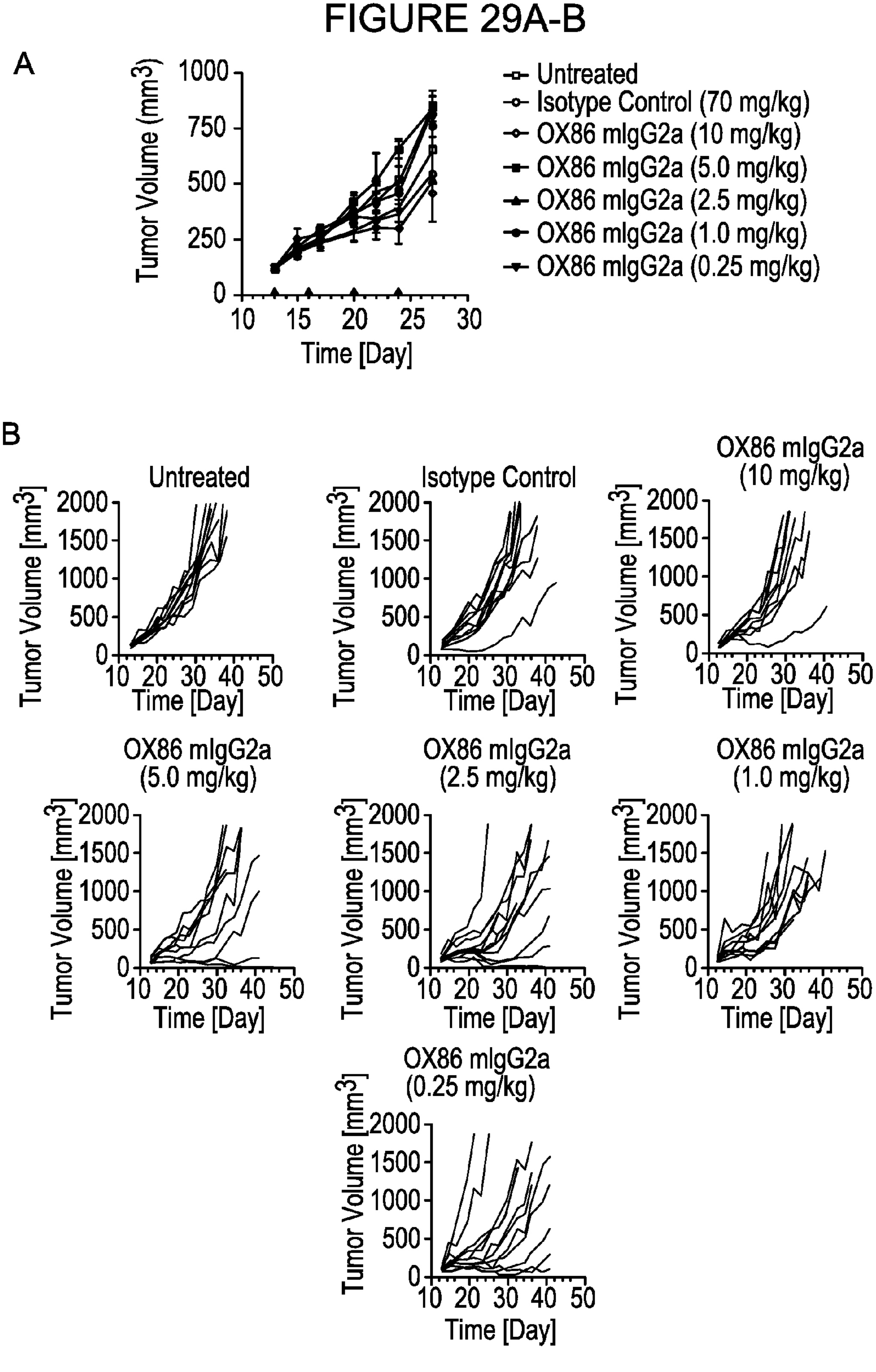

FIGURE 30

```
                                                        CRD1
Human_OX40   MCVGARRLGRGPCAALLLLGLGLSTVTG-LHCVGDTYPSNDRCCHECRPGNGMVSRCSRS 59
Mouse_OX40   MYVWVQQP-----TALLLLALTLGVTARRLNCVKHTYPSGHKCCRECQPGHGMVSRCDHT 55
             * * .::      :*****.* *...:  *:** .****..:**:**:**:******.::

                                                          111   [116]
                                   CRD2                    ↓      ↓
Human_OX40   QNTVCRPCGPGFYNDVVSSKPCKPCTWCNLRSGSERKQLCTATQDTVCRCRAGTQP-LDS 118
Mouse_OX40   RDTLCHPCETGFYNEAVNYDTCKQCTQCNHRSGSELKQNCTPTQDTVCRCRPGTQPRQDS 115
             ::*:*:** .****:.*. ..** ** ** ***** ** **.*********.****  **

               121 [126]       137
                ↓    ↓  CRD3    ↓               CRD4
Human_OX40   -YKPGVDCAPCPPGHFSPGDNQACKPWTNCTLAGKHTLQPASNSSDAICEDRDPPATQPQ 177
Mouse_OX40   GYKLGVDCVPCPPGHFSPGNNQACKPWTNCTLSGKQTRHPASDSLDAVCEDRSLLATLLW 175
              ** ****.**********:***********:**:* :***:* **:****.  **
```

A (FIGURE 32A con't)
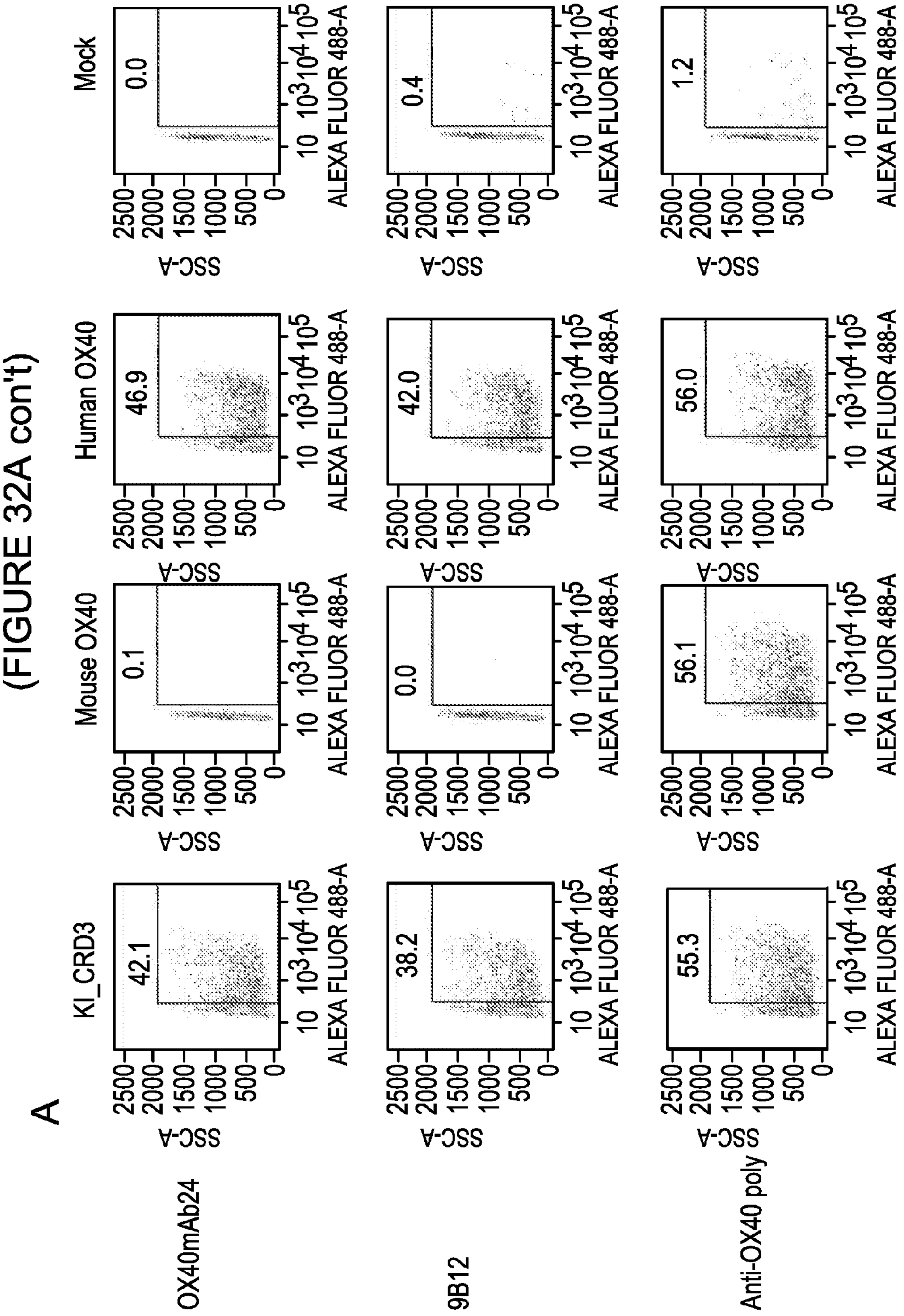

Figure 32A:
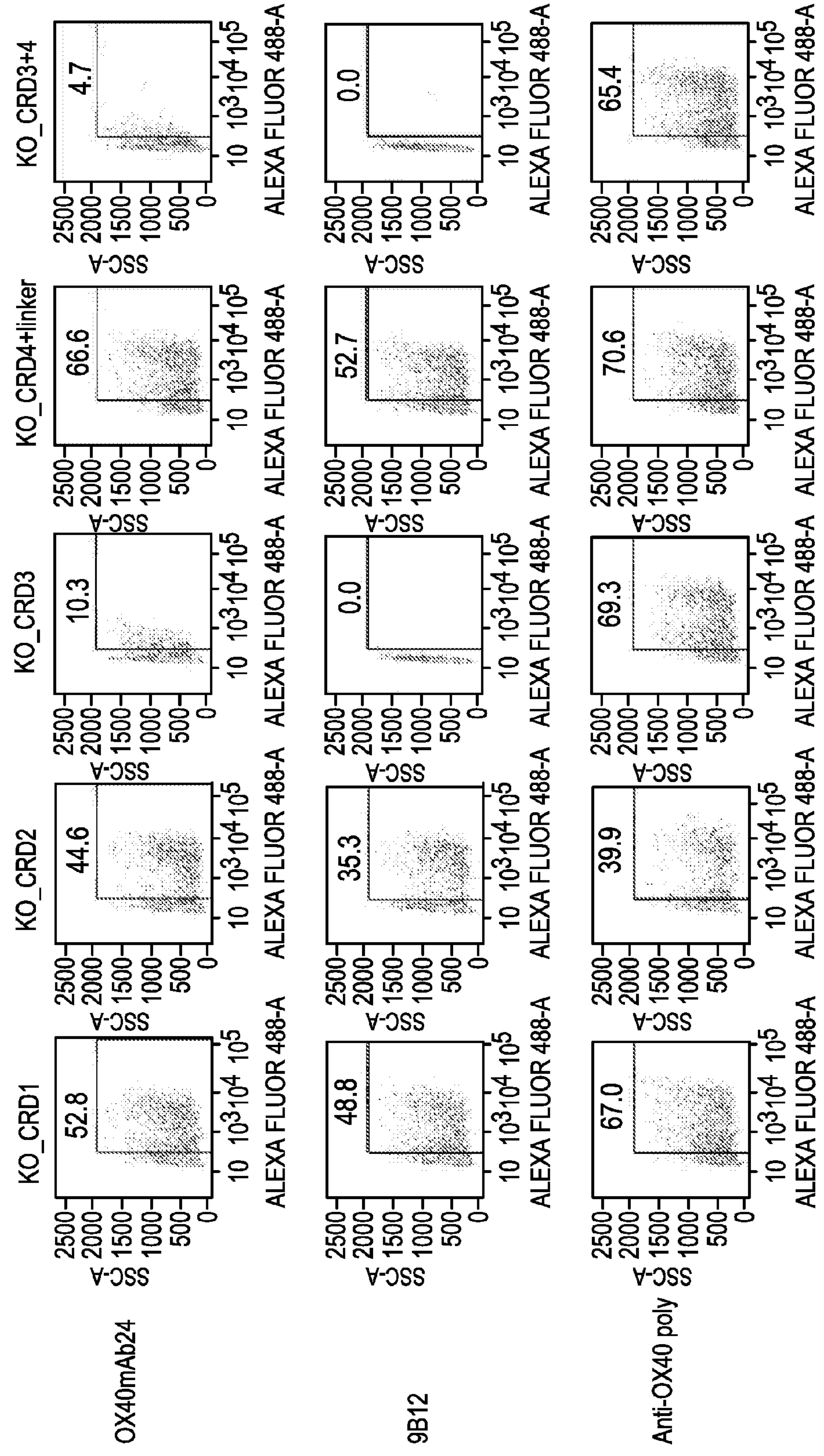
Figure 32B:
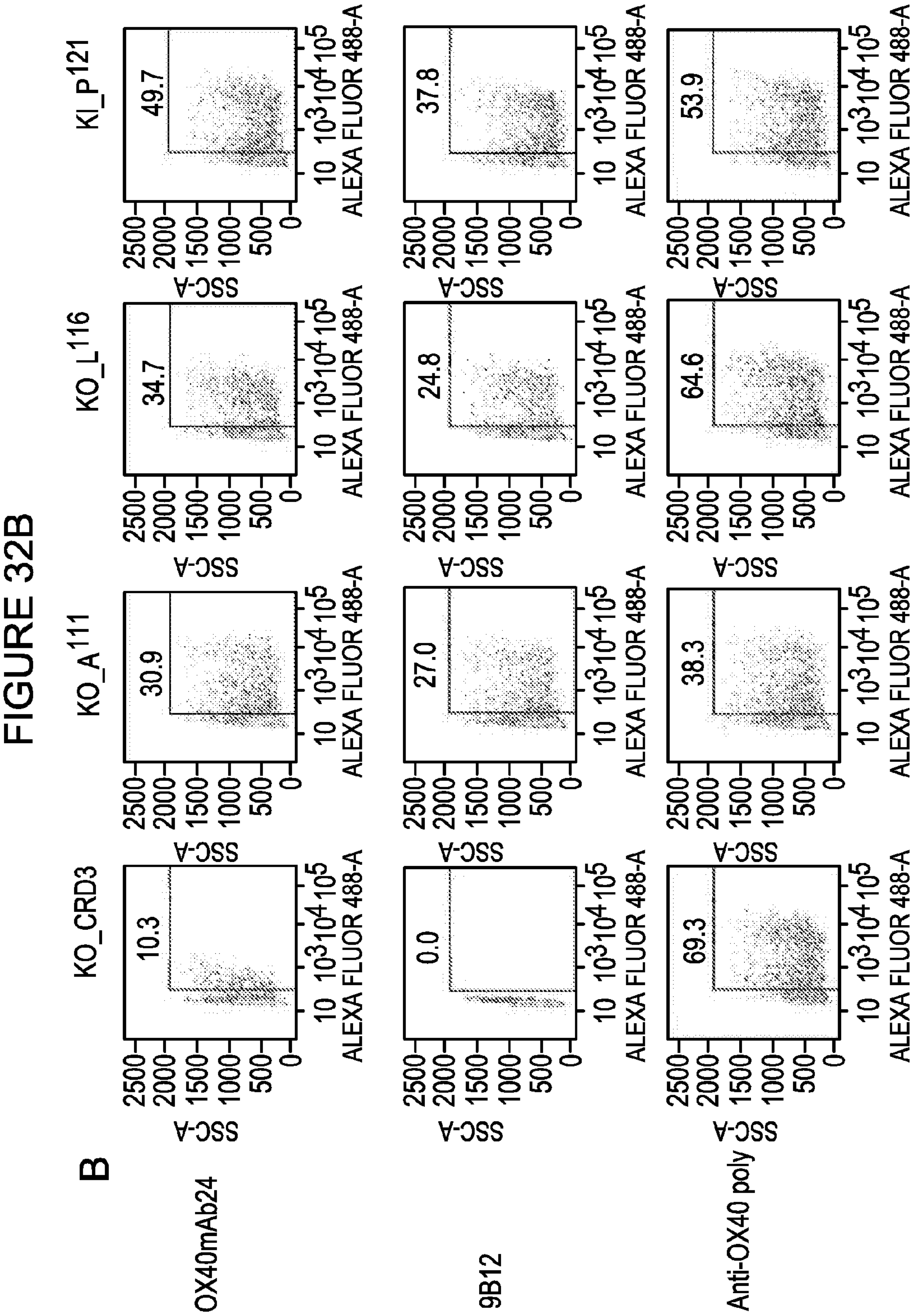

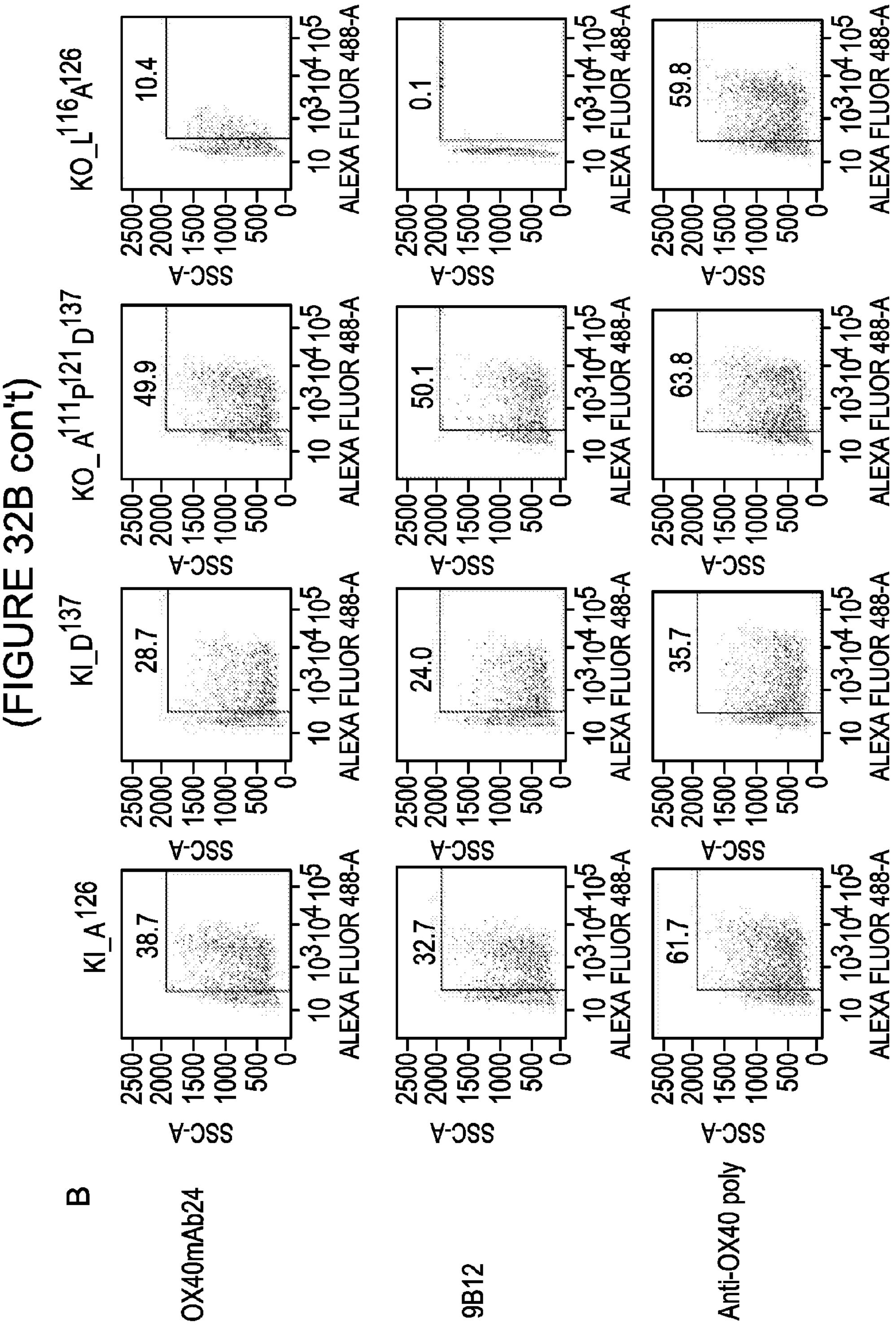
(FIGURE 32B con't)

(FIGURE 32B con't)
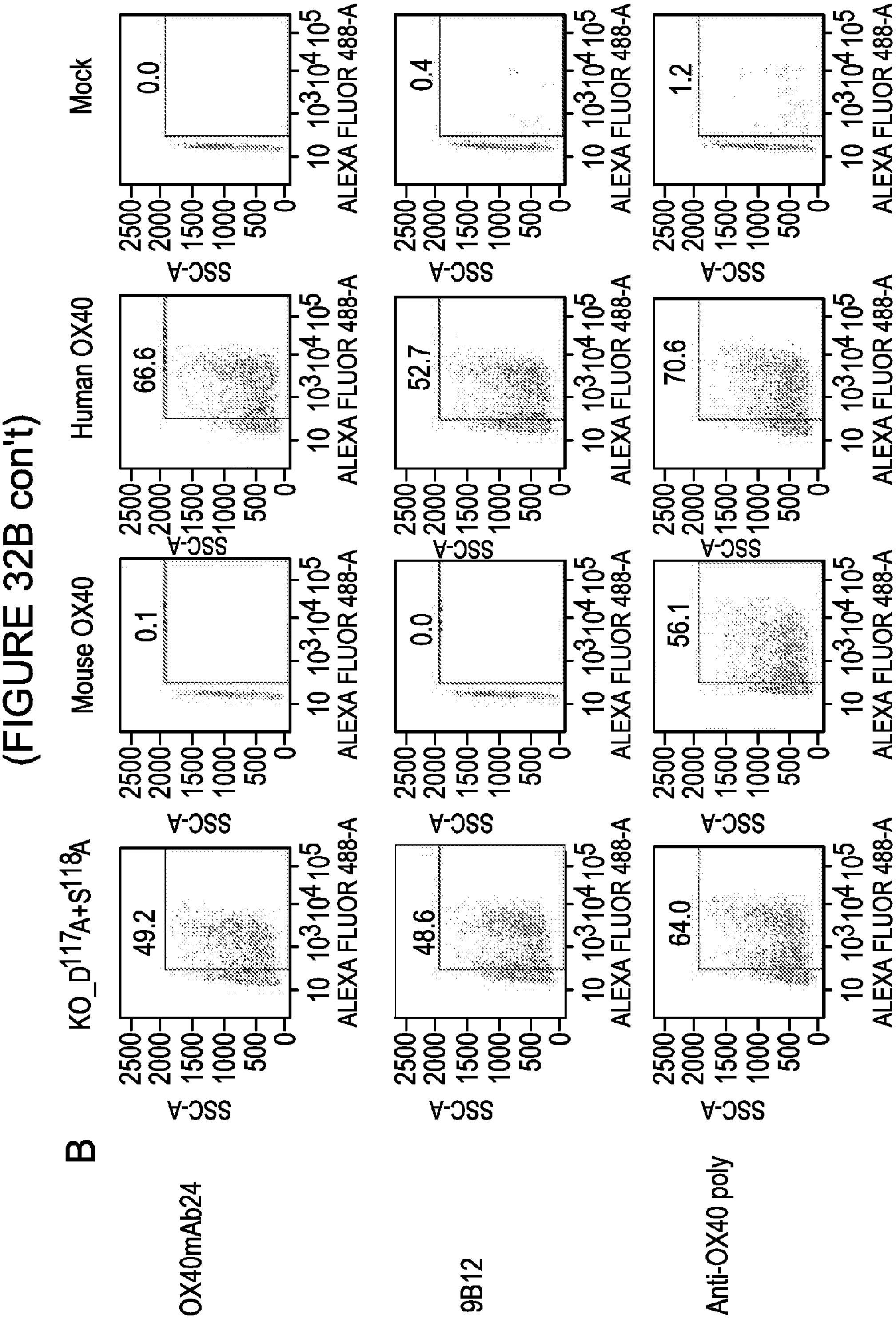

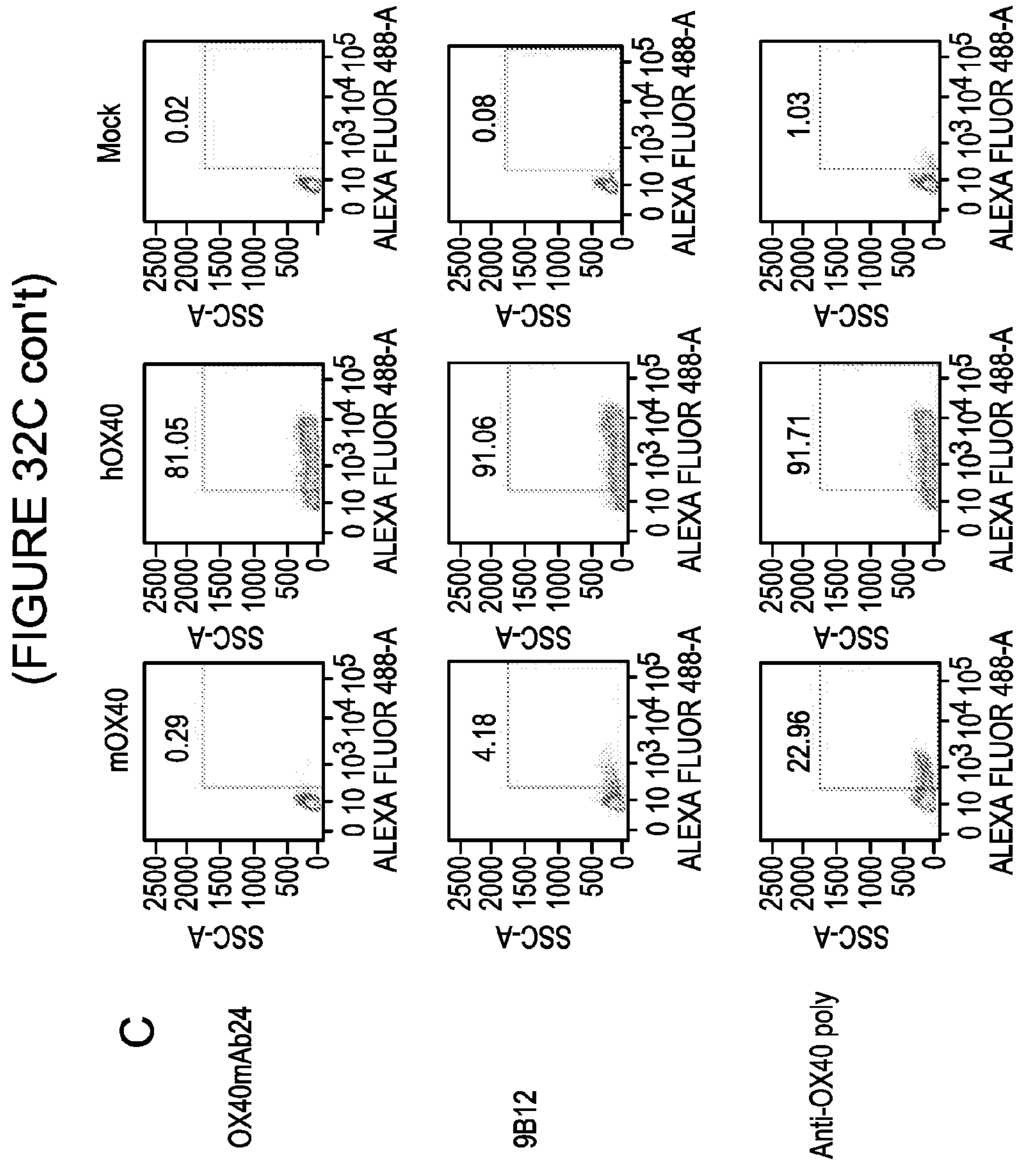
(FIGURE 32C con't)
C
mOX40
hOX40
Mock
OX40mAb24
9B12
Anti-OX40 poly
0.29
81.05
0.02
4.18
91.06
0.08
22.96
91.71
1.03
SSC-A
2500 2000 1500 1000 500 0
0 10 $10^3$ $10^4$ $10^5$
ALEXA FLUOR 488-A FIGURE 33A-D
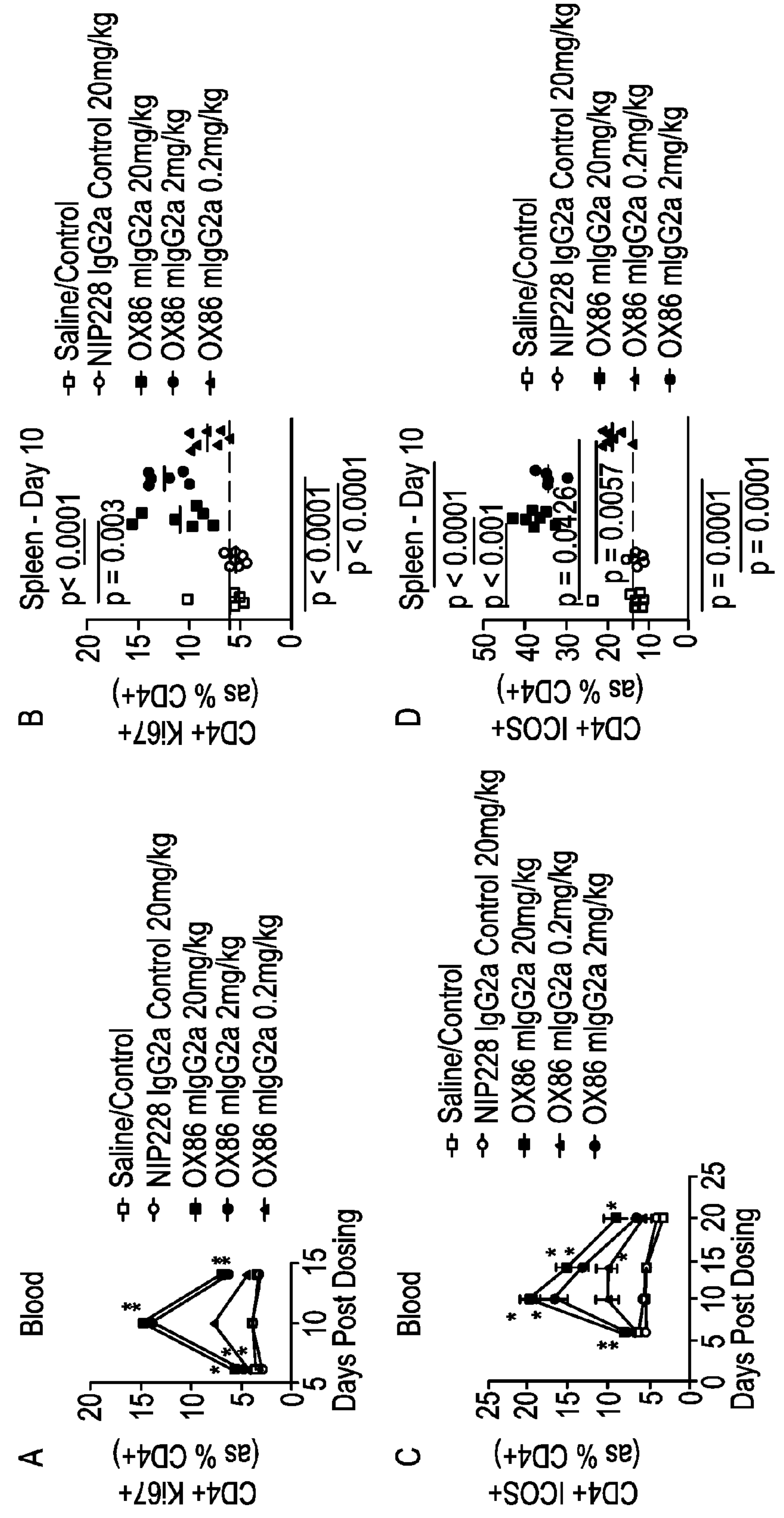

FIGURE 34A-B
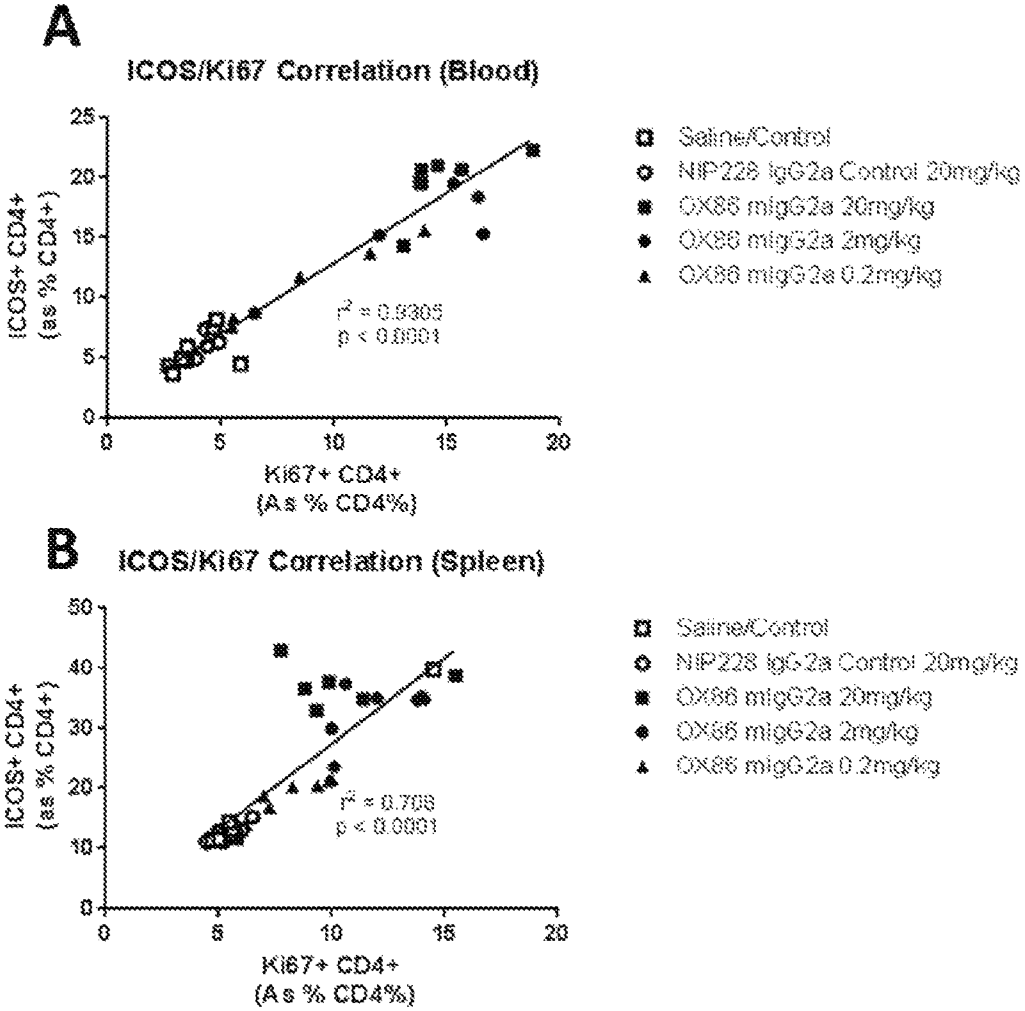

FIGURE 35A-D
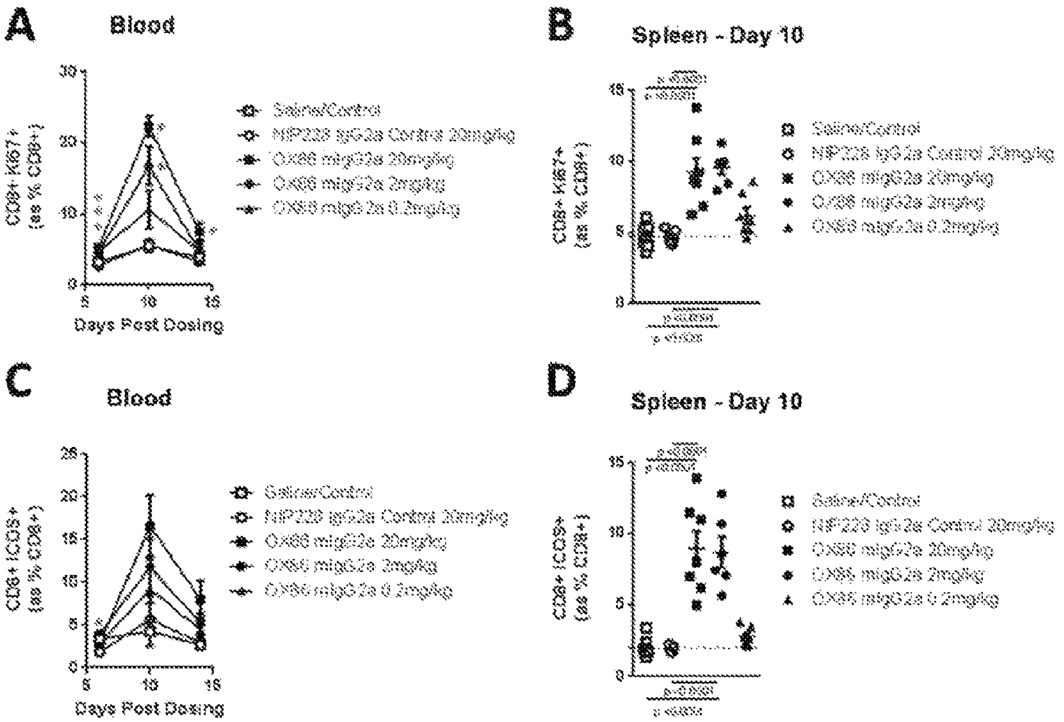

FIGURE 36A-B
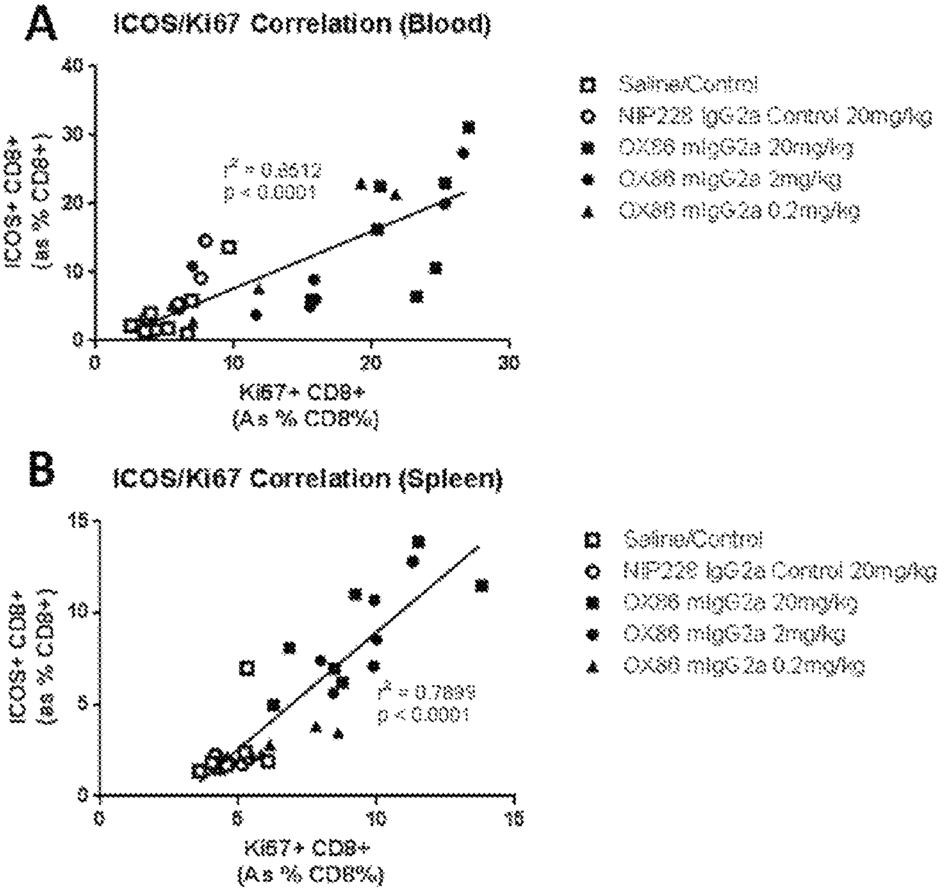

FIGURE 37A-D
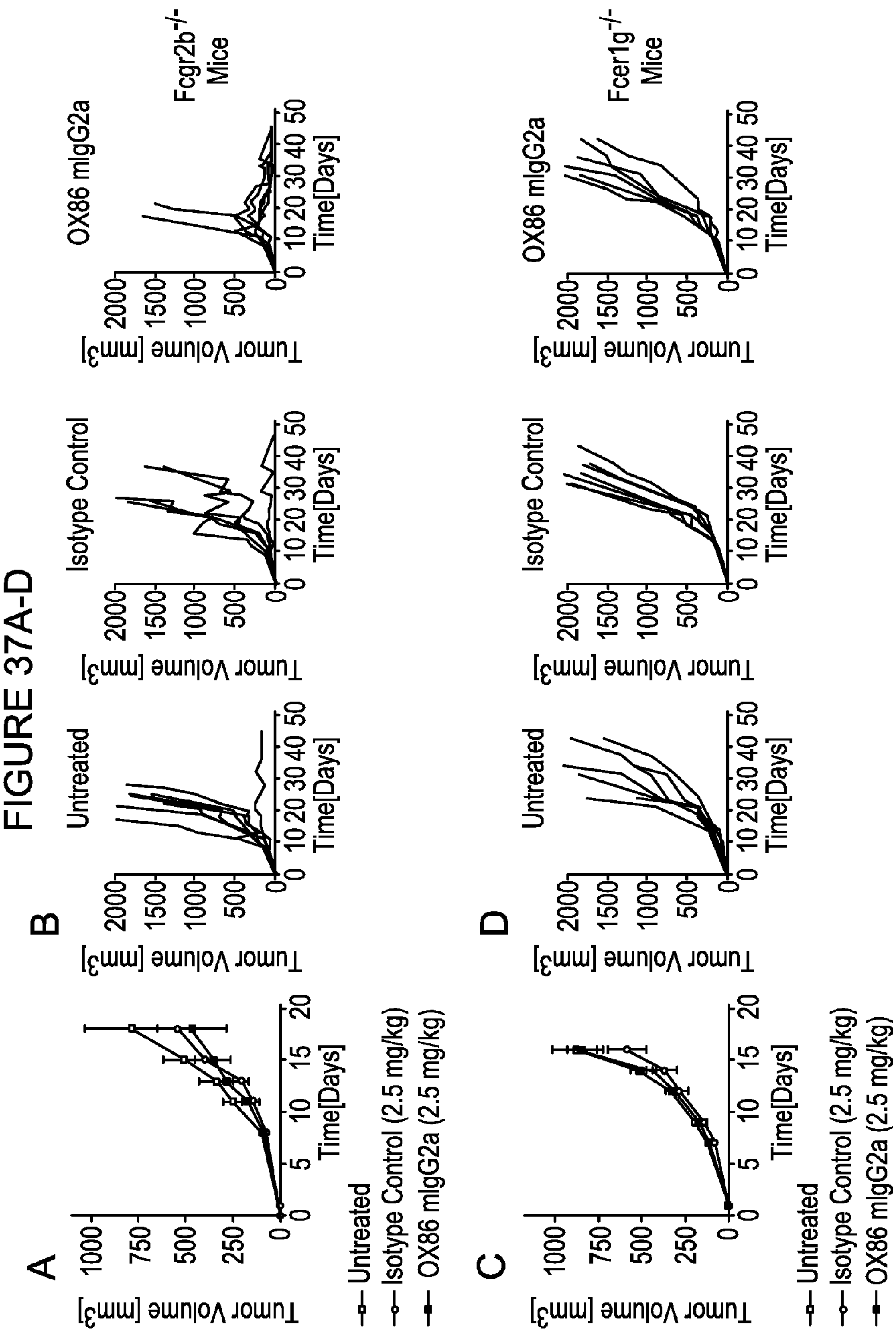

FIGURE 38A-D
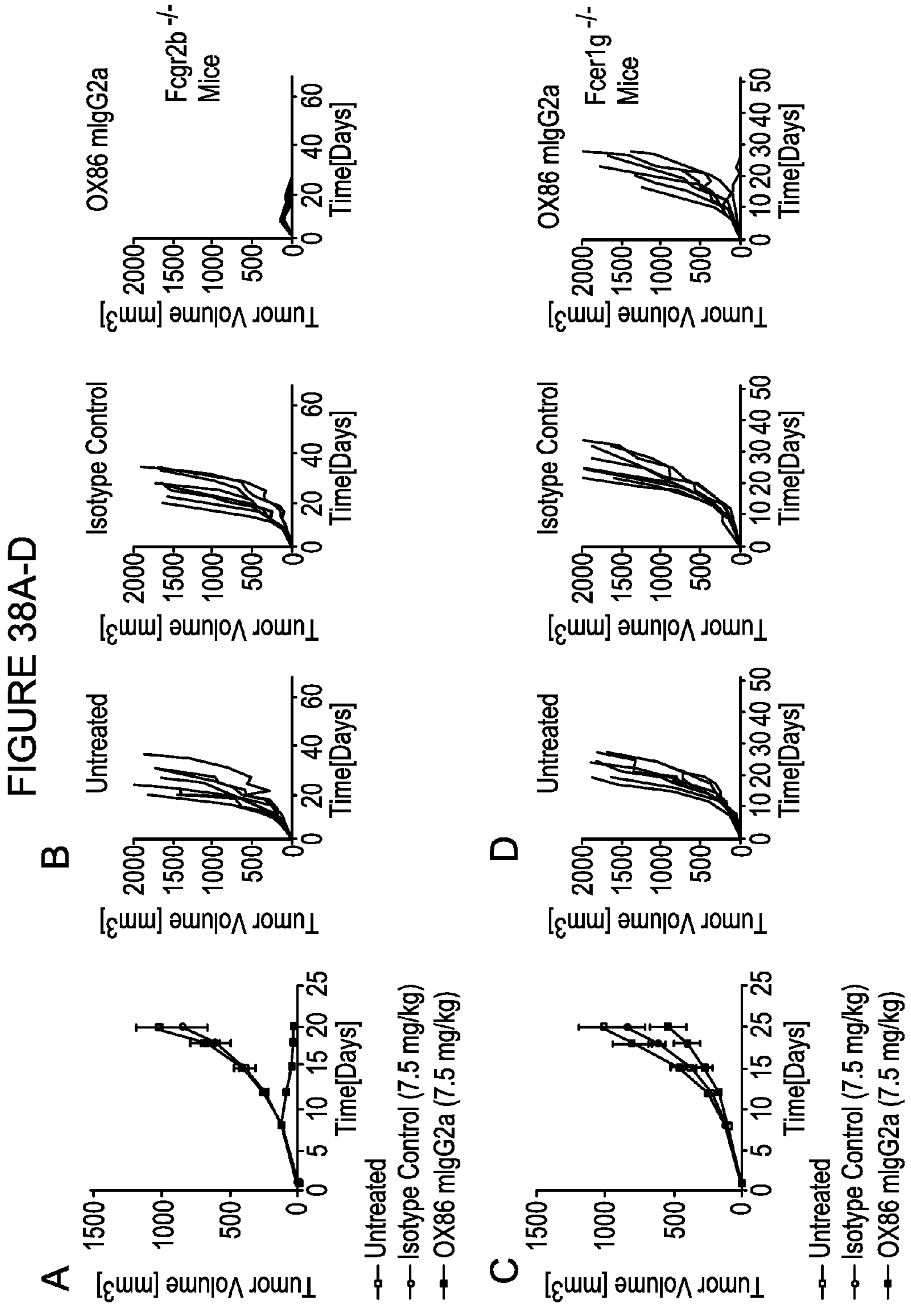

FIGURE 39A-B
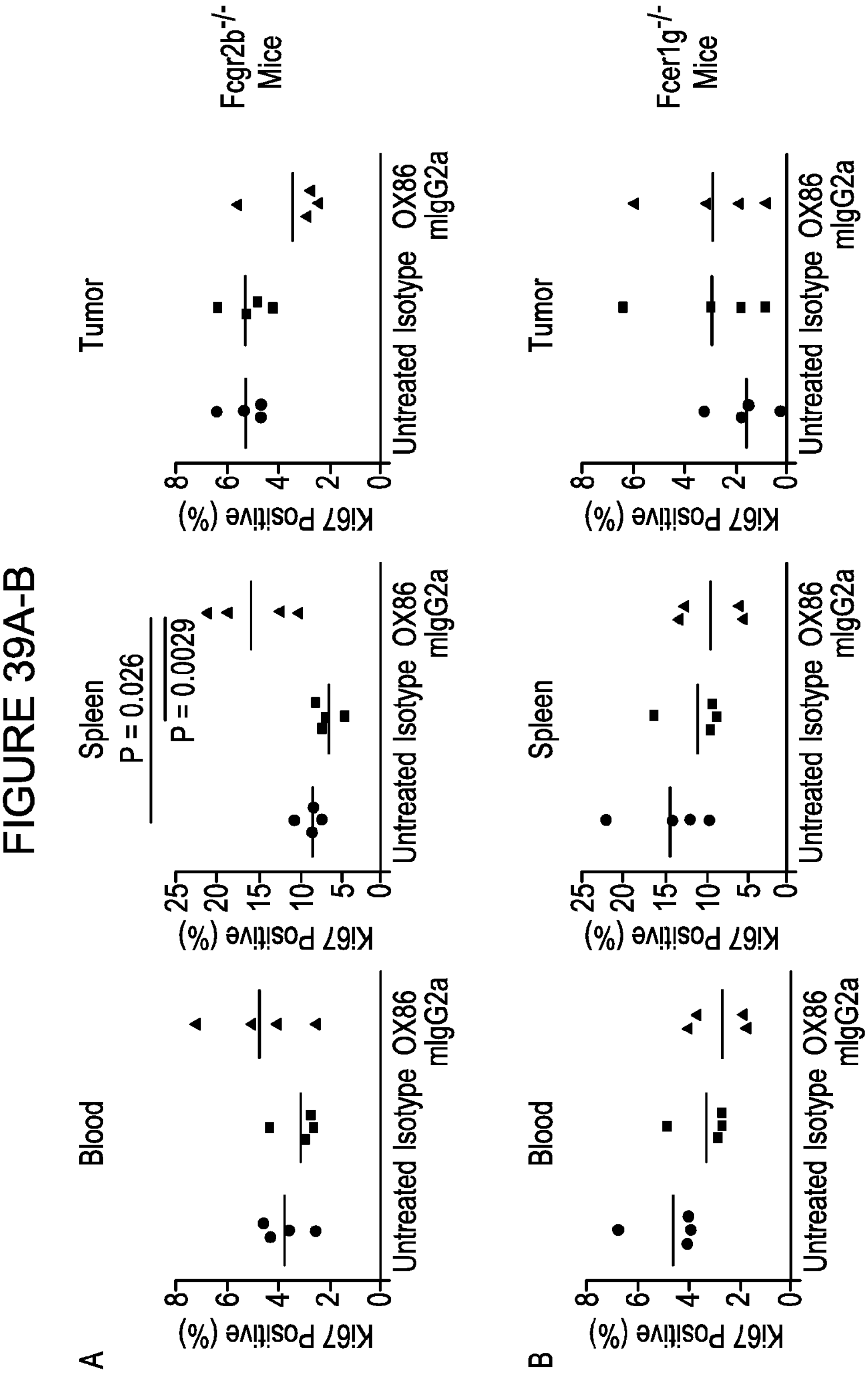

FIGURE 40A-B
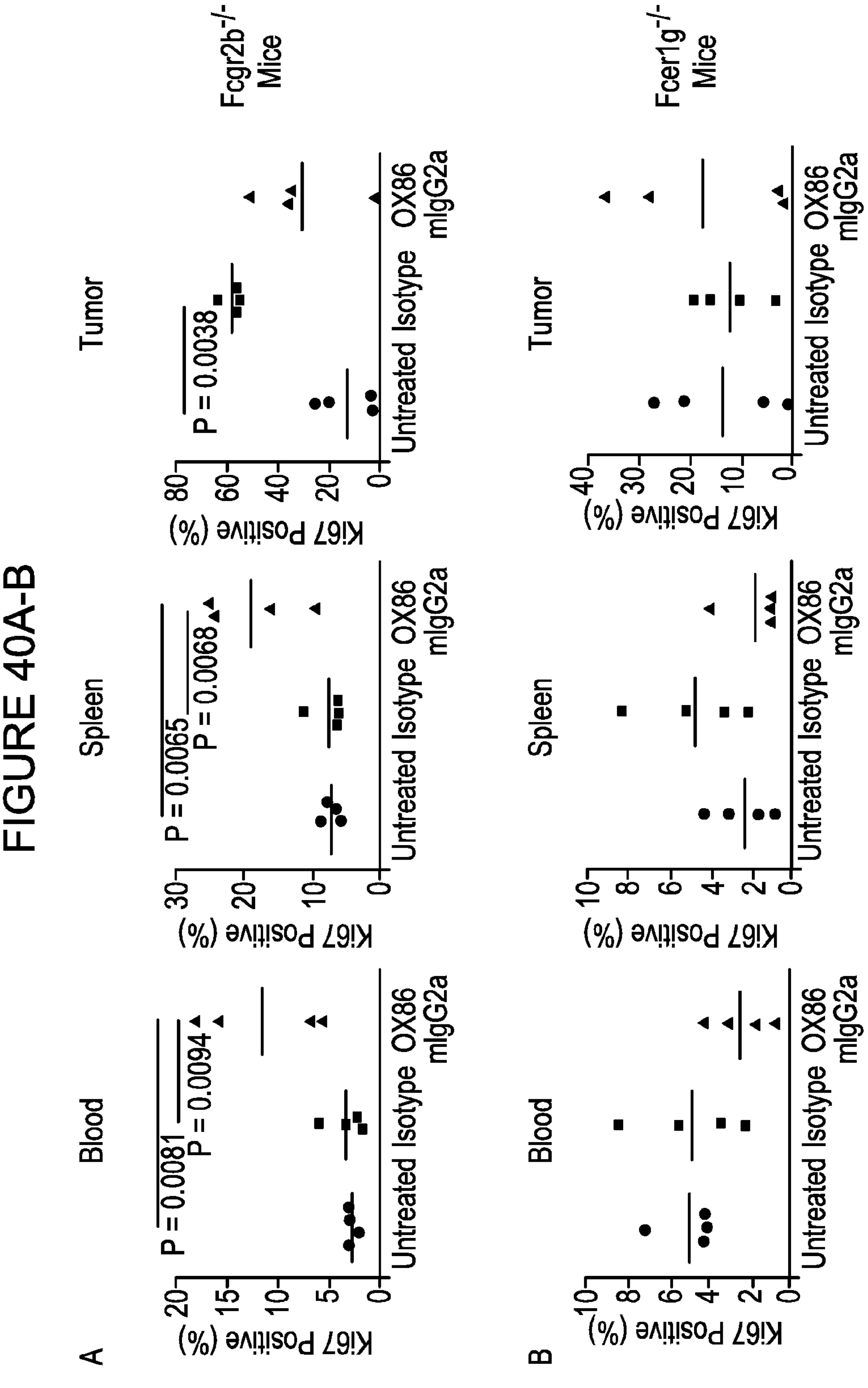

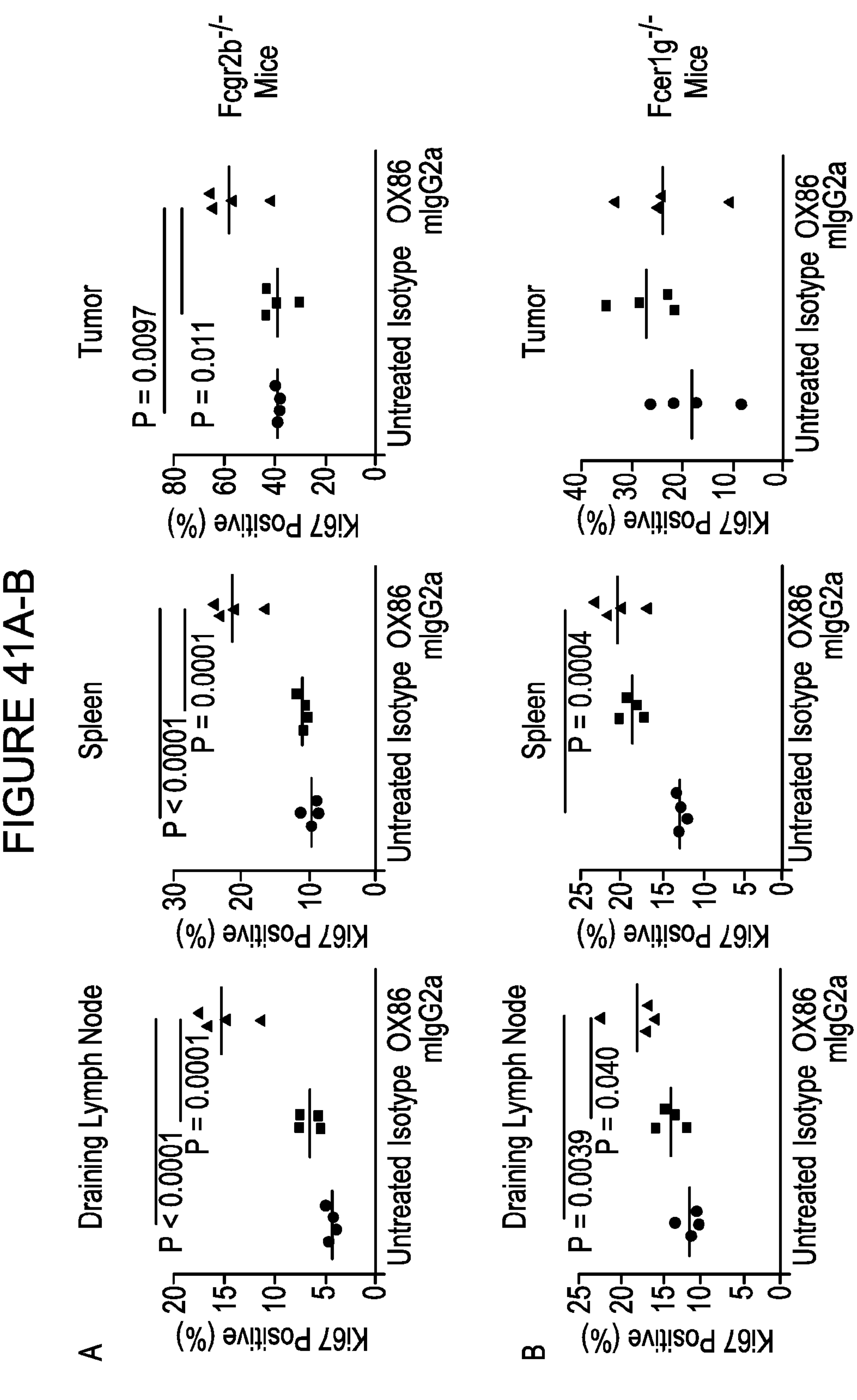
FIGURE 41A-B

FIGURE 42A-B
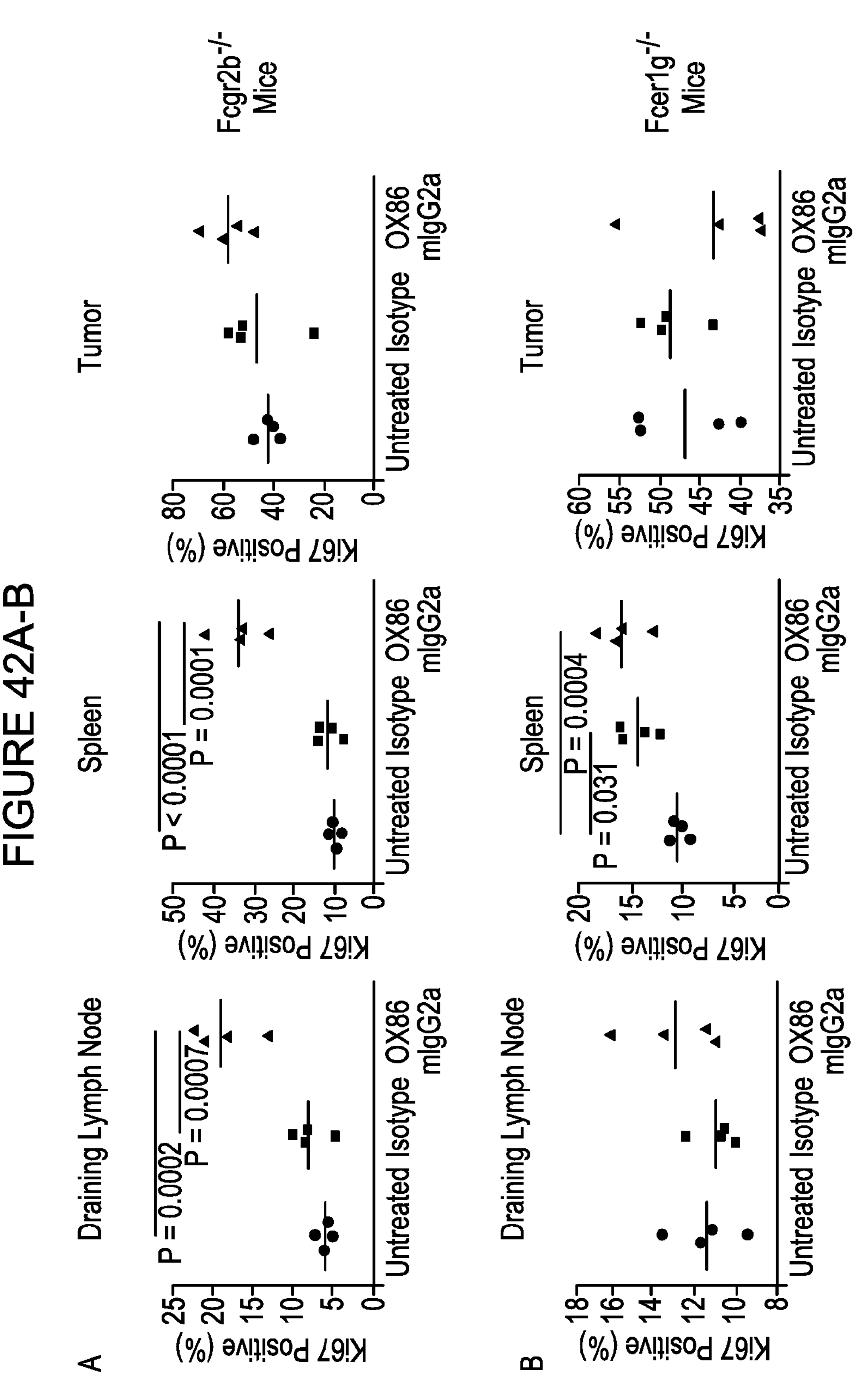

FIGURE 43A-B
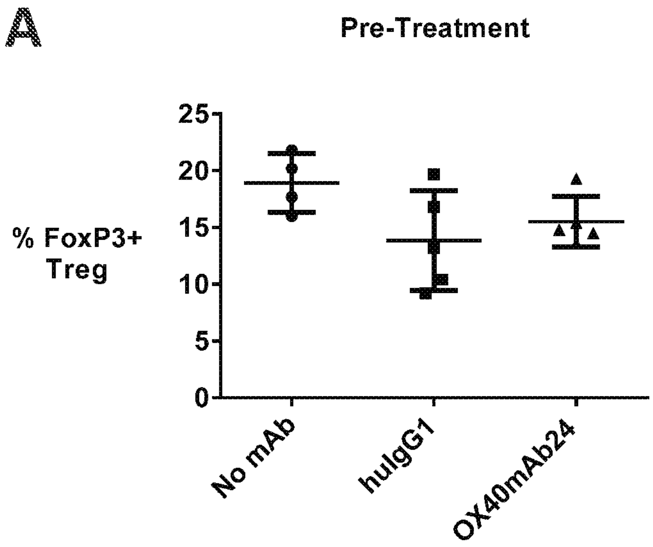
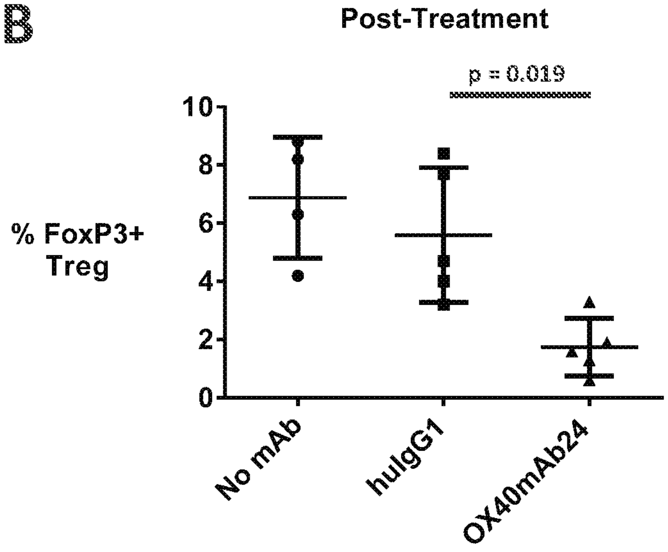

FIGURE 44A-D
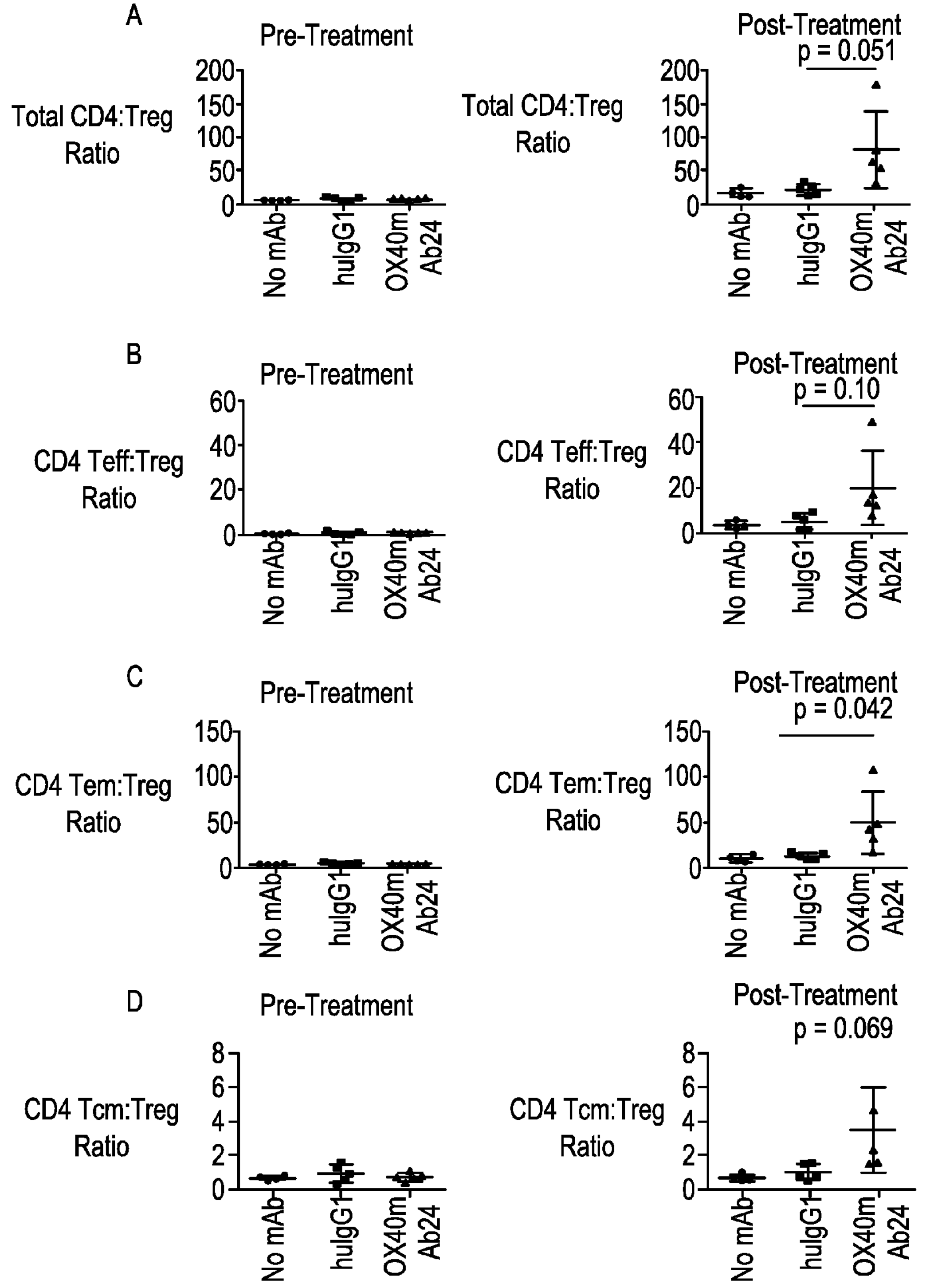

FIGURE 45A-B
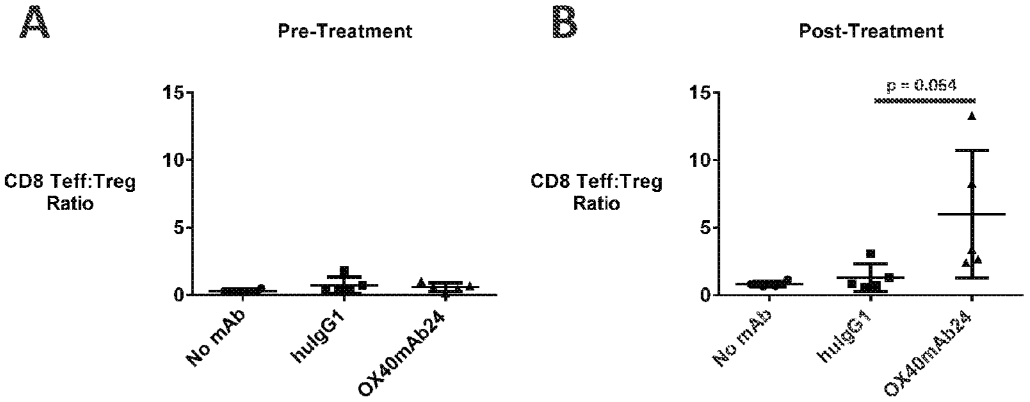

FIGURE 46A-C
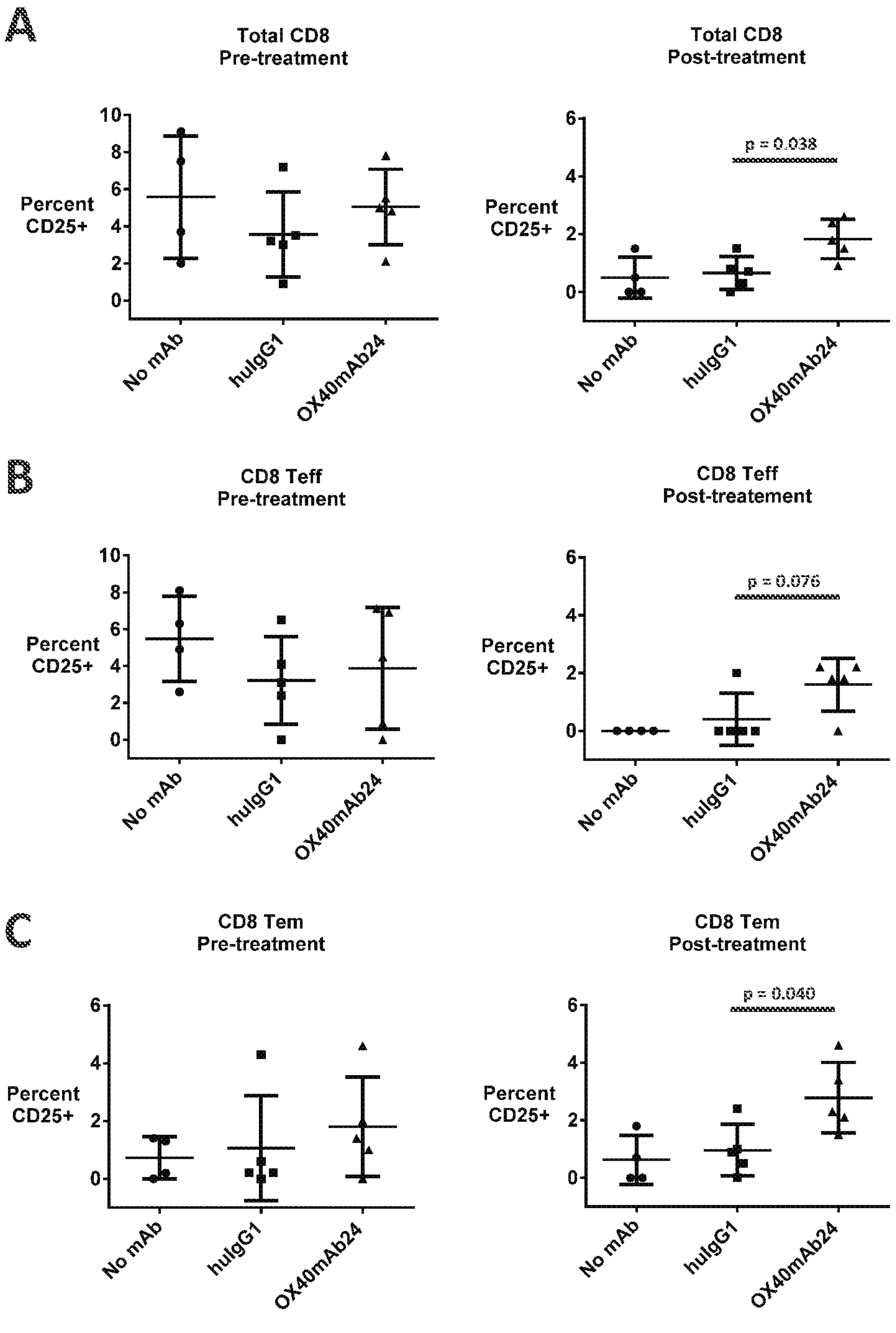

HUMANIZED ANTI-OX40 ANTIBODIES AND USES THEREOF

CROSS REFERENCE TO RELATED APPLICATIONS

This claims benefit of U.S. Provisional Application No. 62/062,431 filed Oct. 10, 2014. The above listed application is incorporated by reference herein in its entirety for all purposes.

REFERENCE TO THE SEQUENCE LISTING

This application incorporates by reference a Sequence Listing submitted with this application as text file entitled OX40H-100US1_SL.txt created on Oct. 6, 2015 and having a size of 865 kilobytes.

BACKGROUND

OX40 (CD134; TNFRSF4) is a tumor necrosis factor receptor found primarily on activated $CD4^+$ and $CD8^+$ T cells, regulatory T (Treg) cells and natural killer (NK) cells (Croft et al., 2009, *Immunol Rev.* 229:173-91). OX40 has one known endogenous ligand, OX40 ligand (OX40L; CD152; TNFSF4), which exists in a trimeric form and can cluster OX40, resulting in potent cell signaling events within T cells. Id. Signaling through OX40 on activated $CD4^+$ and $CD8^+$ T cells leads to enhanced cytokine production, granzyme and perforin release, and expansion of effector and memory T cell pools (Jensen et al., 2010, *Semin Oncol.* 37:524-32). In addition, OX40 signaling on Treg cells inhibits expansion of Tregs, shuts down the induction of Tregs and blocks Treg-suppressive function (Voo et al., 2013, *J Immunol.* 191:3641-50; Vu et al., 2007, *Blood.* 110:2501-10).

Immunohistochemistry studies and early flow cytometry analyses showed that OX40 is expressed on T cells infiltrating a broad range of human cancers (Baruah et al., 2011, *Immunobiology* 217:668-675; Curti et al, 2013, *Cancer Res.* 73:7189-98; Ladanyi et al, 2004, *Clin Cancer Res.* 10:521-30; Petty et al, 2002, *Am J Surg.* 183:512-8; Ramstad et al, 2000, *Am J Surg.* 179:400-6; Sarff et al, 2008, *Am J Surg.* 195:621-5; discussion 625; Vetto et al, 1997, *Am J Surg.* 174:258-65). While not wishing to be bound by theory, OX40 expression on tumor-infiltrating lymphocytes correlates with longer survival in several human cancers, suggesting that OX40 signals can play a role in establishing an antitumor immune response (Ladanyi et al., 2004, *Clin Cancer Res.* 10:521-30; Petty et al., 2002, *Am J Surg.* 183:512-8).

In a variety of nonclinical mouse tumor models, agonists of OX40, including antibodies and OX40 ligand fusion proteins, have been used successfully with promising results (Kjaergaard et al., 2000, *Cancer Res.* 60:5514-21; Ndhlovu et al., 2001, *J Immunol.* 167:2991-9; Weinberg et al., 2000, *J Immunol.* 164:2160-9). Co-stimulating T cells through OX40 promoted anti-tumor activity that in some cases was durable, providing long-lasting protection against subsequent tumor challenge (Weinberg et al., 2000, *J Immunol.* 164:2160-9). Treg-cell inhibition and co-stimulation of effector T cells were shown to be necessary for tumor growth inhibition of OX40 agonists (Piconese et al., 2008, *J Exp Med.* 205:825-39). Many strategies and technologies have been explored to enhance the anti-tumor effect of OX40 agonist therapy through combinations with vaccines, chemotherapy, radiotherapy, and immunotherapy (Jensen et al., 2010, *Semin Oncol.* 37:524-32; Melero et al., 2013, Clin *Cancer Res.* 19:997-1008).

SUMMARY

This disclosure provides antibodies that bind to OX40, e.g., human OX40. In certain aspects the antibodies provided are humanized antibodies. For example, this disclosure provides an antibody or antigen-binding fragment thereof that includes a humanized heavy chain variable region (VH) and a humanized light chain variable region (VL), where the VH includes an amino acid sequence with the formula:

HFW1-HCDR1-HFW2-HCDR2-HFW3-HCDR3-HFW4, where HFW1 is SEQ ID NO: 6 or SEQ ID NO: 7, HCDR1 is SEQ ID NO: 8, HFW2 is SEQ ID NO: 9 (WIR$X_{39}$HPGKGLE$X_{47}X_{48}$G; where $X_{39}$ is Q or K, $X_{47}$ is W or Y, and $X_{48}$ is I or M), HCDR2 is SEQ ID NO: 14, SEQ ID NO: 15 or SEQ ID NO: 16, HFW3 is SEQ ID NO: 17 (RITINX$_{71}$DTSKNQX$_{78}$SLQLNSVTPEDTAVYX$_{91}$CAR; where $X_{71}$ is P or R, $X_{78}$ is F or Y, and $X_{91}$ is Y or F, HCDR3 is SEQ ID NO: 25, SEQ ID NO: 26, or SEQ ID NO: 27), and HFW4 is SEQ ID NO: 28, where the VL includes the amino acid sequence SEQ ID NO: 29 or SEQ ID NO: 32; and where the antibody or fragment thereof can specifically bind to human OX40. In certain aspects, the amino acid sequence of HFW2 is SEQ ID NO: 10, SEQ ID NO: 11, SEQ ID NO: 12, or SEQ ID NO: 1, and in certain aspects the the amino acid sequence of HFW3 is SEQ ID NO: 18, SEQ ID NO: 19, SEQ ID NO: 20, SEQ ID NO: 21, SEQ ID NO: 22, SEQ ID NO: 23, or SEQ ID NO: 24.

In certain aspects, the VH of the provided antibody or fragment thereof includes the amino acid sequence SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, or SEQ ID NO: 67. In certain aspects, the VL of the provided antibody or fragment thereof includes the amino acid sequence SEQ ID NO: 29 and the VH includes the amino acid sequence SEQ ID NO: 59.

In certain aspects, the provided antibody or fragment thereof further includes a light chain constant region or fragment thereof fused to the C-terminus of the VL, e.g., a human kappa constant region or a human lambda constant region. In certain aspects, the provided antibody or fragment thereof further includes a heavy chain constant region or fragment thereof fused to the C-terminus of the VH, e.g., a human IgG1 constant region, a human IgG4P constant region, a human IgG1TM constant region or a murine IgG1 constant region. In certain aspects the heavy chain constant region is a human IgG1 constant region. In certain aspects, the provided antibody or fragment thereof includes the heavy chain amino acid sequence SEQ ID NO: 71 and the light chain amino acid sequence SEQ ID NO: 30. An antigen-binding fragment of an antibody as provided by this disclosure can be, e.g., an Fv fragment, an Fab fragment, an F(ab')2 fragment, an Fab' fragment, a dsFv fragment, an scFv fragment, or an sc(Fv)2 fragment, or any combination thereof.

In certain aspects, the provided antibody or fragment thereof can specifically bind to human, cynomolgus monkey, or rhesus monkey OX40, e.g., can specifically bind to OX40 as expressed on Jurkat cells, primary activated $CD4^+$ or $CD8^+$ T cells from human, cynomolgus monkey, rhesus monkey, or any combination thereof. In certain aspects, the provided antibody or fragment thereof does not bind to murine or rat OX40. In certain aspects, the provided antibody or fragment thereof does not cross react with related TNFRSF proteins.

In certain aspects, the provided antibody or fragment thereof can have a binding affinity for human OX40 expressed on primary activated human $CD4^+$ T cells of about 250 pM to about 370 pM as measured by flow cytometry, e.g., about 312 pM. In certain aspects, the provided antibody or fragment thereof can achieve 20% receptor occupancy on primary activated human $CD4^+$ T cells ($EC_{20}$) at about 63 to about 93 pM, 50% receptor occupancy on primary activated human $CD4^+$ T cells ($EC_{50}$) at about 250 to about 370 pM, and 90% receptor occupancy on primary activated human $CD4^+$ T cells ($EC_{90}$) at about 2290 to about 3330 pM as measured by flow cytometry. For example, in certain aspects, $EC_{20}$ is about 78 pM, $EC_{50}$ is about 312 pM, and $EC_{90}$ is about 2810 pM.

In certain aspects, the provided antibody or fragment thereof can have a binding affinity for human OX40 expressed on OX40-overexpressing Jurkat cells of about 250 pM to about 600 pM as measured by flow cytometry, e.g., about 424 pM. In certain aspects, the provided antibody or fragment thereof can achieve $EC_{20}$ on OX40-overexpressing Jurkat cells at about 60 to about 150 pM, $EC_{50}$ on OX40-overexpressing Jurkat cells at about 250 to about 600 pM, and $EC_{90}$ on OX40-overexpressing Jurkat cells at about 2260 to about 4380 pM as measured by flow cytometry. For example, in certain aspects, $EC_{20}$ is about 106 pM, $EC_{50}$ is about 424 pM, and $EC_{90}$ is about 3820 pM.

In certain aspects, the provided antibody or fragment thereof can have a binding affinity for cynomolgus monkey OX40 expressed on primary activated cynomolgus monkey $CD4^+$ T cells of about 340 pM to about 820 pM as measured by flow cytometry, e.g., about 580 pM. In certain aspects, the provided antibody or fragment thereof can have a binding affinity for rhesus monkey OX40 expressed on primary activated rhesus monkey $CD4^+$ T cells of about 130 pM to about 600 pM as measured by flow cytometry, e.g., about 370 pM.

In certain aspects, the provided antibody or fragment thereof can induce dose-dependent proliferation of activated $CD4^+$ T cells and dose-dependent cytokine release in primary activated $CD4^+$ T cells in a plate-based assay. For example, in certain aspects, a 20% maximal proliferation response ($EC_{20}$) can be achieved in primary activated human $CD4^+$ T cells at an antibody concentration of about 14 pM to about 28 pM, a 50% maximal proliferation response ($EC_{50}$) can be achieved in primary activated human $CD4^+$ T cells at an antibody concentration of about 0.3 pM to about 130 pM, and a 90% maximal proliferation response ($EC_{90}$) can be achieved in primary activated human $CD4^+$ T cells at an antibody concentration of about 50 pM to about 90 pM, all as measured by flow cytometry. In certain aspects, $EC_{20}$ is about 21 pM, $EC_{50}$ is about 28 pM, and $EC_{90}$ is about 72 pM. The released cytokine in primary activated human $CD4^+$ T cells can be one, two, three or more of, without limitation, IFNγ, TNFα, IL-5, IL-10, IL-2, IL-4, IL-13, IL-8, IL-12 p70, IL-1β, or any combination thereof, for example, IFNγ, TNFα, IL-5, IL-10, IL-13, or any combination thereof. In certain aspects, the provided antibody or fragment thereof can achieve $CD4^+$ T cell proliferation and cytokine release in primary activated cynomolgus monkey $CD4^+$ T cells and in primary activated rhesus monkey $CD4^+$ T cells.

In certain aspects, the provided antibody or fragment thereof can activate the NFκB pathway in OX40 expressing T cells in the presence of FcγR-expressing cells. For example, the OX40-expressing T cells can be OX40-overexpressing Jurkat NFκB-luciferase reporter cells that produce luciferase in response to stimulation of the NFκB signaling pathway. In certain aspects, the provided antibody or fragment thereof can trigger complement-dependent or antibody-dependent cellular cytotoxicity against OX40-expressing cells. In certain aspects, the provided antibody or fragment thereof can bind to human C1q and trigger NK-mediated antibody-dependent cellular cytotoxicity against the OX40-expressing cells.

In certain aspects, administration of an effective dose of the provided antibody or fragment thereof to a subject in need of cancer treatment can inhibit tumor growth in the subject. For example, the tumor growth inhibition can be achieved in the presence of T cells. In certain aspects, tumor growth is inhibited by at least 10%, at least 20%, at least 30%, at least 40%, and least 50%, at least 60%, or at least 70% compared to administration of an isotype-matched control antibody or fragment thereof.

This disclosure further provides a composition including the antibody or fragment thereof as described above, and a carrier.

This disclosure further provides a polynucleotide that includes a nucleic acid that encodes the provided antibody or fragment thereof, or encodes a polypeptide subunit of the provided antibody or fragment thereof. In certain aspects, the provided polynucleotide includes the nucleic acid of SEQ ID NO: 60, the nucleic acid of SEQ ID NO: 31, the nucleic acid of SEQ ID NO: 72, or any combination thereof. This disclosure further provides a vector that includes the provided polynucleotide and a host cell that includes the provided polynucleotide or the provided vector. In another aspect, the disclosure provides a method of producing an antibody or fragment thereof, where the method includes culturing the provided host cell under conditions in which the antibody or fragment thereof encoded by the polynucleotide is expressed, and recovering the antibody or fragment thereof.

In additional aspects, the disclosure provides a method to promote survival or proliferation of activated T cells, where the method includes contacting activated T cells with the provided antibody or fragment thereof, and where the antibody or fragment thereof can specifically bind to OX40 on the surface of the T cells.

In additional aspects, the disclosure provides a method of inducing cytokine release from activated T cells, where the method includes contacting activated T cells with the provided antibody or fragment thereof, and where the antibody or fragment thereof can specifically bind to OX40 on the surface of the T cells. In certain aspects the released cytokine can be one, two, three or more of, without limitation, IFNγ, TNFα, IL-5, IL-10, IL-2, IL-4, IL-13, IL-8, IL-12 p70, IL-1θ , or any combination thereof, e.g., IFNγ, TNFα, IL-5, IL-10, IL-13, or any combination thereof. In certain aspects, the activated T cells are activated $CD4^+$ T cells, activated $CD8^+$ T cells, or a combination thereof. In certain aspects, the activated $CD4^+$ T cells are human $CD4^+$ T cells, cynomolgus monkey $CD4^+$ T cells, rhesus monkey $CD4^+$ T cells, or a combination thereof.

In additional aspects, the disclosure provides a method of promoting T cell activation, where the method includes contacting T cells with the provided antibody or fragment thereof, where the antibody or fragment thereof can specifically bind to OX40 on the surface of the T cells. In certain aspects, T cell activation can be measured through stimulation of the NFκB signal transduction pathway. In certain aspects, the T cells are activated $CD4^+$ T cells, activated $CD8^+$ T cells, or a combination thereof. In certain aspects, the activated $CD4^+$ T cells are human $CD4^+$ T cells, cynomolgus monkey $CD4^+$ T cells, rhesus monkey $CD4^+$ T cells, or a combination thereof. In certain aspects, the contacting includes administering an effective amount of the antibody or fragment thereof to a subject.

In additional aspects, the disclosure provides a method of treating cancer in a subject, where the method includes administering to a subject in need of treatment an effective amount of the provided antibody or fragment thereof, or the provided composition. In certain aspects, the cancer is a solid tumor. In certain aspects, administration of the antibody or fragment thereof or composition can inhibit tumor growth, can promote tumor reduction, or both. In certain aspects, tumor growth inhibition is achieved in the presence of T cells.

In additional aspects, the disclosure provides a method of enhancing an immune response in a subject, where the method includes administering to a subject in need thereof a therapeutically effective amount of the provided antibody or fragment thereof, or the provided composition.

In the therapeutic methods provided by this disclosure, the subject to be treated can be a human subject.

In certain aspects, the provided antibody or fragment thereof can bind to an epitope of human OX40 that falls within amino acids 108 to 146 of SEQ ID NO: 91. In certain aspects, the epitope includes at least amino acids leucine 116 (L116) and alanine 126 (A126) of SEQ ID NO: 91. In certain aspects, the provided antibody or fragment thereof can bind to a mouse OX40 variant that has the amino acid sequence of SEQ ID NO: 92, except for a Q113L mutation and a V124A mutation.

This disclosure further provides an isolated peptide consisting of 100 or fewer amino acids, where the peptide can be specifically bound by the provided antibody or fragment thereof. In certain aspects, the peptide includes amino acids 116 to 126 of SEQ ID NO: 91. In certain aspects, the peptide includes amino acids 108 to 146 of SEQ ID NO: 91 except for one, two, three, four, five, or six single amino acid substitutions, deletions, or insertions at any position except L116 and A126.

BRIEF DESCRIPTION OF THE DRAWINGS/FIGURES

FIG. 1. Mutations in humanized 9B12 VH regions: Numbers in the clonal nick name represent the position of the amino acid in VH, according to Kabat numbering. Mabs 1, 2, 5 and 8 are VH chimeric variants paired with humanized VL. Mabs 10-17 are humanized VH variants with mouse back mutations. Mabs 18-27 are variants engineered to remove potential sequence liabilities. Variable regions of Mab24 and mAb27 were grafted onto different heavy constant regions for the resulting isotype variants named mAb28-30 and mAb31-32, mAb37, respectively.

FIGS. 2A-D. Binding of OX40mAb24 and 9B12 to OX40 Expressed on the Surface of Primary Activated Human $CD4^+$ T cells. MFI=mean fluorescence intensity of AlexaFluor® 647 labeled secondary anti-human antibody binding to OX40mAb24 (2A-B) or AlexaFluor® 488 labeled anti-mouse secondary antibody binding to 9B12 (2C-D) on primary human $CD4^+$ T cells.

FIGS. 3A-F. Binding of OX40mAb24 and 9B12 to Human OX40 Expressed on Jurkat T cells. MFI=mean fluorescence intensity of AlexaFluor® 647 labeled secondary anti-human antibody binding to OX40mAb24 (3A-C) or AlexaFluor® 488 labeled anti-mouse secondary antibody binding to 9B12 (3D-F) on Jurkat T cells.

FIGS. 4A-B. Binding of OX40mAb24 to TNFRSF-expressing HEK293 cells and OX40-expressing Jurkat T cells. (4A) Transient expression of TNFRSF members, as indicated to left of histograms, in HEK293 cells, and binding to TNFRSF-specific mAbs or to OX40mAb24, as indicated above histograms. Gray histogram, fluorochrome-conjugated isotype control antibody binding for TNFRSF-specific mAb, or goat anti-human AlexaFluor® 647 secondary antibody binding control for OX40mAb24; Open histogram, TNFRSF-specific mAb or OX40mAb24 binding. (4B): Binding of OX40mAb24 to OX40-expressing Jurkat as a positive control. Gray histogram, goat anti-human AlexaFluor® 647 secondary antibody binding control; Open histogram, OX40mAb24 binding.

FIGS. 5A-B. Binding of OX40mAb24 (OX40mAb29) (complementarity-determining regions) CDRs and 9B12 to recombinant human TNFRSF members by ELISA. Results of ELISA assays demonstrating specific binding of OX40 by OX40mAb29 (5A) and 9B12 (5B). OX40mAb29 contains the CDRs of OX40mAb24. Antibody binding of OX40 was compared to binding of other human TNFRSF proteins.

FIG. 6. Schematic diagram of the OX40mAb24 plate-bound bioactivity assay. Q=OX40mAb24; Y=anti-human CD3 antibody clone OKT3.

FIGS. 7A-C. Human $CD4^+$ T cell Proliferation in response to OX40mAb24 and 9B12. (7A) CD4 T cell proliferation of four independent donors mediated by plate-immobilized OX40mAb24 in combination with sub-mitogenic TCR stimulation (anti-CD3). Data points were normalized to the lower asymptotic value of raw data curves prior to graphing to enhance visualization of the dynamic range of each response. (7B) Representative raw data from Donor 651 demonstrating proliferation-driven by OX40mAb24 plus sub-mitogenic TCR stimulation (anti-CD3) and the relative lack of proliferation mediated by the R347 human IgG1 control mAb, soluble OX40mAb24 in the presence or absence of concomitant TCR signaling, anti-CD3 mAb alone without OX40mAb24, and by plate-immobilized OX40mAb24 in the absence of anti-CD3 mAb. (7C) CD4 T cell proliferation of four independent donors mediated by plate-immobilized 9B12 in combination with sub-mitogenic TCR stimulation. Symbols, mean values; Error bars, standard deviation of the mean; n=3 technical replicates for OX40mAb24, R347 human IgG1 control mAb, and 9B12 all in combination with anti-CD3; n=2 technical replicates for soluble OX40mAb24, and CD3 in the absence of OX40mAb24, plate bound OX40mAb24 with no anti-CD3, and soluble OX40mAb24 with no anti-CD3.

FIGS. 8A-E. Human $CD4^+$ T cell Cytokine Release in Response to OX40mAb24. Representative OX40mAb24 induced human CD4 T cell cytokine release for Donor 651, including (8A) IFNγ, (8B) TNFα (8C) IL-10 (8D) IL-13, and (8E) IL-5. Symbols, mean values; Error bars, standard deviation of the mean; n=3 technical replicates for OX40mAb24 and R347 human IgG1 control mAb, both in combination with anti-CD3; n=2 technical replicates for soluble OX40mAb24, soluble OX40mAb24 with no anti-CD3, and anti-CD3 in the absence of OX40mAb24.

FIGS. 9A-E. Human $CD4^+$ T cell Cytokine Release in Response to 9B12. Representative 9B12 induced human CD4 T cell cytokine release for Donor 651, including (9A) IFNγ, (9B) TNFα (9C) IL-10 (9D) IL-13, and (9E) IL-5. Symbols, mean values; Error bars, standard deviation of the mean; n=3 technical replicates for 9B12 and mouse IgG1 control mAb, both in combination with anti-CD3; n=2 technical replicates for soluble 9B12, soluble 9B12 with no anti-CD3, and anti-CD3 in the absence of 9B12.

Figure 10:
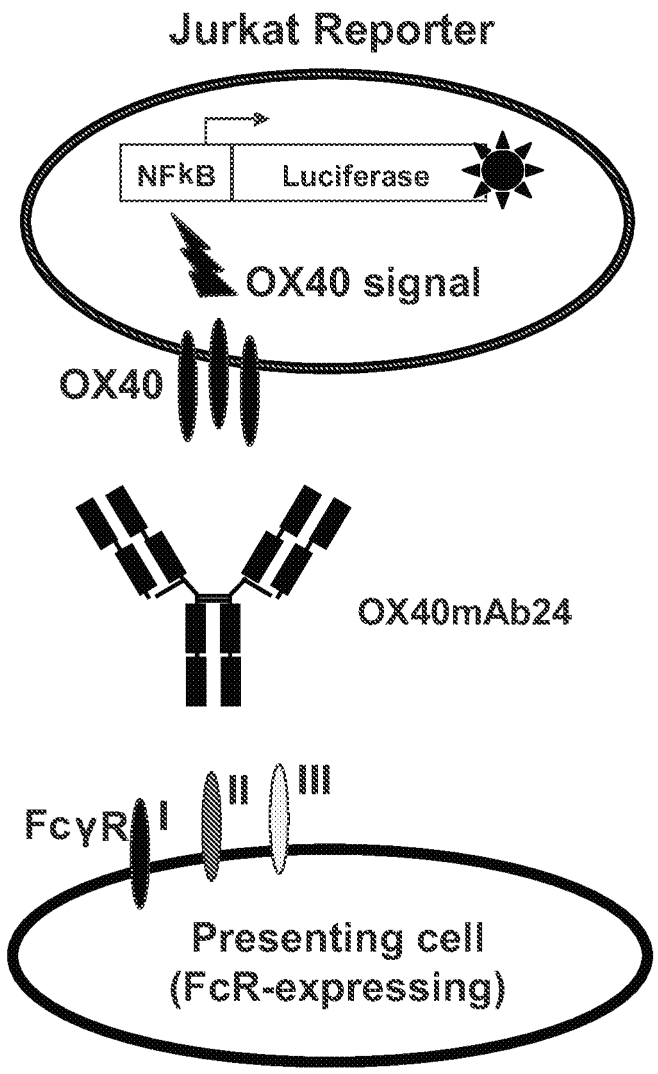

FIG. 10 is a schematic illustrating cell systems used for measuring OX40mAb24 and 9B12 bioactivity. OX40mAb24 cross linking by FcγR-expressing cells mediates the clustering and activation of OX40 on the cell surface of an OX40-expressing Jurkat NFκB-luciferase reporter cell line, resulting in the NFκB-mediated production of luciferase that can be measured as a surrogate for OX40 activation. FcγR=fragment crystallizable gamma receptor; NFκB=nuclear factor kappa B.

FIGS. 11A-D. Bioactivity of OX40mAb24 in OX40-expressing Jurkat NFκB Reporter Cells With and Without Cross-linking by FcγR. Concentration-dependent activity (in RLU) of OX40mAb24-induced signaling through human OX40 expressed on the cell surface of a Jurkat NFκB-luciferase reporter cell line in a 2-cell bioassay. Reporter activity after cross-linking of OX40mAb24 by (11A) CD32A-expressing HEK293 cells, and HEK293 parental cells (HEK), or in the presence of (11B) CD32B-expressing HEK293 cells, (11C) Raji B cells, or (11D) $CD45^+$ cells isolated from a primary lung tumor. Data is representative of other results found in Table 5-2. mAb=monoclonal antibody, RLU=relative light units.

FIGS. 12A-D. Bioactivity of 9B12 in OX40-expressing Jurkat NFκB Reporter Cells using FcγR Cross-linking by Different Cell Types in 2-Cell Bioactivity Assays. Concentration-dependent activity (in RLU) of 9B12 induced signaling through human OX40 expressed on the cell surface of a Jurkat NFκB-luciferase reporter cell lines in a two-cell bioassay. Reporter activity after cross-linking of 9B12 by (12A) CD32A-expressing HEK293 cells, (12B) CD32B-expressing HEK293 cells, (12C) Raji B cells, or (12D) $CD45^+$ cells isolated from a primary lung tumor. Data is representative of other results found in Table 5-3. mAb=monoclonal antibody; RLU=relative light units.

FIGS. 13A-B. Natural Killer Cell-mediated Antibody-Dependent Cellular Cytotoxicity of OX40mAb24, Experiment 1. (13A) Specific killing of OX40-expressing activated $CD4^+$ T cells by human NK cells from an allogeneic, left, or autologous, right, NK and $CD4^+$ T cell donor pairs using 10 μ/mL of 9B12, OX40mAb24, or the IgG1 triple mutant (mAb29) or human IgG4P (mAb28) versions of OX40mAb24. (13B) Lysis of Toledo B cells by NK cells from donors 350 and 351 in the presence of rituximab, but not R347 human IgG1 isotype control antibody. Technical replicates were conducted in triplicate. Error bars represent standard error of the mean. ADCC=antibody-drug-dependent-cytotoxicity; mAb=monoclonal antibody; NK=natural killer.

FIGS. 14A-B. Natural Killer Cell-mediated Antibody-Dependent Cellular Cytotoxicity of OX40mAb24, Experiment 2. (14A) Specific killing of OX40-expressing activated CD4 T cells by human NK cells from an allogeneic, left, or autologous, right, NK and CD4 T cell donor pairs using 10 μ/mL of control R347 human IgG1, 9B12, OX40mAb24, the human IgG4P (mAb28) or the IgG1 triple mutant (mAb29) versions of OX40mAb24. (14B) Lysis of Toledo B cells by NK cells from donors 558 and 589 in the presence of rituximab, but not R347 human IgG1 isotype control antibody. Technical replicates were conducted in triplicate. Error bars represent standard error of the mean. ADCC=antibody-drug-dependent-cytotoxicity; mAb=monoclonal antibody; NK=natural killer.

FIGS. 15A-D. Assessment of Natural Killer Cell-mediated Antibody-Dependent Cellular Cytotoxicity of OX40mAb24 and 9B12, Experiment 3. (15A-B) Specific killing of OX40-expressing human CD4 T cells mediated by OX40mAb24, but not by 9B12, using primary human NK cells from two separate donors as indicated. (15C-D) Lysis of Toledo B cells by NK cells from donors 363 and 504 in the presence of rituximab, but not R347 human IgG1 isotype control antibody. Technical replicates were conducted in duplicate. Error bars represent standard error of the mean. ADCC=antibody-drug-dependent-cytotoxicity; mAb=monoclonal antibody; NK=natural killer.

FIGS. 16A-D. Assessment of Natural Killer Cell-mediated Antibody-Dependent Cellular Cytotoxicity of OX40mAb24, Experiment 4. (16A-B) Specific killing of OX40-expressing human CD4 T cells mediated by OX40mAb24 using primary human NK cells from two separate donors as indicated. (16C-D) Lysis of Toledo B cells by NK cells from donors 464 and 532 in the presence of rituximab, but not R347 human IgG1 isotype control antibody. Technical replicates were conducted in duplicate. Error bars represent standard error of the mean. ADCC=antibody-drug-dependent-cytotoxicity; mAb=monoclonal antibody; NK=natural killer.

FIGS. 17A-B. Assessment of Natural Killer Cell-mediated Antibody-Dependent Cellular Cytotoxicity of OX40mAb24, Experiment 5. Specific killing of OX40-expressing human $CD4^+$ T cells mediated by OX40mAb24, using primary human NK cells from donors 601 (panel A) and 602 (panel B) as indicated. Error bars represent standard error of the mean. ADCC=antibody-drug-dependent-cytotoxicity; mAb=monoclonal antibody; NK=natural killer.

FIGS. 18A-B. Assessment of OX40mAb24 and 9B12 binding to purified human C1q protein. The indicated concentrations of purified human C1q protein were injected onto the biosensor chip. Blank represents injections of PBS/0.005% Tween 20 vehicle alone. Panel A: OX40mAb24 binding to purified human C1q. Panel B: 9B12 binding to purified human C1q.

FIGS. 19A-B. OX40mAb24 Activity in Cyno/Rhesus OX40-expressing Jurkat NFκB-luciferase Clone B2 and LCL8664 Rhesus B-Cell Bioactivity Assays. Concentration-dependent induction of NFκB activity by OX40mAb24 (in RLU) in a cyno/rhesus OX40 expressing Jurkat NFκB-luciferase reporter cell line combined with rhesus B-cell line LCL8664. Data shown for 2 independent assays with 4 replicates for each data point. Error bars represent standard error of the mean are not visible due to scale. RLU=relative light units.

FIGS. 20A-B. 9B12 Activity in Cyno/Rhesus OX40-expressing Jurkat NFκB-luciferase Clone B2 and LCL8664 Rhesus B-Cell Bioactivity Assays. Concentration-dependent induction of NFκB activity by 9B12 (in RLU) in a cyno/rhesus OX40 expressing Jurkat NFκB-luciferase reporter cell line combined with rhesus B-cell line LCL8664. Data shown for 2 independent assays with 4 replicates for each data point. Error bars represent standard error of the mean. RLU=relative light units.

FIGS. 21A-B. OX40mAb24 and 9B12 Activity in Cyno/Rhesus OX40-expressing Jurkat NFκB-luciferase Clone B2 and Fc Gamma Receptor-Expressing Rhesus Immune Cells Bioactivity Assay. Concentration-dependent induction of NFκB activity by OX40mAb24 (Panel A) and 9B12 (Panel B) (in RLU) in a cyno/rhesus OX40 expressing Jurkat NFκB-luciferase reporter cell line combined with Fcγ receptor-expressing rhesus immune cells. Two replicates per data point. RLU=relative light units.

FIGS. 22A-D. OX40mAb24 and 9B12 Cause Proliferation of Primary Rhesus CD4 T Cells. OX40mAb24 (22A-B) and 9B12 (22C-D) induced cell division in primary activated rhesus $CD4^+$ T cells. Data is shown for 2 independent assays with triplicate wells. Error bars represent standard error of the mean.

FIGS. 23A-B. Effect of OX40mAb24 and 9B12 on Growth of A375 Cells in a Mouse Xenograft Model—Experiment 1. Six NOD/SCID mice in each group were engrafted SC on Day 1 with A375 cells mixed with alloreactive human $CD4^+$ and $CD8^+$ T cell lines at E:T ratio 1:6. OX40mAb24 (23A) and 9B12 (23B) and isotype control (23A-B) were administered IP on Days 3, 5, 7, 10 and 12. Mean values of tumor volumes are shown. A comparison between OX40mAb24-treated (23A) or 9B12-treated (23B) and the isotype control-treated animals was made on Day 25 and 18, respectively, and intergroup differences were analyzed for statistical significance by a Mann-Whitney rank sum test. Error bars represent standard error of the mean. *: TGI>68%, P<0.05 as compared to the isotype-control group. E:T=effector-to-target ratio; IP intraperitoneal; NOD/SCID=non-obese diabetic/severe combined immunodeficient; SC=subcutaneous; TGI=tumor growth inhibition.

FIGS. 24A-B. Effect of OX40mAb24 and 9B12 on Growth of A375 Cells in a Mouse Xenograft Model—Experiment 2. Six NOD/SCID mice in each group were engrafted SC on Day 1 with A375 cells mixed with alloreactive human $CD4^+$ and $CD8^+$ T cell lines at E:T ratio 1:6. OX40mAb24 (24A) and 9B12 (24B) and isotype control (24A-B) were administered IP on Days 3, 5, 7, 10 and 12. Mean values of tumor volumes are shown. A comparison between OX40mAb24-treated (12A) or 9B12-treated (12B) and the isotype control-treated animals was made on Day 18, and intergroup differences were analyzed for statistical significance by a Mann-Whitney rank sum test. Error bars represent standard error of the mean. #: TGI>75%, P<0.0004 as compared to the isotype-control group. *: TGI=53%, P<0.05 as compared to the isotype-control group. E:T=effector-to-target ratio; IP=intraperitoneal; NOD/SCID=non-obese diabetic/severe combined immunodeficient; SC=subcutaneous; TGI=tumor growth inhibition.

Figure 25:
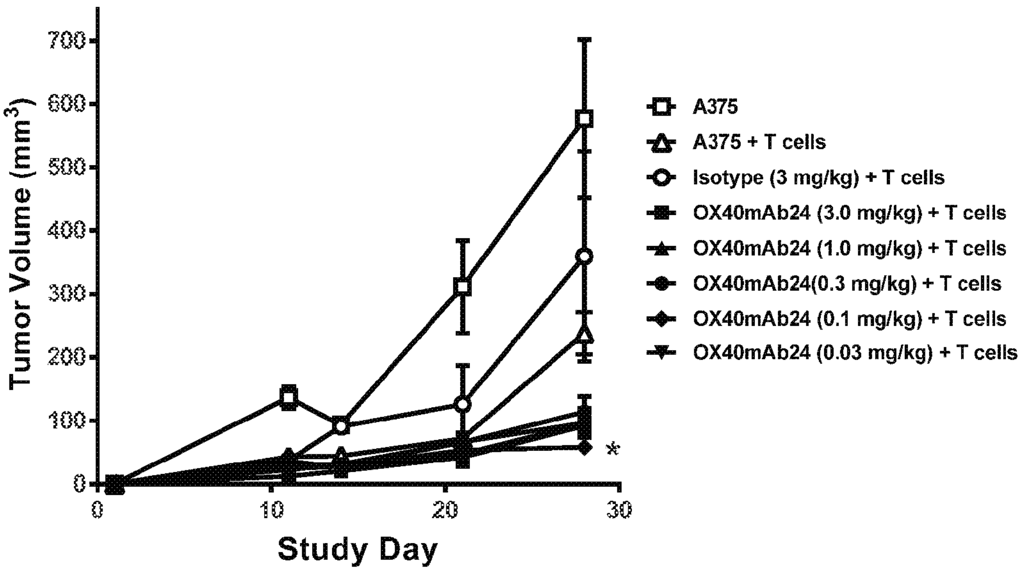

FIG. 25. Effect of OX40mAb24 on Growth of A375 Cells in a Mouse Xenograft Model—Experiment 3. Six NOD/SCID mice in each group were engrafted SC on Day 1 with A375 cells mixed with alloreactive human $CD4^+$ and $CD8^+$ T cell lines at E:T ratio 1:6. OX40mAb24 was administered IP on Days 3, 6, 8, 10 and 13. Mean values of tumor volumes are shown. A comparison between OX40mAb24-treated and the isotype control-treated animals was made on Day 28, and intergroup differences were analyzed for statistical significance by a Mann-Whitney rank sum test. Error bars represent standard error of the mean. *: TGI=75%, P<0.05 as compared to the isotype-control group; E:T=effector-to-target ratio; IP=intraperitoneal; NOD/SCID=non-obese diabetic/severe combined immunodeficient; SC=subcutaneous; TGI=tumor growth inhibition.

FIGS. 26A-B. Effect of OX86 mIgG2a on Growth of CT26 Cell Line in a Mouse Syngeneic Model. Ten BALB/c mice in each group were inoculated SC on Day 1 with CT26 cells. Control (negative control) and test article (OX86 mIgG2a) were administered IP on Days 9 and 12 (arrows in (26A)). Mean (26A) and individual (26B) values of tumor volumes are shown. A comparison between OX86 mIgG2a-treated and the negative control-treated animals was made, and intergroup differences were analyzed for statistical significance by aone-way ANOVA using GraphPad Prism 6.0 software. Error bars represent standard error of the mean. *: TGI>50%, P<0.0001 as compared to the isotype-control group on Day 21. IP=intraperitoneal; SC=subcutaneous; TGI=tumor growth inhibition.

FIGS. 27A-B. Effect of OX86 mIgG2a on Growth of CT26 Cell Line in a Mouse Syngeneic Model. Twelve BALB/c mice in each group were inoculated SC on Day 1 with CT26 cells. Test article (OX86 mIgG2a) was administered IP on Days 13 and 16 (arrows in (27A)). Mean (27A) and individual (27B) values of tumor volumes are shown. A comparison between OX86 mIgG2a-treated and the untreated control animals was made, and intergroup differences were analyzed for statistical significance by a one-way ANOVA using GraphPad Prism 6.0 software. Error bars represent standard error of the mean. *: TGI>50%, P<0.0001 as compared to the untreated control group on Day 24. IP=intraperitoneal; SC=subcutaneous; TGI=tumor growth inhibition.

FIGS. 28A-B. Effect of OX86 mIgG2a on Growth of MCA205 Cell Line in a Mouse Syngeneic Model. Fourteen C57BL/6 mice in each group were inoculated SC on Day 1 with MCA205 cells. Control article (isotype control) and test article (OX86 mIgG2a) were administered IP on Days 11 and 14. Mean (28A) and individual (28B) values of tumor volumes are shown. A comparison between OX86 mIgG2a-treated and the isotype control-treated animals was made, and intergroup differences were analyzed for statistical significance by a one-way ANOVA using GraphPad Prism 6.0 software. Error bars represent standard error of the mean. *: TGI>50%, P<0.0001 as compared to the isotype-control group on Day 27. IP=intraperitoneal; SC=subcutaneous; TGI=tumor growth inhibition.

FIGS. 29A-B. Effect of OX86 mIgG2a on Growth of 4T1 Cell Line in a Mouse Syngeneic Model. Twelve BALB/c mice in each group were inoculated S on Day 1 with 4T1 cells. Control article (isotype control) and test article (OX86 mIgG2a) were administered IP on Days 13, 16, 20, and 23. Mean (29A) and individual (29B) values of tumor volumes are shown. A comparison between OX86 mIgG2a-treated and the isotype control-treated animals was made, and intergroup differences were analyzed for statistical significance by a one-way ANOVA using GraphPad Prism 6.0 software. Error bars represent standard error of the mean. IP=intraperitoneal; SC=subcutaneous; TGI=tumor growth inhibition.

FIG. 30. Amino Acid Alignment of the Extracellular Domains of Human and Mouse OX40 molecules. Human OX40 (NCBI reference sequence NP_003318.1) shares 60% sequence identity with mouse OX40 (NCBI reference sequence NP_035789.1). The alignment was performed using the method of Clustal W. The extracellular domains of OX40 are detailed. Amino acids that differ between human and mouse in the CRD3 domain are shown with arrows. The two critical epitope residues L116 and A126 are boxed. CRD=cysteine-rich domain.

Figure 31:
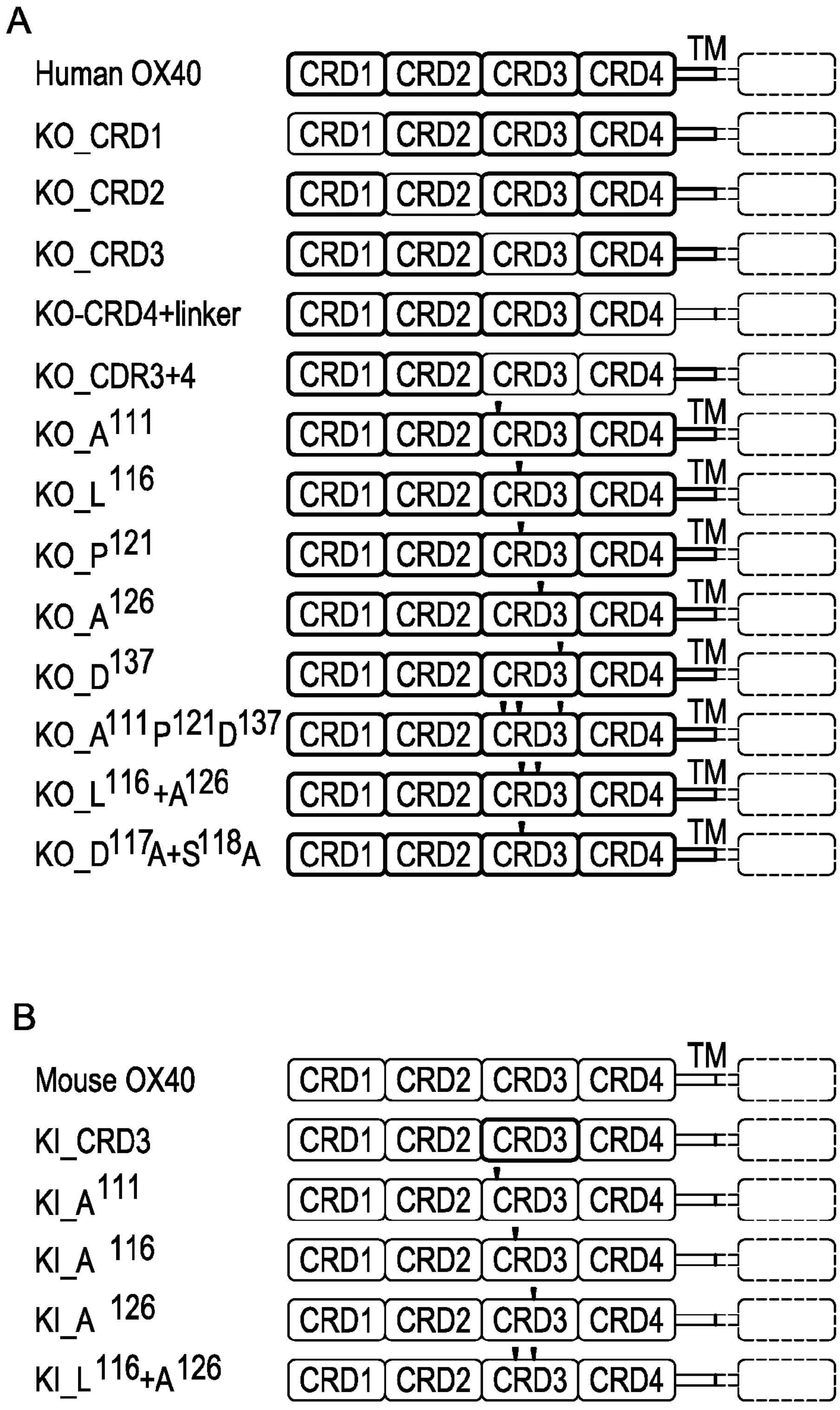

FIG. 31. Nomenclature and Schematic Representation of Chimeric Human/Mouse OX40 Variants. Chimeric human/mouse OX40 variants were constructed by swapping in or out various domains or residues of mouse OX40 (open) into human (solid) (KO) or of human OX40 amino acids into mouse OX40 (KI). Mutations for individual amino acids or combinations were shown with a red (KO) and green (KI) arrows. CRD=cysteine-rich domain; KI=knock-in; KO=knock-out; TM=transmembrane domain.

Figure 32C:
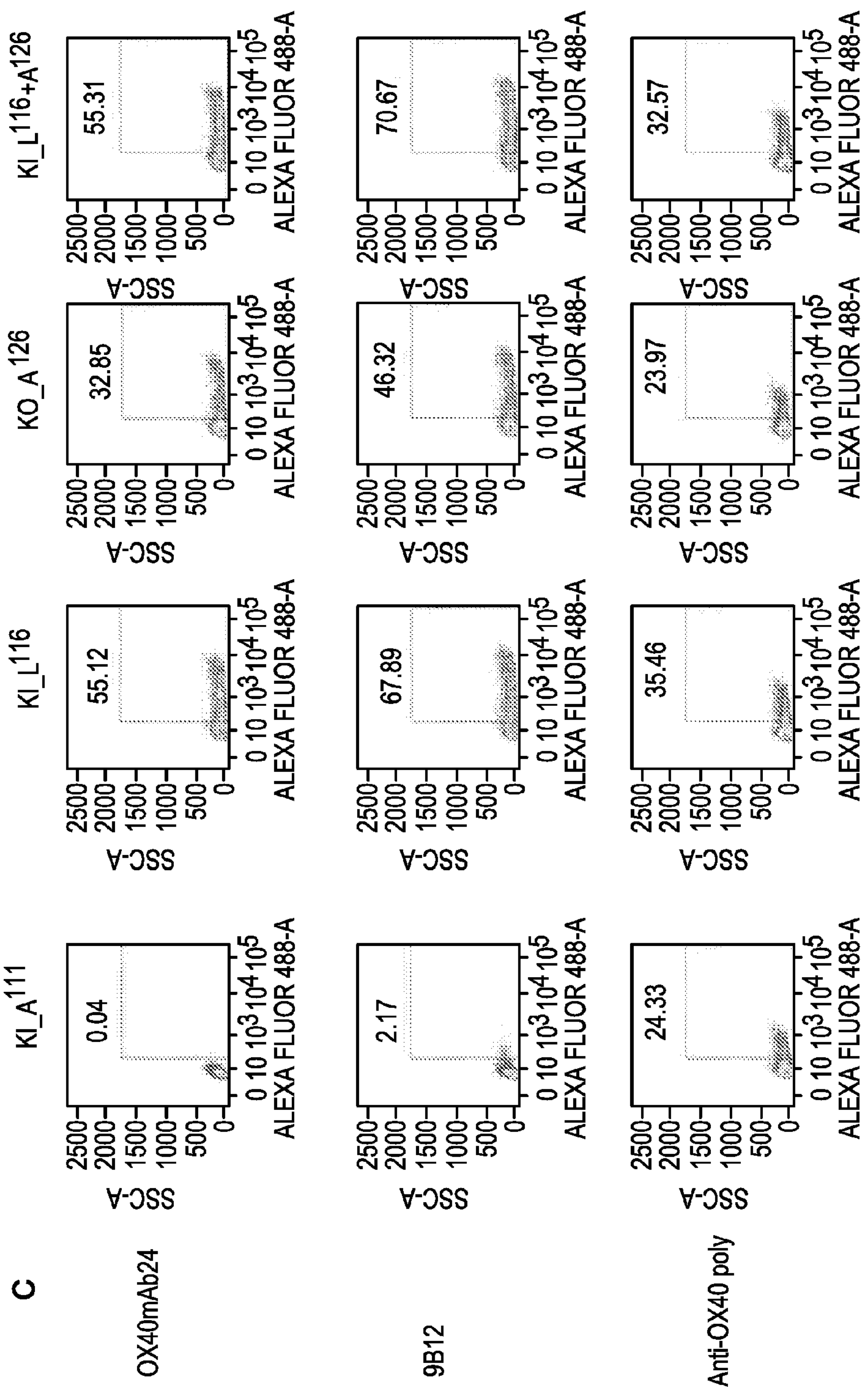

FIGS. 32A-C. FACS Analysis of Binding of OX40mAb24 to Chimeric Human/Mouse OX40 Variants. All variants were transiently expressed using 293F cells for binding characterization with FACS analysis using OX40mAb24 and its parental mouse mAb, 9B12. Expression levels were monitored using anti-human and mouse OX40 polyclonal antibodies. (A) Using domain-swapped chimeric variants, the CRD3 domain was identified as the epitope-containing domain. OX40mAb24 and 9B12 do not bind the KO variants encoding for mouse CRD3 domain (KO_CRD3 and KO_CRD3+4), and recognize the KI variant (KI_CRD3) encoding for human CRD3 domain. (B) Additionally, critical epitope residues were determined as L116 and A126 in CRD3 domain by mutating individual or combinations of amino acids, which differ between human and mouse in the CRD3 domain (FIG. 1). The binding of OX40mAb24 and 9B12 was abolished when replacing human residues L116 and A126 with the mouse counterparts (KO_L116+A126). (C) The KI/gain-of-function variants confirm the importance of these two critical residues. Grafting L116, A126, or the combination to mouse OX40 led to the binding of OX40mAb24 and 9B12.

FIGS. 33A-D. Expression Levels of Ki67 and ICOS on Peripheral Blood and Splenic $CD4^+$ T cells Following Administration of OX86 mIgG2a to Naïve Mice. Seven naïve BALB/c mice in each group were inoculated intraperitoneally on Day 1 with control articles (saline and NIP228 IgG2a isotype control) and test article (OX86 mIgG2a) at the indicated dose levels. Blood (panels A and C) was collected on the indicated Days and spleens from five groups were isolated on Day 10. Expression levels of Ki67 (panel A and B) and ICOS (panels C and D) on $CD4^+$ T cells were measured by flow cytometry. Mean values of the percentage of CD4 cells in blood expressing Ki67 (panel A) and ICOS (panel C) are shown for each group. Percentage of CD4 cells in the spleen expressing Ki67 (panel B) and ICOS (panel D) were plotted for each animal of individual groups. Error bars represent the standard error of the mean. *: $P<0.05$ are marked in Panels A and C; P values are listed for each group with significance in Panels B and D.

FIGS. 34A-B. Correlation of Ki67 and ICOS Expression on Peripheral Blood and Splenic $CD4^+$ T cells Following Administration of OX86 mIgG2a to Naïve Mice. A comparison was made between the percentage of Ki67 and ICOS positive CD4 T cells isolated from peripheral blood (panel A) and spleens (panel B) of individual animals shown in FIGS. 12A-D 10 days following treatment with control articles (saline and NIP228 IgG2a isotype control) and test article (OX86 mIgG2a) at the indicated dose levels. Measurements for individual mice were plotted. Linear regression analysis was performed using GraphPad Prism 6.0 software on the resulting group of data sets to determine a best-fit line for the data. The coefficient of determination (r2) and significance that the slope is non-zero (P value) are provided for each graph.

FIGS. 35A-D. Expression Levels of Ki67 and ICOS on Peripheral Blood and Splenic $CD8^+$ T cells Following Administration of OX86 mIgG2a to Naïve Mice. Seven naïve BALB/c mice in each group were inoculated intraperitoneally on Day 1 with control articles (saline and NIP228 IgG2a isotype control) and test article (OX86 mIgG2a) at the indicated dose levels. Blood (panels A and C) was collected on the indicated Days and spleens from five groups were isolated on Day 10. Expression levels of Ki67 (panel A and B) and ICOS (panels C and D) on $CD8^+$ T cells were measured by flow cytometry. Mean values of the percentage of CD8 cells in blood expressing Ki67 (panel A) and ICOS (panel C) are shown for each group. Percentage of CD8 cells in the spleen expressing Ki67 (panel B) and ICOS (panel D) were plotted for each animal of individual groups. Error bars represent the standard error of the mean. *: $P<0.05$ are marked in Panels A and C; P values are listed for each group with significance in Panels B and D.

FIGS. 36A-B. Correlation of Ki67 and ICOS Expression on Peripheral Blood and Splenic $CD8^+$ T cells Following Administration of OX86 mIgG2a to Naïve Mice. A comparison was made between the percentage of Ki67 and ICOS positive $CD8^+$ T cells isolated from peripheral blood (panel A) and spleens (panel B) of individual animals shown in FIGS. 12A-D 10 days following treatment with control articles (saline and NIP228 IgG2a isotype control) and test article (OX86 mIgG2a) at the indicated dose levels. Measurements for individual mice were plotted. Linear regression analysis was performed using GraphPad Prism 6.0 software on the resulting group of data sets to determine a best-fit line for the data. The coefficient of determination (r2) and significance that the slope is non-zero (P value) are provided for each graph.

FIGS. 37A-D. Effect of Mouse OX86 IgG2a on Growth of the CT26 Cell Line in Syngeneic Mouse Model Lacking Inhibitory (Fcgr2b−/−) or Activating (Fcer1g−/−) Fc Gamma Receptors. Groups of eight Balb/c mice genetically engineered to lack the inhibitory Fcγ receptor IIb (Fcgr2b−/−; panels A and B) or the activating Fcγ receptors (Fcer1g−/−; panels C and D) were inoculated SC on Day 1 with CT26 cells. Control articles (saline/untreated and OX86 mIgG1 D265A mutant/isotype control) and test article (OX86 mIgG2a) were administered IP on Days 4 and 7. Mean (panel A and C) and individual (panel B and D) tumor volumes are shown. A comparison between OX86 mIgG2a-treated and the untreated and isotype control-treated animals was made, and intergroup differences were analyzed for statistical significance by a one-way ANOVA using GraphPad Prism 6.0 software. Error bars represent standard error of the mean. SC=subcutaneous; IP=intraperitoneal; TGI=tumor growth inhibition FIGS. 38A-D. Effect of Mouse OX86 IgG2a on Growth of the MCA205 Cell Line in a Syngeneic Mouse Model Lacking Inhibitory (Fcgr2b−/−) or Activating (Fcer1g−/−) Fc Gamma Receptors. Groups of eight C57BL/6 mice genetically mutated to lack the inhibitory Fcγ receptor IIb (Fcgr2b−/−; panels A and B) or the activating Fcγ receptors (Fcer1g−/−; panels C and D were inoculated SC on Day 1 with MCA205 cells. Control articles (saline/untreated and OX86 mIgG1 D265A mutant/isotype control) and test article (mOX40L FP) were administered IP on Days 4 and 7. Mean (panel A and C) and individual (panel B and D) tumor volumes are shown. A comparison between mOX40L FP-treated and the untreated and isotype control-treated animals was made, and intergroup differences were analyzed for statistical significance by a one-way ANOVA using GraphPad Prism 6.0 software. Error bars represent standard error of the mean. *: TGI>95%, $P<0.023$ as compared to the untreated and isotype-control groups on study day 20. SC=subcutaneous; IP=intraperitoneal; TGI=tumor growth inhibition.

FIGS. 39A-B. Expression Levels of Ki67 in $CD4^+$ T cells Isolated from Peripheral Blood, Spleen and CT26 Tumor Following Administration of OX86 Mouse IgG2a to Mice Lacking Inhibitory (Fcgr2b−/−) or Activating (Fcer1g−/−) Fc Gamma Receptor. Groups of four Balb/c mice genetically engineered to lack the inhibitory Fcγ receptor IIb (Fcgr2b−/−; panels A) or the activating Fcγ receptors (Fcer1g−/−; panels B) were inoculated SC on Day 1 with CT26 cells; this study is independent of, but was conducted similarly to, the study presented in FIGS. 12A-D. Control articles (saline/untreated and OX86 mIgG1 D265A mutant/isotype control) and test article (OX86 mIgG2a) were administered IP on Days 4 and 7. Blood, spleens and tumors were isolated on Day 14 for panel A and Day 13 for panel B. Expression levels of Ki67 in $CD4^+$ T cells were measured by flow cytometry. Symbols represent the percentage of Ki67 positive $CD4^+$ T cells from each tissue of individual mice; horizontal bar represents the mean values for each group. Intergroup differences were analyzed for statistical significance by a one-way ANOVA using GraphPad Prism 6.0 software, and indicated with a horizontal bar with the calculated P values. SC=subcutaneous; IP=intraperitoneal.

FIGS. 40A-B. Expression Levels of Ki67 in $CD8^+$ T cells Isolated from Peripheral Blood, Spleen and CT26 Tumor Following Administration of OX86 Mouse IgG2a to Mice Lacking Inhibitory (Fcgr2b−/−) or Activating (Fcer1g−/−) Fc Gamma Receptors. Groups of four Balb/c mice, genetically engineered to lack the inhibitory Fcγ receptor IIb (Fcgr2b−/−; panels A) or the activating Fcγ receptors (Fcer1g−/−; panels B), were inoculated SC on Day 1 with CT26 cells; this study is independent of but was conducted similarly to the study presented in FIGS. 12A-D. Control articles (saline/untreated and OX86 mIgG1 D265A mutant/isotype control) and test article (OX86 mIgG2a) were administered IP on Days 4 and 7. Blood, spleens and tumor were isolated on Day 14 for panel A and Day 13 for panel B. Expression levels of Ki67 on $CD8^+$ T cells were measured by flow cytometry. Symbols represent the percentage of Ki67 positive $CD8^+$ T cells from each tissue of individual mice; horizontal bar represents the mean values. Intergroup differences were analyzed for statistical significance by a one-way ANOVA using GraphPad Prism 6.0 software, and indicated with a horizontal bar with the calculated P values. SC=subcutaneous; IP=intraperitoneal.

FIGS. 41A-B. Expression Levels of Ki67 in CD4 T cells Isolated from Draining Lymph Node, Spleen and MCA205 Tumor Following Administration of OX86 Mouse IgG2a to Mice Lacking Inhibitory ($Fcgr2b^{-/-}$) or Activating ($Fcer1g^{-/-}$) Fc Gamma Receptors. Groups of four C57BL/6 mice, genetically engineered to lack the inhibitory Fcγ receptor IIb ($Fcgr2b^{-/-}$; panels A) or the activating Fcγ receptors ($Fcer1g^{-/-}$; panels B), were inoculated SC on Day 1 with MCA205 cells; study is independent but conducted similarly to the study presented in FIGS. 12A-D. Control articles (saline/untreated and OX86 mIgG1 D265A mutant/isotype control) and test article (OX86 mIgG2a) were administered IP on Days 4 and 7. Draining lymph nodes, spleens and tumor were isolated on Day 20 for panel B. Expression levels of Ki67 in $CD4^+$ T cells were measured by flow cytometry. Symbols represent the percentage of Ki67 positive $CD4^+$ T cells from each tissue of individual mice; horizontal bar represents the mean values. Intergroup differences were analyzed for statistical significance by a one-way ANOVA using GraphPad Prism 6.0 software, and indicated with a horizontal bar with the calculated P values. SC=subcutaneous; IP=intraperitoneal.

FIGS. 42A-B. Expression Levels of Ki67 in CD8 T cells Isolated from Draining Lymph Node, Spleen and MCA205 Tumor Following Administration of OX86 Mouse IgG2a to Mice Lacking Inhibitory (Fcgr2b−/−) or Activating (Fcer1g−/−) Fc Gamma Receptors. Groups of four C57BL/6 mice, genetically engineered to lack the inhibitory Fcγ receptor IIb (Fcgr2b−/−; panels A) or the activating Fcγ receptors (Fcer1g−/−; panels B), were inoculated SC on Day 1 with MCA205 cells; this study is independent of but was conducted similarly to the study presented in FIGS. 12A-D. Control articles (saline and mOX40L FP D265A mutant control) and test article (OX86 mIgG2a) were administered IP on Days 4 and 7. Draining lymph nodes, spleens and tumor were isolated on Day 20. Expression levels of Ki67 on $CD8^+$ T cells were measured by flow cytometry. Symbols represent the percentage of Ki67 positive $CD8^+$ T cells from each tissue of individual mice; horizontal bar represents the mean values. Intergroup differences were analyzed for statistical significance by a one-way ANOVA using GraphPad Prism 6.0 software, and indicated with a horizontal bar with the calculated P values. SC=subcutaneous; IP=intraperitoneal FIGS. 43A-B. Reduction of Regulatory T Cells by OX40mAb24. Panel A: Percentages of human $CD4^+$ $Foxp3^+$ Treg cells measured in the peripheral blood of mice engrafted with human immune cells just prior to KLH immunization and treatment with NIP228 huIgG1 control (huIgG1) or OX40mAb24. No mAb indicates no immunization and no mAb treatment. Panel B: Percentages of human $CD4^+FoxP3^+$ Treg cells in the peripheral blood of mice in the same groups after immunization and treatment with mAbs. Statistical p values are from one-way ANOVA. Hu=human; mAb=monoclonal antibody; Treg=regulatory T cells FIGS. 44A-D. Expansion of Effector and Memory CD4 T Cells Relative to Regulatory T Cells after OX40mAb24 Treatment. Ratios of human $CD4^+$ T cells to human Treg cells in the peripheral blood of mice engrafted with human immune cells either pre-treatment (left) or post-treatment (right) with KLH immunization followed by NIP228 huIgG1 mAb (huIgG1) or OX40mAb24, as indicated, for Total $CD4^+$ (Panel A); $CD4^+$ effector (Teff) (Panel B); $CD4^+$ effector memory (Tem) (Panel C); and $CD4^+$ central memory T cells (Tcm) (Panel D). No mAb indicates no immunization as well as no mAb treatment. Statistical p values are from one-way ANOVA. Hu=human; mAb=monoclonal antibody; Tcm=central memory Tcell; Teff=effector T cell; Tem=effector memory T cell FIGS. 45A-B. Increased $CD8^+$ Effector to Regulatory T Cell Ratio in Mice Treated with OX40mAb24. Ratios of human $CD8^+$ effector T cells to human Treg cells in the peripheral blood of mice engrafted with human immune cells either pre-treatment (left) or post-treatment (right) with KLH immunization followed by NIP228 huIgG1 mAb (huIgG1) or OX40mAb24, as indicated. No mAb indicates no immunization as well as no mAb treatment. Statistical p value from one-way ANOVA comparing all groups is indicated. Hu=human; mAb=monoclonal antibody; Teff=effector T cell; Treg=regulatory T cell FIGS. 46A-C. Increased CD25 (IL-2 Receptor) Levels on $CD8^+$ T Cells in Mice Treated with OX40mAb24. Percentage of human CD25 (IL-2 receptor) positive cells among human $CD8^+$ T cells in the peripheral blood of mice engrafted with human immune cells either post-treatment (left) or pre-treatment (right) with no treatment (no mAb), or KLH immunization followed by NIP228 huIgG1 mAb (huIgG1) or OX40MAB24, as indicated, for (A) Total $CD8^+$, (B) $CD8^+$ effector (Teff), (C) $CD8^+$ effector memory (Tem) T cells. No mAb indicates no immunization as well as no mAb treatment. Statistical p values are from one-way ANOVA. Hu=human; mAb=monoclonal antibody; Teff=effector T cell; Tem=effector memory T cell.

DETAILED DESCRIPTION

Engagement of the OX40 receptor on T cells, e.g., $CD4^+$ T cells during, or shortly after, priming by an antigen results in an increased response of the T cells, e.g., $CD4^+$ T cells to the antigen. In the context of the present disclosure, the term "engagement" refers to binding to and stimulation of at least one activity mediated by the OX40 receptor. For example, engagement of the OX40 receptor on antigen specific T cells, e.g., $CD4^+$ T cells can result in increased T cell proliferation as compared to the response to antigen alone, and increased cytokine production. The elevated response to the antigen can be maintained for a period of time substantially longer than in the absence of OX40 receptor engagement. Thus, stimulation via the OX40 receptor enhances the antigen specific immune response by boosting T cell recognition of antigens, e.g., tumor antigens.

OX40 agonists can enhance antigen specific immune responses in a subject, such as a human subject, when administered to the subject during or shortly after priming of T cells by an antigen. OX40 agonists include OX40 ligand ("OX40L"), such as soluble OX40L fusion proteins and anti-OX40 antibodies or fragments thereof. A specific example is a humanized antibody that specifically binds to OX40, thereby triggering signaling. A collection of humanized anti-OX40 monoclonal antibodies are provided by this disclosure. Also described are nucleic acids including polynucleotide sequences that encode such antibodies. This disclosure also provides methods for enhancing an antigen specific immune response in a subject using humanized anti-OX40 monoclonal antibodies.

Definitions

It is to be noted that the term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone) Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are, or that might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are, or that might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides which retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10): 879-884 (1999); and Burks et al., *Proc. Natl. Acad. Sci. USA* 94:412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature.

Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are, or that might be at any time, determined or interpreted by a judge or an administrative or judicial body to be, "naturally-occurring."

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit B-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Disclosed herein are certain binding molecules, or antigen-binding fragments, variants, or derivatives thereof. Unless specifically referring to full-sized antibodies, the term "binding molecule" encompasses full-sized antibodies as well as antigen-binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a receptor, e.g., an epitope or an antigenic determinant. As described further herein, a binding molecule can comprise one of more "antigen binding domains" described herein. A non-limiting example of a binding molecule is an antibody or fragment thereof that retains antigen-specific binding.

As used herein, the terms "binding domain," "receptor binding domain," or "antigen binding domain" refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain." Other binding domains include, without limitation, the variable heavy chain (VHH) of an antibody derived from a camelid species, or six immunoglobulin complementarity determining regions (CDRs) expressed in a heterologous framework, e.g., a different germline or species, or in a different scaffold, e.g., a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable domain of a heavy chain (for camelid species) or at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and optionally includes a J chain and/or a secretory component, or an IgM antibody that includes ten or twelve complete heavy chains and ten or twelve complete light chains and optionally includes a J chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$ or $\alpha1$-$\alpha2$)). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, $IgA_2$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda ($\kappa$, $\lambda$). Each heavy chain class can be associated with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure.

Both the light and heavy chains are divided into regions of structural and functional homology. The terms "constant" and "variable" are used functionally. In this regard, it will be appreciated that the variable domains of both the variable light (VL) and variable heavy (VH) chain portions determine antigen recognition and specificity. Conversely, the constant domains of the light chain (CL) and the heavy chain (CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains actually comprise the carboxy-terminus of the heavy and light chain, respectively.

As indicated above, a binding domain, e.g., an antibody variable region allows the binding molecule to selectively recognize and specifically bind a receptor, or an epitope on an antigen. That is, the VL domain and VH domain, or subset of the complementarity determining regions (CDRs), of a binding molecule, e.g., an antibody combine to form the variable region that defines a three dimensional antigen binding site. More specifically, the antigen binding site is defined by three CDRs on each of the VH and VL chains. Certain antibodies form larger structures. For example, IgA can form a molecule that includes two H2L2 units, a J chain, and a secretory component, all covalently connected via disulfide bonds, and IgM can form a pentameric or hexameric molecule that includes five or six H2L2 units and optionally a J chain covalently connected via disulfide bonds.

The six "complementarity determining regions" or "CDRs" present in an antibody antigen-binding domain are short, non-contiguous sequences of amino acids that are specifically positioned to form the binding domain as the antibody assumes its three dimensional configuration in an aqueous environment. The remainder of the amino acids in the binding domain, referred to as "framework" or "FW" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., J. Mol. Biol. 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

CDR Definitions[1]

| | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for antibody heavy and light chains, e.g., antibody variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to, e.g., $5\times10^{-2}$ $sec^{-1}$, $10^{-2}$ $sec^{-1}$, $5\times10^{-3}$ $sec^{-1}$, $10^{-3}$ $sec^{-1}$, $5\times10^{-4}$ $sec^{-1}$, $10^{-4}$ $sec^{-1}$, $5\times10^{-5}$ $sec^{-1}$, or $10^{-5}$ $sec^{-1}5\times10^{-6}$ $sec^{-1}$, $10^{-6}$ $sec^{-1}$, $5\times10^{-7}$ $sec^{-1}$ or $10^{-7}$ $sec^{-1}$.

A binding molecule, e.g., an antibody or antigen-binding fragment, variant, or derivative disclosed herein can be said to bind a target antigen with an on rate (k(on)) of greater than or equal to, e.g., $10^3$ $M^{-1}$ $sec^{-1}$, $5\times10^3M^{-1}$ $sec^{-1}$, $10^4$ $M^{-1}$ $sec^{-1}$, $5\times10^4$ $M^{-1}$ $sec^{-1}$, $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of binding domains and an antigen. See, e.g., Harlow at pages 29-34. Avidity is related to both the affinity of individual binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than, e.g., $5\times10^{-2}$ M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$ M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$ M, $5\times10^{-13}$M, $10^{-13}$M, $5\times10^{-14}$M, $10^{-14}$M, $5\times10^{-15}$M, or $10^{-15}$M.

Antibody fragments including single-chain antibodies or other binding domains can exist alone or in combination with one or more of the following: hinge region, CH1, CH2, CH3, or CH4 domains, J chain, or secretory component. Also included are antigen-binding fragments that can include any combination of variable region(s) with one or more of a hinge region, CH1, CH2, CH3, or CH4 domains, a J chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" includes amino acid sequences derived from an immunoglobulin heavy chain, a binding molecule, e.g., an antibody comprising a heavy chain subunit includes at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include, in addition to a VH domain, a CH1 domain; CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH domain, a CH3 domain and a CH4 domain; or a CH3 domain, a CH4 domain, and a J chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

The heavy chain subunits of a binding molecule, e.g., an antibody or fragment thereof, can include domains derived from different immunoglobulin molecules. For example, a heavy chain subunit of a polypeptide can include a CH1 domain derived from an IgG1 molecule and a hinge region derived from an IgG3 molecule. In another example, a heavy chain subunit can include a hinge region derived, in part, from an IgG1 molecule and, in part, from an IgG3 molecule. In another example, a heavy chain subunit can comprise a chimeric hinge derived, in part, from an IgG1 molecule and, in part, from an IgG4 molecule.

As used herein, the term "light chain subunit" includes amino acid sequences derived from an immunoglobulin light chain. The light chain subunit includes at least one of a VL or CL (e.g., Cκ or Cλ) domain.

Binding molecules, e.g., antibodies or antigen-binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of a typical immunoglobulin heavy chain molecule.

As used herein the term "CH2 domain" includes the portion of a heavy chain molecule that extends, e.g., from about amino acid 244 to amino acid 360 of an IgG antibody using conventional numbering schemes (amino acids 244 to 360, Kabat numbering system; and amino acids 231-340, EU numbering system; see Kabat E A et al. op. cit. The CH3 domain extends from the CH2 domain to the C-terminal of the IgG molecule and comprises approximately 108 amino acids. Certain immunoglobulin classes, e.g., IgM, further include a CH4 region.

As used herein, the term "hinge region" includes the portion of a heavy chain molecule that joins the CH1 domain to the CH2 domain. This hinge region comprises approximately 25 amino acids and is flexible, thus allowing the two N-terminal antigen binding regions to move independently.

As used herein the term "disulfide bond" includes the covalent bond formed between two sulfur atoms. The amino acid cysteine comprises a thiol group that can form a disulfide bond or bridge with a second thiol group. In certain IgG molecules, the CH1 and CL regions are linked by a disulfide bond and the two heavy chains are linked by two disulfide bonds at positions corresponding to 239 and 242 using the Kabat numbering system (position 226 or 229, EU numbering system). In certain aspects provided herein, a human IgG4 Fc domain can be mutated in the hinge region to insure disulfide bond formation between two hinge regions, specifically, a serine to proline mutation at position 228 (according to EU numbering). Human IgG4 Fc domains comprising the S228P mutation are referred to herein as "IgG4P Fc domains."

As used herein, an "Fc-TM region" is a human IgG Fc region that comprises amino acid substitutions of L234F, L235E and P331S as numbered by the EU index as set forth in Kabat and exhibits reduced or ablated effector (ADCC and/or CDC) function, reduced or ablated binding to Fc receptors, and/or reduced or ablated toxicities. See, e.g., U.S. Patent Application Publication No. 2011/0059078, which is incorporated herein by reference in its entirety.

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody, or "bispecific antibody" refer to an antibody that has binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Ströhlein and Heiss, *Future Oncol.* 6:1387-94 (2010); Mabry and Snavely, IDrugs. 13:543-9 (2010)). A bispecific antibody can also be a diabody.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide. A portion of a polypeptide that is "amino-terminal" or "N-terminal" to another portion of a polypeptide is that portion that comes earlier in the sequential polypeptide chain. Similarly a portion of a polypeptide that is "carboxy-terminal" or "C-terminal" to another portion of a polypeptide is that portion that comes later in the sequential polypeptide chain. For example in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

OX40, or "OX40 receptor" is a protein (also variously termed CD134, tumor necrosis factor receptor superfamily member 4, and ACT-35) expressed on the surface of activated T cells, e.g., $CD4^+$ and $CD8^+$ T cells, as well as on $Foxp3^+CD4^+$ regulatory T cells (Tregs). Naive $CD4^+$ and $CD8^+$ T cells do not express OX40 (Croft, M., (2010) Ann Rev Immunol 28:57-78).

"OX40 ligand" ("OX40L") (also variously termed tumor necrosis factor ligand superfamily member 4, gp34, TAX transcriptionally-activated glycoprotein-1, and CD252) is found largely on antigen presenting cells (APCs), and can be induced on activated B cells, dendritic cells (DCs), Langerhans cells, plamacytoid DCs, and macrophages (Id.). Other cells, including activated T cells, NK cells, mast cells, endothelial cells, and smooth muscle cells can express OX40L in response to inflammatory cytokines (Id.). OX40L specifically binds to the OX40 receptor. The human protein is described in PCT Publication No. WO 95/21915. The mouse OX40L is described in U.S. Pat. No. 5,457,035. OX40L is expressed on the surface of cells and includes an intracellular, a transmembrane and an extracellular receptor-binding domain. A functionally active soluble form of OX40L can be produced by deleting the intracellular and transmembrane domains as described, e.g., in U.S. Pat. Nos. 5,457,035 and 6,312,700, and WO 95/21915, the disclosures of which are incorporated herein for all purposes. A functionally active form of OX40L is a form that retains the capacity to bind specifically to OX40, that is, that possesses an OX40 "receptor binding domain." Methods of determining the ability of an OX40L molecule or derivative to bind specifically to OX40 are discussed below. Methods of making and using OX40L and its derivatives (such as derivatives that include an OX40 binding domain) are described in WO 95/21915, which also describes proteins comprising the soluble form of OX40L linked to other peptides, such as human immunoglobulin ("Ig") Fc regions, that can be produced to facilitate purification of OX40 ligand from cultured cells, or to enhance the stability of the molecule after in vivo administration to a mammal (see also, U.S. Pat. No. 5,457,035 and PCT Publication No. WP 2006/121810, both of which are incorporated by reference herein in their entireties).

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of a humanized anti-OX40 antibody. Such antibodies, can be used, e.g., for a diagnostic procedures and/or for treatment or prevention of a disease, e.g., cancer.

Humanized Anti-OX40 Antibodies and Antigen-Binding Fragments Thereof

The present disclosure relates to antibodies, e.g., humanized antibodies, which specifically bind to OX40. In certain aspects, an antibody or fragment thereof as provided herein can be isolated. In certain aspects, an antibody or fragment thereof as provided herein can be substantially pure. In certain aspects an antibody or fragment thereof as provided herein can be non-naturally occurring.

In certain aspects, this disclosure provides a humanized anti-OX40 antibody or an antigen-binding fragment thereof comprising the VH and VL of OX40mAb5, OX40mAb8, OX40mAb10, OX40mAb11, OX40mAb12, OX40mAb13, OX40mAb14, OX40mAb15, OX40mAb16, OX40mAb17, OX40mAb18, OX40mAb19, OX40mAb20, OX40mAb21, OX40mAb22, OX40mAb23, OX40mAb24, OX40mAb25, OX40mAb25a, OX40mAb26, OX40mAb27, OX40mAb28, OX40mAb29, OX40mAb30, OX40mAb31, OX40mAb32, or OX40mAb37. In certain aspects, this disclosure provides a humanized anti-OX40 antibody or an antigen-binding fragment thereof comprising the heavy chain and light chain of OX40mAb5, OX40mAb8, OX40mAb10, OX40mAb11, OX40mAb12, OX40mAb13, OX40mAb14, OX40mAb15, OX40mAb16, OX40mAb17, OX40mAb18, OX40mAb19, OX40mAb20, OX40mAb21, OX40mAb22, OX40mAb23, OX40mAb24, OX40mAb25, OX40mAb25a, OX40mAb26, OX40mAb27, OX40mAb28, OX40mAb29, OX40mAb30, OX40mAb31, or OX40mAb32.

In certain aspects this disclosure provides a humanized anti-OX40 antibody or an antigen-binding fragment thereof comprising an antibody VH and an antibody VL, wherein the VL comprises an amino acid sequence at least 70%, 75%, 80%, 85%, 90%, 95%, or 100% identical to the reference amino acid sequence SEQ ID NO: 29 or SEQ ID NO: 32.

In certain aspects this disclosure provides a humanized anti-OX40 antibody or an antigen-binding fragment thereof comprising an antibody VH and an antibody VL, where the VL comprises SEQ ID NO: 29 or SEQ ID NO: 32.

The disclosure further provides a humanized anti-OX40 antibody or an antigen-binding fragment thereof comprising an antibody VH and an antibody VL, wherein the VH comprises VH-CDR1, VH-CDR2, and VH-CDR3 amino acid sequences identical to, or identical except for eight, seven, six, five, four, three, two, or one single amino acid substitutions, deletions, or insertions in one or more of the VH-CDRS to: the VHCDR1 amino acid sequence SEQ ID NO: 8, the VHCDR2 amino acid sequence SEQ ID NO: 14, SEQ ID NO: 15, or SEQ ID NO: 16, and the VHCDR3 amino acid sequence SEQ ID NO: 25, SEQ ID NO: 26, or SEQ ID NO: 27.

The disclosure further provides a humanized anti-OX40 antibody or an antigen-binding fragment thereof comprising an antibody VH and an antibody VL, wherein the VH comprises an amino acid sequence with the formula:

HFW1-HCDR1-HFW2-HCDR2-HFW3-HCDR3-HFW4, wherein HFW1 is SEQ ID NO: 6 or SEQ ID NO: 7, HCDR1 is SEQ ID NO: 8, HFW2 is SEQ ID NO: 9, HCDR2 is SEQ ID NO: 14, SEQ ID NO: 15 or SEQ ID NO: 16, HFW3 is SEQ ID NO: 17, HCDR3 is SEQ ID NO: 25, SEQ ID NO: 26, or SEQ ID NO: 27, and HFW4 is SEQ ID NO: 28. In certain aspects the amino acid sequence of HFW2 is SEQ ID NO: 10, SEQ ID NO: 11, SEQ ID NO: 12, or SEQ ID NO: 13. In certain aspects the amino acid sequence of HFW3 is SEQ ID NO: 18, SEQ ID NO: 19, SEQ ID NO: 20, SEQ ID NO: 21, SEQ ID NO: 22, SEQ ID NO: 23, or SEQ ID NO: 24.

Moreover, the disclosure provides a humanized anti-OX40 antibody or an antigen-binding fragment thereof comprising an antibody VH and an antibody VL, wherein the VH comprises an amino acid sequence at least 70%, 75%, 80%, 85%, 90%, 95%, or 100% identical to the reference amino acid sequence SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, or SEQ ID NO: 67.

In one aspect, the disclosure provides a humanized anti-OX40 antibody or an antigen-binding fragment thereof comprising an antibody VH and an antibody VL, where the VL comprises the amino acid sequence SEQ ID NO: 29 and the VH comprises the amino acid sequence SEQ ID NO: 59.

A humanized anti-OX40 antibody or an antigen-binding fragment thereof as provided herein can include, in addition to a VH and a VL, a heavy chain constant region or fragment thereof. In certain aspects the heavy chain constant region is a human heavy chain constant region, e.g., a human IgG constant region, e.g., a human IgG1 constant region or a human IgG4 constant region. As described elsewhere herein, in certain aspects a heavy chain constant region or fragment thereof, e.g., a human IgG constant region or fragment thereof, can include one or more amino acid substitutions relative to a wild-type IgG constant region, where the modified IgG has one or more desirable properties relative to a wild-type IgG constant region. For example, the human IgG constant region can be an IgG4P constant region, or an IgG1-TM constant region, as described elsewhere herein.

A humanized anti-OX40 antibody or an antigen-binding fragment thereof as provided herein can include, in addition to a VH and a VL, and optionally a heavy chain constant region or fragment thereof, a light chain constant region or fragment thereof. In certain aspects the light chain constant region is a kappa or lambda light chain constant region, e.g., a human kappa constant region or a human lambda constant region. In a specific aspect, the light chain constant region is a human kappa constant region.

In certain aspects the disclosure provides a humanized anti-OX40 antibody or an antigen-binding fragment thereof comprising an antibody heavy chain or fragment thereof and an antibody light chain or fragment thereof, where the heavy chain comprises the amino acid sequence SEQ ID NO: 71, and the light chain comprises the amino acid sequence SEQ ID NO: 30.

A humanized anti-OX40 antibody or an antigen-binding fragment thereof as provided herein can be, e.g., monoclonal, polyclonal, recombinant, multispecific, or any combination thereof. A humanized anti-OX40 antibody or antigen-binding fragment can be, e.g., an Fv fragment, an Fab fragment, an F(ab')2 fragment, an Fab' fragment, a dsFv fragment, an scFv fragment, an sc(Fv)2 fragment, an Fd fragment, a disulfide linked Fv fragment, a V-NAR domain, an IgNar, an intrabody, an IgGACH2, a minibody, a F(ab')3 fragment, a tetrabody, a triabody, a diabody, a single-domain antibody, a DVD-Ig, a Fcab fragment, an mAb2 fragment, an (scFv)2 fragment, or a scFv-Fc fragment.

In certain aspects, a humanized anti-OX40 antibody or an antigen-binding fragment thereof as provided herein can specifically bind to human, cynomolgus monkey, or rhesus monkey OX40. In certain aspects, a humanized anti-OX40 antibody or an antigen-binding fragment thereof as provided herein can specifically bind to the surface of primary human, cyno, or rhesus CD4 T cells or Jurkat cells. In certain aspects, a humanized anti-OX40 antibody or an antigen-binding fragment thereof as provided herein can specifically bind to OX40 as expressed on activated $CD4^+$ or $CD8^+$ T cells from human, cynomolgus monkey, rhesus monkey, or any combination thereof. In certain aspects, a humanized anti-OX40 antibody or an antigen-binding fragment thereof as provided herein can specifically bind to OX40 as expressed on primary activated $CD4^+$ T cells from human, cynomolgus monkey, rhesus monkey, or any combination thereof. In certain aspects, a humanized anti-OX40 antibody or an antigen-binding fragment thereof as provided herein does not bind to murine or rat OX40. In certain aspects, a humanized anti-OX40 antibody or an antigen-binding fragment thereof as provided herein does not cross react with related TNFRSF proteins, e.g., the TNFRSF proteins listed in Table 3-1 in Example 3 below.

A humanized anti-OX40 antibody or antigen-binding fragment thereof as provided herein can contain one or more conservative amino acid changes, e.g., up to ten conservative changes (e.g., two substituted amino acids, three substituted amino acids, four substituted amino acids, or five substituted amino acids, etc.), provided that the changes can be made in the polypeptide without changing a biochemical function of the humanized anti-OX40 antibody or antigen-binding fragment thereof, e.g., specifically binding to OX40, thereby triggering signaling. For example, one or more conservative changes can be made in a receptor binding domain of an antibody as provided herein without blocking its ability to bind to OX40.

Additionally, part of a polypeptide domain can be deleted without impairing or eliminating all of its functions. Similarly, insertions or additions can be made in the polypeptide chain, for example, adding epitope tags, without impairing or eliminating its functions, as described below. Other modifications that can be made without materially impairing one or more functions of a polypeptide include, for example, in vivo or in vitro chemical and biochemical modifications that incorporate unusual amino acids. Such modifications include, for example, acetylation, carboxylation, phosphorylation, glycosylation, labeling, e.g., with radionuclides, and various enzymatic modifications, as will be readily appreciated by those of ordinary skill in the art. A variety of methods for labeling polypeptides, and labels useful for such purposes, are well known in the art, and include radioactive isotopes such as $^{32}P$, fluorophores, chemiluminescent agents, enzymes, and antiligands.

A humanized anti-OX40 antibody or antigen-binding fragment thereof as provided herein can further include a heterologous agent, e.g., a stabilizing agent, an immune response modifier, or a detectable agent. In certain aspects the heterologous agent comprises one or more additional polypeptide sequences fused to the polypeptide subunit via a peptide bond, such as a signal sequence (e.g., a secretory signal sequence), a linker sequence, an amino acid tag or label, or a peptide or polypeptide sequence that facilitates purification. In certain aspects, the heterologous polypeptide can be fused to the N-terminus or the C-terminus of either a heavy chain or light chain antibody subunit, or fragment thereof, as long as the functional characteristics of the domains are maintained.

In certain aspects, the heterologous agent can be chemically conjugated to a humanized anti-OX40 antibody or antigen-binding fragment thereof as provided herein. Exemplary heterologous agents that can be chemically conjugated to the polypeptide subunit include, without limitation, linkers, drugs, toxins, imaging agents, radioactive compounds, organic and inorganic polymers, and any other compositions which can provide a desired activity that is not provided by the polypeptide subunit itself. Specific agents include, without limitation, polyethylene glycol (PEG), a cytotoxic agent, a radionuclide, an imaging agent, biotin.

In certain aspects, the disclosure provides certain anti-OX40 antibodies to be used as controls or research tools. For example, the disclosure provides a humanized anti-OX40 antibody or antigen-binding fragment thereof as described above, in which the VH and VL are fused to a murine IgG1 heavy chain and a murine kappa light chain, respectively. This "reverse chimera" is useful for in vivo characterization in rhesus monkeys. In another example, the VH region on a humanized anti-OX40 antibody as provided herein can be attached to various heavy chain constant regions with altered effector functions, e.g., human IgG4P or human IgG1TM, described elsewhere herein.

A humanized anti-OX40 antibody or antigen-binding fragment thereof as provided herein can specifically bind to OX40 as expressed on primary activated T cells, e.g., primary activated $CD4^+$ T cells, primary activated $CD8^+$ T cells and/or regulatory T cells, from human, cynomolgus monkey, rhesus monkey, or any combination thereof. In certain aspects, a humanized anti-OX40 antibody or antigen-binding fragment thereof as provided herein, e.g., OX40mAb24, can bind to human OX40 expressed on primary activated human $CD4^+$ T cells with a binding affinity of about 0.01 pM to about 1 nM, e.g., about 1 pM to about 500 pM, e.g., about 100 pM to about 400 pM, e.g., about 250 pM to about 370 pM, all as measured by flow cytometry. For example, a humanized anti-OX40 antibody or an antigen-binding fragment thereof can bind to human OX40 expressed on primary activated human $CD4^+$ T cells with a binding affinity of about 0.1 pM, about 0.5 pM, about 1 pM, about 10 pM, about 50 pM, about 100 pM, about 150 pM, about 200 pM, about 250 pM, about 275 pM, about 300 pM, about 325 pM, about 350 pM, about 370 pM, about 400 pM, about 425 pM, about 450 pM, about 475 pM, about 500 pM, about 550 pM, about 600 pM, about 650 pM, about 700 pM, about 750 pM, or about 1 nM, all as measured by flow cytometry. In certain aspects, a humanized anti-OX40 antibody or antigen-binding fragment thereof as provided herein can bind to human OX40 expressed on primary activated human $CD4^+$ T cells with a binding affinity of about 312 pM. Binding affinity can be measured by a number of different methods and/or instruments, and the relative binding affinities can vary depending on the method or instrument, as is well understood by persons or ordinary skill in the art.

A humanized anti-OX40 antibody or antigen-binding fragment thereof as provided herein can occupy and cross-link some or all of the OX40 molecules on the surface of a cell, e.g., a primary activated human $CD4^+$ T cell. In certain aspects, a humanized anti-OX40 antibody or antigen-binding fragment thereof as provided herein can bind to human OX40 expressed on primary activated human $CD4^+$ T cells, and can achieve 20% receptor occupancy on primary activated human $CD4^+$ T cells ($EC_{20}$) at a concentration of about 0.01 pM to about 1 nM, e.g., about 0.1 pM to about 500 pM, e.g., about 1 pM to about 200 pM, e.g., about 10 pM to about 100 pM, e.g., about 50 pM to about 100 pM, e.g., about 63 pM to about 93 pM, e.g., about 1 pM, about 10 pM, about 20 pM, about 30 pM, about 40 pM, about 50 pM, about 60 pM, about 70 pM, about 78 pM, about 80 pM, about 90 pM, about 100 pM, or about 150 pM, as measured by flow cytometry. In certain aspects, a humanized anti-OX40 antibody or antigen-binding fragment thereof as provided herein can achieve 20% receptor occupancy on primary activated human $CD4^+$ T cells ($EC_{20}$) at a concentration of about 78 pM., as measured by flow cytometry. In certain aspects, a humanized anti-OX40 antibody or antigen-binding fragment thereof as provided herein can bind to human OX40 expressed on primary activated human $CD4^+$ T cells, and can achieve 50% receptor occupancy on primary activated human $CD4^+$ T cells ($EC_{50}$) at a concentration of about 0.01 pM to about 1 nM, e.g., about 1 pM to about 500 pM, e.g., about 100 pM to about 400 pM, e.g., about 250 pM to about 370 pM, e.g., about 100 pM, about 150 pM, about 200 pM, about 250 pM, about 275 pM, about 300 pM, about 325 pM, about 350 pM, about 370 pM, about 400 pM, about 425 pM, about 450 pM, about 475 pM, or about 500 pM, all as measured by flow cytometry. In certain aspects, a humanized anti-OX40 antibody or antigen-binding fragment thereof as provided herein can achieve 50% receptor occupancy on primary activated human $CD4^+$ T cells ($EC_{50}$) at a concentration of about 312 pM., as measured by flow cytometry. In certain aspects, a humanized anti-OX40 antibody or an antigen-binding fragment thereof can bind to human OX40 expressed on primary activated human $CD4^+$ T cells, and can achieve 90% receptor occupancy on primary activated human $CD4^+$ T cells ($EC_{90}$) at a concentration of about 100 pM to about 100 nM, e.g., about 500 pM to about 10 nM, e.g., about 1 nM to about 500 nM, e.g., about 2 nM to about 4 nM, e.g., about 1 nM, about 2 nM, about 3 nM, about 4 nM, or about 5 nM, as measured by flow cytometry. In certain aspects, a humanized anti-OX40 antibody or antigen-binding fragment thereof as provided herein can achieve 90% receptor occupancy on primary activated human $CD4^+$ T cells ($EC_{90}$) at a concentration of about 2290 pM to about 3330 pM, e.g., about 2810 pM., as measured by flow cytometry.

In certain aspects, a humanized anti-OX40 antibody or antigen-binding fragment thereof as provided herein can bind to human OX40 expressed on OX40-overexpressing Jurkat cells with a binding affinity of about 250 pM to about 600 pM, e.g., about 424 pM as measured by flow cytometry.

In certain aspects, a humanized anti-OX40 antibody or an antigen-binding fragment thereof can bind to human OX40 expressed on OX40-overexpressing Jurkat cells, and can achieve $EC_{20}$ at a concentration of about 60 to about 150 pM, $EC_{50}$ at a concentration of about 250 to about 600 pM, and $EC_{90}$ at a concentration about 2260 to about 4390 pM as measured by flow cytometry. In certain aspects, a humanized anti-OX40 antibody or antigen-binding fragment thereof as provided herein can bind to human OX40 expressed on OX40-overexpressing Jurkat cells and can achieve $EC_{20}$ at a concentration of about 106 pM, $EC_{50}$ at a concentration of about 424 pM, and $EC_{90}$ at a concentration of about 3820 pM, as measured by flow cytometry.

In another example, a humanized anti-OX40 antibody or antigen-binding fragment thereof as provided herein can bind to cynomolgus monkey OX40 expressed on primary activated cynomolgus monkey $CD4^+$ T cells with a binding affinity of about 340 pM to about 820 pM, e.g., about 580 pM, as measured by flow cytometry. In another example, a humanized anti-OX40 antibody or antigen-binding fragment thereof as provided herein can bind to rhesus monkey OX40 expressed on primary activated rhesus monkey $CD4^+$ T cells with a binding affinity of about 130 pM to about 600 pM, e.g., about 370 pM, as measured by flow cytometry.

In certain aspects, a humanized anti-OX40 antibody or antigen-binding fragment thereof as provided herein can induce dose-dependent proliferation of activated $CD4^+$ T cells in a plate-based assay. For example, in an in vitro assay a humanized anti-OX40 antibody or antigen-binding fragment thereof as provided herein, e.g., OX40mAb24, a 20% maximal proliferation response ($EC_{20}$) can be achieved in primary activated human $CD4^+$ T cells at an antibody concentration of about 14 pM to about 28 pM, e.g., about 21 pM, a 50% maximal proliferation response ($EC_{50}$) can be achieved in primary activated human $CD4^+$ T cells at an antibody concentration of about 0.3 pM to about 130 pM, e.g., about 28 pM, and a 90% maximal proliferation response ($EC_{90}$) can be achieved in primary activated human $CD4^+$ T cells at an antibody concentration of about 50 pM to about 90 pM, e.g., about 72 pM, all as measured by flow cytometry.

In certain aspects, a humanized anti-OX40 antibody or antigen-binding fragment thereof as provided herein can induce dose-dependent cytokine release from activated $CD4^+$ T cells, e.g., human primary activated $CD4^+$ T cells. In certain aspects, the released cytokine is IFNγ, TNFα, IL-5, IL-10, IL-2, IL-4, IL-13, IL-8, IL-12 p70, IL-1β, or any combination thereof. In certain aspects, the cytokine is IFNγ, TNFα, IL-5, IL-10, IL-13 or any combination thereof. Similarly, a humanized anti-OX40 antibody or antigen-binding fragment thereof as provided herein can achieve $CD4^+$ T cell proliferation and cytokine release in primary activated cynomolgus monkey $CD4^+$ T cells and in primary activated rhesus monkey $CD4^+$ T cells.

In additional aspects, a humanized anti-OX40 antibody or antigen-binding fragment thereof as provided herein can activate the NFκB pathway in OX40 expressing T cells in the presence of FcγR-expressing cells. For example, a humanized anti-OX40 antibody or antigen-binding fragment thereof as provided herein can activate the NFκB pathway in OX40-expressing Jurkat NFκB-luciferase reporter cells that produce luciferase in response to stimulation of the NFκB signaling pathway. Alternatively, a humanized anti-OX40 antibody or antigen-binding fragment thereof as provided herein can activate the NFκB pathway in cells expressing human OX40, cynomolgus monkey OX40 or rhesus monkey OX40.

In yet another aspect a humanized anti-OX40 antibody or antigen-binding fragment thereof as provided herein can facilitate cancer treatment, e.g., by slowing tumor growth, stalling tumor growth, or reducing the size of existing tumors, when administrated as an effective dose to a subject in need of cancer treatment. In certain aspects the facilitation of cancer treatment can be achieved in the presence of T cells. In certain aspects, a humanized anti-OX40 antibody or antigen-binding fragment thereof as provided herein, when administered as an effective dose to a subject in need of treatment, can reduce tumor growth by at least 10%, at least 20%, at least 30%, at least 40%, and least 50%, at least 60%, or at least 70% compared to administration of an isotype-matched control antibody.

In yet further aspects, a humanized anti-OX40 antibody or antigen-binding fragment thereof as provided herein can induce proliferation of activated, OX40-expressing T cells through binding to OX40, and at the same time trigger complement-dependent or antibody-dependent cellular cytotoxicity against the OX40-expressing T cells, e.g., activated $CD4^+$ T cells, activated $CD8^+$ T cells and/or regulatory T cells. Moreover in certain aspects, a humanized anti-OX40 antibody or antigen-binding fragment thereof as provided herein can induce proliferation of OX40-expressing T cells, e.g., activated, OX40-expressing $CD4^+$, $CD8^+$ T cells and/or regulatory T cells through binding to OX40, and at the same time bind to C1q or trigger NK cell-mediated antibody-dependent cellular cytotoxicity of OX40-expressing T cells, e.g., activated $CD4^+$ T cells, activated CD8+ T cells and/or regulatory T cells.

In certain aspects the disclosure provides an anti-OX40 antibody or fragment thereof comprising a humanized VH attached to a murine heavy chain constant region and a humanized VL attached to a murine light chain constant region, wherein the heavy chain comprises SEQ ID NO: 81 and the light chain comprises SEQ ID NO: 83. In certain aspects the heavy chain constant region can be, e.g., a murine IgG1 constant region. In certain aspects the light chain constant region can be, e.g., a murine kappa constant region.

In certain aspects the disclosure provides a rat-anti-mouse OX40 antibody or antigen-binding fragment thereof comprising a rat VH and a rat VL, where the VH comprises the amino acid sequence SEQ ID NO: 85 and the VL comprises the amino acid sequence SEQ ID NO: 88. In certain aspects, this antibody or fragment thereof further comprises a light chain constant region or fragment thereof fused to the C-terminus of the VL. The light chain constant region can be, e.g., a murine kappa constant region. In certain aspects, this antibody or fragment thereof further comprises a heavy chain constant region or fragment thereof fused to the C-terminus of the VH. The heavy chain constant region can be, e.g., a murine IgG2a constant region. In certain aspects this rat-anti-mouse OX40 antibody comprises the heavy chain amino acid sequence SEQ ID NO: 86 and the light chain amino acid sequence SEQ ID NO: 89. In certain aspects, a rat-anti-mouse OX40 antibody or fragment thereof as provided herein can specifically bind to mouse OX40. In certain aspects, administration of an effective dose of a rat-anti-mouse OX40 antibody or fragment thereof as provided herein to mouse can inhibit mouse cancer cell line growth in the mouse.

In certain aspects a rat-anti-mouse OX40 antibody fragment as provided herein can be, e.g., an Fv fragment, an Fab fragment, an F(ab')2 fragment, an Fab' fragment, a dsFv fragment, an scFv fragment, or an sc(Fv)2 fragment, or any combination thereof.

Polynucleotides Encoding Humanized Anti-OX40 Antibodies, Fragments, or Subunits

This disclosure provides polynucleotides comprising nucleic acid sequences that encode a humanized anti-OX40 antibody or an antigen-binding fragment thereof. For example, the disclosure provides a polynucleotide, or two or more polynucleotides, comprising a nucleic acid sequence that encodes a humanized anti-OX40 antibody or a subunit of a humanized anti-OX40 antibody, or encodes an antigen-binding fragment of such an antibody. The polynucleotides of the disclosure can be in the form of RNA or in the form of DNA. DNA includes cDNA, genomic DNA, e.g., modified genomic DNA, and synthetic DNA; and can be double-stranded or single-stranded, and if single stranded can be the coding strand or non-coding (anti-sense) strand.

In certain aspects, a polynucleotide can be isolated. In certain aspects, a polynucleotide can be substantially pure. In certain aspects a polynucleotide can be non-naturally occurring. In certain aspects a polynucleotide can be cDNA or derived from cDNA. In certain aspects a polynucleotide can be recombinantly produced. In certain aspects a polynucleotide can comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In certain aspects the disclosure provides a polynucleotide comprising a nucleic acid that encodes a humanized anti-OX40 antibody or an antigen-binding fragment thereof as provided herein, or a polypeptide subunit of a humanized anti-OX40 antibody or an antigen-binding fragment thereof as provided herein.

Also provided are polynucleotides comprising nucleic acid sequences comprising one or a small number of deletions, additions and/or substitutions. Such changes can be contiguous or can be distributed at different positions in the nucleic acid. A substantially identical nucleic acid sequence can, for example, have 1, or 2, or 3, or 4, or even more nucleotide deletions, additions and/or substitutions. In certain aspects, the one or more deletions, additions and/or substitutions do not alter the reading frame encoded by the polynucleotide sequence, such that a modified ("mutant") but substantially identical polypeptide is produced upon expression of the nucleic acid.

In certain aspects this disclosure provides an isolated polynucleotide comprising a nucleic acid encoding an antibody VL, wherein the VL comprises an amino acid sequence at least 70%, 75%, 80%, 85%, 90%, 95%, or 100% identical to the reference amino acid sequence SEQ ID NO: 29 or SEQ ID NO: 32. In certain aspects, the polynucleotide encodes an antibody light chain and comprises a nucleotide sequence at least 70%, 75%, 80%, 85%, 90%, 95%, or 100% identical to the reference nucleic acid sequence SEQ ID NO: 31.

In certain aspects this disclosure provides an isolated polynucleotide comprising a nucleic acid encoding an antibody VL, wherein the VL comprises SEQ ID NO: 29 or SEQ ID NO: 32.

The disclosure further provides an isolated polynucleotide comprising a nucleic acid encoding an antibody VH, wherein the VH comprises VH-CDR1, VH-CDR2, and VH-CDR3 amino acid sequences identical to, or identical except for eight, seven, six, five, four, three, two, or one single amino acid substitutions, deletions, or insertions in one or more of the VH-CDRS to: the VHCDR1 amino acid sequence SEQ ID NO: 8, the VHCDR2 amino acid sequence SEQ ID NO: 14, SEQ ID NO: 15, or SEQ ID NO: 16, and the VHCDR3 amino acid sequence SEQ ID NO: 25, SEQ ID NO: 26, or SEQ ID NO: 27.

The disclosure further provides an isolated polynucleotide comprising a nucleic acid encoding an antibody VH, wherein the VH comprises an amino acid sequence with the formula:

HFW1-HCDR1-HFW2-HCDR2-HFW3-HCDR3-HFW4, wherein HFW1 is SEQ ID NO: 6 or SEQ ID NO: 7, HCDR1 is SEQ ID NO: 8, HFW2 is SEQ ID NO: 9, HCDR2 is SEQ ID NO: 14, SEQ ID NO: 15 or SEQ ID NO: 16, HFW3 is SEQ ID NO: 17, HCDR3 is SEQ ID NO: 25, SEQ ID NO: 26, or SEQ ID NO: 27, and HFW4 is SEQ ID NO: 28. In certain aspects the amino acid sequence of HFW2 is SEQ ID NO: 10, SEQ ID NO: 11, SEQ ID NO: 12, or SEQ ID NO: 13. In certain aspects the amino acid sequence of HFW3 is SEQ ID NO: 18, SEQ ID NO: 19, SEQ ID NO: 20, SEQ ID NO: 21, SEQ ID NO: 22, SEQ ID NO: 23, or SEQ ID NO: 24.

Moreover, the disclosure provides an isolated polynucleotide comprising a nucleic acid encoding an antibody VH, wherein the VH comprises an amino acid sequence at least 70%, 75%, 80%, 85%, 90%, 95%, or 100% identical to the reference amino acid sequence SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, or SEQ ID NO: 67. In certain aspects, the polynucleotide comprises a nucleotide sequence at least 70%, 75%, 80%, 85%, 90%, 95%, or 100% identical to the reference nucleic acid sequence SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, or SEQ ID NO: 68.

In certain aspects the disclosure provides a polynucleotide comprising the nucleic acid of SEQ ID NO: 60, the nucleic acid of SEQ ID NO: 31, the nucleic acid of SEQ ID NO: 72, or any combination thereof.

Further provided is a vector comprising a polynucleotide as described above. Suitable vectors are described elsewhere herein, and are known to those of ordinary skill in the art.

In certain aspects, the disclosure provides a composition, e.g., a pharmaceutical composition, comprising a polynucleotide or vector as described above, optionally further comprising one or more carriers, diluents, excipients, or other additives.

In certain aspects, the disclosure provides a polynucleotide composition comprising: a polynucleotide that comprises a nucleic acid encoding a VH, and polynucleotide that comprises a nucleic acid encoding a VL. According to this aspect, the VL and VH together can comprise a VL amino acid sequence at least 70%, 75%, 80%, 85%, 90%, 95%, or 100% identical to the reference amino acid sequence SEQ ID NO: 29 or SEQ ID NO: 32, and a VH comprising: (a) VH-CDR1, VH-CDR2, and VH-CDR3 amino acid sequences identical to, or identical except for eight, seven, six, five, four, three, two, or one single amino acid substitutions, deletions, or insertions in one or more of the VH-CDRS to: the VHCDR1 amino acid sequence SEQ ID NO: 8, the VHCDR2 amino acid sequence SEQ ID NO: 14, SEQ ID NO: 15, or SEQ ID NO: 16, and the VHCDR3 amino acid sequence SEQ ID NO: 25, SEQ ID NO: 26, or SEQ ID NO: 27; (b) an amino acid sequence with the formula:

HFW1-HCDR1-HFW2-HCDR2-HFW3-HCDR3-HFW4, wherein HFW1 is SEQ ID NO: 6 or SEQ ID NO: 7, HCDR1 is SEQ ID NO: 8, HFW2 is SEQ ID NO: 9, HCDR2 is SEQ ID NO: 14, SEQ ID NO: 15 or SEQ ID NO: 16, HFW3 is SEQ ID NO: 17, HCDR3 is SEQ ID NO: 25, SEQ ID NO: 26, or SEQ ID NO: 27, and HFW4 is SEQ ID NO: 28; or (c) an amino acid sequence at least 70%, 75%, 80%, 85%, 90%, 95%, or 100% identical to the reference amino acid sequence SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, or SEQ ID NO: 67. For VH (b), the amino acid sequence of HFW2 can be SEQ ID NO: 10, SEQ ID NO: 11, SEQ ID NO: 12, or SEQ ID NO: 13; and/or the amino acid sequence of HFW3 can be SEQ ID NO: 18, SEQ ID NO: 19, SEQ ID NO: 20, SEQ ID NO: 21, SEQ ID NO: 22, SEQ ID NO: 23, or SEQ ID NO: 24.

In a polynucleotide composition as described above, the polynucleotide comprising a nucleic acid encoding a VH and the polynucleotide comprising a nucleic acid encoding a VL can reside in a single vector, or can be on separate, non-identical vectors. Accordingly the disclosure provides one or more vectors comprising the polynucleotide composition described above.

In some cases, a polynucleotide composition encoding a VH and VL as described above can encode a humanized antibody or antigen-binding fragment thereof that can specifically bind to OX40, e.g., human OX40, cynomolgus monkey OX40, and/or rhesus monkey OX40.

In certain aspects the disclosure provides an isolated polynucleotide comprising a nucleic acid that encodes an anti-OX40 antibody or fragment thereof comprising a humanized VH attached to a murine heavy chain constant region and a humanized VL attached to a murine light chain constant region, wherein the heavy chain comprises SEQ ID NO: 81 and the light chain comprises SEQ ID NO: 83. In certain aspects the heavy chain constant region can be, e.g., a murine IgG1 constant region. In certain aspects the light chain constant region can be, e.g., a murine kappa constant region.

In certain aspects the disclosure provides an isolated polynucleotide comprising a nucleic acid that encodes a rat-anti-mouse OX40 antibody or antigen-binding fragment thereof comprising a rat VH and a rat VL, where the VH comprises the amino acid sequence SEQ ID NO: 85 and the VL comprises the amino acid sequence SEQ ID NO: 88. In certain aspects, this antibody or fragment thereof further comprises a light chain constant region or fragment thereof fused to the C-terminus of the VL. The light chain constant region can be, e.g., a murine kappa constant region. In certain aspects, this antibody or fragment thereof further comprises a heavy chain constant region or fragment thereof fused to the C-terminus of the VH. The heavy chain constant region can be, e.g., a murine IgG2a constant region. In certain aspects this rat-anti-mouse OX40 antibody comprises the heavy chain amino acid sequence SEQ ID NO: 86 and the light chain amino acid sequence SEQ ID NO: 89. In certain aspects, a rat-anti-mouse OX40 antibody or fragment thereof as provided herein can specifically bind to mouse OX40. In certain aspects, administration of an effective dose of a rat-anti-mouse OX40 antibody or fragment thereof as provided herein to mouse can inhibit mouse cancer cell line growth in the mouse.

This disclosure further provides a host cell comprising a polynucleotide, polynucleotide composition, or vector as provided above, where the host cell can, in some instances, express an antibody or antigen-binding fragment thereof that specifically binds to OX40, e.g., human OX40, cynomolgus monkey OX40, or rhesus monkey OX40. Such a host cell can be utilized in a method of making an antibody or antigen-binding fragment thereof as provided herein, which method includes (a) culturing the host cell and (b) isolating the antibody or antigen-binding fragment thereof expressed from the host cell.

Polynucleotide variants are also provided. Polynucleotide variants can contain alterations in the coding regions, non-coding regions, or both. In some aspects polynucleotide variants contain alterations that produce silent substitutions, additions, or deletions, but do not alter the properties or activities of the encoded polypeptide. In some aspects, polynucleotide variants are produced by silent substitutions due to the degeneracy of the genetic code. Polynucleotide variants can be produced for a variety of reasons, e.g., to optimize codon expression for a particular host (change codons in the human mRNA to those by a bacterial host such as *E. coli*). Vectors and cells comprising the polynucleotides described herein are also provided.

In some aspects, a DNA sequence encoding a humanized anti-OX40 antibody or an antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides can contain 5' or 3' overhangs for complementary assembly.

Once assembled (by synthesis, site-directed mutagenesis or another method), the polynucleotide sequences encoding a particular isolated polypeptide of interest can be inserted into an expression vector and operatively linked to an expression control sequence appropriate for expression of the protein in a desired host. Proper assembly can be confirmed, e.g., by nucleotide sequencing, restriction mapping, and/or expression of a biologically active polypeptide in a suitable host. In order to obtain high expression levels of a transfected gene in a host, the gene can be operatively linked to or associated with transcriptional and translational expression control sequences that are functional in the chosen expression host.

In certain aspects, recombinant expression vectors are used to amplify and express DNA encoding a humanized anti-OX40 antibody or an antigen-binding fragment thereof. Recombinant expression vectors are replicable DNA constructs which have synthetic or cDNA-derived DNA fragments encoding a polypeptide chain of a humanized anti-OX40 antibody or an antigen-binding fragment thereof, operatively linked to suitable transcriptional or translational regulatory elements derived from mammalian, microbial, viral or insect genes. In one example, a transcriptional unit can comprise an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, conferred, e.g., by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine. This methionine can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of a humanized anti-OX40 antibody or an antigen-binding fragment thereof include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be employed to express a humanized anti-OX40 antibody or an antigen-binding fragment thereof. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

A humanized anti-OX40 antibody or an antigen-binding fragment thereof produced by a transformed host, can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a humanized anti-OX40 antibody or an antigen-binding fragment thereof. Some or all of the foregoing purification steps, in various combinations, can also be employed to provide a homogeneous recombinant protein.

A humanized anti-OX40 antibody or an antigen-binding fragment thereof produced in bacterial culture, can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

Pharmaceutical Compositions and Administration Methods

Methods of preparing and administering a humanized anti-OX40 antibody or an antigen-binding fragment thereof as provided herein, to a subject in need thereof, e.g., to enhance an immune response in a cancer patient, e.g., to inhibit or reduce tumor growth, are well known to or can be readily determined by those skilled in the art. The route of administration of a humanized anti-OX40 antibody or an antigen-binding fragment thereof can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as suitable forms, another example of a form for administration would be a solution for injection, in particular for intravenous or intraarterial injection or drip. Usually, a suitable pharmaceutical composition can comprise, without limitation, a buffer (e.g. acetate, phosphate or citrate buffer), a surfactant (e.g. polysorbate), a stabilizer agent (e.g. human albumin), etc. In other methods compatible with the teachings herein, a humanized anti-OX40 antibody or an antigen-binding fragment thereof as provided herein can be delivered directly to the site of the adverse cellular population thereby increasing the exposure of the diseased tissue to the therapeutic agent.

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a humanized anti-OX40 antibody or an antigen-binding fragment thereof that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

By "therapeutically effective dose or amount" or "effective amount" is intended an amount of a humanized anti-OX40 antibody or an antigen-binding fragment thereof, that when administered brings about a positive therapeutic response with respect to treatment of a patient with a disease or condition to be treated.

Kits

This disclosure further provides kits that comprise a humanized anti-OX40 antibody or an antigen-binding fragment thereof as described herein and that can be used to perform the methods described herein. In certain embodiments, a kit comprises at least one purified humanized anti-OX40 antibody or an antigen-binding fragment thereof, in one or more containers. One skilled in the art will readily recognize that the disclosed humanized anti-OX40 antibody can be readily incorporated into one of the established kit formats that are well known in the art.

Immunoassays

A humanized anti-OX40 antibody or an antigen-binding fragment thereof can be assayed for specific and/or selective binding by any method known in the art. The immunoassays that can be used include but are not limited to competitive and non-competitive assay systems using techniques such as Western blots, radioimmunoassays, ELISA (enzyme linked immunosorbent assay), fluorescent focus assay (FFA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

Methods and reagents suitable for determination of binding characteristics of a humanized anti-OX40 antibody as provided herein are known in the art and/or are commercially available. Equipment and software designed for such kinetic analyses are commercially available (e.g., BIAcore®, BIAevaluation® software, GE Healthcare; KINEXA® Software, Sapidyne Instruments).

Methods of Immune Enhancement and Treatment

The enhancement of an antigen-specific immune response in a subject (e.g., a mammalian subject, such as a human subject) by engaging OX40 on activated T cells, e.g., activated $CD4^+$ T cells and/or activated $CD8^+$ T cells, during or after antigen activation can be accomplished using a wide variety of methods. The method of choice will primarily depend upon the type of antigen against which it is desired to enhance the immune response, and various methods available are discussed below. Whatever method is selected, a humanized anti-OX40 antibody or an antigen-binding fragment thereof can be administered to a subject, e.g., a human patient such that it is presented to T cells of the subject during or shortly after priming of the T cells by antigen.

In certain aspects, the disclosure provides a method to promote survival or proliferation of activated T cells, e.g., activated $CD4^+$ T cells and/or activated $CD8^+$ T cells, comprising contacting the activated T cells, e.g., activated $CD4^+$ T cells and/or activated $CD8^+$ T cells, with a humanized anti-OX40 antibody or an antigen-binding fragment thereof, under conditions where the humanized anti-OX40 antibody can specifically bind to OX40 on the surface of the T cells, e.g., activated $CD4^+$ T cells and/or activated $CD8^+$ T cells. In certain aspects the contacting is in vitro. In certain aspects the contacting is in vivo, e.g. via administration of an effective dose of the humanized anti-OX40 antibody to a subject in need of treatment. In certain aspects the contacting can occur at the same time as T cell activation, e.g., antigen activation, in certain aspects the contacting can occur after T cell activation.

In further aspects, the disclosure provides a method of inducing cytokine release from activated T cells, e.g., activated $CD4^+$ T cells and/or activated $CD8^+$ T cells, comprising contacting the activated T cells, e.g., activated $CD4^+$ T cells and/or activated $CD8^+$ T cells, with a humanized anti-OX40 antibody or an antigen-binding fragment thereof as provided herein, wherein the humanized anti-OX40 antibody can specifically bind to OX40 on the surface of the activated T cells, e.g., activated $CD4^+$ T cells and/or activated $CD8^+$ T cells. In certain aspects the contacting is in vitro. In certain aspects the contacting is in vivo, e.g. via administration of an effective dose of the humanized anti-OX40 antibody to a subject in need of treatment. In certain aspects the contacting can occur at the same time as T cell activation, e.g., antigen activation, in certain aspects the contacting can occur after T cell activation. In certain aspects the cytokine can be IFNγ, TNFα, IL-5, IL-10, IL-2, IL-4, IL-13, IL-8, IL-12 p70, IL-1β, or any combination thereof. In certain aspects the cytokine is IFNγ, TNFα, IL-5, IL-10, IL-13, or any combination thereof.

In certain aspects, the activated T cells, e.g., activated $CD4^+$ T cells and/or activated $CD8^+$ T cells are human T cells, cynomolgus monkey T cells, rhesus monkey T cells, or a combination thereof.

The disclosure further provides a method of promoting T cell activation, comprising contacting T cells with a humanized anti-OX40 antibody as provided herein, wherein the humanized anti-OX40 antibody can specifically bind to OX40 on the surface of the T cells. In certain aspects the contacting occurs in the presence of antigen, e.g., a tumor antigen. In certain aspects the method further comprises interaction of an Fc domain of the humanized anti-OX40 antibody with a cell expressing FcγR, e.g., a B cell, monocyte, macrophage, myeloid or plasmacytoid dendritic cell, follicular dendritic cell, Langerhans cell, endothelial cell, NK cell, activated T cell, neutrophil, eosinophil, platelet, mast cell, a $CD45^+$ cell from a primary human tumor or tumor-draining or non-draining lymph node, a $CD45^+$ cell from other secondary or tertiary lymphoid structures, or a combination thereof. In certain aspects, the T cell activation can be measured through stimulation of the NFκB signal transduction pathway. In certain aspects the contacting is in vitro. In certain aspects the contacting is in vivo, e.g. via administration of an effective dose of the humanized anti-OX40 antibody to a subject in need of treatment.

The disclosure further provides a method of treating cancer in a subject, comprising administering to a subject in need of treatment an effective amount of a humanized anti-OX40 antibody or an antigen-binding fragment thereof, or a composition or formulation comprising the humanized anti-OX40 antibody. In certain aspects, the cancer is a solid tumor. According to this method, administration of humanized anti-OX40 antibody or composition can inhibit tumor growth; can promote tumor reduction, or both. In certain aspects, the tumor growth inhibition is achieved in the presence of T cells.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer including, but not limited to, squamous cell cancers, and cancers of mucinous origins, such as, mucinous ovarian cancer, cholangiocarcinoma (liver) and renal papillary carcinoma.

This disclosure further provides a method of preventing or treating a cancer in a subject in need thereof, comprising administering to the subject an effective amount of a humanized anti-OX40 antibody or an antigen-binding fragment thereof, a composition or formulation comprising the humanized anti-OX40 antibody, or a polynucleotide, a vector, or a host cell as described herein.

Effective doses of compositions for treatment of cancer vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

The compositions of the disclosure can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The disclosure further provides a method of enhancing an immune response in a subject comprising administering to a subject in need thereof a therapeutically effective amount of a humanized anti-OX40 antibody or an antigen-binding fragment thereof, or a composition or formulation comprising the humanized anti-OX40 antibody.

The subject to be treated can be any animal, e.g., mammal, in need of treatment, in certain aspects, subject is a human subject.

In its simplest form, a preparation to be administered to a subject is a humanized anti-OX40 antibody or an antigen-binding fragment thereof, administered in conventional dosage form, which can be combined with a pharmaceutical excipient, carrier or diluent as described elsewhere herein.

A humanized anti-OX40 antibody or an antigen-binding fragment thereof can be administered by any suitable method as described elsewhere herein, e.g., via IV infusion. In certain aspects, a humanized anti-OX40 antibody or an antigen-binding fragment thereof can be introduced into a tumor, or in the vicinity of a tumor cell.

All types of tumors are potentially amenable to treatment by this approach including, without limitation, carcinoma of the breast, lung, pancreas, ovary, kidney, colon and bladder, as well as melanomas, sarcomas and lymphomas.

Engagement of the OX40 receptor on activated T cells, e.g., activated $CD4^+$ T cells and/or activated $CD8^+$ T cells during, or shortly after, priming by an antigen results in an increased response of the activated T cells, e.g., activated $CD4^+$ T cells and/or activated $CD8^+$ T cells to the antigen. In the context of the present disclosure, the term "engagement" refers to binding to and stimulation of at least one activity mediated by the OX40 receptor. For example, engagement of the OX40 receptor on antigen specific activated T cells, e.g., activated $CD4^+$ T cells and/or activated $CD8^+$ T cells, results in increased T cell proliferation as compared to the response to antigen alone, and increased cytokine production. The elevated response to the antigen can be maintained for a period of time substantially longer than in the absence of OX40 receptor engagement. Thus, stimulation via the OX40 receptor enhances the antigen specific immune response by boosting T cell recognition of antigens, e.g., tumor antigens.

OX40 agonists can enhance antigen specific immune responses in a subject, such as a human subject, when administered to the subject during or shortly after priming of T cells by an antigen. OX40 agonists include OX40 ligand ("OX40L"), such as soluble OX40L fusion proteins and anti-OX40 antibodies or fragments thereof. A specific example is a humanized antibody that specifically binds to OX40, thereby triggering signaling. A collection of humanized anti-OX40 monoclonal antibodies are provided by this disclosure. Also described are nucleic acids including polynucleotide sequences that encode such antibodies. This disclosure also provides methods for enhancing an antigen specific immune response in a subject using humanized anti-OX40 monoclonal antibodies.

OX40 Epitopes

The portion of a target molecule, e.g., an OX40 polypeptide, which specifically interacts with the antigen binding domain of an antibody is an "epitope," or an "antigenic determinant." A target molecule, e.g., a polypeptide, can be a single epitope, but typically includes at least two epitopes, and can include any number of epitopes, depending on the size, conformation, and type of target molecule.

The minimum size of an epitope that can be bound by an antibody on a target polypeptide is thought to be about four to five amino acids. Peptide or polypeptide epitopes can contain at least seven, at least nine, at least ten, or at least about 15 or more amino acids. Since an antibody can recognize a polypeptide antigen in its tertiary form, the amino acids comprising an epitope need not be contiguous. An epitope of OX40, e.g., human OX40 as provided herein can include at least 4, at least 5, at least 6, at least 7, at least 8, at least 9, at least 10, at least 15, at least 20, at least 25, or between about 10 to about 30 contiguous or non-contiguous amino acids of OX40, e.g., human OX40. In certain aspects, an epitope of OX40, e.g., human OX40 as provided herein consists of a peptide of 100 or fewer amino acids, 75 or fewer amino acids, 50 or fewer amino acids, 40 or fewer amino acids, 35 or fewer amino acids, 30 or fewer amino acids, 25 or fewer amino acids, 20 or fewer amino acids, or 15 or fewer amino acids, and can include at least 4, at least 5, at least 6, at least 7, at least 8, at least 9, at least 10, at least 15, at least 20, at least 25, or between about 10 to about 30 contiguous or non-contiguous amino acids of OX40, e.g., human OX40. On the other hand, an epitope of OX40, e.g., human OX40 as provided herein can include no more than 4, no more than 5, no more than 6, no more than 7, no more than 8, no more than 9, no more than 10, no more than 15, no more than 20, no more than 25, or can consist of between about 10 to about 30 contiguous or non-contiguous amino acids of OX40, e.g., human OX40.

In certain aspects, an anti-OX40 antibody or fragment thereof as provided herein binds to an epitope of OX40, e.g., human OX40, rhesus monkey OX40, or cynomolgus monkey OX40 that falls within the third cysteine rich domain (CRD3) of OX40, e.g., within amino acids 108 to 146 of human OX40 (SEQ ID NO: 91), or a peptide at least 17%, at least 75%, at least 80%, at least 85%, and least 90%, at least 95%, or at least 100% identical to amino acids 108 to 146 of SEQ ID NO: 91. By "falls within" the CRD3 of OX40, means that the means that the epitope can include 4 or more, 5 or more, 6 or more 7 or more 8 or more 9 or more, 10 or more, 15 or more, or 30 or more contiguous or non-contiguous amino acids amino acids of the region of OX40 consisting of the CRD3 region, e.g., amino acids 108 to 146 of SEQ ID NO: 91, or a peptide at least 70%, at least 75%, at least 80%, at least 85%, and least 90%, at least 95%, or at least 100% identical to amino acids 108 to 146 of SEQ ID NO: 91.

In certain aspects the OX40 CRD3 peptide that binds the antibody provided herein retains a leucine at the position corresponding to amino acid 116 of SEQ ID NOL 91, and an alanine at the position corresponding to amino acid 126 of SEQ ID NO: 91. For example, certain anti-OX40 antibodies or fragments thereof as provided herein bind to human OX40 but do not bind to mouse or rat OX40. The CRD3 region of mouse OX40 stretches from about amino acid 104 to about amino acid 144 of SEQ ID NO: 92. Amino acid Q113 of mouse OX40, SEQ ID NO: 92, corresponds to amino acid L116 of human OX40, SEQ ID NO: 91, and amino acid V124 of mouse OX40, SEQ ID NO: 92, corresponds to amino acid A126 of human OX40, SEQ ID NO: 91. As shown in Example 10, an OX40 antibody as provided herein, e.g., OX40mAb24, can bind to a variant of mouse OX40 comprising SEQ ID NO: 92 except for a Q113L mutation and a V124A.

In certain aspects an isolated peptide is provided, the peptide consisting of or comprising an epitope that specifically binds an OX40 antibody as provided herein, e.g., OX40mAb24. In certain aspects, the peptide consists of 100 or fewer amino acids, 75 or fewer amino acids, 50 or fewer amino acids, 40 or fewer amino acids, 35 or fewer amino acids, 30 or fewer amino acids, 25 or fewer amino acids, 20 or fewer amino acids, or 15 or fewer amino acids, and includes at least 4, at least 5, at least 6, at least 7, at least 8, at least 9, at least 10, at least 15, at least 20, at least 25, or between about 10 to about 30 contiguous or non-contiguous amino acids of the CRD3 of OX40, e.g., an OX40 region at least 70%, at least 75%, at least 80%, at least 85%, and least 90%, at least 95%, or at least 100% identical to amino acids 108 to 146 of SEQ ID NO: 91. In certain aspects, the peptide retains a leucine at the position corresponding to amino acid 116 of SEQ ID NO: 91, and an alanine at the position corresponding to amino acid 126 of SEQ ID NO: 91.

Such an isolated peptide can be used, e.g., for screening libraries for binding molecules that specifically bind to OX40, or as an immunogen to raise anti-OX40 antibodies in a subject animal.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Abbreviations and definitions of terms are listed in Table 2.

TABLE 2

List of Abbreviations and Definitions of Terms

| Abbreviation or Term | Definition |
|---|---|
| 1A7 | Isotype control mouse IgG1 kappa antibody |
| 9B12 | Mouse anti-human OX40 IgG1κ monoclonal antibody |
| A375 | human melanoma cell line |
| Aa | amino acid |
| ADCC | Antibody-dependent cellular cytotoxicity |
| ADPE | Antibody Development and Protein Engineering |
| ANOVA | Analysis of variance |
| Asp | aspartic acid |
| BSA | Bovine serum albumin |
| BLASTP | protein sequence homology Basic Local Alignment Search Tool |
| C | Final tumor volumes from the control group |
| CD | cluster of differentiation |
| CDC | Complement-dependent cytotoxicity |
| $CD4^+$, $OX40^+$ | CD4 positive, OX40 positive |
| CDR | complementarity-determining regions |
| CFA | Complete Freund's adjuvant |
| CFSE | Carboxyfluorescein succinimidyl ester |
| CI | Confidence Interval |
| Clq | Complement component Clq |
| CR | Complete response |
| CRD | Cysteine rich domain |
| Cyno | cynomolgus |
| DM-L | density media-lymphocyte |
| E:T | effector-to-target (ratio) |
| EC | effective concentration |
| ECf | effective concentration resulting in f % of maximal effect |
| $EC_{20}$ | effective concentration resulting in 20% of maximal effect |

TABLE 2-continued

List of Abbreviations and Definitions of Terms

| Abbreviation or Term | Definition |
|---|---|
| $EC_{50}$ | half maximal effective concentration |
| $EC_{90}$ | effective concentration resulting in 90% of maximal effect |
| F | fraction of maximal |
| FACS | fluorescence activated cell sorting |
| FBS | fetal bovine serum |
| Fc | Fragment, crystallizable |
| Fcerlg−/− | Genetically engineered mouse strain; lacks expression of activating Fc gamma receptors (Fc gamma I, III, and IV) |
| Fcgr2b−/− | Genetically engineered mouse strain; lacks expression of inhibitory Fc gamma IIb receptor |
| FCS | Flow cytometry standard |
| Fcγ | fragment, crystallizable gamma |
| FMO | Fluorescence minus-one |
| FP | Fusion protein |
| G | Force of gravity |
| H | hour |
| $H^+L$ | heavy plus light chains |
| HEK293 | Human embryonic kidney cell line |
| Hr | hour |
| HSC | Hematopoietic stem cell |
| Hu | Human |
| ICOS | Inducible T-cell co-stimulator |
| IgG | Immunoglobulin |
| IgG1 | Immunoglobulin G1 |
| IL-2 | interleukin 2 |
| IP | intraperitoneal |
| IU | International Units |
| $K_d$ | equilibrium binding dissociation constant |
| KI | knock-in |
| KLH | Keyhole limpet hemocyanin |
| KO | knock-out |
| $K_p$ | equilibrium dissociation constant |
| Leu | Leucine |
| M | Mouse |
| mAb | monoclonal antibody |
| mL | milliliter |
| OX40mAb24 | Humanized anti-human OX40 IgG1κ monoclonal antibody |
| MFI | mean fluorescence intensity |
| mOX40L FP | Mouse OX40 ligand mouse IgG1 fusion protein |
| mOX40L FP (Y182A) | Mouse OX40 ligand mouse IgG1 fusion protein engineered to have reduced binding to OX40 |
| NFκB | Nuclear factor kappa-light-chain-enhancer of activated B cells |
| NIP228 | Mouse IgG1 kappa monoclonal antibody against 4-hydroxy-3-iodo-5-nitrophenylacetic acid |
| NK | natural killer |
| NOD/SCID | non-obese diabetic/severe combined immunodeficient |
| NSG | Mice with genetic background Nod.Cg-$Prkd^{cscid}112rg^{tm/Wy}$/SzJ |
| OX40L | OX40 ligand |
| OX40L FP IgG4P Y180A | human OX40 ligand IgG4P fusion protein engineered to have reduced binding to OX40 |
| OX40mAb24 | Humanized anti-human OX40 IgG1 κ monoclonal antibody |
| OX86 | Rat anti-mouse OX40 IgG1κ monoclonal antibody |
| PBMC | peripheral blood mononuclear cells |
| PBS | Phosphate buffered saline |
| PHA-L | Phytohemagglutinin-Leucoagglutinin |
| PI | Propidium iodide |
| PK/PD | Pharmacokinetic/pharmacodynamics |
| RBC | red blood cell |
| RBCL | Red blood cell lysis |
| RBD | receptor binding domain |
| Rh | recombinant human |
| RLU | Relative light units |
| RPMI | Roswell Park Memorial Institute 1640 medium |
| ROA | Route of administration |
| SC | subcutaneous |
| SD | Standard Deviation |
| SEM | Standard Error of the Mean |
| Ser | serine |
| T | Final tumor volumes from the test group |

TABLE 2-continued

| List of Abbreviations and Definitions of Terms | |
|---|---|
| Abbreviation or Term | Definition |
| Tcm | Central Memory T cell |
| TCR | T cell receptor |
| Teff | Effector T cell |
| Tem | Effector memory T cell |
| TGI | tumor growth inhibition |
| TIL | tumor infiltrating leukocyte |
| TM | transmembrane domain |
| TNFR | tumor necrosis factor receptor |
| TNFRSF | tumor necrosis factor receptor superfamily |
| TRAF2 | tumor necrosis factor receptor-associated factor 2 |
| Treg | regulatory T cells |
| μL | microliter |
| μg | Microgram |
| V | volume |

Example 1

Humanization of Anti-human OX40 Murine MAb 9B12

Murine mAb 9B12 was humanized by grafting its CDRs onto selected human germline frameworks. The sequences of the heavy chain variable region (VH) and the light chain variable region (VL) of murine mAb 9B12 were compared with the human antibody germline sequences available in the public NCBI databases. Human acceptor frameworks (FR) were identified based on the highest sequence homology. When selecting an optimal acceptor framework several criteria were considered such as matching residues that could impact binding (residues in the Vernier zone, canonical class residues, and VH/VL interface residues), and the potential for immunogenicity (low germline frequency). An optimal hybrid human acceptor FR sequence was designed for VH and VL independently by selecting the most homologous human immunoglobulin germline segment for each individual framework region. Three different germline acceptor sequences were combined to form the humanized VH framework backbone, while two different germline acceptor sequences were selected for VL. The fully human germline acceptor template chosen for the VH chain (9B12VH-hu) was a combination of IGVH4-34*09 (FR 1), VH4-39 (FR 2), VH6-1(FR 3) and JH4 (FR 4). VL (9B12VL-hu1) was a combination of 018 (FR 1), 018 (FR 2), L23 (FR 3) and JK1 (FR 4). The framework homology between the murine sequence and human template acceptor sequence was approximately 72% for VH and 77% for VL.

Murine framework residues which could influence or maintain the functional conformation of the parent CDR and did not match the human germline sequence were identified and selectively reintroduced into the human acceptor FR to best preserve the 9B12 binding affinity and functionality. In this case, mouse FR residues 27D, 39K, 47Y, 48M, 71R, 78Y and 91F in the VH chain and 44V and 68R in the VL chain were mutated back in the human template. CDR residues as defined by Kabat were fused into the designed acceptor frameworks for both VH and VL for generating the humanized antibody. Two humanized VH genes (9B12VH-hu and 9B12VH-hu39K71R) and two VL genes (9B12VL-hu1 and 9B12VL-hu2) were synthesized by GeneART (Thermo Fisher Scientific, Waltham, Mass.), then cloned into the in-house pOE IgG1 expression vector.

A panel of humanized variants has been generated and characterized in T cell-based binding and proliferation assays. The humanized variants, containing several framework amino acids reverted to mouse FR residues in the heavy chain variable region, bound to OX40 on activated $CD4^+$ T cells with comparable affinities and similar potencies (T cell proliferation) to 9B12. The variable light chain paired with all humanized VH variants encodes for fully humanized frameworks. To reduce the risk of immunogenicity, the number of mouse residues in the VH human FR was further reduced to 3 or 4 by replacing non-influential mouse residues with the corresponding human residues. To remove potential sequence liabilities, the NG deamidation site in VH-CDR2, the RYD integrin binding site and the DG isomerization site in VH-CDR3 were proactively removed either independently or in combination. To avoid ADCC mediated by human IgG1 Fc effector function, IgG4P and IgG1TM Fc variants were made for the humanized lead mAbs. The resultant IgG4P and IgG1TM variants exhibited the same binding activity to OX40 as the IgG1 variants, but significantly reduced ADCC activity which is most similar to the murine mAb 9B12. In summary, the humanized variants exhibited cell-binding affinities and in vitro potencies comparable to the parent mouse mAb 9B12. The amino acid differences among the humanized VH variant, all of which are paired with the humanized VL, are summarized in FIG. 1.

Reverse chimera was engineered for in vivo characterization in rhesus monkeys. Briefly, the VH and VL of humanized mAb24 were grafted onto the constant heavy and constant light chains of murine 9B12. In vitro characterization demonstrated the Fab portions of the reverse chimera bound to human OX40 comparable to mAb24.

Example 2

Binding Affinity and Receptor Occupancy of OX40mAb24 to Native OX40 Expressed on the Surface of Activated Human, Non-human Primate, Rat and Mouse T Cells 2.1 Materials Materials used in this example are listed in Table 2-1.

TABLE 2-1

| Materials | |
|---|---|
| Item | Source |
| AlexaFluor ® A488 goat anti-human IgG (H + L) | Life Technologies, Carlsbad, CA |
| AlexaFluor ® A488 goat anti-mouse IgG (H + L) | Life Technologies, Carlsbad, CA |
| AlexaFluor ® A488 goat anti-rat IgG (H + L) | Life Technologies, Carlsbad, CA |
| Antibiotic/antimycotic solution, 100X | Life Technologies, Carlsbad, CA |
| Anti-rat CD134 (OX40 clone) antibody | Biolegend, San Jose, CA |
| Anti-rat CD3 antibody | BD Biosciences, San Jose, CA |

TABLE 2-1-continued

| Materials | |
|---|---|
| Item | Source |
| Anti-mouse CD134 (OX86 clone) antibody | MedImmune, Gaithersburg, MD |
| Anti-rat IgG1, κ isotype control mAb clone RTK2071 | Biolegend, San Jose, CA |
| Balb/C mouse | Harlan, Indianapolis, IN |
| Beta mercaptoethanol (BME) | Life Technologies, Carlsbad, CA |
| Concanavalin A | Sigma, St. Louis, MO |
| Ethylenediaminetetraacetic acid (EDTA) | Life Technologies, Carlsbad, CA |
| Heat inactivated newborn calf serum (FBS) | Life Technologies, Carlsbad, CA |
| Hamster anti-mouse CD3 antibody | BD Biosciences, San Jose, CA |
| Hamster anti-mouse CD28 antibody | BD Biosciences, San Jose, CA |
| IL-2, recombinant human | Preprotech, Rocky Hill, NJ |
| Lymphocyte separation medium (LSM) | MP Biomedicals, Santa Ana, CA |
| Magcellect rat CD4 T cell isolation kit | R&D Systems, Minneapolis, MN |
| Miltenyi MACS buffer | Miltenyi San, Diego, CA |
| Mouse CD4 T cell isolation kit | Miltenyi San, Diego, CA |
| Mouse IgG1, κ isotype control mAb clone MOPC-21 | Biolegend, San Jose, CA |
| Non-human primate CD4 T cell isolation kit | Miltenyi San, Diego, CA |
| Non-TC treated round-bottom 96 well plates | VWR, Radnor, PA |
| Percoll | Sigma, St. Louis, MO |
| Phytohemagglutinin-Leucoagglutinin (PHA-L) | Roche Applied Science, Indianapolis, IN |
| Phosphate buffered saline, pH 7.2 (PBS) | Life Technologies, Carlsbad, CA |
| RosetteSep CD4 T cell enrichment kit | Stem Cell Technologies, Vancouver, BC |
| RPMI-1640 | Life Technologies, Carlsbad, CA |
| Sprague Dawley rat | Harlan, Indianapolis, IN |
| Whole blood, sodium heparin anti-coagulated | MedImmune Blood Donor Program, Gaithersburg, MD |

In this example, cell-based equilibrium binding assays were performed to measure the apparent affinity of OX40mAb24 binding to OX40 expressed on the cell surface of human, non-human primate, rat and mouse T cells. Additionally, the equilibrium binding assays were utilized to determine the concentrations of OX40mAb24 that achieve 20%, 50%, or 90% human OX40 receptor occupancy on activated human $CD4^+$ T cells.

OX40mAb24 concentrations required to achieve 20%, 50% or 90% receptor occupancy were also determined for binding of 9B12, the murine anti-human OX40 monoclonal antibody from which OX40mAb24 was derived, to human and non-human primate OX40 expressed on the surface of $CD4^+$ T cells for a comparison of OX40mAb24 and 9B12 binding.

2.2 Assays 2.2.1 Binding of OX40mAb24 to Primary Human $CD4^+$ T Cells and OX40-expressing Jurkat T Cells The apparent equilibrium binding consent ($K_d$) for OX40mAb24 binding to human OX40 and the concentrations required to bind 20%, 50%, or 90% of cell surface human OX40 receptor at equilibrium were calculated from binding curves of OX40mAb24 to OX40-expressing activated primary human $CD4^+$ T cells or human OX40-overexpressing Jurkat T cells. Similar experiments were performed at the same time to assess binding of 9B12 to these cells for comparison with OX40mAb24 values.

Primary human $CD4^+$ T cells were first isolated from sodium heparin anti-coagulated whole blood obtained from healthy donors through the MedImmune Blood Donor Program using a RosetteSep $CD4^+$ T cell enrichment kit (Stem Cell Technologies, Vancouver, BC) and a modified manufacturer's protocol.

Primary human $CD4^+$ T cells were cultured for 48 h with 2 μg/mL PHA-L and 20 IU/mL rhIL-2 to activate T cells and up-regulate OX40. Activated T cells, which were >95% viable, were subsequently used in OX40mAb24 binding experiments. All donors represent unique individuals; that is, repeat binding experiments were not performed with $CD4^+$ T cells from the same donor.

Human OX40-overexpressing Jurkat NFκB-luciferase clone 64 cells were cultured in complete RPMI+10% FBS prior to binding experiments, without the need for activation.

OX40mAb24 (10 μg/mL) or 9B12 (10 μg/mL) was diluted over a 17 point 2-fold dilution series. OX40mAb24 was added to 100,000 cells (activated primary $CD4^+$ T cells or human OX40-overexpressing Jurkat NFkB-luciferase clone 64 cells) per well and incubated for one hour at 4° C. For background binding subtraction, cells were incubated in the presence of secondary antibody alone. The control R347 human IgG1 monoclonal antibody and mouse IgG1 isotype clone MOPC-21 were used in experiments with OX40 over-expressing Jurkat T cells to demonstrate the specificity for OX40 binding of OX40mAb24 or 9B12, respectively. Following incubation, cells were washed three times with 200 μL of cold (4° C.) FACS buffer and incubated with 100 μL of FACS buffer (PBS+2% heat-inactivated newborn calf serum) containing 10 μg/mL AlexaFluor® 647 labeled goat anti-human IgG secondary antibody (for binding to OX40mAb24) or 10 μg/mL AlexaFluor® 488 labeled goat anti-mouse IgG secondary antibody (for binding to 9B12) and 5 μg/mL propidium iodide (PI). Following secondary antibody incubation, cells were washed and suspended in 100 μL FACS buffer for flow cytometry analysis on a BD LSRII flow cytometer as described below.

2.2.2 OX40mAb24 Binding to Mouse $CD4^+$ T Cells

OX40mAb24 was investigated for binding to mouse OX40 expressed on activated primary $CD4^+$ T cells. Similar experiments were performed at the same time to assess binding of 9B12 to these cells in comparison with OX40mAb24. Mouse $CD4^+$ T cells were isolated from harvested normal Balb/C mouse spleens according to the following protocol:

Spleens were mashed against a 70 μM nylon filter to release splenocytes and the filter rinsed with 1 mL complete medium (RPMI-1640 plus 10% FBS, 1% antibiotic/antimycotic solution and 55 μM beta mercaptoethanol [BME]). Splenocytes were pelleted and the supernatant discarded. The pellet was treated with 5 mL of 1× red blood cell (RBC) lysis buffer and incubated to lyse RBCs. Osmolarity was restored by addition of complete medium at the end of incubation time.

Cells were pelleted, washed in Miltenyi MACS buffer (PBS pH 7.2+0.5% bovine serum albumin (BSA)+2 mM ethylenediaminetetraacetic acid [EDTA]) and the supernatant was discarded. The pellet was suspended in cold MACS buffer and counted with a ViCell counter to determine cell number and viability.

Mouse $CD4^+$ T cell isolation was performed with a Miltenyi process kit (San Diego, Calif.) according to manufacturer's instructions, and isolated cells were suspended in complete medium Mouse $CD4^+$ T cells (150,000 per well in 100 μL complete medium) were cultured overnight in 96-well plates coated with 2 μg/mL each hamster anti-mouse CD3 and hamster anti-mouse CD28 antibodies to activate T cells and induce OX40 expression. Activated $CD4^+$ T cells were removed from the incubation plate and 100,000 cells were transferred to each well of a non-tissue culture-treated 96-well round-bottom plate for binding assays and washed once with FACS buffer. Binding was performed with 10 μg/mL of OX40mAb24, 9B12 and rat anti-mouse OX40, clone OX86 (positive control) antibodies each serially diluted 3-fold in FACS buffer for a 10-point data curve. For negative controls, 10 μg/mL R347 human IgG1, MOPC-21 mouse IgG1 or RTK2071 rat IgG1 were diluted 6-fold for a 3 point data curve. FACS buffer (50 μL) containing OX40mAb24, or antibodies, was added to $CD4^+$ T cells in duplicate and incubated. Following primary incubation, cells were washed with 200 μL of 4° C. FACS buffer and incubated with 50 μL of FACS buffer containing 10 μg/mL AlexaFluor® 488 labeled goat anti-human secondary, 10 μg/mL AlexaFluor® 488 labeled goat anti-mouse secondary or AlexaFluor® 488 labeled goat anti-rat secondary antibody and 5 μg/mL PI. Following secondary antibody incubation, cells were washed with 4° C. FACS buffer (200 μL per wash) and suspended in 100 μL FACS buffer for flow cytometry analysis on a BD LSRII flow cytometer as described in Section 2.3.

2.2.3 OX40mAb24 Binding to Rat $CD4^+$ T cells

OX40mAb24 was investigated for binding to rat OX40 expressed on activated primary $CD4^+$ T cells. Similar experiments were performed at the same time with 9B12 to allow comparison with OX40mAb24. Rat $CD4^+$ cells were isolated from freshly harvested normal Sprague-Dawley rat spleens according to the protocol described above for the isolation of mouse splenocytes, except that rat $CD4^+$ T cell isolation was performed with an R&D Systems Magellect kit (Minneapolis, Minn.) according to manufacturer's instructions.

Rat $CD4^+$ T cells ($1\times10^6$ per mL complete medium) were cultured overnight in a T75 cell culture flask with 1 μg/mL concanavalin A (Con A) and 500 IU/mL IL-2, to activate T cells and induce OX40 expression, and incubated overnight. Activated $CD4^+$ T cells were removed from the flask and 100,000 cells were transferred to each well of a non-tissue culture treated 96-well round-bottom plate for binding assays and washed with FACS buffer. Binding was performed with 10 μg/mL OX40mAb24, 9B12 or mouse anti-rat CD134, clone OX40 (positive control) antibody serially diluted 3-fold for a 10 point data curve in FACS buffer. For negative controls, 10 μg/mL R347 human IgG1 or mouse IgG1 clone MOPC-21 were serially diluted 6-fold for a 3 point data curve. 100 μL of OX40mAb24 control protein, 9B12 or clone OX40 antibody was added to $CD4^+$ T cells in duplicate and incubated. Following primary incubation, cells were washed with 200 μL of 4° C. FACS buffer per wash and incubated with 100 μL of FACS buffer containing 10 μg/mL AlexaFluor® 488 labeled goat and human, or AlexaFluor® 488 labeled goat anti-mouse secondary antibody and 5 μg/mL PI. Following secondary antibody incubation, cells were processed for flow cytometry as described in Section 2.3.

2.2.4 OX40mAb24 Binding to Cynomolgus Monkey $CD4^+$ T Cells

OX40mAb24 was investigated for binding to cynomolgus monkey (cyno) OX40 expressed on activated primary $CD4^+$ T cells. Similar experiments were performed at the same time with 9B12 to allow comparison with OX40mAb24 values. Cyno $CD4^+$ T cells were isolated from sodium heparin anti-coagulated whole blood obtained from healthy cyno donors (N=2) from World Wide Primates (Miami, Fla.) according to the following protocol:

Whole blood was layered onto 30 mL of 60% Percoll in a 50 mL conical centrifuge tube. Blood was centrifuged and peripheral blood mononuclear cells (PBMC) were collected at the interface and washed with cold (4° C.) Miltenyi MACS buffer at 1200 RPM for 10 minutes. Supernatant was discarded and the pellet was treated with 5 mL of 1× RBC lysis buffer and incubated. Complete medium (RPMI with 10% FBS and 1% antibiotics/antimycotics) was added to the pellet to stop the lysis process at the end of incubation time.

Cells were pelleted and washed with 20 mL of cold (4° C.) Miltenyi MACS buffer. The supernatant was discarded and the cell pellet was suspended in cold (4° C.) MACS buffer and counted with a ViCell counter to determine cell number and viability.

Cyno $CD4^+$ T cell isolation was performed with a Miltenyi non-human primate kit according to manufacturer's instructions, then $CD4^+$ T cells counted on a ViCell counter and suspended at $1\times10^6$ per mL in complete medium as described above.

Cyno $CD4^+$ T cells ($1\times10^6$ per mL in complete medium) were incubated for 48 hours in a T75 cell culture flask with 2 μg/mL PHA-L and 20 IU/mL IL-2, to activate T cells and induce OX40 expression. Activated $CD4^+$ T cells were removed from the flask and 100,000 cells were transferred to each well of a non-tissue culture treated 96-well round-bottom plate for binding assays and washed with 200 μL FACS buffer. Binding was performed with 10 μg/mL OX40mAb24 or 9B12 serially diluted 4-fold in FACS buffer for an 11-point data curve, or both R347 human IgG1 or mouse IgG1 clone MOPC-21 (negative controls) serially diluted 6-fold for a 3 point data curve. OX40mAb24, 9B12 or control protein was added to $CD4^+$ T cells and incubated. Following primary incubation, cells were washed with 200 μL of cold (4° C.) FACS buffer per wash and incubated with 100 μL of FACS buffer containing 10 μg/mL AlexaFluor® 488 labeled goat anti-human secondary antibody or 10 μg/mL AlexaFluor® 488 labeled goat anti-mouse secondary and 5 μg/mL PI. Following secondary antibody incubation, cells were processed for flow cytometry as described in Section 2.3.

2.2.5 OX40mAb24 Binding to Rhesus Monkey $CD4^+$ T Cells

OX40mAb24 was investigated for binding to rhesus macaque OX40 expressed on activated primary $CD4^+$ T cells. Similar experiments were performed at the same time with 9B12 to allow comparison with OX40mAb24 values. Rhesus $CD4^+$ T cells were isolated from sodium heparin anti-coagulated whole blood obtained from healthy rhesus donors (N=2) from World Wide Primates (Miami, Fla.) according to the following protocol:

Heparinized rhesus blood (20 mL) was diluted 1:1 with PBS and layered onto 15 ml of 95% LSM in a 50 ml conical centrifuge tube. Blood was centrifuged, PBMC were collected at the interface and washed twice with cold Miltenyi MACS buffer at 400×g for 30 minutes. Supernatant was discarded and the pellet was treated with 5 mL of 1× RBC lysis buffer and incubated. Complete medium (RPMI with 10% FBS and 1% antibiotics/antimycotics) was added to the pellet to stop the lysis process at the end of incubation time. Cells were pelleted and washed with 20 mL of cold Miltenyi MACS buffer. Supernatant was discarded and the pellet was suspended in cold MACS buffer and counted with a ViCell counter to determine cell number and viability. Rhesus $CD4^+$ T cell isolation was performed with a Miltenyi non-human primate kit (San Diego, Calif.) according to manufacturer's instructions.

Rhesus $CD4^+$ T cells ($1\times10^6$ per mL in complete medium) were cultured for 48 hours in a T75 cell culture flask with 5 μg/mL Con-A and 1000 IU/mL IL-2 to activate T cells and induce OX40 expression. Binding to 100,000 activated rhesus $CD4^+$ T cells was performed with 10 μg/mL OX40mAb24 and 9B12 serially diluted 3-fold in FACS buffer for a 10 point (experiment 1) or 12 point data curve (experiment 2) and 10 μg/mL human and mouse isotype controls diluted 6-fold for 2 data points (experiment 1) or 4 data points (experiment 2). AlexaFluor® 488-labeled goat anti-human secondary antibody and AlexaFluor® 488 labeled goat anti-mouse secondary binding were as described above for cyno $CD4^+$ T cells, and flow cytometry as described in Section 2.3.

2.3 Flow Cytometry

Flow cytometry in the assays described in Section 2.1 was performed using an LSRII flow cytometer (Becton-Dickinson, San Jose, Calif.). Flow Jo cytometry analysis software (TreeStar, Ashland, Oreg.) was used to determine OX40mAb24, 9B12 and control protein binding to cells. Wells containing OX40-expressing cells (unstained, no PI or secondary antibody), cells bound to AlexaFluor® 488- or AlexaFluor® 647-labeled secondary antibody reagent only or cells permeabilized with 0.1% saponin and treated with 10 μg/mL PI were prepared for single-stain compensation controls. After fluorescence compensation, live (PI negative) cells were gated and the mean fluorescence intensity (MFI) of secondary antibody was determined.

2.4 Calculations 2.4.1 Determination of Apparent Equilibrium Dissociation Constant ($K_d$)

GraphPad Prism version 5.01 for Windows, GraphPad Software, San Diego Calif. USA, www.graphpad.com, was used to plot MFI of OX40mAb24 binding versus protein concentration (M) to create binding curves from which apparent $K_d$ was determined. To determine the apparent $K_d$ for OX40mAb24 and 9B12 binding to human, mouse, rat, cyno, or rhesus monkey OX40, a non-linear regression (curve fit) equation for one site (specific) binding was employed.

2.4.2 Determination of 20%, 50%, and 90% Receptor Occupancy Values

The amount of a monoclonal antibody (mAb) bound to its receptor can be estimated from the following binding relationship:

Receptor(A)+mAb(B)↔receptor-mAb complex (AB) Equation 1

The binding dissociation constant ($K_d$) of the respective antibody is represented by:

$$Kd = \frac{[A][B]}{[AB]} \quad \text{Equation 2}$$

Where [A] and [B] represent the concentrations of free receptor and antibody, respectively. Finally, the fractional occupancy, fraction (F) of all receptor molecules that are bound to the antibody, can be calculated by:

$$F = \frac{[AB]}{[A]+[AB]} \quad \text{Equation 3}$$

Formation of Equation 2 and Substitution into Equation 3 Results in:

$$F = \frac{[A][B]/Kd}{[A]+([A][B]/Kd)} \quad \text{Equation 4}$$

Simplification of Equation 4 Results in:

$$F = \frac{[B]}{[B]+Kd} \quad \text{Equation 5}$$

Therefore, at equilibrium condition, the fraction of all receptor molecules that are bound to the antibody can be calculated if the concentration of free mAb and the dissociation constant $K_d$ of the respective antibody are known.

Derivation of this formula for the calculation of the concentration of antibody required for a fractional receptor occupancy expressed as F, leads to the following formula:

$$[B]=F*Kd/(1-F) \quad \text{Equation 6}$$

Where [B] equals the concentration of mAb, in this case OX40mAb24. This formula (Equation 6) was used for the calculation of the concentrations of OX40mAb24 required for 20, 50, and 90% receptor occupancy (F=0.20, 0.50 or 0.90) from cell binding experiments from which the $K_d$ value was calculated using the non-linear regression (curve fit) equation for one site (specific) binding described above.

2.5 Statistical Methods

A 2-sided unpaired Student's t test with 95% confidence level and Welch's correction to account for data sets with different standard deviations was utilized in Graphpad Prism software to determine statistically significant differences between apparent $K_d$ values or apparent receptor occupancy values determined for OX40mAb24 binding to OX40 on activated primary human CD4 T cells versus OX40-expressing Jurkat T cells. Descriptive statistics (i.e., mean and standard error of the mean) are presented in the summary figures and tables.

2.6 Results 2.6.1 Binding of OX40mAb24 to Primary Human $CD4^+$ T Cells

OX40mAb24 bound to activated human $CD4^+$ T cells with a mean apparent $K_d$ of 312 pM and 20%, 50% and 90% receptor occupancy values of 78.1, 312, and 2810 pM, respectively; n=6 binding assays with six independent T cell donors (FIGS. 2A and 2B, and Table 2-2).

In comparison, 9B12 bound to activated human $CD4^+$ T cells with a mean $K_d$ of 669 pM, and 20%, 50% and 90% receptor occupancy values of 167, 669, and 6020 pM, respectively (FIGS. 2C and 2D and Table 2-2). The ratio between 9B12 and OX40mAb24 apparent $K_d$ values was therefore 2.1 to 1, and reflects a similar binding affinity to human OX40 for the murine and humanized monoclonal antibodies

TABLE 2-2

Apparent Affinity ($K_d$) and Receptor Occupancy Values for Binding of OX40mAb24 or 9B12 to OX40-expressing Activated Primary Human CD4+ T cells

| Binding Protein | N donors | $K_d$ (StdErr), pM | $EC_{20}$ (StdErr), pM | $EC_{50}$ (StdErr), pM | $EC_{90}$ (StdErr), pM |
|---|---|---|---|---|---|
| OX40mAb24 | 6 | 312 (57.9) | 78.1 (14.5) | 312 (57.9) | 2810 (521) |
| 9B12 | 6 | 669 (137) | 167 (34.3) | 669 (137) | 6020 (1230) |

$EC_{20}$ = effective concentration resulting in 20% of maximal effect;
$EC_{50}$ = half maximal effective concentration;
$EC_{90}$ = effective concentration resulting in 90% of maximal effect;
$K_d$ = equilibrium binding dissociation constant;
StdErr = standard error of the mean.

2.6.2 Binding of OX40mAb24 to a Jurkat T Cell Line Engineered to Over-Express Human OX40

OX40mAb24 bound to OX40-expressing Jurkat T cells with a mean $K_d$ of 424 pM and 20%, 50% and 90% receptor occupancy values of 106, 424, and 3820 pM, respectively. FIGS. 3A-C and Table 2-3. There were no statistically significant differences in apparent binding affinity or receptor occupancy of OX40mAb24 to OX40 expressed by activated primary human $CD4^+$ T cells and OX40 over-expressing Jurkat T cells (p=0.59).

In comparison, 9B12 bound these cells with a mean $K_d$ of 726 pM and 20%, 50% and 90% receptor occupancy values of 182, 726, and 6540 pM, respectively (FIGS. 3D-F and Table 2-3). The ratio between the apparent $K_d$ values for 9B12 and OX40mAb24 was therefore 1.7 to 1, similar to the ratio calculated for binding to OX40 on activated human $CD4^+$ T cells

TABLE 2-3

Apparent Affinity ($K_d$) and Receptor Occupancy Values for Binding of OX40mAb24 or 9B12 to Human OX40-overexpressing Jurkat NFkB-luciferase Clone 64 cells

| Binding Protein | N experiments | $K_d$ (StdErr), pM | $EC_{20}$ (StdErr), pM | $EC_{50}$ (StdErr), pM | $EC_{90}$ (StdErr), pM |
|---|---|---|---|---|---|
| OX40mAb24 | 3 | 424 (173) | 106 (43.3) | 424 (173) | 3820 (1560) |
| 9B12 | 3 | 726 (308) | 182 (76.9) | 726 (308) | 6540 (2770) |

$EC_{20}$ = effective concentration resulting in 20% of maximal effect;
$EC_{50}$ = half maximal effective concentration;
$EC_{90}$ = effective concentration resulting in 90% of maximal effect;
$K_d$ = equilibrium binding dissociation constant;
StdErr = standard error of the mean.

2.6.3 Binding of OX40mAb24 to Mouse or Rat $CD4^+$ T Cells

Neither OX40mAb24 nor 9B12 bound to activated mouse or rat $CD4^+$ T cells (data not shown). Positive staining of activated mouse and rat $CD4^+$ T cells was observed with commercial anti-mouse and anti-rat OX40 antibodies, clones OX86 and OX40, respectively. 9B12 did not bind activated mouse nor rat $CD4^+$ T cells (data not shown).

2.6.4 Binding of OX40mAb24 to Cynomolgus and Rhesus Monkey $CD4^+$ T Cells

OX40mAb24 bound to activated cynomolgus cells with a mean $K_d$ of 581 pM. The cyno $K_d$ was 1.9-fold higher than the human $K_d$ (Table 2-4).

9B12 bound the activated cyno $CD4^+$ T cells with a mean $K_d$ of 1088 pM (Table 2-4), which resulted in a ratio between 9B12 and OX40mAb24 apparent $K_d$ values of 1.9 to 1.

OX40mAb24 bound to activated rhesus monkey $CD4^+$ T cells with a mean $K_d$ of 369 pM (Table 2-4). The rhesus $K_d$ was 1.2-fold higher than the human $K_d$.

9B12 bound the activated rhesus monkey $CD4^+$ T cells with a mean $K_d$ of 713 pM (Table 2-4), which results in a ratio between 9B12 and OX40mAb24 apparent $K_d$ values not shown of 2.8 to 1

TABLE 2-4

Apparent Affinity ($K_d$) for Binding of OX40mAb24 or 9B12 to Cynomolgus and Rhesus Monkey OX40-expressing Activated Primary CD4+ T cells

| | Cynomolgus | | Rhesus | |
|---|---|---|---|---|
| Binding Protein | N experiments | $K_d$ (StdErr), pM | N experiments | $K_d$ (StdErr), pM |
| OX40mAb24 | 2 | 581 (238) | 2 | 369 (236) |
| 9B12 | 2 | 1088 (37) | 2 | 713 (559) |

$K_d$ = equilibrium binding dissociation constant;
StdErr = standard error of the mean.

Example 3

Binding Specificity of OX40mAb24 for Human OX40

In this example, flow cytometry-based cell binding assays were performed to determine the specificity of OX40mAb24 for human OX40, relative to other human TNFRSF members with related amino acid sequences, which included: NGFR (TNFRSF16), LTBR (TNFRSF3), TNFR2 (TNFRSF1B), GITR (TNFRSF18), CD137 (TNFRSF9), and HVEM (TNFRSF14). In addition, the binding specificity of OX40mAb24 for recombinant human TNFRSF members was tested in an ELISA format, which included those mentioned above as well as DR6 (TNFRSF21), osteoprotegerin (OPG; TNFRSF11B), RANK (TNFRSF11A), FAS (TNFRSF6), and CD40 (TNFRSF5).

3.1 Materials

Materials used in this study are listed in Table 3-1.

TABLE 3-1

| Materials | |
|---|---|
| Item | Source |
| AlexaFluor ® 647 goat anti-human IgG (H + L) | Life Technologies, Carlsbad, CA |
| BioTek ® plate washer | BioTek ®, Wincoski, VT |
| CD137 (TNFRSF9) pCMV6-XL5 expression vector | Origene Technologies, Inc., Rockville, MD |
| GITR (TNFRSF18) pCMV6-XL5 expression vector | Origene Technologies, Inc., Rockville, MD |
| Goat anti-human IgG kappa light chain HRP conjugate | Sigma-Aldrich, St. Louis, MO |
| Goat-antimouse IgG (Fab specific) HRP conjugate | Sigma-Aldrich, St. Louis, MO |
| HVEN (TNFRSF14) pCMV6-XL4 expression vector | Origene Technologies, Inc., Rockville, MD |
| Lipofectamine 2000 | Life Technologies, Carlsbad, CA |
| AF488 anti-mouse IgG1 isotype | Biolegend, San Diego, CA |
| AF488 anti-human GITR | Ebioscience, San Diego, CA |
| AF647 anti-human NGFR | BD, San Jose, CA |
| APC anti-human CD137 | BD, San Jose, CA |
| APC anti-mouse IgG1 isotype | Biolegend, San Diego, CA |
| Clone Manager v9 software | Sci-Ed Software, Cary, NC |
| Fetal bovine serum (FBS), heat inactivated | Life Technologies, Carlsbad, CA |
| LTβR (TNFRSF3) pCMV6-XL4 expression vector | Origene Technologies, Inc., Rockville, MD |
| MaxiSorp 96 well flat bottom plate | VWR, Radnor, PA |
| Newborn calf serum, heat inactivated | Life Technologies, Carlsbad, CA |
| NGFR (TNFRSF16) pCMV6-XL5 expression vector | Origene Technologies, Inc., Rockville, MD |
| PE anti-human HVEM | Ebioscience, San Diego, CA |
| PE anti-human LtβR | R&D systems, Minneapolis, MN |
| PE anti-human TNFRSF 1B | BD, San Jose, CA |
| PE anti-mouse IgG1 isotype | Biolegend, San Diego, CA |
| PE anti-rat isotype | Ebioscience, San Diego, CA |
| PBS, pH 7.2 without calcium and magnesium | Life Technologies, Carlsbad, CA |
| Recombinant human TNFRSF1β (TNFRII) | R&D systems, Minneapolis, MN |
| Recombinant human TNFRSF3 (LTβR) | R&D systems, Minneapolis, MN |
| Recombinant human TNFRSF4 (OX40) | R&D systems, Minneapolis, MN |
| Recombinant human TNFRSF5 (CD40) | R&D systems, Minneapolis, MN |
| Recombinant human TNFRSF6 (FAS) | R&D systems, Minneapolis, MN |
| Recombinant human TNFRSF9 (CD137) | In house protein; lot# AMPur19 |
| Recombinant human TNFRSF11A (RANK) | R&D systems, Minneapolis, MN |
| Recombinant human TNFRSF11B (OPG) | R&D systems, Minneapolis, MN |
| Recombinant human TNFRSF14 (HVEM) | R&D systems, Minneapolis, MN |
| Recombinant human TNFRSF16 (NGFR) | R&D systems, Minneapolis, MN |
| Recombinant human TNFRSF18 (GITR) | In house protein; lot# LBPur0025 |
| Recombinant human TNFRSF21 (DR6) | R&D systems, Minneapolis, MN |
| TNFRSF1β pCMV6-XL5 expression vector | Origene Technologies, Inc., Rockville, MD |
| Tween-20 | Sigma-Aldrich, St. Louis, MO |

3.2 Methods 3.2.1 Search for Proteins with Close Sequence Homology to Human OX40

In order to identify human proteins with amino acid sequence identity to human OX40, a protein sequence homology Basic Local Alignment Search Tool (BLASTP) search was conducted using the protein sequence of OX40 (CCDS 11/UniProt P43489). Nineteen TNFRSF family members/isoforms were identified. The full-length sequences of these proteins were verified using both the CCDS and UniProt databases (www.uniprot.org). Clone Manager version 9 software was used to perform an assembled alignment against the human OX40 reference using a blosum62 scoring matrix to determine the percentage of amino acid identity between human OX40 and the proteins identified in the BLASTP search (Table 3-2).

3.2.2 Binding Specificity of OX40mAb24 for OX40 Relative to Other TNFRSF Members Expressed in HEK293 Cells cDNA constructs capable of directing the expression of individual TNFRSF members, when transfected into mammalian cells, were obtained from Origene Technologies, Rockville, Md. These cDNA constructs were amplified and purified by the Protein Sciences group at MedImmune in Gaithersburg, Md. for use in transient transfections. For individual expression of each of the TNFRSF members, HEK293 cells were transfected using Lipofectamine 2000 (Life Technologies, Carlsbad, Calif.) combined with 0.5 μg DNA of an expression vector encoding one of the TNFRSF members, according to the manufacturer's suggested protocol for Lipofectamine 2000. Forty-eight hours post transfection, cells were removed from tissue culture plates by trypsinization. Trypsin was neutralized by the addition of serum-containing complete medium RPMI-1640 plus 10% FBS), followed by cell pelleting and washes in complete medium. Cells were then suspended in cold FACS buffer (PBS+2% FBS) and plated into 96 well non-tissue culture-treated plates for binding studies with TNFRSF member-specific mAbs (Table 3-3) and OX40mAb24.

For binding of antibodies or OX40mAb24, HEK cells were pelleted, FACS buffer removed, and cells suspended in FACS buffer containing 2 μg/mL propidium iodide (PI) and either a fluorochrome-labeled mAb, specific for the transfected TNFRSF member, at a concentration recommended by the manufacturer or with OX40mAb24 at a concentration of 1 μg/mL. For binding controls, cells were separately incubated with fluorochrome-labeled isotype control antibodies. Cells were incubated with antibodies for 1 hour at 4° C. in the dark. Thereafter, cells incubated with fluorochrome-labeled monoclonal antibodies were washed in cold FACS buffer and then binding events collected and analyzed by flow cytometry using an LSRII flow cytometer (BD Biosciences, San Jose, Calif.) and FlowJo software, as described in Section 3.2.3. Cells incubated with OX40mAb24 were washed in ice cold FACS buffer and then suspended 25 μg/mL of Alexa Fluor® 647 goat antihuman IgG (H+L) secondary antibody and incubated for a further 30 minutes at 4° C. in the dark. For a secondary antibody binding control cells were incubated in the absence of OX40mAb24, but in the presence of fluorochrome-labeled secondary antibody alone. Thereafter, cells were washed and suspended in cold FACS buffer for analysis on an LSRII flow cytometer.

3.2.3 Flow Cytometry Analysis

Flow cytometry standard (FCS) data was examined using FlowJo software (Ashland, Oreg.). To analyze mAb binding, cells were first gated for viable (PI negative) cells, and then the mean fluorescence intensity (MFI) of events was plotted versus total number of events to generate binding histograms. The geometric MFI of all viable cells was determined for each sample so that the fold MFI over background (isotype control or secondary antibody alone) could be determined.

3.2.4 OX40mAb24 Binding Specificity ELISA

An eight point, two-fold dilution series of each recombinant human TNFRSF protein was prepared after dilution of stock proteins to 5 μg/mL in PBS. Subsequently, 50 μL of each antigen dilution was transferred in duplicate to wells of a Nunc 96-well MaxiSorp flat bottom plate, and incubated overnight at 4° C. to adsorb proteins to the plate. Afterwards, plates were washed three times with PBS in a BioTek® plate washer to remove unbound protein. Anti OX40 mAb29, 9B12, and control antibodies were diluted in PBS to a final concentration of 10 μg/mL, and 50 μL of mAb were added to each well and incubated at room temperature for one hour to bind mAb to plate-bound protein. Thereafter, wells were washed with PBS/Tween-20 0.1% (volume/volume) using a BioTek® plate washer. HRP conjugated goat anti-human or goat anti-mouse secondary antibodies at 10 μg/mL was added to each well and incubated at room temperature for 1 hour. After three washes in PBS/Tween-20 0.1%, 50 μL of TMB substrate was added to each well and incubated at room temperature for 5 minutes to develop the colorimetric product. Reactions were stopped by adding 50 μL of 0.5 molar $H_2SO_4$ to wells, and plates read immediately at 450 nm using an Envision C plate reader for detection of the colorimetric product. Results were graphed in GraphPad Prism software for Windows, version 5.01, and binding curves generated using non-linear regression analysis for single site binding.

3.3 Results

The protein sequence homology BLASTP search on human OX40 identified 19 human TNFRSF proteins or isoforms that shared 15-27% amino acid sequence identity with the full-length OX40 sequence. The proteins and their percentages of sequence identity are listed in Table 3-2.

TABLE 3-2

Amino Acid Sequence Identity of Twelve TNFRSF Members with the Highest Homology to Human OX40.

| TNFRSF member | Alternate names | % identity with OX40 | UniProt protein sequence ID |
|---|---|---|---|
| TNFRSF11A | RANK, CD265 | 27 | Q9Y6Q6 iso 2 (delta 7, 8, 9) |
| TNFRSF6B | DcR3 | 25 | O95407 |
| TNFRSF18 | GITR, AITR | 25 | Q9Y5U5 iso 2 |
| TNFRSSF10C | DCR1, TRAIL-R3 | 24 | O14798 |

TABLE 3-2-continued

Amino Acid Sequence Identity of Twelve TNFRSF Members with the Highest Homology to Human OX40.

| TNFRSF member | Alternate names | % identity with OX40 | UniProt protein sequence ID |
|---|---|---|---|
| TNFRSF5 | CD40 | 23 | P25942 iso 2 |
| TNFRSF18 | GITR, AITR | 23 | Q9Y5U5 iso 3 |
| TNFRSF18 | GITR, AITR | 23 | Q9Y5U5 |
| TNFRSF9 | CD137, 4-1BB | 22 | Q07011 |
| TNFRSF5 | CD40 | 21 | P25942 |
| TNFRSF14 | TR2, HVEM-A | 21 | Q92956 |
| TNFRSF16 | NGF receptor | 21 | P08138 |
| TNFRSF3 | LTβR, TNFRIII | 20 | P36941 |
| TNFRSF6 | Fas | 20 | P25445 iso 6 Tmdcl (A) |
| TNFRSF6 | Fas | 20 | P25445 |
| TNFRSF3 | LTβR, TNFRIII | 19 | P36941 iso 2 |
| TNFRSF6 | Fas | 19 | P25445 iso 7 FasExo8Del |
| TNFRSF11B | Osteoprotegerin | 18 | O0030 |
| TNFRSF1B | TNFR1b, TNFR2, CD120b | 18 | P20333 |
| TNFRSF11A | RANK, CD265 | 16 | Q9Y6Q6 |

CCDS = consensus coding sequence;
ID = identifier;
NA = not applicable;
TNFRSF = tumor necrosis factor receptor superfamily;
UniProt—Universal Protein Resource Binding of OX40mAb24 to transiently transfected HEK293 cells that expressed human NGFR, LTBR, TNFR2, GITR, CD137 or HVEM was assessed by flow cytometry as described in Section 3.1.3 above. Cell surface expression of human NGFR, LTBR, TNFR2, GITR, CD137 and HVEM was confirmed using commercially available antibodies specific for each human TNFRSF protein; fold increase in MFI compared to isotype control antibodies for each TNFRSF protein is shown in Table 3-3. Binding of OX40mAb24 to HEK293 cells that expressed human NGFR, LTBR, TNFR2, GITR, CD137 or HVEM was not substantially above that seen for binding of the secondary antibody alone to those same cells (Table 3-3, FIG. 4A). In contrast, binding of OX40mAb24 to a Jurkat cell line that constitutively overexpresses OX40 was 48-fold greater, by mean MFI, than the binding of fluorochrome labeled secondary antibody alone (Table 3-3 and FIG. 4B).

TABLE 3-3

Fold Binding of Fluorochrome-labeled TNFRSF-specific Monoclonal Antibodies and OX40mAb24 to TNFRSF-overexpressing HEK293 Cells or OX40mAb24 to OX40-overexpressing Jurkat Cells.

| TNFRSF member expressed | Cell Line Transferred with TNFRSF Member | Receptor-Specific Commercial mAb binding (ratio to isotype control MFI) | OX40mAb24 binding (ratio to secondary antibody alone MFI) |
|---|---|---|---|
| OX40 | Jurkat | ND | 48 |
| TNFRSF16 (NGFR) | HEK293 | 17 | 2.2 |
| TNFRSF3 (LTβR) | HEK293 | 146 | 1.0 |
| TNFRSF1β | HEK293 | 5.0 | 1.0 |
| TNFRSF18 (GITR) | HEK293 | 37 | 1.1 |
| TNFRSF9 (CD137) | HEK293 | 24 | 1.2 |
| TNFRSF14 (HVEM) | HEK293 | 69 | 1.1 |

mAb = monoclonal antibody;
MFI = mean fluorescence intensity;
ND = not determined;
TNFRSF = tumor necrosis factor receptor superfamily In an ELISA format, binding of an antibody containing the Fab arms of OX40mAb24 but with IgG1 Fc domain containing three amino acid modifications (mAb29) was specific for OX40 (FIG. 5A), showing no specific binding above background to recombinant human NGFR (TNFRSF16), LTβR (TNFRSF3), TNFR2 (TNFRSF1β), GITR (TNFRSF18), CD137 (TNFRSF9), HVEM (TNFRSF14), DR6 (TNFRSF21), osteoprotegerin (OPG; TNFRSF11B), RANK (TNFRSF11A), FAS (TNFRSF6), and CD40 (TNFRSF5). 9B12, the mouse anti-human OX40 IgG1 monoclonal antibody that was "humanized" to create OX40mAb24, demonstrated similar lack of binding to these TNFRSF proteins (FIG. 5B).

3.4: Conclusions

Binding of OX40mAb24 and 9B12 to human OX40 is specific, and do not cross-react with highly related TNFRSF proteins.

Example 4

Ability of OX40mAb24 to Co-stimulate Primary Human $CD4^+$ T Cells Through OX40 In Vitro In this example, the ability of OX40mAb24 to enhance activation of T cells, in combination with activation through the CD3/T cell receptor (TCR) complex, was assessed using a plate-based human $CD4^+$ T cell proliferation and cytokine release assay. Soluble OX40mAb24 activity was also examined, as were the activity of soluble and plate-bound OX40mAb24 in the absence of CD3/TCR signaling.

4.1 Materials

Materials used in this study are listed in Table 4-1.

TABLE 4-1

| Materials | |
|---|---|
| Item | Source |
| AlexaFluor ® 647 goat anti-human IgG (H + L) | Life Technologies, Carlsbad, CA |
| Anti-human CD4 EFluor450 ® | eBioscience, San Diego, CA |
| Bovine serum albumin (BSA) | Sigma, Saint Louis, MO |
| CFSE cell labeling kit | Life Technologies, Carlsbad, CA |
| Complete RPMI medium: RPMI-1640 + 10% FBS | Materials from Life Technologies, Carlsbad, CA |
| Deep well plates, polypropylene, 2 mL | VWR, Radnor, PA |
| EasySep $CD4^+$ T cell enrichment kit | Stem Cell Technologies, Vancouver, BC Canada |
| FlowJo software | TreeStar, Ashland, OR |
| Goat anti-human IgG, Fcγ-specific | Jackson ImmunoResearch, West Grove, PA |
| Goat anti-mouse IgG, Fcγ-specific | Jackson ImmunoResearch, West Grove, PA |
| Heat inactivated newborn calf serum | Life Technologies, Carlsbad, CA |
| IL-2, recombinant human | Preprotech, Rocky Hill, NJ |
| Leuko Pak | AllCells, Alameda, CA |
| LSM | MP Biomedicals, Santa Ana, CA |
| LSR II flow cytometer | BD Biosciences, San Jose, CA |
| Mouse anti-human CD3 antibody clone OKT3 | Biolegend, San Diego, CA |
| Newborn calf serum, beat inactivated (FBS) | Life Technologies, Carlsbad, CA |
| Non-issue culture treated round-bottom 96 well plates | VWR, Radnor, PA |
| PHA-L | Roche Applied Science, Indianapolis, IN |
| Phosphate Buffered Saline (PBS) pH 7.2 without Calcium and Magnesium | Life Technologies, Carlsbad, CA |
| Prism software, v 5.01 | Graphpad Software, San Diego, CA |
| Propidium iodide (1 mg/mL solution) | Sigma, Saint Louis, MO |
| RosetteSep $CD4^+$ T cell enrichment kit | StemCell Technologies, Vancouver, BC Canada |
| RPMI-1640 | Life Technologies, Carlsbad, CA |
| Thl/Th2 multi-cytokine detection array | Mesoscale Discovery (MSD), Rockville, MD |
| Vi-Cell counter | Beckman Coulter, Indianapolis, IN |
| Whole blood, sodium heparin anti-coagulated | MedImmune Blood Donor Program, Gaithersburg, MD |

4.2 Assays 4.2.1 Plate-immobilized Bioactivity of OX40mAb24

The bioactivity of OX40mAb24 was determined by measurement of human $CD4^+$ T cell proliferation and cytokine production in a plate-based drug capture assay (FIG. 6).

Enriched human $CD4^+$ T cells were isolated from healthy donor whole blood using a RosetteSep $CD4^+$ T cell enrichment kit, according to the manufacturer's protocol. Assays were performed with cells from four independent donors.

$CD4^+$ T cells were suspended in complete RPMI culture medium and the cell concentration adjusted to $1.0\times10^6$ per mL. Final concentrations of 2 μg/mL phytohemagglutinin-leucoagglutinin (PHA-L) and 20 IU/mL recombinant human IL-2 were added, and cells were cultured at 37° C. and 5% $CO_2$ in a humidified tissue culture incubator for 2 days to activate T cells and up-regulate OX40.

Non-tissue culture treated round-bottom 96 well assay plates were coated with 100 μL of 2 μg/mL goat anti-mouse Fcγ-specific IgG and 2 μg/mL goat anti-human Fcγ-specific IgG in PBS. Goat anti-human IgG capture antibodies were not added to wells intended for assay of soluble OX40mAb24 activity. Plates were incubated overnight at 4° C., washed with 200 μL of PBS, and blocked for 90 minutes at 37° C. with 1% BSA in PBS (1% BSA/PBS). The plates were washed with PBS and 2 ng/mL of mouse anti-human CD3 clone OKT3 reconstituted in 1% BSA/PBS was added to the plates for 90 minutes at 37° C. The plates were washed with PBS to remove unbound OKT3, OX40mAb24, R347 human IgG1 control mAb, 9B12, and mouse IgG1 control mAb clone MOPC-21 were each reconstituted in 1% BSA/PBS starting at 0.918 μg/mL (3.0 nM) and serially diluted over a 3-fold dilution series and then added to assay plates and incubated for 90 minutes at 37° C.

Activated primary human $CD4^+$ T cells were collected, washed in complete RPMI medium, and the concentration adjusted to $1.0\times10^6$ viable cells/mL. Cells were labelled with carboxyfluorescein succinimidyl ester (CFSE), according to the manufacturer's instructions, with the exception of using 1.25 μM CFSE as opposed to the recommended 5 μM with an incubation of 10 minutes at 37° C. After labeling, cells were suspended in complete RPMI medium and the concentration was adjusted to $0.5\times10^6$ per mL. The plates were washed with PBS and 200 μL of $CD4^+$ T cells (100,000/well) were added to each well. For wells containing soluble OX40mAb24, OX40mAb24 was diluted in complete RPMI medium to the highest final concentrations used for plate-bound OX40mAb24. Cells in the plate were pelleted by centrifugation at 380×g and incubated at 37° C. for 3 days. After 72 hours incubation time, 40 μL of cell culture supernatant was removed for cytokine release measurement. $CD4^+$ T cells were pelleted, and washed once with PBS containing 2% FBS (FACS buffer). Cells were suspended in binding mix containing anti-human CD4 eFluor450® labeled antibody for identification of $CD4^+$ T cells, and propidium iodide (PI) for live/non-viable cell discrimination, and incubated for 30 minutes. Following incubation, cells were washed in FACS buffer, re-suspended in FACS buffer and analyzed by flow cytometry using an LSRII flow cytometer and FlowJo software for analysis of Flow Cytometry Standard (FCS) formatted data.

To analyze T cell proliferation, live (PI negative) events were gated using FlowJo software, and the percentage of CD4-gated cells showing dilution of CFSE determined as a measure of the percentage of cells undergoing proliferation.

To analyze cytokine release, cell culture supernatants obtained after 72 hours of culture were measured for cytokine content using a 10-plex human Th1/Th2 cytokine analysis kit from MesoScale Discovery (Gaithersburg, Md.) according to the manufacturer's protocol. This kit employs an electrochemical detection method to quantitatively measure the following human cytokines: IFNγ, IL-2, IL4, IL-5, IL-8, IL-10, IL-12 p70, IL-13, and IL-1β.

GraphPad Prism version 5.01 for Windows, GraphPad Software, San Diego Calif. USA, www.graphpad.com was used to plot the log of mAb concentration versus either proliferation or cytokine release values. The effective concentrations resulting in 20%, 50% and 90% maximal effect ($EC_{20}$, $EC_{50}$, and $EC_{90}$) values for OX40mAb24 bioactivity were calculated from sigmoidal dose-response bioactivity curves using the ECAnything function.

4.3 Results

Proliferation data from each of the four donors and cytokine release data from one donor are shown in FIGS. 7A-C and FIGS. 8A-E. $EC_{20}$, $EC_{50}$, and $EC_{90}$ potency values for human primary $CD4^+$ T cell proliferation are shown in Table 4-2; potency values for human primary $CD4^+$ T cell cytokine release assays in Table 4-3 through Table 4-7; Mean proliferation and cytokine release values for OX40mAb24 and 9B12 are shown in Table 4-8 and Table 4-9, respectively.

OX40mAb24 co-stimulated proliferation of primary human $CD4^+$ T cells (n=4) in a concentration-dependent manner with $EC_{20}$, $EC_{50}$, and $EC_{90}$ values of 21, 28, and 72 pM, respectively. 9B12 co-stimulated proliferation of $CD4^+$ T cells with $EC_{20}$, $EC_{50}$, and $EC_{90}$ values of 106, 218, and 622 pM. Therefore, the ratio of 9B12 to OX40mAb24 concentrations required to induce a 50% of maximum proliferative response was 8 to 1 (Table 4-2).

OX40mAb24 and 9B12 co-stimulated primary human $CD4^+$ T cells to release cytokines (n=4). Mean $EC_{20}$, $EC_{50}$, and $EC_{90}$ values were less potent than values for proliferation, and are summarized in Table 4-8 and Table 4-9. Non-linear regression analysis could not be conducted for IL-2, IL-4, IL-8, IL-12 p70, and IL-1β assay results for both mAbs, due to poorly formed or non-existent sigmoidal dose-response curves.

TABLE 4-2

Mean $EC_{20}$, $EC_{50}$ and $EC_{90}$ Values for OX40mAb24 and 9B12 in a Primary Human $CD4^+$ T cell Proliferation Assay

| Donor Number | Monoclonal Antibody | $EC_{20}$ (95% CI), pM | $EC_{50}$ (95% CI), pM | $EC_{90}$ (95% CI), pM | Soluble activity | Activity in absence of TCR stimulation |
|---|---|---|---|---|---|---|
| 367 | OX40mAb24 | 32 (22, 46) | 38 (20, 72) | 71 (17, 29) | Not Tested | None |
| 661 | OX40mAb24 | 33 (28, 39) | 51 (33, 77) | 128 (96, 172) | Not Tested | None |
| 645 | OX40mAb24 | 7.5 (2.7, 21) | 8.3 (2.8, 25) | 35 (7.1, 173) | None | Not Tested |
| 651 | OX40mAb24 | 9.6 (6.3, 15) | 16 (9.1, 26) | 54 (30, 99) | None | Not Tested |
| Mean (Standard Error of the Mean), pM | OX40mAb24 | 21 (6.9) | 28 (9.8) | 72 (20) | | |
| 367 | 9B12 | 99.8 (80.0, 125) | 156 (90.2, 269) | 337 (214, 530) | Not Tested | Not Tested |
| 661 | 9B12 | 128 (113, 144) | 237 (164, 342) | 535 (464, 617) | Not Tested | Not Tested |
| 645 | 9B12 | 77.5 (30.2, 199) | 169 (67.0, 425) | 686 (152, 3080) | Not Tested | Not Tested |
| 651 | 9B12 | 118 (80.8, 173) | 309 (201, 475) | 929 (511, 1690) | Not Tested | Not Tested |
| Mean (Standard Error of the Mean), pM | 9B12 | 106 (11.1) | 218 (35.2) | 622 (125) | | |

CI = confidence interval;

$EC_{20}$ = effective concentration resulting in 20% of maximal effect;

$EC_{50}$ = half maximal effective concentration;

$EC_{90}$ = effective concentration resulting in 90% of maximal effect;

TCR = T cell receptor.

TABLE 4-3

Mean $EC_{20}$, $EC_{50}$ and $EC_{90}$ Values for IFNγ Induced by OX40mAb24 or 9B12 in a Primary Human $CD4^+$ T Cell Bioactivity Assay

| Donor Number | Monoclonal Antibody | $EC_{20}$ (95% CI), pM | $EC_{50}$ (95% CI), pM | $EC_{90}$ (95% CI), pM | Soluble activity | Activity in absence of TCR stimulation |
|---|---|---|---|---|---|---|
| 367 | OX40mAb24 | 38.6 (21.3, 70.0) | 57.2 (31.2, 105) | 106 (34.6, 328) | Not Tested | None |
| 661 | OX40mAb24 | ND | ND | ND | Not Tested | None |
| 645 | OX40mAb24 | 32.1 (20.8, 49.7) | 58.2 (42.0, 80.8) | 150 (77.6, 289) | None | Not Tested |
| 651 | OX40mAb24 | 47.5 (24.5, 91.8) | 77.4 (51.4, 116) | 168 (86.7, 324) | None | Not Tested |
| Mean (Standard Error of the Mean), pM | OX40mAb24 | 39.4 (4.46) | 64.3 (6.57) | 141 (18.4) | | |
| 367 | 9B12 | ND | ND | ND | Not Tested | Not Tested |
| 661 | 9B12 | ND | ND | ND | Not Tested | Not Tested |
| 645 | 9B12 | 706 (518, 963) | 2380 (1420, 3970) | 16300 (5480, 48300) | Not Tested | Not Tested |
| 651 | 9B12 | 344 (274, 430) | 758 (639, 900) | 2660 (780, 3990) | Not Tested | Not Tested |
| Mean (Standard Error of the Mean), pM | 9B12 | 525 (148) | 1570 (662) | 9480 (5569) | | |

CI = confidence interval;
$EC_{20}$ = effective concentration resulting in 20% of maximal effect;
$EC_{50}$ = half maximal effective concentration;
$EC_{90}$ = effective concentration resulting in 90% of maximal effect;
TCR = T cell receptor.

TABLE 4-4

Mean $EC_{20}$, $EC_{50}$ and $EC_{90}$ Values for TNFα Induced by OX40mAb24 or 9B12 in a Primary Human $CD4^+$ T cell Bioactivity Assay

| Donor Number | Monoclonal Antibody | $EC_{20}$ (95% CI), pM | $EC_{50}$ (95% CI), pM | $EC_{90}$ (95% CI), pM | Soluble activity | Activity in absence of TCR stimulation |
|---|---|---|---|---|---|---|
| 367 | OX40mAb24 | ND | ND | ND | Not Tested | None |
| 661 | OX40mAb24 | ND | ND | ND | Not Tested | None |
| 645 | OX40mAb24 | 37.6 (22.5, 62.7) | 54.1 (29.1, 101) | 96.2 (26.7, 347) | None | Not Tested |
| 651 | OX40mAb24 | ND | ND | ND | None | Not Tested |
| Mean (Standard Error of the Mean), pM | OX40mAb24 | ND | ND | ND | | |
| 367 | 9B12 | ND | ND | ND | Not Tested | Not Tested |
| 661 | 9B12 | ND | ND | ND | Not Tested | Not Tested |
| 645 | 9B12 | 306 (258, 503) | 670 (527, 853) | 1800 (1100, 2920) | Not Tested | Not Tested |
| 651 | 9B12 | 388 (300, 502) | 764 (640, 919) | 2260 (1500, 3410) | Not Tested | Not Tested |
| Mean (Standard Error of the Mean), pM | 9B12 | 347 (33.5) | 717 (38.4) | 2030 (188) | | |

CI = confidence interval;
$EC_{20}$ = effective concentration resulting in 20% of maximal effect;
$EC_{50}$ = half maximal effective concentration;
$EC_{90}$ = effective concentration resulting in 90% of maximal effect;
ND = not determined due to poor curve fit ($EC_{20}$, $EC_{50}$, $EC_{90}$) or lack of sufficient in values to determine mean and standard error of the mean;
TCR = T cell receptor.

TABLE 4-5

Mean $EC_{20}$, $EC_{50}$ and $EC_{90}$ Values for IL10 Induced by OX40mAb24 or 9B12 in a Primary Human $CD4^+$ T Cell Bioactivity Assay

| Donor Number | Monoclonal Antibody | $EC_{20}$ (95% CI), pM | $EC_{50}$ (95% CI), pM | $EC_{90}$ (95% CI), pM | Soluble activity | Activity in absence of TCR stimulation |
|---|---|---|---|---|---|---|
| 367 | OX40mAb24 | 41.6 (17.8, 97.0) | 59.5 (25.4, 139) | 105 (25.0, 440) | Not Tested | None |
| 661 | OX40mAb24 | 63.5 (29.6, 136) | 89.5 (64.2, 125) | 154 (93.3, 255) | Not Tested | None |
| 645 | OX40mAb24 | ND | ND | ND | None | Not Tested |
| 651 | OX40mAb24 | 53.0 (31.0, 90.6) | 86.4 (65.0, 115) | 188 (110, 321) | None | Not Tested |
| Mean (Standard Error of the Mean), pM | OX40mAb24 | 52.7 (6.32) | 78.5 (9.53) | 149 (24.1) | | |
| 367 | 9B12 | 130 (83.3, 204) | 198 (139, 284) | 385 (224, 662) | Not Tested | Not Tested |
| 661 | 9B12 | ND | ND | ND | Not Tested | Not Tested |
| 645 | 9B12 | 528 (363, 767) | 1220 (858, 1740) | 4630 (2050, 10400) | Not Tested | Not Tested |
| 651 | 9B12 | 405 (300, 547) | 796 (649, 976) | 2320 (1440, 3730) | Not Tested | Not Tested |
| Mean (Standard Error of the Mean), pM | 9B12 | 354 (118) | 738 (296) | 2445 (1227) | | |

CI = confidence interval;
$EC_{20}$ = effective concentration resulting in 20% of maximal effect;
$EC_{50}$ = half maximal effective concentration;
$EC_{90}$ = effective concentration resulting in 90% of maximal effect;
ND = not determined due to poor curve fit ($EC_{20}$, $EC_{50}$, $EC_{90}$) or lack of sufficient in values to determine mean and standard error of the mean;
TCR = T cell receptor.

TABLE 4-6

Mean EC20, EC50 and EC90 Values for IL13 Induced by OX40mAb24 or 9B12 in a Primary Human $CD4^+$ T Cell Bioactivity Assay

| Donor Number | Monoclonal Antibody | $EC_{20}$ (95% CI), pM | $EC_{50}$ (95% CI), pM | $EC_{90}$ (95% CI), pM | Soluble activity | Activity in absence of TCR stimulation |
|---|---|---|---|---|---|---|
| 367 | OX40mAb24 | ND | ND | ND | Not Tested | None |
| 661 | OX40mAb24 | ND | ND | ND | Not Tested | None |
| 645 | OX40mAb24 | 44.7 (26.5, 75.5) | 73.8 (52.2, 104) | 163 (93.3, 286) | None | Not Tested |
| 651 | OX40mAb24 | 36.2 (24.9, 52.7) | 65.0 (49.6, 85.3) | 164 (99.2, 273) | None | Not Tested |
| Mean (Standard Error of the Mean), pM | OX40mAb24 | 40.5 (4.25) | 69.4 (4.40) | 164 (0.50 | | |
| 367 | 9B12 | ND | ND | ND | Not Tested | Not Tested |
| 661 | 9B12 | 154 (841, 283) | 238 (166, 341) | 472 (278, 800) | Not Tested | Not Tested |
| 645 | 9B12 | 1100 (413, 2910) | 5450 (1060, 2800) | 6930 (4310, 1110000) | Not Tested | Not Tested |
| 651 | 9B12 | 495 (324, 756) | 1770 (896, 3510) | 13400 (2980, 60400) | Not Tested | Not Tested |
| Mean (Standard Error of the Mean), pM | 9B12 | 583 (277) | 2486 (1550) | 6930 (3730) | | |

CI = confidence interval;
$EC_{20}$ = effective concentration resulting in 20% of maximal effect;
$EC_{50}$ = half maximal effective concentration;
$EC_{90}$ = effective concentration resulting in 90% of maximal effect;
ND = not determined due to poor curve fit ($EC_{20}$, $EC_{50}$, $EC_{90}$) or lack of sufficient in values to determine mean and standard error of the mean;
TCR = T cell receptor.

TABLE 4-7

Mean $EC_{20}$, $EC_{50}$ and $EC_{90}$ Values for IL5 Induced by OX40mAb24 or 9B12 in a Primary Human $CD4^+$ T cell Bioactivity Assay

| Donor Number | Monoclonal Antibody | $EC_{20}$ (95% CI), pM | $EC_{50}$ (95% CI), pM | $EC_{90}$ (95% CI), pM | Soluble activity | Activity in absence of TCR stimulation |
|---|---|---|---|---|---|---|
| 367 | OX40mAb24 | 33.2 (21.2, 52.1) | 46.7 (24.7, 88.0) | 79.8 (12.3, 519) | Not Tested | None |
| 661 | OX40mAb24 | 43.4 (27.6, 68.4) | 69.0 (49.7, 95.7) | 144 (86.8, 238) | Not Tested | None |
| 645 | OX40mAb24 | ND | ND | ND | None | Not Tested |
| 651 | OX40mAb24 | 56.2 (35.5, 88.9) | 95.9 (76.1, 121) | 224 (128, 391) | None | Not Tested |
| Mean (Standard Error of the Mean), pM | OX40mAb24 | 44.3 (6.65) | 70.5 (14.2) | 149 (41.7) | | |
| 367 | 9B12 | ND | ND | ND | Not Tested | Not Tested |
| 661 | 9B12 | ND | ND | ND | Not Tested | Not Tested |
| 645 | 9B12 | ND | ND | ND | Not Tested | Not Tested |
| 651 | 9B12 | 423 (285, 627) | 1090 (742, 1600) | 4870 (1900, 12500) | Not Tested | Not Tested |
| Mean (Standard Error of the Mean), pM | 9B12 | ND | ND | ND | | |

CI = confidence interval;
$EC_{20}$ = effective concentration resulting in 20% of maximal effect;
$EC_{50}$ = half maximal effective concentration;
$EC_{90}$ = effective concentration resulting in 90% of maximal effect;
ND = not determined due to poor curve fit ($EC_{20}$, $EC_{50}$, $EC_{90}$) or lack of sufficient in values to determine mean and standard error of the mean;
TCR = T cell receptor.

TABLE 4-8

Summary of Mean $EC_{20}$, $EC_{50}$ and $EC_{90}$ Values for Proliferation and Cytokine Release for OX40mAb24

| Bioactivity Readout | $EC_{20}$ (StdErr), pM | $EC_{50}$ (StdErr), pM | $EC_{90}$ (StdErr), pM |
|---|---|---|---|
| CD4 T cell proliferation | 21 (6.9) | 28 (98) | 72 (20) |
| IFNγ release | 39.4 (4.46) | 64.3 (6.57) | 141 (18.4) |
| TNFα release | ND | ND | ND |
| IL10 | 52.7 (6.32) | 78.5 (9.53) | 149 (24.1) |
| IL13 | 40.5 (4.25) | 69.4 (4.40) | 164 (0.50) |
| IL5 | 44.3 (6.65) | 70.5 (14.2) | 149 (41.7) |

$EC_{20}$ = effective concentration resulting in 20% of maximal effect;
$EC_{50}$ = half maximal effective concentration;
$EC_{90}$ = effective concentration resulting in 90% of maximal effect;
ND = not determined due to insufficient n value to calculate a mean and standard error of the mean;
StdErr = standard error of the mean.

TABLE 4-9

Summary of Mean $EC_{20}$, $EC_{50}$ and $EC_{90}$ Values for Proliferation and Cytokine Release for 9B12

| Bioactivity Readout | $EC_{20}$ (StdErr), pM | $EC_{50}$ (StdErr), pM | $EC_{90}$ (StdErr), pM |
|---|---|---|---|
| CD4 T cell proliferation | 106 (11.1) | 218 (35.2) | 622 (125) |
| IFNγ release | 525 (148) | 1570 (662) | 9480 (5569) |
| TNFα release | 347 (33.5) | 717 (38.4) | 2030 (188) |
| IL10 | 354 (118) | 738 (296) | 2445 (1227) |
| IL13 | 583 (277) | 2486 (1547) | 6934 (3732) |
| IL5 | ND | ND | ND |

$EC_{20}$ = effective concentration resulting in 20% of maximal effect;
$EC_{50}$ = half maximal effective concentration;
$EC_{90}$ = effective concentration resulting in 90% of maximal effect;
ND = not determined due to insufficient n value to calculate a mean and standard error of the mean;
StdErr = standard error of the mean.

The activity of non-plate bound, soluble OX40mAb24 was determined. Soluble OX40mAb24 did not induce either primary human $CD4^+$ T cell proliferation (FIG. 7A-C) or cytokine release (FIGS. 8A-E) above levels observed for either anti-CD3 antibody alone or in the presence of R347 human IgG1 control mAb. Plate bound anti-CD3 antibody alone produced a minimal-to-moderate level of proliferation and cytokine release. The lack of activity demonstrated here by soluble OX40mAb24 is in agreement with the absence of activity observed for soluble OX40mAb24 without cell-based cross-linking in a 2-cell bioactivity assay that measured OX40 mediated NFκB signaling (see Example 5 below).

Likewise, OX40mAb24, either immobilized on the plate surface or added as a soluble unbound protein, in the absence of a sub-mitogenic anti-CD3 antibody signal induced little-to-no $CD4^+$ T cell proliferation (FIGS. 7A-C) or cytokine release (FIGS. 8A-E). These results demonstrated that, in this study, OX40mAb24 does not have activity in primary human $CD4^+$ T cells in the absence of simultaneous CD3/TCR ligation.

4.4 Conclusions

OX40mAb24 induced proliferation and cytokine release of primary human $CD4^+$ T cells in a concentration-dependent manner similar to that of the antibody from which it was humanized 9B12 (FIGS. 8A-E and FIGS. 9A-E). OX40mAb24 demonstrated activity as a plate-bound, but not as a soluble, protein. Furthermore, OX40mAb24 activity occured concurrent with CD3/TCR signaling.

Example 5

Determination of the In Vitro Activity of OX40mAb24 in 2-cell Based Bioactivity Assays Using Jurkat NFκB-luciferase Reporter T Cells In this example, the ability of OX40mAb24 and 9B12 to signal through human OX40 was assessed using a set of two-cell reporter bioactivity assays. Measurement of T cell activation through OX40 co-stimulation was accomplished by using an OX40-overexpressing Jurkat NFκB-luciferase T cell reporter line that produces luciferase in response to stimulation of the NFκB signaling pathway (FIG. 10). NFκB signaling has been reported to occur downstream of OX40 engagement, and can correlate with other measures of T cell activation, such as proliferation and cytokine release (Croft M, et al., *Immunol Rev.* 229:173-91 (2009)). The amount of luciferase, and thus T cell activation, was measured by adding a luciferase substrate to cell lysates and measuring light emitted by the reaction product using a luminometer. Bioactivity of OX40mAb24 cross-linked using cells engineered to express different Fcγ receptor complements, as well as soluble, non-FcγR-crosslinked OX40mAb24 was measured.

5.1 Materials

Materials used in this study are listed in Table 5-1.

TABLE 5-1

| Materials | |
|---|---|
| Item | Source |
| $CD45^+$ microbeads | Miltenyi, San Diego, CA |
| Collagenase III | Worthington Biochemical Corporation, Lakewood, NJ |
| DNAse I, from b ovine pancreas | Sigma, Saint Louis, MO |
| EDTA, 0 5M pH 8.0 | Life Technologies, Carlsbad, CA |
| Envision luminescence reader | Perkin Elmer, Waltham, MA |
| Heat inactivated newborn calf serum (FBS) | Life Technologies, Carlsbad, CA |
| LS column | Miltenyi, San Diego, CA |
| MACS buffer: PBS + 0.5% BSA + 2 mM EDTA | Materials from Life Technologies, Carlsbad, CA |
| Non-TC treated round-bottom 96 well plates | VWR, Radnor, PA |
| Prism v5.01 software | GraphPad, San Diego, CA |
| Steady-Glo Luciferase Assay Solution | Promega, Madison, WI |
| ViCell counter | Beckman Coulter, Indianapolis, IN |

5.2 Two-cell Bioactivity Assay 5.2.1 Isolation of Primary Human $CD45^+$ Cells

Primary human $CD45^+$ cells were isolated from human tumors. Tumor samples were removed from transport media and placed in sterile petri dish. Hank's Buffered Salt Solution was added and visible necrotic tissue or any normal tissue from tumor sample was dissected. Tissue was minced into small pieces (~1 mm) and placed in a 50 mL conical tube, and Collagenase III enzyme mix (250 IU/mL collagenase III, 3 mM $CaCl_2$, 315 μg/mL DNAase 1) was added, mixed and incubated. The digested sample was filtered through a 70 micron filter and washed with MACS buffer. Dissociated cells were pelleted and the cell number and viability were determined using a ViCell counter. Cells were suspended in MACS buffer with CD45 microbeads and incubated on ice. Cells were washed and re-suspended in MACS buffer for positive selection of $CD45^+$ cells using an LS column. Bead-bound $CD45^+$ cells were eluted by removing the column from the magnet and adding MACS buffer to the column. Cells were pelleted and re-suspended in complete RPMI medium and used in bioactivity assays as described above.

5.2.2 Assay Protocol

OX40mAb24 and 9B12 were tested for bioactivity using a 2-cell bioactivity assay. Human OX40-overexpressing Jurkat NFκB-luciferase reporter clone 64 (OX40 Jurkat reporter) was used to measure OX40 agonism (NFκB activity). A second, FcγR-expressing cell line, was used to mediate OX40mAb24 cross-linking, which clusters and activates OX40 on the OX40 Jurkat reporter cells (FIG. 10). The FcγR-expressing cell lines used for cross-linking included the Raji human B cell lymphoma line, CD32A-expressing HEK293, CD32B-expressing HEK293 or $CD45^+$ immune cells isolated from primary human tumors.

To determine the soluble activity of OX40mAb24, bioactivity assays were also conducted using either parental HEK293 cells, which are FcγR null and therefore are unable to cross-link OX40mAb24, or in the absence of cross-linking cells altogether.

Prior to use, OX40 Jurkat reporter cells were cultured in complete RPMI medium in a tissue culture incubator at a density of $0.5\text{-}1.5\times10^6$ per mL. Cells were passaged the day prior to the bioassay at a final density of $10^6$ cells per mL.

OX40 Jurkat reporter cells, FcγR-expressing cell lines, or HEK parental cells were collected, and pelleted. To isolate $CD45^+$ cells from primary human tumors and normal adjacent tissues, tissues were dissociated and $CD45^+$ cells isolated and re-suspended in complete RPMI medium for use in bioactivity assays, as described below.

OX40mAb24, 9B12 and various control antibodies were serially diluted 3-fold in complete RPMI medium.

OX40 Jurkat reporter cells plus FcγR-expressing cells, or HEK parental cells, were added to a 96 well plate at 100,000 cells per well. OX40mAb24, 9B12 or control antibodies were added to cells in a dilution series with a starting concentration of 10 μg/mL, and incubated at 37° C. in a tissue culture incubator.

After 16-24 hours incubation time, 100 μL reconstituted Steady-Glo luciferase assay solution (Promega, Madison, Wis.) was added to each well and mixed to lyse cells and then incubated to equilibrate luciferase signal. Steady-Glo/sample lysate (150 μL) was transferred from each well to a 96 well, white walled assay plate for detection and luminescence read using a Perkin Elmer Envision luminescence reader.

GraphPad Prism version 5.01 for Windows (GraphPad Software, San Diego, Calif.), was used to plot the concentration of OX40mAb24, 9B12, R347 human IgG1, mouse IgG1 clone MOPC-21 (x-axis is log 10 of protein concentration) versus luminescence RLU (y-axis). The $EC_{20}$, $EC_{50}$, and $EC_{90}$ values for bioactivity were determined using ECAnything (ECf) for f=20, f=50 and f=90 from sigmoidal dose-response (variable slope) bioactivity curves).

5.3 Results of 2-Cell Bioactivity Assays

Results for the bioactivity of OX40mAb24 and control antibodies are shown in FIG. 11A-D, FIGS. 12A-D and Table 5-2.

In the presence of an FcγR-expressing cell line (e.g., CD32A-expressing HEK293, CD32B-expressing HEK293, Raji B cells, or $CD45^+$ cells isolated from primary human tumors), OX40mAb24 demonstrated potent stimulation of OX40-overexpressing Jurkat NFκB reporter cells, as measured by NFκB pathway activation. In the absence of a second cell type or in the presence of HEK293 cells lacking exogenously expressed FcγRs, OX40mAb24 exhibited minimal reporter activity (FIG. 11A-D).

Potency values ($EC_{20}$, $EC_{50}$, and $EC_{90}$) for the two-cell bioassays are summarized in Table 5-2. The mean $EC_{20}$, $EC_{50}$, and $EC_{90}$ values across all assays were 228, 751, and 5630 pM, respectively.

Results for the bioactivity of 9B12 and control antibodies are shown in FIGS. 12A-D and the potency values are summarized in Table 5-3. The mean $EC_{20}$, $EC_{50}$, and $EC_{90}$ values for all assays were 519, 2530, and 41100 pM, respectively. Therefore, the ratio of 2-cell bioactivity ($EC_{50}$) for 9B12 relative to that of OX40mAb24 was calculated to be 3.4 to 1.

TABLE 5-2

Two-cell Bioactivity of OX40mAb24

| Experiment Number | FcγR-expressing cell* | $EC_{20}$ (95% CI) pM | $EC_{50}$ (95% CI) pM | $EC_{90}$ (95% CI) pM |
|---|---|---|---|---|
| 1 | Raji | 298 (236, 378) | 1140 (982, 1340) | 9850 (6500, 14300) |
| 2 | CD32A-expressing HEK | 104 (78.8, 138) | 437 (370, 517) | 4250 (2900, 6240) |
| 3 | CD32A-expressing HEK | 100 (79.5, 126) | 322 (281, 370) | 2060 (1530, 2780) |
| 4 | Raji | 350 (259, 467) | 1040 (855, 1270) | 5930 (3740, 9400) |
| 5 | CD32B-expressing HEK | 90.6 (75.4, 109) | 270 (242, 301) | 1520 (1200, 1920) |
| 6 | Raji | 180 (109, 296) | 796 (577, 1100) | 8410 (3820, 18500) |
| 7 | CD32B-expressing HEK | 280 (198, 394) | 899 (710, 1140) | 5730 (3290, 9970) |
| 8 | CD32B-expressing HEK | 237 (196, 286) | 671 (592, 762) | 3510 (2630, 4670) |
| 9 | Raji | 676 (443, 1030) | 1320 (970, 1800) | 3820 (2000, 7320) |
| 10 | Raji | 297 (127, 694) | 1260 (666, 2390) | 12500 (2570, 60500) |
| 11 | CD32B-expressing HEK | 144 (113, 184) | 700 (598, 818) | 8540 (5770, 12600) |
| 12 | $CD45^+$ cells, NSCLC | 33.6 (24.7, 45.8) | 81.6 (68.5, 97.3) | 334 (236, 471) |
| 13 | $CD45^+$ cells, RCC | 92.2 (75.4, 113) | 337 (296, 383) | 2630 (1940, 3550) |
| 14 | $CD45^+$ cells, NSCLC | 247 (207, 295) | 772 (688, 867) | 4700 (3600, 6140) |
| 15 | $CD45^+$ cells, RCC | 351 (155, 798) | 1410 (782, 2530) | 12700 (2960, 54500) |
| 16 | CD32A-expressing HEK | 166 (145, 191) | 553 (507, 603) | 3720 (3060, 4530) |
| | Mean (Standard Error of the Mean) | 228 (38.9) | 751 (101) | 5630 (937) |

NSCLC = non-small cell lung cancer;
RCC = renal cell carcinoma
*As indicated, assays used Raji, CD32A-expressing HEK293, CD32B-expressing HEK293 cells, or $CD45^+$ cells isolated from primary human tumor samples with OX40-expressing Jurkat NFκB-luciferase clone 64 reporter cells.

TABLE 5-3

Two-cell Bioactivity of 9B12

| Experiment Number | FcγR-expressing cell* | $EC_{20}$ pM | $EC_{50}$ pM | $EC_{90}$ pM |
|---|---|---|---|---|
| 1 | Raji | 1110 (791, 1570) | 9280 (4460, 19300) | 267000 (57900, 1230000) |
| 2 | CD32A-expressing HEK | 74.1 (53.0, 104) | 338 (279, 410) | 3760 (2440, 5790) |
| 3 | CD32A-expressing HEK | 66.7 (43.3, 103) | 225 (175, 289) | 1550 (914, 2630) |
| 4 | Raji | 1040 (834, 1300) | 5040 (3880, 6550) | 61200 (32200, 116000) |
| 5 | CD32B-expressing HEK | 249 (206, 303) | 726 (641, 823) | 3950 (2980, 5240) |
| 6 | Raji | 548 (408, 736) | 2700 (2070, 3620) | 33700 (17000, 66700) |
| 7 | CD32B-expressing HEK | 585 (520, 658) | 1770 (1620, 1930) | 10200 (8280, 12500) |
| 8 | CD32B-expressing HEK | 518 (449, 598) | 1340 (1210, 1480) | 6050 (4800, 7630) |
| 9 | Raji | 872 (504, 1510) | 3070 (1910, 4950) | 22600 (7000, 73100) |
| 10 | Raji | 571 (212, 1540) | 3330 (1080, 10200) | 54400 (3400, 872000) |
| 11 | CD32B-expressing HEK | 650 (458, 923) | 2360 (1790, 3100) | 18200 (9200, 36000) |
| 12 | $CD45^+$ cells, NSCLC | 104 (76.3, 143) | 223 (185, 269) | 741 (501, 1100) |
| 13 | $CD45^+$ cells, RCC | ND | ND | ND |
| 14 | $CD45^+$ cells, NSCLC | ND | ND | ND |
| 15 | $CD45^+$ cells, RCC | 356 (132, 964) | 2420 (938, 6250) | 50500 (4140, 616000) |
| | Mean (Standard Error of the Mean) | 519 (96.2) | 2530 (687) | 41100 (19700) |

ND = not determined;
NSCLC = non-small cell lung cancer;
RCC = renal cell carcinoma
*As indicated, assays used Raji, CD32A-expressing HEK293, CD32B-expressing HEK293 cells, or $CD45^+$ cells isolated from primary human tumor samples with OX40-expressing Jurkat NFκB-luciferase clone 64 reporter cells.

5-4: Conclusions

OX40mAb24 and 9B12 mediate the activation of human T cells as measured by the stimulation of the NFκB pathway in an OX40-overexpressing Jurkat NFκB-luciferase reporter cell line. In the absence of cells that express FcγRs capable of cross linking via the Fc domains of OX40mAb24, minimal reporter cell-line activity was measured. However, in a 2-cell system comprising cells that express FcγR that are capable of cross-linking the mAb, and a Jurkat overexpressing NFκB-luciferase reporter line for readout of T cell activation, OX40mAb24 and 9B12 mediated potent OX40 activation with mean $EC_{50}$ values of 751 pM and 2530 pM, respectively. Therefore, the bioactivity of OX40mAb24 in the 2-cell assay system was similar to that of 9B12.

Example 6

Ability of OX40mAb24 to Trigger Effector Function

In this example OX40mAb24 was assessed with respect to its ability to trigger Fc effector function namely, the ability of OX40mAb24 to trigger human natural killer (NK) cell-mediated antibody-dependent cellular cytotoxicity (ADCC) against primary human $CD4^+$ T cells expressing high levels of OX40, or to bind C1q, a prerequisite for complement-dependent cellular cytotoxicity (CDC) by the classical complement pathway. Versions of OX40mAb24 containing either a human IgG4P Fc domain (mAb28), or a triple mutation in the IgG1 Fc domain that reduces Fcγ RIIIa binding (mAb29) were utilized to assess the contribution of the OX40mAb24 IgG1 Fc domain to mediate ADCC activity. Also, the effector functions of OX40mAb24 were compared to that of 9B12, a mouse anti-human OX40 IgG1 monoclonal antibody that was humanized to create OX40mAb24. The anti-CD20 antibody rituximab binds to B cells expressing CD20 and was used as a positive control for ADCC experiments. Because primary activated human $CD4^+$ T cells do not express CD20, a separate assay using the Toledo B cell line, which does express CD20, was conducted to validate the activity of NK cells used in the ADCC assay system.

6.1 Materials

Materials used in this study are listed in Table 7-1.

TABLE 6-1

| Materials | |
|---|---|
| Item | Source |
| Complement protein C1q | Quidel, San Diego, CA |
| Complete RPMI medium: RPMI-1640+ 10% FBS | Materials from Life Technologies, Carlsbad, CA |
| DM-L medium | Stem Cell Technologies, Vancouver, BC Canada |
| GLC biosensor chip | Bio-Rad, Hercules, CA |
| FlowJo Software | FlowJo, Ashland, OR |
| IL-2, recombinant human | Preprotech, Rocky Hill, NJ |
| LSR II flow cytometer | BD Biosciences, San Jose, CA |
| Prism software, v 5.01 | Graphpad Software, San Diego, CA |
| Propidium iodide (1 mg/mL solution) | Sigma, Saint Louis, MO |
| ProteOn Manager 2.1 software | Bio-Rad, Hercules, CA |
| ProteOn XPR36 instrument | Bio-Rad, Hercules, CA |
| RosetteSep CD4 T cell enrichment kit | Stem Cell Technologies, Vancouver, BC Canada |
| RosetteSep Human NK cell enrichment | Stem Cell Technologies, Vancouver, BC Canada |
| ViCell counter | Beckman Coulter, Indianapolis, IN |
| Vybrant DiO cell labeling solution | Life Technologies, Carlsbad, CA |
| Whole blood, sodium heparin anti-coagulated | MedImmune Blood Donor Program, MedImmune, Gaithersburg, MD |

6.2 Assays 6.2.1 Antibody-dependent Cellular Cytotoxicity

The ADCC activity of OX40mAb24 relative to that of 9B12 and monoclonal antibodies containing the Fab arms of OX40mAb24 with either an IgG4P Fc domain or a triple mutant (TM) human IgG1 Fc domain, was tested using enriched primary human NK cells as effectors and OX40-expressing primary human $CD4^+$ T cells as targets. As a positive control, the activity of each NK cell preparation was tested using rituximab directed killing of the Toledo B cell line.

For the isolation of primary human $CD4^+$ T cells, heparin anti-coagulated, whole blood obtained from healthy donors through the MedImmune Blood Donor Program was processed according to the following protocol: Stem Cell Technologies RosetteSep CD4 T cell isolation kit antibody mix (1 mL, Stem Cell Technologies, Vancouver, BC Canada) was added per 20 mL of whole blood, mixed, and incubated for 20 minutes (mm) at room temperature (RT). Blood was diluted 1:1 with sterile room temperature FACS buffer (PBS, pH 7.2 plus 2% heat inactivated newborn calf serum) and layered onto DM-L medium followed by centrifugation for 20 min. After centrifugation, the buffy coat containing human $CD4^+$ T cells was removed and the cells were washed once with RT FACS buffer and once with RT complete RPMI medium. Cells were counted on a ViCell counter to determine cell number and viability and $CD4^+$ T cells were suspended in complete RPMI medium at a concentration of $1.0\times10^6$ per mL.

Primary human $CD4^+$ T cells ($1.0\times10^6$ per mL in complete RPMI medium) were cultured in a humidified tissue culture incubator at 37° C. and 5% $CO_2$ for 48 hours with 2 μg/mL PHA-L and 20 IU/mL rhIL-2 to activate T cells and up-regulate OX40 and were subsequently used in OX40mAb24 ADCC assays. All donors in the figures referenced below represent unique individuals; that is, $CD4^+$ T cells were not isolated from the same donor for repeat ADCC experiments.

To discriminate target T cells, or cultured Toledo B cells, from purified human NK cells in cytotoxicity assays, the fluorescent dye, DiO, was incorporated into the cell membrane of target cells using the Vybrant DiO cell labeling solution (according to the manufacturer's protocol for suspension cell labeling). After activation and DiO labeling of primary human $CD4^+$ T cells and Toledo B cells, effector NK cells were isolated from sodium heparin anticoagulated blood from the MedImmune Blood Donor Program using the same protocol as above for human $CD4^+$ T cells, with the exception that 1 mL of RosetteSep NK cell isolation kit antibody mix was used in place of 1 mL of RosetteSep $CD4^+$ T cell isolation kit antibody mix. Isolated primary human NK cells were washed two times with warm complete RPMI medium (RPMI-1640 plus 10% FBS), and then suspended in complete RPMI at a concentration of $2.67\times10^6$ per mL. Likewise, activated primary human $CD4^+$ T cells were also washed two times in warm complete RPMI and suspended at a concentration of $2.67\times10^5$ per mL. Thereafter, 75 μL of primary human NK cells (200,000) and 75 μL of activated primary human $CD4^+$ T cells (20,000) were added to wells of sterile non-tissue culture treated round bottom 96-well plates for an effector-to-target ratio of 10:1. In some experiments, complete RPMI medium (50 μL) containing OX40mAb24 or control mAb was added to give a final concentration of 10 μg/mL. In others, complete RPMI (50 μL) containing a 3-fold dilution series of OX40mAb24 or control mAbs, resulting in a final concentration of 67 nM, or a 27-fold dilution series of 9B12 or R347 human IgG1 starting from 67 nM, was added to the plated cells. Rituximab (10 μg/mL, control antibody) was used as a positive control in wells containing DiO labeled, CD20-expressing Toledo B cells, in place of OX40-expressing, activated primary human $CD4^+$ T cells, because activated $CD4^+$ T cells do not express CD20. Cells in the ADCC assay were gently pelleted by centrifugation at RT and subsequently cultured for 24 hours.

At the end of the incubation period, cells were pelleted by centrifugation and then suspended in FACS buffer containing 10 μg/mL of propidium iodide (PT) for flow cytometry analysis on a BD LSRII flow cytometer. Non-viable (PT positive) cells among DiO-positive target $CD4^+$ T cells or Toledo B cells were discriminated using FlowJo software after fluorescence compensation.

Graphical representation of the data for NK cell ADCC assays, including determination of mean values and standard error of the mean, was generated using GraphPad Prism version 5.01 for Windows.

6.2.2 OX40mAb24 Binding to C1q

A ProteOn XPR36 instrument was used to determine the binding of OX40mAb24 or 9B12 to human complement protein C1q purified from pooled human sera to OX40mAb24 or 9B12 by surface plasmon resonance. Standard amine coupling was used to immobilize OX40mAb24 or 9B12 to the surface of a GLC biosensor chip. Human C1q was suspended in PBS/0.005% Tween 20, pH 7.4 at five concentrations ranging from 26 nM to 1.6 nM. The samples were injected at 30 μL/min for 200 seconds, and the dissociation phase was followed for 600 seconds. Sensorgram data was processed using ProteOn Manager 2.1 software (Bio-Rad) using 1:1 fitting.

6.3 Results

The ability of OX40mAb24, 9B12, and human IgG4P (mAb28) and IgG1-TM (mAb29) versions of OX40mAb24 to mediate ADCC was tested at saturating levels (10 μg/mL [67 nM]) for OX40 binding (see Example 2), using both allogeneic and autologous mixtures of NK cells and OX40-expressing target cells (FIG. 13A and FIG. 14A). OX40mAb24 showed measurable ADCC activity against activated human $CD4^+$ T cells. In contrast, 9B12, mAb28 and mAb29 showed no ADCC activity above that of the negative controls. A positive-control antibody against human CD20 (rituximab) demonstrated ADCC activity using the same NK cells, demonstrating that the NK cells were all capable of robust ADCC activity (FIG. 13B and FIG. 14B).

In dose-response experiments, OX40mAb24 demonstrated concentration-dependent ADCC activity against activated human $CD4^+$ T cells (FIGS. 15A-D, FIGS. 16A-D, FIGS. 17A-B, and Table 6-2. In contrast, 9B12 did not show any detectable ADCC activity. In addition, the R347 human IgG1 control mAb did not show any detectable ADCC activity, which confirms that ADCC activity mediated by OX40mAb24 was dependent on engagement with OX40 on the target cells. A positive-control antibody against human CD20 also demonstrated ADCC against a CD20-expressing B cell lymphoma cell line (FIG. 13B and FIG. 14B); this supports the validity of the assay. Collectively, the results of these experiments confirmed that OX40mAb24 is capable of ADCC against target cells that have been cultured under conditions previously shown to stimulate expression of cell surface OX40.

TABLE 6-2

Summary of OX40mAb24-mediated NK cell ADCC Potency

| Experiment Number | Donor Number | EC20 (pM) | EC50 (pM) | EC90 (pM) |
|---|---|---|---|---|
| 3 | 363 | 134 | 2380 | 225000 |
| 3 | 504 | 309 | 1370 | 14600 |
| 4 | 464 | 37.0 | 3050 | 3330000 |
| 4 | 532 | 111 | 1310 | 66100 |
| 5 | 601 | 54.4 | 501 | 16900 |
| 5 | 602 | 61.4 | 527 | 16000 |

TABLE 6-2-continued

Summary of OX40mAb24-mediated NK cell ADCC Potency

| Experiment Number | Donor Number | EC20 (pM) | EC50 (pM) | EC90 (pM) |
|---|---|---|---|---|
| Mean (standard error of the mean), pM | | 118 (41.1) | 1520 (415) | 611000 (545000) |

The potential for OX40mAb24 to bind to the human complement component C1q was assessed using a surface plasmon resonance assay. In this assay, binding to C1q was used as a surrogate for activity in a complement dependent cytotoxicity assay (Dall'Acqua et al., J. Immunol 177:1129-1138 (2006)). 9B12 was used as a negative control antibody. OX40mAb24 demonstrated a concentration-dependent ability to bind to purified human C1q protein (FIG. 18A). In contrast, 9B12 did not demonstrate any detectable binding to C1q protein (FIG. 18B).

6.4 Conclusions

OX40mAb24 binds to C1q and triggers NK-mediated ADCC against activated $CD4^+$ T cells.

Example 7

In Vitro Comparability Studies with OX40mAb24 and Cynomolgus and Rhesus Monkey T Cells In this example, the ability of OX40mAb24 to enhance activation of T cells was determined using two-cell reporter bioactivity assays with a Jurkat NFκB-luciferase T cell reporter line expressing cynomolgus (cyno)/rhesus monkey OX40. Fcγ receptor-mediated drug cross-linking was mediated by either a rhesus B cell line, or by rhesus Fcγ receptor-expressing cells in a post-red blood cell lysis whole blood sample. OX40 activation was measured as increased luciferase activity in response to stimulation of the NFκB signaling pathway downstream of primary human T cell activation. NFκB signaling is a well-studied downstream event in OX40 signaling, and can correlate with other measures of T cell activation such as proliferation and cytokine release (Croft M, et al., *Immunol Rev.* 229:173-91 (2009)). In addition, the ability of OX40mAb24 to enhance T cell receptor-mediated activation (co-stimulation) of rhesus T cells was tested using a plate-based bioactivity assay in which $CD4^+$ T cell proliferation was assessed. An isotype control (NIP228 IgG1), was used to demonstrate specific OX40 engagement.

In parallel, the bioactivity of 9B12, the murine anti-OX40 monoclonal antibody from which OX40mAb24 was derived, was measured to provide for a comparison of OX40mAb24 and 9B12 activity on non-human primate OX40.

7.1 Materials

Materials used in this study are listed in Table 7.1

TABLE 7-1

Materials

| Item | Source |
|---|---|
| Ammonium Chloride | StemCell Technologies, Vancouver, BC |
| Anti-human CD3 antibody, clone SP34-2 | BD Biosciences, San Jose, CA |
| Anti-human CD4-V450 antibody, clone L200 | BD Biosciences, San Jose, CA |
| Anti-human CD28 antibody, clone CD28.2 | BD Biosciences, San Jose, CA |
| CFSE cell labeling kit | Life Technologies, Carlsbad, CA |
| Concanavalin A | Sigma, Saint Louis, MO |
| Envision multilabel plate reader | Perkin Elmer, Waltham, MA |
| Goat anti-human Fcγ antibody | Jackson Immunoresearch, West Grove, PA |
| Goat anti-mouse Fcγ antibody | Jackson Immunoresearch, West Grove, PA |

TABLE 7-1-continued

| Materials | |
|---|---|
| Item | Source |
| Heat inactivated fetal bovine serum | Life Technologies, Carlsbad, CA |
| Interleukin-2, recombinant human | Preprotech, Rocky Hill, NJ |
| LSR II flow cytometer | BD Biosciences, San Jose, CA |
| Lymphocyte separation medium (LSM) | MP Biomedicals, Santa Ana, CA |
| MACS buffer | Miltenyi, San Diego, CA |
| Nonhuman primate CD4 T cell isolation kit | Miltenyi, San Diego, CA |
| Propidium iodide (1 mg/mL solution) | Sigma, Saint Louis, MO |
| Rhesus monkey (Indian Origin) whole blood, sodium heparin anti-coagulated | Worldwide Primates, Miami, FL |
| RPMI-1640 medium | Life Technologies, Carlsbad, CA |
| SteadyGlo Luciferase Assay Solution | Promega, Madison, WI |
| ViCell counter | Beckman Coulter, Indianapolis, IN |

7.2 Assays 7.2.1 Cyno/Rhesus 2-Cell Bioactivity Assays

OX40mAb24 was tested for bioactivity using a 2-cell reporter assay. As cyno and rhesus monkeys share identical OX40 amino acid sequences, a cyno/rhesus OX40-expressing Jurkat NFκB-luciferase reporter cell line (clone B2) was used for readout of OX40 agonism (NFκB activity). To mediate OX40mAb24 cross-linking and, consequently, OX40 clustering on Jurkat reporter cells, either an Fcγ receptor-expressing rhesus B-cell line, LCL8664, or leukocytes from whole blood of a normal rhesus monkey, which contain FcγR expressing cells, were used. Background bioactivity was assessed both without the addition of OX40mAb24, and also in the absence of the FcγR-expressing cells. To demonstrate the role of OX40 engagement on reporter cells, an isotype control was used in place of OX40mAb24.

The OX40mAb24 2-cell bioactivity assay with LCL8664 was performed according to the following protocol:

The day prior to use, cyno/rhesus OX40-expressing Jurkat NFκB-luciferase reporter clone B2 and LCL8664 were cultured in complete RPMI medium (RPMI with 10% fetal bovine serum [FBS] and 1% antibiotics/antimycotics) to achieve cell densities of approximately $5\times10^6$ cells/mL and $4\times10^5$ cells/mL, respectively. The next day, OX40 Jurkat reporter cells and LCL8664 were pelleted, suspended in complete medium and counted using a ViCell counter before cell concentrations for both cell lines were adjusted to $2.5\times10^6$ in complete medium.

Clone B2 and LCL8664 cells were each added to a 96 well round bottom non tissue-culture treated plate at 100, 000 cells per well. OX40mAb24 was added to cells in complete RPMI medium, to a final concentration starting at 30 μg/mL and diluted in 3-fold increments. Similarly, R347 IgG1 (isotype control) was used at a final concentration of 10 μg/mL and diluted in 6-fold increments. 9B12 and MOPC-21 (isotype control) were diluted in the same manner. Plates were transferred to a 37° C. incubator with a humidified 5% $CO_2$ atmosphere.

After 16 hours incubation time, 100 μL reconstituted Steady-Glo luciferase assay solution was added to each well and mixed to lyse cells and then incubated to equilibrate luciferase signal. Steady-Glo/sample lysate (150 μL) was transferred from each well to a 96 well, white walled assay plate for detection and luminescence read using a Perkin Elmer Envision luminescence reader.

The following protocol was used to acquire RBC-lysed rhesus cells from sodium heparin anti-coagulated whole blood obtained from a healthy Indian-origin rhesus macaque:

Fresh whole blood (5 mL) was added to a 50-mL conical tube and 45 mL of ammonium chloride solution was added. The cell mixture was incubated for 10 minutes on ice, then pelleted, and washed with complete RPMI medium after which the cells were ready for use in the 2-cell bioactivity assay.

The 2-cell bioactivity assay with rhesus RBC-lysed whole blood cells was performed as described with the LCL8664 rhesus B-cell line, but 10 μg/mL NIP228 IgG1 was used as the negative-control antibody.

7.2.2 Rhesus CD4 T Cell Proliferation Assay

OX40mAb24 bioactivity was determined in a $CD4^+$ T cell proliferation assay using activated primary rhesus $CD4^+$ T cells and plate-captured drug according to the following protocol. Rhesus $CD4^+$ T cells isolated from sodium heparin anti-coagulated whole blood obtained from healthy rhesus monkeys (N=2) from World Wide Primates were used as the source of responding cells.

Fresh heparinized rhesus blood was diluted 1:1 with PBS at room temperature (RT). Then 20 mL of diluted whole blood was overlayed onto 15 mL of 95% lymphocyte separation medium (LSM) in a 50-mL conical centrifuge tube. Blood was centrifuged at 400×g for 30 minutes at room temperature without the brake. Peripheral blood mononuclear cells were collected at the interface and washed twice with Miltenyi MACS buffer and pelleted. The cell pellet was treated with red cell lysis buffer for 5 minutes, and lysis buffer was deactivated with the addition of complete RPMI medium. The cells were washed and suspended in MACS buffer and counted with a ViCell counter to determine cell number and viability.

Rhesus $CD4^+$ T cells were isolated with a Miltenyi nonhuman primate kit according to manufacturer's instructions. Then, $CD4^+$ T cells were counted on a ViCell counter, suspended at $1\times10^6$ cells/mL in complete RPMI medium with 51 μg/mL Concanavalin A and 1000 IU/mL of IL-2 and cultured at 37° C. and 5% $CO_2$ in a humidified incubator for 2 days to activate T cells and induce OX40 expression. Non-tissue culture treated round-bottom 96 well assay plates were coated with 100 μL of 2 μg/mL goat anti-mouse Fcγ-specific IgG and 2 μg/mL goat anti-human Fcγ-specific IgG in PBS. Goat anti-human IgG capture antibodies were not added to wells intended for assay of soluble OX40mAb24 activity. Plates were incubated overnight at 4° C., washed with 200 μL of PBS, and blocked for 90 minutes at 37° C. with 1% BSA in PBS (1% BSA/PBS). The plates were washed with PBS and 2 ng/mL of anti-CD3 (clone SP34-2) reconstituted in 1% BSA/PBS was added to the plates for 90 minutes at 37° C. The plates were washed with PBS to remove unbound OX40mAb24, R347 human IgG1 control mAb, 9B12, and mouse IgG1 control mAb (clone MOPC-21) were each reconstituted in 1% BSA/PBS starting at 1.01 μg/mL (6.67 nM; experiment 1) or 1.5 μg/mL (10.0 nM; experiment 2) and serially diluted over a 3-fold dilution series and then added to assay plates and incubated for 90 minutes at 37° C.

Activated primary rhesus $CD4^+$ T cells were collected, washed in complete RPMI medium, and the concentration adjusted to $1.0\times10^6$ viable cells/mL. Cells were labelled with carboxyfluorescein succinimidyl ester (CFSE), according to the manufacturer's instructions, with the exception of using 1.25 μM CFSE instead of the recommended 5 μM, with an incubation of 10 minutes at 37° C. After labeling, cells were suspended in complete RPMI and the concentration was adjusted to $1.0\times10^6$ per mL. The plates were washed with PBS and 200 μL of $CD4^+$ T cells (200,000/well) was added to each well. Then, the plate was incubated at 37° C. for 3 days.

After 72 hours incubation time, $CD4^+$ T cells were pelleted, and washed once with PBS containing 2% FBS (FACS buffer). Cells were suspended in binding mix containing anti-CD4 V450® labeled antibody for identification of $CD4^+$ T cells, and propidium iodide (PI) for live/non-viable cell discrimination, and incubated for 30 minutes. Following incubation, cells were washed in FACS buffer, re-suspended in FACS buffer and analyzed by flow cytometry using an LSRII flow cytometer and FlowJo software for analysis of Flow Cytometry Standard (FCS) formatted data.

The assay was repeated in two independent experiments using primary rhesus $CD4^+$ T cells.

To assess cell proliferation, live (propidium iodide-negative) events were gated using FlowJo software and the percentage of $CD4^+$-gated cells showing dilution of CFSE was determined. Specific activity of OX40mAb24 was calculated by subtracting the percentage of $CD4^+$-gated cells showing dilution of CFSE in response to anti-CD3 alone from the percentage of $CD4^+$-gated cells showing dilution of CSFE in response to anti-CD3 antibody plus OX40mAb24.

The concentrations of OX40mAb24 that achieved half-maximal ($EC_{50}$) responses in the Jurkat NFκB reporter assay and the primary rhesus $CD4^+$ T cell assay were determined using non-linear regression analysis (log dose-response, 4-parameter fit curves) in GraphPad Prism, version 5.01 (San Diego, Calif.).

7.3 Results 7.3.1 Cyno/Rhesus 2-Cell Bioactivity Assay

Results of the cyno/rhesus 2-cell bioactivity assays are shown in Table 7-2, FIGS. 19A-B, FIGS. 20A-B and FIGS. 21A-B. OX40mAb24 activated the OX40 signaling pathway, as measured by NFκB signaling, in cyno/rhesus OX40-expressing Jurkat T cells in the presence of the rhesus B-cell line, LCL8664, with a mean $EC_{50}$ of 1450 pM (N=2 experiments). As shown in Table 7-2, the $EC_{50}$ value of OX40mAb24 activity in the cyno/rhesus 2-cell assay was 1.3 fold higher than in human 2-cell assays with the Raji B-cell line, while 9B12 had limited activity in cyno/rhesus 2-cell assays and an $EC_{50}$ value could not be determined.

In addition, as shown in Table 7-2, OX40mAb24 activated the OX40 signaling pathway in Jurkat T cells in the presence of rhesus RBC-lysed whole blood, which is expected to contain Fcγ receptor-expressing cells, with an $EC_{50}$ of 550 pM (N=1 experiment). As Table 7-2 also shows, the $EC_{50}$ value of 9B12 in the same assay was 6052 pM, and was 4680 pM in a human 2-cell assay with the Raji B-cell line.

TABLE 7-2

Mean Half Maximal Effective Concentration for OX40mAb24 and 9B12 in 2-cell Bioactivity Assays

| | 2-cell assay format | | |
|---|---|---|---|
| Test or Control Article | Rhesus LCL8664 B cells + cyno/rhesus OX40-expressing Jurkat NFκB-luciferase clone B2 bioactivity [mean $EC_{50}$ (Std Err); n] | Rhesus RBC-lysed whole blood + cyno/rhesus OX40-expressing Jurkat NFκB-luciferase clone B2 bioactivity [mean $EC_{50}$ (Std Err); n] | Human Raji B cells + human OX40 Jurkat NFκB-luciferase clone 64 bioactivity[a] [mean $EC_{50}$ (Std Err); n] |
| OX40mAb24 | 1450 (204); n = 2 | 550; n = 1 | 1110 (92.5); n = 5 |
| R347 human IgG1 | no activity; n = 2 | NT | no activity |
| NIP228 human IgG1 | NT | no activity; n = 1 | NT |
| 9B12 | ND | 6052; n = 1 | 4680 (1220); n = 5 |

Std Err = standard error of the mean.
n = number of experiments.
NT = Not tested.
ND = Not Determined.
[a]Data from Example 5.

7.3.2 Rhesus Primary C-cell Proliferation Assay

Results for the rhesus primary T cell proliferation assay are shown in Table 7-3, Table 7-4, and FIGS. 22A-D. OX40mAb24 induced proliferation of primary rhesus $CD4^+$ T cells with a mean $EC_{50}$ of 436 pM (Table 7-3; N=2 experiments). As shown in Table 7-5, the $EC_{50}$ value for 9B12 was 110 pM (Table 7-4; N=2 experiments). In OX40mAb24 induced proliferation of activated primary human $CD4^+$ T cells in a similar assay format with a mean $EC_{50}$ of 28 pM (Table 7-5; data from Example 4).

TABLE 7-3

Mean Half Maximal Effective Concentration for OX40mAb24 in Primary Rhesus CD4 T cell Proliferation Assays

| Test or control antibody | No. of Experiments | Mean $EC_{50}$ (Std Err) |
|---|---|---|
| OX40mAb24 | 2 | 436 (309) |
| NIP228 IgG1 | 2 | No activity |

Std Err = standard error of the mean.

TABLE 7-4

Mean Half Maximal Effective Concentration for 9B12 in Primary Rhesus CD4 T cell Proliferation Assays

| Test or control antibody | No. of Experiments | Mean $EC_{50}$ (Std Err) |
|---|---|---|
| 9B12 | 2 | 110 (13) |
| MOPC-21 mouse IgG1 | 2 | No activity |

Std Err = standard error of the mean.

TABLE 7-5

Mean Half Maximal Effective Concentration for OX40mAb24 and 9B12 in Rhesus and Human CD4 T cell Proliferation Assays

| Test or control antibody | Rhesus Mean (Std Err) | Human Mean (Std Err) |
|---|---|---|
| OX40mAb24 | 436 (309) | 28 (98) |
| 9B12 | 110 (13) | 218 (35) |

Std Err = standard error of the mean.

7.4 Conclusions

OX40mAb24 activated the OX40 signaling pathway in a cyno/rhesus OX40 expressing Jurkat T cell NFκB reporter cell line in the presence of rhesus B cells or Fcγ receptor-expressing cells contained within RBC-lysed rhesus whole blood. In addition, OX40mAb24 induced proliferation of primary rhesus $CD4^+$ T cells.

Example 8

Activity of OX40mAb24 in Mouse Models of Human Cancers

This example was designed to determine if OX40mAb24 is effective as a single-agent therapy for the treatment of cancers. This study was conducted in xenograft models of human cancers mixed with alloreactive human T cells in immunocompromised non-obese diabetic/severe combined immunodeficient (NOD/SCID) mice.

8.1 Materials

Materials used in this study, and their source, are listed in Table 8-1.

TABLE 8-1

Materials

| Item | Source |
|---|---|
| DMEM medium | Invitrogen, Carlsbad, CA |
| FBS | Invitrogen, Carlsbad, CA |
| Lymphocyte separation medium | VWR, West Chester, PA |
| PBS | Invitrogen, Carlsbad, CA |
| RPMI 1640 | Invitrogen, Carlsbad, CA |
| RosetteSep $CD4^+$ T cell enrichment kit | Stem Cell Technologies, Vancouver, BC, Canada |
| RosetteSep $CD8^+$ T cell enrichment kit | Stem Cell Technologies, Vancouver, BC, Canada |
| RosetteSep DML medium | Stem Cell Technologies, Vancouver, BC, Canada |
| Mitomycin C | Sigma-Aldrich, St. Louis, MO |

8.2 Experimental Protocols 8.2.1 Test Animals

Female NOD/SCID mice aged 5 to 9 weeks, were obtained from Harlan Laboratories, Inc. The animals were humanely treated and housed according to Iristithtional Animal Care and Use Committee approved protocols in the Laboratory Animal Resources facility at MedImmune, an Association for Animal Accreditation of Laboratory Animal Care and United States Department of Agriculture-licensed facility. The animals were kept in sterile micro-isolator units, provided with sterile bedding and food, and acidified drinking water ad libitum. Environmental conditions were standardized (room temperature: 20° C.+/−1° C.; relative humidity: 50%±10%; 12-hour light-dark cycle). The animals were monitored daily for adverse clinical signs and weekly for body weight.

8.2.2 Establishment of Xenografts

Human cancerous A375 cells originating from a human melanoma cell line were obtained from ATCC. The cells were grown in DMEM with 10% FCS at 37° C. under 5% $CO_2$ in a humidified incubator. They were then harvested, washed once with PBS, then resuspended in PBS.

Human cancerous A375 cells were harvested from cell cultures. They were resuspended in PBS. A375 cells were subsequently mixed with $CD4^+$ and $CD8^+$ T cell lines alloreactive to A375 tumor cell lines before implantation into animals.

To generate $CD4^+$ and $CD8^+$ T cell lines, human peripheral blood mononuclear cells (PBMCs) from healthy donors were enriched for $CD4^+$ or $CD8^+$ T cells by the addition of 1 mL RosetteSep T cell enrichment product per 20 mL of whole blood. This was followed by a 20-minute incubation and subsequent isolation by density gradient centrifugation using RosetteSep DM-L density medium. After centrifugation, the cells were washed 3 times with PBS supplemented with 2% fetal bovine serum (FBS) and resuspended in RPMI1640 medium supplemented with 10% FBS. Enriched $CD4^+$ and $CD8^+$ T cells were cultured separately for 7 to 10 days in medium supplemented with recombinant human interleukin 2 (rhIL-2) and each combined with mitomycin C-treated A375 cells. T cells were collected and separately cultured again for 7 to 10 days in medium supplemented with rhIL-2 and combined with mitomycin C-treated A375 cells. $CD4^+$ and $CD8^+$ T cells were collected and combined at a 2:1 ratio.

A375 cells and PMBCs enriched for $CD4^+$ and $CD8^+$ T cells were mixed at a ratio of 6 A375 cells to 1 T cell immediately before implantation.

Xenografts were established by subcutaneous (SC) injection of $3.5\times10^6$ cells (human T cells mixed with A375 cells at an effector-to-target (E:T) ratio of 1:6 and suspended in 200 μL of PBS) into the right flanks of the animals.

8.2.3 Randomization, Group Designation, and Dose Levels

Six animals were randomly assigned to each experimental group prior to SC injection of cells. There were no animal substitutions. Group designations and dose levels for each experiment are listed in Table 8-2, Table 8-3 and Table 8-4. Test and control antibodies were diluted in PBS to appropriate concentrations and administered intraperitoneally (IP) in a total volume of 200 μL. The first dose of test and control antibodies was administered on Day 3 or 4 after implantation of cancer/effector T cells. The animals received up to 3 additional doses of the test and control antibodies, as indicated in the figures and described in the corresponding figure description. The formation of tumors was observed in each animal 1 or 2 times a week. The primary endpoints in this study was either a tumor volume of 2000 $mm^3$ or gross tumor necrosis.

8.2.4 Tumor Measurements

Tumors were measured at intervals indicated in the figures and tables for each experiment by caliper and tumor volumes (V) were calculated using the following formula:

$$V(mm^3)=(\text{length [mm]}\times\text{width [mm]}\times\text{width [mm]})/2.$$

For each group, the results are reported as the arithmetic mean. Antitumor effects were expressed as percent tumor growth inhibition (% TGI), which was calculated as follows:

% TGI=(1−[mean tumor *V* of treatment group]÷[mean tumor *V* of control group])×100

8.3 Statistical Methods

A comparison between OX40mAb24-treated or 9B12-treated, and isotype control-treated animals was made, and intergroup differences were analyzed for statistical significance by a Mann-Whitney rank sum test.

Significant p-values obtained from the Mann-Whitney rank sum test are presented in the summary tables and figures adjacent to the arithmetic mean and standard deviation of the mean.

8.4 Results

The activity of OX40mAb24 on growth of tumors in mouse models of human cancer was investigated in this study. Immunodeficient NOD/SCID female animals were implanted with human cancer cell lines mixed with alloreactive human $CD4^+$ and $CD8^+$ T cell lines. $CD4^+$ and $CD8^+$ T cells were derived from PBMCs isolated from healthy human donors. Animals received the first dose of the test and control antibodies there or four days after implantation of xenographs, and were administered additional doses of the test and control antibodies as indicated.

In three separate experiments, OX40mAb24 plus alloreactive human T cells significantly inhibited growth of A375 cells by up to 85% as compared to the isotype-control group (Table 8-2, Table 8-3, and Table 8-4; FIG. 23A, FIG. 24A and FIG. 25). The control 9B12 plus alloreactive human T cells also significantly inhibited growth of A375 cells by up to 77% as compared to the isotype-control group (Tables 8-2 to 8-4, FIG. 23B and FIG. 24B.

TABLE 8-2

Treatment Groups and Percent TGI in A375 Xenograft Model on Day 18 (Experiment 2)

| Group [a] | Test Antibody | Dose [b] (mg/kg) | % TGI [c] |
|---|---|---|---|
| 1 | None; no T cells | NA | NA |
| 2 | None | NA | NA |
| 3 | Isotype control | 5 | NA |
| 4 | OX40mAb24 | 5 | 79 |
| 5 | OX40mAb24 | 2.5 | 75 |
| 6 | OX40mAb24 | 1.0 | 85 |
| 7 | 9B12 | 5 | 53 |

IP = intraperitoneal;
NA = not applicable;
TGI = tumor growth inhibition;
V = volume
[a] Number of animals per group: 6.
[b] All animals received 200 μl of test antibody IP on Days 4, 7, 9, and 12
[c] % TGI = [1 − (mean tumor V of treatment group) ÷ (mean tumor V of isotype control group)] × 100

TABLE 8-3

Treatment Groups and Percent TGI in A375 Xenograft Model on Day 25 (Experiment 1)

| Group [a] | Test Antibody | Dose [b] (mg/kg) | % TGI [c] |
|---|---|---|---|
| 1 | None; no T cells | NA | NA |
| 2 | None | NA | NA |
| 3 | Isotype control | 5 | NA |
| 4 | OX40mAb24 | 5 | 68 |
| 5 | OX40mAb24 | 2.5 | 83 |
| 6 | OX40mAb24 | 1.0 | 84 |
| 7 | 9B12 | 5 | 80 |

IP = intraperitoneal;
NA = not applicable;
TGI = tumor growth inhibition;
V = volume
[a] Number of animals per group: 6.
[b] All animals received 200 μl of test antibody IP on Days 4, 7, 9, and 12
[c] % TGI = [1 − (mean tumor V of treatment group) ÷ (mean tumor V of isotype control group)] × 100

TABLE 8-4

Treatment Groups and Percent TGI in A375 Xenograft Model on Day 28 (Experiment 3)

| Group [a] | Test Antibody | Dose [b] (mg/kg) | % TGI [c] |
|---|---|---|---|
| 1 | None; no T cells | NA | NA |
| 2 | None | NA | NA |
| 3 | Isotype control | 3.0 | NA |
| 4 | OX40mAb24 | 3.0 | 75 |
| 5 | OX40mAb24 | 1.0 | 73 |
| 6 | OX40mAb24 | 0.3 | 68 |
| 7 | OX40mAb24 | 0.1 | 84 |
| 8 | OX40mAb24 | 0.03 | 73 |

IP = intraperitoneal;
NA = not applicable;
TGI = tumor growth inhibition;
V = volume
[a] n = 6.
[b] All animals received 200 μl of test antibody IP on Days 3, 6, 8, and 10
[c] % TGI = [1 − (mean tumor V of treatment group) ÷ (mean tumor V of isotype control group)] × 100

8.5 Conclusions

OX40mAb24 demonstrated potent antitumor activity in mouse models of human cancer mixed with alloreactive human T cells. The antitumor activity of OX40mAb24 was similar to the antitumor activity of 9B12. These results provide evidence that OX40mAb24 can be effective as a single-agent therapy for the treatment of patients with cancer with a T cell infiltrate.

Example 9

Rat/Mouse Anti-Mouse OX40 IgG2a Chimera Antibody Clone OX86 Inhibits the Growth of Mouse Cancer Cell Lines in Syngeneic Models OX40mAb24 does not cross-react to mouse (m)OX40 (See Example 2); therefore, it is not possible to test its activity in immunocompetent mouse models. OX86 is a rat anti-mOX40 IgG1 antibody that specifically binds to and triggers signaling of mOX40 (al-Shamkhani et al., *Eur. J. Immunol.* 26:1695-1699 (1996)), and has anti-tumor activity in immunocompetent mouse models of cancer (Weinberg A D, et al., J. Immunol. 164:2160-2169 (2000)). To more fully study the effects of OX40 agonism using a mouse surrogate antibody with functional properties similar to OX40mAb24, a rat/mouse anti-mOX40 IgG2a chimera antibody (OX86 mIgG2a; rat anti-OX40 light and heavy chain variable regions with mouse IgG2a constant regions) was generated from OX86. This example evaluates the single-agent anti-tumor activity of OX86 mIgG2a in three mouse models of cancer.

9.1 Materials

Materials used in this study, and their source, are listed in Table 9-1.

TABLE 9-1

| Materials | |
|---|---|
| Item | Source |
| Phosphate-buffered saline, pH 7.2 | Life Technologies, Carlsbad, CA |
| Fetal bovine serum, heat inactivated | Life Technologies, Carlsbad, CA |
| Roswell Park Memorial Institute 1640 medium | Life Technologies, Carlsbad, CA |
| 0.25% Trypsin-EDTA (1x) | Life Technologies, Carlsbad, CA |

EDTA = Ethylenediaminetetraacetic acid.

9.2 Experimental Protocols 9.2.1 Test Animals

BALB/c and C57BL/6 mice of 6-8 weeks of age were received at MedImmune from Harlan Laboratories, Inc. (Indianapolis, Ind.) and allowed to acclimatize for 3 days prior to study start. Thereafter, mice were shaved at tumor implantation sites and implanted with microchip transponders for identification.

The animals were housed according to Institutional Animal Care and Use Committee approved protocols in the Laboratory Animal Resources facility at MedImmune, an Association for Animal Accreditation of Laboratory Animal Care and United States Department of Agriculture-licensed facility. The animals were kept in sterile micro-isolator units, provided with sterile bedding and food, and acidified drinking water ad libitum. Environmental conditions were standardized (room temperature: 20° C.±1° C.; relative humidity: 50%±10%; 12-hour light-dark cycle). The animals were monitored daily for adverse clinical signs and bi-weekly for body weight. If hind limb paralysis, respiratory distress, 20% body weight loss, or tumor volume greater than 2000 $mm^3$ were noted, the animals were immediately sacrificed humanely by asphyxiation with $CO_2$.

9.2.2 Establishment and Implantation of Syngeneic Tumors

CT26 and 4T1 were obtained from ATCC in Manassas, Va. MCA205 cells were obtrained from Providence Cancer Center, Portland, Oreg. All cells were cultured in RPMI 1640 cell culture medium supplemented with 10% FBS and grown at 37° C. at 5% $CO_2$ in a humidified tissue culture chamber, then harvested, washed once in FBS and then resuspended in PBS.

Allografts were established by subcutaneous (SC) injection of $5.0\times10^5$ CT26 cells, or $1.0\times10^5$ 4 T1 cells suspended in 0.1 mL of PBS into the right flank of 7- to 9-week-old BALB/c mice, while $2.5\times10^5$ MCA205 cells suspended in 0.1 mL of phosphate-buffered saline were injected into the right flank of 7- to 9-week-old C57BL/6 mice.

9.2.3 Randomization, Group Designation, and Dose Levels

BALB/c (total of 216) and C57BL/6 (total of 70) female mice were used in this study. BALB/c mice implanted with CT26 tumor cells were randomly assigned after tumors grew to a mean volume of 120 $mm^3$ per cohort, 9 days after implantation or 200 $mm^3$ per cohort, 13 days after implantation. BALB/c mice implanted with 4T1 tumor cells were randomly assigned after tumors grew to a mean volume of 120 $mm^3$ per cohort, 13 days after implantation. C57BL/6 mice were randomly assigned after tumors grew to a mean-volume of 95 $mm^3$ per cohort, 11 days after implantation. Group designations number of animals, dose levels, and dose schedule are presented in Table 9-2, Table 9-3, Table 9-4, and Table 9-5. All test antibodies and control antibodies were administered by intraperitoneal (IP) injection. There were no animal substitutions.

Animals from each group were sacrificed when tumor volumes reached approximately 2000 $mm^3$ or when tumors became ulcerated or necrotic.

TABLE 9-2

Study Design: CT26 Syngeneic Model

| Group | Number of animals (M/F) | Treatment | Dose schedule (study day) | Dose level (mg/kg)[a] | ROA |
|---|---|---|---|---|---|
| 1 | 10 (F) | None | NA | NA | IP |
| 2 | 10 (F) | Negative control (OX86 mIgG1 D265A) | 9, 12 | 2.5 | IP |
| 3 | 10 (F) | OX86 mIgG2a | 9, 12 | 2.5 | IP |
| 4 | 10 (F) | OX86 mIgG2a | 9, 12 | 1.0 | IP |
| 5 | 10 (F) | OX86 mIgG2a | 9, 12 | 0.25 | IP |
| 6 | 10 (F) | OX86 mIgG2a | 9, 12 | 0.1 | IP |

F = female; IgG1 = immunoglobulin G1; IP = intraperitoneal; mAb = monoclonal antibody; OX86 mIgG2a = rat anti-OX40 light and heavy chain variable regions of clone OX86 with mouse IgG2a constant regions; OX86 mIgG1 D265A = mouse anti-mouse OX40 mIgG1 with a point mutation in the Fc domain that reduces its ability to bind Fcγ receptors; NA = not applicable because the animals were not treated; ROA = route of administration.

[a]Dose volume: 0.2 mL.

TABLE 9-3

Study Design: CT26 Syngeneic Model

| Group | Number of animals (M/F) | Treatment | Dose schedule (study day) | Dose level (mg/kg)[a] | ROA |
|---|---|---|---|---|---|
| 1 | 12 (F) | None | NA | NA | IP |
| 2 | 12 (F) | OX86 mIgG2a | 13, 16 | 10 | IP |
| 3 | 12 (F) | OX86 mIgG2a | 13, 16 | 3 | IP |
| 4 | 12 (F) | OX86 mIgG2a | 13, 16 | 1 | IP |
| 5 | 12 (F) | OX86 mIgG2a | 13, 16 | 0.3 | IP |
| 6 | 12 (F) | OX86 mIgG2a | 13, 16 | 0.1 | IP |

F = female; IP = intraperitoneal; 0X86 mIgG2a = rat anti-OX40 light and heavy chain variable regions of clone OX86 with mouse IgG2a constant regions; NA = not applicable because the animals were not treated; ROA = route of administration.

[a]Dose volume: 0.2 mL.

TABLE 9-4

Study Design: MCA205 Syngeneic Model

| Group | Number of animals (M/F) | Treatment | Dose schedule (study day) | Dose level (mg/kg)[a] | ROA |
|---|---|---|---|---|---|
| 1 | 14 (F) | None | NA | NA | IP |
| 2 | 14 (F) | Isotype control (mixture)[b] | 11, 14 | 20 | IP |
| 3 | 14 (F) | OX86 mIgG2a | 11, 14 | 10 | IP |
| 4 | 14 (F) | OX86 mIgG2a | 11, 14 | 10 | IP |
| 5 | 14 (F) | OX86 mIgG2a | 11, 14 | 5 | IP |

F = female; IP = intraperitoneal; 0X86 mIgG2a = rat anti-OX40 light and heavy chain variable regions of clone OX86 with mouse IgG2a constant regions; NA = not applicable because the animals were not treated; ROA = route of administration.

[a]Dose volume: 0.2 mL.

[b]Mixture contains isotype control antibodies with Fc domains of mIgG2a (10 mg/kg) and mIgG2b (10 mg/kg).

TABLE 9-5

| Study Design: 4T1 Syngeneic Model | | | | | |
|---|---|---|---|---|---|
| Group | Number of animals (M/F) | Treatment | Dose schedule (study day) | Dose level (mg/kg)[a] | ROA |
| 1 | 12 (F) | None | NA | NA | IP |
| 2 | 12 (F) | Isotype control (mixture)[b] | 13, 16, 20, 23 | 70 | IP |
| 3 | 12 (F) | OX86 mIgG2a | 13, 16, 20, 23 | 10 | IP |
| 4 | 12 (F) | OX86 mIgG2a | 13, 16, 20, 23 | 5 | IP |
| 5 | 12 (F) | OX86 mIgG2a | 13, 16, 20, 23 | 2.5 | IP |
| 6 | 12 (F) | OX86 mIgG2a | 13, 16, 20, 23 | 1.0 | IP |
| 7 | 12 (F) | OX86 mIgG2a | 13, 16, 20, 23 | 0.25 | IP |

F = female; IP = intraperitoneal; 0X86 mIgG2a = rat anti-OX40 light and heavy chain variable regions of clone OX86 with mouse IgG2a constant regions; NA = not applicable because the animals were not treated; ROA = route of administration.

[a]Dose volume: 0.2 mL.

[b]Mixture contains isotype control antibodies with Fc domains of mIgG2a (10 mg/kg), mIgG2b (20 mg/kg), rat IgG2a (20 mg/kg) and rat IgG2b (20 mg/kg).

9.2.4 Tumor Measurements

Tumors were measured by caliper twice weekly and tumor volumes were calculated using the following formula:

$$\text{tumor volume } (V)=[\text{length (mm)}\times\text{width (mm)}^2]/2$$

where length was defined as the larger side and width as the smaller side perpendicular to the length.

Antitumor effects of each group were expressed as tumor growth inhibition (TGI), which was calculated as follows:

$$\%\ \text{TGI}=(1-[\text{mean } V \text{ of treatment group}]\div[\text{mean } V \text{ of control group}]\times 100$$

Tumor growth responses were categorized as a complete response (CR) if there was no measureable tumor.

9.3 Statistical Methods

One-way ANOVA was used to determine mean tumor volume differences. In the event of a significant F test a Dunnett's or Sidak's multiple comparison test was utilized (where appropriate). Where applicable, a log 10 transformation was applied to tumor volumes to account for heteroscedasticity. A p value<0.05 was considered significant.

9.4 Results

Treatment of mice with the OX86 mIgG2a results in significantly reduced growth of CT26 and MCA205 tumor cells compared to untreated or negative, or isotype control antibody-treated mice control, (Table 9-6, Table 9-7 and Table 9-8; FIG. 26A, FIG. 27A, and FIG. 28A). Treatment of mice with the OX86 mIgG2a results in delayed and reduced growth of 4T1 tumor cells compared to untreated or isotype control antibody (Table 9-9 and FIG. 29A).

A mixed response is often shown in syngeneic models; however, the dramatic response of the treatment with OX86 mIgG2a is clearer from the individual animal tumor growth graphs (FIG. 26B, FIG. 27B, FIG. 28B and FIG. 29B). A dose response was not observed in mice treated with OX86 mIgG2a based on TGI (Table 9-6, Table 9-7, Table 9-8 and Table 9-9; FIG. 26A, FIG. 27A, FIG. 28A and FIG. 29A) or with respect to increasing the number of animals exhibiting complete responses (Table 9-6, Table 9-7, Table 9-8 and Table 9-9).

TABLE 9-6

| Treatment Groups, Percent Tumor Growth Inhibition on Day 22, and number of Complete Responders in CT26 Syngeneic Model | | | | |
|---|---|---|---|---|
| Group [a] | Test/Control Antibody | Dose [b] (mg/kg) | % TGI [c] | Number of Complete Responders out of 12 mice [d] |
| 1 | None | NA | NA | 0 |
| 2 | OX86 mIgG2a | 10 | 67 | 8 |
| 3 | OX86 mIgG2a | 3 | 67 | 6 |
| 4 | OX86 mIgG2a | 10 | 75 | 8 |
| 5 | OX86 mIgG2a | 0.3 | 65 | 8 |
| 6 | OX86 mIgG2a | 0.1 | 70 | 8 |

IP = intraperitoneal; NA = not applicable; TGI = tumor growth inhibition; V volume.

[a] n = 12.

[b] All animals received 200 μL of test antibody IP on Days 13 and 16.

[c] % TGI = [1 − (mean tumor V of treatment group) ÷ (mean tumor V of control group)] × 100.

[d] Number of animals in a group with a tumor volume measurement recorded as zero at the end of the study.

TABLE 9-7

| Treatment Groups, Percent Tumor Growth Inhibition on Day 26, and number of Complete Responders in CT26 Syngeneic Model | | | | |
|---|---|---|---|---|
| Group [a] | Test/Control Antibody | Dose [b] (mg/kg) | % TGI [c] | Number of Complete Responders out of 10 mice [d] |
| 1 | None | NA | NA | 1 |
| 2 | Negative control (OX86 mIgG1 D265A) | 2.5 | NA | 1 |
| 3 | OX86 mIgG2a | 2.5 | 94 | 7 |
| 4 | OX86 mIgG2a | 1.0 | 97 | 8 |
| 5 | OX86 mIgG2a | 0.25 | 95 | 6 |
| 6 | OX86 mIgG2a | 0.1 | 92 | 7 |

IP = intraperitoneal; NA = not applicable; TGI = tumor growth inhibition; V volume.

[a] n = 10.

[b] All animals received 200 μL of test antibody IP on Days 9 and 12.

[c] % TGI = [1 − (mean tumor V of treatment group) ÷ (mean tumor V of control group)] × 100.

[d] Number of animals in a group with a tumor volume measurement recorded as zero at the end of the study.

TABLE 9-8

| Treatment Groups, Percent Tumor Growth Inhibition on Day 22, and Number of Complete Responders in MCA205 Syngeneic Model | | | | |
|---|---|---|---|---|
| Group [a] | Test/Control Antibody | Dose [b] (mg/kg) | % TGI [c] | Number of Complete Responders out of 14 mice [d] |
| 1 | None | NA | NA | 0 |
| 2 | Isotype control (mixture) | 20 | NA | 0 |
| 3 | OX86 mIgG2a | 20 | 65 | 0 |
| 4 | OX86 mIgG2a | 10 | 76 | 4 |
| 5 | OX86 mIgG2a | 5 | 70 | 2 |

TABLE 9-9

| Treatment Groups, Percent Tumor Growth Inhibition on Day 25, and number of Complete Responders in 4T1 Syngeneic Model | | | | |
|---|---|---|---|---|
| Group [a] | Test/Control Antibody | Dose [b] (mg/kg) | % TGI [c] | Number of Complete Responders out of 12 mice [d] |
| 1 | None | NA | NA | 0 |
| 2 | Isotype control (mixture) | 70 | NA | 0 |
| 3 | OX86 mIgG2a | 10 | 5 | 0 |

TABLE 9-9-continued

| Treatment Groups, Percent Tumor Growth Inhibition on Day 25, and number of Complete Responders in 4T1 Syngeneic Model | | | | |
|---|---|---|---|---|
| Group [a] | Test/Control Antibody | Dose [b] (mg/kg) | % TGI [c] | Number of Complete Responders out of 12 mice [d] |
| 4 | OX86 mIgG2a | 5 | 34 | 2 |
| 5 | OX86 mIgG2a | 2.5 | 37 | 0 |
| 6 | OX86 mIgG2a | 1.0 | 22 | 0 |
| 7 | OX86 mIgG2a | 0.25 | ND | 0 |

IP = intraperitoneal; NA = not applicable; TGI = tumor growth inhibition; V volume; ND = not determined.
[a] n = 12.
[b] All animals received 200 μL of test antibody IP on Days 13, 16, 20 and 23.
[c] % TGI = [1 − (mean tumor V of treatment group) ÷ (mean tumor V of control group)] × 100.
[d] Number of animals in a group with a tumor volume measurement recorded as zero at the end of the study.

9-5 Conclusions

Single-agent treatment of tumor-bearing mice with OX86 mIgG2a results in anti-tumor activity that significantly reduces growth of multiple tumors as compared to untreated, negative control, and/or isotype control treated groups.

Example 10

Characterization of the Epitope of OX40mAb24

This example examines the epitope of OX40mAb24 using a series of human/mouse OX40 chimeric variants.

10.1 Materials Used in this Study, and their Source, are Listed in Table 10-1.

TABLE 10-1

| Materials | |
|---|---|
| Item | Source |
| Anti-human IgG-Alexa480 | Invitrogen (Carlsbad, CA) |
| Anti-sheep IgG-Alexa-480 | Invitrogen (Carlsbad, CA) |
| Anti-goat IgG-Alexa480 | Invitrogen (Carlsbad, CA) |
| FreeStyle 293F cells (HEK293F cells) | Invitrogen (Carlsbad, CA) |
| Goat anti-mouse OX40 polyclonal antibody | R&D Systems (Minneapolis, MN) |
| LSRII flow cytometer | BD Biosciences (San Jose, CA) |
| Phosphate buffered saline | Invitrogen (Carlsbad, CA) |
| Sheep anti-human OX40 polyclonal antibody | R&D Systems (Minneapolis, MN) |
| 293fectin transfection reagent | Invitrogen (Carlsbad, CA) |

10.2 Generation of Human/Mouse Chimeric Variants

OX40mAb24 binds specifically to human OX40 (SEQ ID NO: 91) and does not recognize mouse OX40 (SEQ ID NO: 92), despite sharing 60% identity in their amino acid (aa) sequence (FIG. 30). Human/mouse chimeric OX40 variants were engineered by swapping portions of the extracellular domain between human and mouse OX40. The cDNA constructs of human and mouse OX40 were used as templates in overlapping extension PCR to construct chimeric variants with a transmembrane domain for cell-surface expression of the recombinant proteins. OX40 is an approximately 45 kDa protein with three complete cysteine-rich domains (CRDs) and one truncated cysteine-rich domain. The structure is characteristic of the TNFR superfamily.

Thirteen chimeric knock-out (KO/loss-of-function) variants were constructed by replacing the following residues of the extracellular domain of human OX40 with the corresponding mouse OX40 aa or Alanine (FIG. 31):

CRD1 (human OX40 aa 29 to 65 replaced with the mouse counterparts);

CRD2 (human OX40 aa 66 to 107 replaced with the mouse counterparts);

CRD3 (human OX40 aa 108 to 146 replaced with the mouse counterparts);

CRD4+linker (human OX40 aa 147 to 214 replaced with the mouse counterparts);

CRD3+4 (human OX40 aa 108 to 167 replaced with its mouse counterparts);

$A^{111}$ (human OX40 aa alanine 111 replaced with its mouse counterpart proline);

$L^{116}$ (human OX40 aa leucine 116 replaced with its mouse counterpart glutamine);

$P^{121}$ (human OX40 aa proline 121 replaced with its mouse counterpart leucine);

$A^{126}$ (human OX40 aa alanine 126 replaced with its mouse counterpart valine);

$D^{137}$ (human OX40 aa aspartic acid 137 replaced with its mouse counterpart asparagine);

$A^{111}P^{121}D^{137}$ (human OX40 aa Ala111, Pro121 and Asp137 replaced with the mouse counterparts);

$L^{116}A^{126}$ (human OX40 aa Leu116 and Ala126 replaced with the mouse counterparts); and $D^{117}S^{118}$ (human OX40 aa Asp117 and Ser118 replaced with Ala mutations).

In addition, five knock-in (KI/gain-of-function) variants were constructed by grafting the following residues of human OX40 into mouse OX40 using the same method as described above for the KO constructs (FIG. 31):

CRD3 (human OX40 aa 108 to 146 grafted into the corresponding mouse regions);

$A^{111}$ (human OX40 aa alanine 111 grafted into the corresponding mouse position);

$L^{116}$ (human OX40 aa leucine 116 grafted into the corresponding mouse position);

$A^{126}$ (human OX40 aa alanine 126 grafted into the corresponding mouse position);

$L^{116}A^{126}$ (human OX40 aa leucine 116 and alanine 126 grafted into the corresponding mouse positions).

The resulting chimeric DNAs were closed into a mammalian expression vector pEBNA for transient mammalian expression. 293F cells were seeded at a density of $0.7 \times 10^6$ cells/mL one day prior to transfection. Three and a half micro grams of each expression vector were transfected into 5 mL of HEK293 F cells using 5 μL of 293fectin transfection reagent following the manufacturer's instructions.

10.3 Characterization of Binding of OX40mAb24 to Chimeric OX40 Variants

Forty-eight hours after transfection, HEK293F cells were incubated with 1 μg/mL of OX40mAb24 for 1 hour on ice in PBS. To detect bound OX40mAb24 by flow cytometry, the cells were washed 3-times with cold PBS, incubated with 1 μg/mL of Alexa480-conjugated anti-human IgG antibody for 1 hr on ice, and then analyzed using the LSRII flow cytometer.

The expression levels of all chimeric OX40 variants were also monitored by flow cytometry; the cells were incubated with a mixture of sheep anti-human OX40 and goat anti-mouse OX40 polyclonal antibodies at 1 μg/mL in PBS for 1 hour on ice. Cells were washed 3-times with cold PBS, and then incubated with a mixture of Alexa480-conjugated anti-goat and anti-sheep IgG polyclonal antibodies. After washing 3 times with cold PBS, cells were analyzed with the LSRII flow cytometer.

10.4 Results

The epitope of OX40mAb24 was characterized using chimeric human/mouse variants. Human OX40 and mouse OX40 share 60% identity in the aa sequence (FIG. 30); yet, OX40mAb24 binds specifically to human OX40 and does not recognize mouse OX40. This specificity was employed to identify the epitope of OX40mAb24. Eighteen chimeric variants were constructed by swapping in or out various domains of the extracellular domain of mouse OX40 into human OX40 (KO/loss-of-function variants) or of human OX40 into mouse OX40 (KI/gain-of-function variants) (FIG. 31). All variants encoded a transmembrane domain for cell-surface expression of the chimeric protein. The binding characteristics of OX40mAb24 to these variants were analyzed by flow cytometry.

The epitope of OX40mAb24 was mapped to the CRD3 domain of human OX40 by swapping individual domains between human and mouse OX40s. The binding of OX40mAb24 to human OX40 was abolished when replacing human CRD3 domain with the mouse counterpart (KO_CRD3 and KO_CRD3-4) (FIGS. 32A-C). Replacement of the other human CRD domains with mouse regions did not affect the binding of OX40mAb24(KO_CRD1, KO_CRD2, and KO_CRD4+linker). Furthermore, grafting the human CRD3 domain into mouse OX40 led to the binding of OX40mAb24 (KI_CRD3). All variants were expressed as monitored by anti-human and mouse OX40s polyclonal antibodies (FIGS. 32A-C). The parental mAb of OX40mAb24, 9B12, was also characterized in the binding study. 9B12 shows the same binding profiles to these variants as OX40mAb24, suggesting both IgGs recognize the same epitope of the CRD3 domain.

Furthermore, critical epitope residues $Leu^{116}$ and $Ala^{126}$ were identified in the CRD3 domain by mutating the amino acids that are different between human and mouse OX40s. Five amino acids, including $Ala^{111}$, $Leu^{116}$, $Pro^{121}$, $Ala^{126}$, and $Asp^{137}$ (FIG. 30) in the human CRD3 domain, were mutated to corresponding mouse residues or Ala as individual amino acids or different combinations (FIG. 31). The binding of OX40mAb24 was abolished when replacing human residues $Leu^{116}$ and $Ala^{126}$ with the mouse counterparts (KO_$L^{116}$+$A^{126}$). Furthermore, the KI/gain-of-function variants confirmed the importance of these two critical residues. Grafting $Leu^{116}$, $Ala^{126}$, or the combination into mouse OX40 led to the binding of OX40mAb24.

10.5 Conclusions

The epitope OX40mAb24 was mapped to the CRD3 domain of human OX40 using human/mouse chimeric variants, with critical residues $Leu^{116}$ and $Ala^{126}$. The binding profiles to all variants between OX40mAb24 and its parental 9B12 are identical, indicating they recognize the same epitope on human OX40.

Example 11

Pharmacodynamic Activity of the Rat/Mouse Anti-Mouse OX40 IgG2a Chimera Antibody Clone OX86 in Naïve Mice and in Mice Bearing Syngeneic Tumors OX86 is a rat anti-mOX40 IgG1 antibody that specifically binds to and triggers signaling of MOX40 (al-Shamkhani et al, 1996), and has anti-tumor activity in immunocompetent mouse models of cancer (Weinberg et al, 2000). To more fully study the effects of OX40 agonism using a mouse surrogate antibody with functional properties similar to OX40mAb24, this example utilizes the rat/mouse anti-mOX40 IgG2a chimera antibody OX86 described in Example 9. However, it is possible to draw some parallels between the species, for example mIgG2a and human IgG1 are often considered equivalent functionally as both isotypes are able to bind multiple Fcγ receptors, are capable of high affinity Fcγ receptor binding and are able to trigger ADCC and bind to human C1q, a prerequisite for complement-dependent cytotoxicity (CDC) by the classical complement pathway (Stewart et al. 2014; Dall'Acqua et al, 2006). OX86 mIGg2a binds to mouse OX40 (see Example 9) and was used as a surrogate mouse OX40 agonist antibody for OX40mAb24.

In this example, the ability of OX86 mIgG2a to induce T cells in naïve and tumor bearing mice, and to enter the cell cycle and proliferate. Further, K167 and ICOS were evaluated as a potential biomarker of OX40 agonist activity, was investigated. T-cell proliferation and anti-tumor activity was determined in two syngeneic mouse models of cancer. Moreover, finally, the role of activating (Fcγ receptors I, III and IV) and/or inhibitory (Cfy receptor IIb) Fcγ receptors play in vivo activity of OX86 mIgG2a was determined.

11.1 Materials and Methods 11.1.1 Animal Receipt and Identification

Wild-type $Fcgr2b^{-/-}$ or $Fcer1g^{-/-}$ BALB/c and $Fcgr2b^{-/-}$ or $Fcer1g^{-/-}$ C57BL/6 mice of 6-8 weeks of age were received at MedImmune from Harlan Laboratories, Inc. (Indianapolis, Ind. or Charles River Laboratories (UK)) and allowed to acclimatize for <15 days prior to study start. Thereafter, mice were implanted with microchip transponders to identify individual mice.

11.1.2 Housing

The animals were humanely treated and housed according to Institutional Animal Care and Use Committee (USA) and Home Office (UK) approved protocols in the Laboratory Animal Resources facility (USA) and Biological Sciences Unit (UK) at MedImmune, an Association for Animal Accreditation of Laboratory Animal Care and United States Department of Agriculture-licensed facility. The animals were kept in sterile micro-isolator units, provided with sterile bedding and food, and acidified drinking water (USA) or tap water (UK) ad libitum. Environmental conditions were standardized (room temperature: 20° C.±1° C. (USA) or 21° C.±1° C. (UK); relative humidity: 50%±10% (USA) or 55±10% (UK); 12-hour light-dark cycle). The animals were monitored daily for adverse clinical signs and bi-weekly for body weight. If hind limb paralysis, respiratory distress, 20% body weight loss, or tumor volume greater than 2000 $mm^3$ were noted, the animals were immediately sacrificed humanely by cervical dislocation or asphyxiation with $CO_2$.

11.1.3 Establishment of Syngeneic Tumors

The CT26 cell line (mouse colon carcinoma) was obtained from ATCC, Manassas, Va., and the cell line MCA 205 (chemically-induced mouse soft tissue sarcoma) was obtained from the Providence Cancer Center, Portland, Oreg. Both cell lines were maintained in RPMI 1640 medium+10% FBS at 37° C., 5% $CO_2$.

Allografts were established by subcutaneous (SC) injection of $5.0\times10^5$ CT26 cells, resuspended in 0.1 mL of PBS, into the right flank of 7- to 9-week-old wild-type, $Fcgr2b^{-/-}$ or $Fcer1g^{-/-}$ BALB/c mice. Allografts were also established by SC injection of $2.5\times10^5$ MCA205 cells, resuspended in 0.1 mL of PBS, into the right flank of 7- to 9-week-old wild-type, $Fcgr2b^{-/-}$ or $Fcer1g^{-/-}$ C57BL/6 mice.

11.1.4 Randomization, Group Designation and Dose Levels

Wild-type (n=70), $Fcgr2b^{-/-}$ (n=36) or $Fcer1g^{-/-}$ (n=36) BALB/c and $Fcgr2b^{-/-}$ (n=36) or $Fcer1g^{-/-}$C57BL/6 female mice (n=36) were used in this study. All mice were randomly assigned into treatment groups. Group designations, number of animals, dose levels and dose schedule are presented in Table 11-1, Table 11-2 and Table 11-3. All test articles and control articles were administered intraperitoneally (IP). There were no animal substitutions.

Animals from each group were sacrificed when tumor volumes reached approximately 2000 $mm^3$ or when tumors became ulcerated or necrotic.

TABLE 11-1

Group Designation and Dose Levels of Naïve Balb/c Mice

| Group | Number of animals (M/F) | Treatment | Dose schedule (study day) | Dose level (mg/kg)$^a$ | ROA |
|---|---|---|---|---|---|
| 1, 9 | 7 (F), 7 (F) | Saline | 1 | NA | IP |
| 3, 11 | 7 (F), 7 (F) | Isotype control (NIP228 IgG2a) | 1 | 20 | IP |
| 4, 12 | 7 (F) | OX86 mIgG2a | 1 | 20 | IP |
| 5, 13 | 7 (F), 7 (F) | OX86 mIgG2a | 1 | 2 | IP |
| 6, 14 | 7 (F), 7 (F) | OX86 mIgG2a | 1 | 0.2 | IP |

F = female;
M = male;
NA = not applicable;
IP = intraperitoneal;
ROA = route of administration;
OX86 mIgG2a = mouse anti-mouse OX40 IgG2a monoclonal antibody variant of OX86
$^a$Dose volume: 0.2 mL for saline or volume adjusted to body weight; 10 mL/kg for all other groups.

TABLE 11-2

Group Designation and Dose Levels in the CT26 Syngeneic Model

| Group | Number of animals (M/F) | Mouse Strain | Treatment | Dose schedule (study day) | Dose level (mg/kg)$^a$ | ROA |
|---|---|---|---|---|---|---|
| 1 | 8 (F) | Balb/c | None | NA | NA | IP |
| 2 | 8 (F) | Fcgr2b$^{-/-}$ | Control (OX86 mIgG1 D265A) | 4, 7 | 2.5 | IP |
| 3 | 8 (F) | | OX86 mIgG2a | 4, 7 | 2.5 | IP |
| 4 | 8 (F) | Balb/c | None | NA | NA | IP |
| 5 | 8 (F) | Fcer1g$^{-/-}$ | Control (OX86 mIgG1 D265A) | 4, 7 | 2.5 | IP |
| 6 | 8 (F) | | OX86 mIgG2a | 4, 7 | 2.5 | IP |

F = female;
M = male;
NA = not applicable because the animals were not treated;
IP = intraperitoneal;
ROA = route of administration;
OX86 mIgG2a = rat anti-OX40 light and heavy chain variable regions of clone OX86 with mouse IgG2a constant regions.
$^a$Dose volume: 0.2 mL.

TABLE 11-3

Group Designation and Dose Levels in the MCA205 Syngeneic Model

| Group | Number of animals (M/F) | Mouse Strain | Treatment | Dose schedule (study day) | Dose level (mg/kg)$^a$ | ROA |
|---|---|---|---|---|---|---|
| 1 | 8 (F) | C57BL/6 | None | NA | NA | IP |
| 2 | 8 (F) | Fcgr2b$^{-/-}$ | Control (OX86 mIgG1 D265A) | 4, 7 | 7.5 | IP |
| 3 | 8 (F) | | OX86 mIgG2a | 4, 7 | 7.5 | IP |
| 4 | 8 (F) | C57BL/6 | None | NA | NA | IP |
| 5 | 8 (F) | Fcer1g$^{-/-}$ | Control (OX86 mIgG1 D265A) | 4, 7 | 7.5 | IP |
| 6 | 8 (F) | | OX86 mIgG2a | 4, 7 | 7.5 | IP |

F = female;
M = male;
NA = not applicable because the animals were not treated;
IP = intraperitoneal;
ROA = route of administration;
OX86 mIgG2a = rat anti-OX40 light and heavy chain variable regions of clone OX86 with mouse IgG2a constant regions.
$^a$Dose volume: 0.2 mL.

11.1.5 Tumor Measurements

Tumors were measured by caliper twice weekly and tumor volumes were calculated using the following formula:

$$\text{tumor volume}=[\text{length(mm)}\times\text{width(mm)}^2]/2$$

where length was defined as the larger side, and width as the smaller side perpendicular to the length.

Antitumor effects of each group were expressed as tumor growth inhibition (TGI), which was calculated as follows:

$$\%\ \text{TGI}=(1-[\text{mean tumor } V \text{ of treatment group}]\div[\text{mean tumor } V \text{ of control group}])\times 100$$

11.1.6 Tissue Collection and Single Cell Isolation 11.1.6.1 Preparation of Mouse Blood Cells for Flow Cytometry Analysis Red blood cell lysis (RBCL) buffer (2 mL) was added to blood (50 μL) and incubated for 5 min. Volumes obtained from in-life bleeds ranged from 20 μL to 50 μL. Terminal bleeds were 50 μL. RPMI+10% fetal bovine serum (FBS) (8 mL) was added to each sample. Cells in each sample were pelleted (300×g, 5 min) and then resuspended in 0.3 mL Flow Buffer. Cell suspensions (200 μL) were added to each well of a 96-well round-bottomed plate for staining with fluorescent antibodies. Pooled group samples were used for unstained, the single antibody staining, isotype staining and the fluorescence-minus-one (FMO) antibody staining controls.

11.1.6.2 Mouse Draining Lymph Node and Spleen Isolation and Generation of Single Cell Suspensions for Flow Cytometry Analysis Spleens were placed in 10 mL of RPMI+1× Pen/Strep solution and passed through a 40 μm cell strainer. Samples were pelleted (300×g, 5 min) and then resuspended in 1 mL RBCL buffer for 3 min. RPMI+FBS 10% (9 mL) was added to each sample. Cell suspensions were pelleted (300×g, 5 min) and resuspended in 1 mL of Flow Buffer. Cell suspensions (100 μL) were added to each well of a 96-well round-bottomed plate for staining with fluorescent antibodies. Pooled group samples were used for unstained, the single antibody staining, isotype staining and FMO antibody staining controls.

11.1.6.3 Preparation of Single-Cell Suspension of Mouse Tumor for Flow Cytometry Analysis Tumors were aseptically excised from euthanized mice, being careful to avoid collecting connective tissue or skin, and placed in collagenase diluted with Hanks balanced salt solution in a 6-well dish. To increase the efficiency of the enzymatic digestion process, each tumor was minced with a scalpel or a small pair of sharp scissors into smaller pieces. Minced tumors were transferred into 15 mL conical tubes and placed on a shaking platform to incubate at 37° C. for 20-30 minutes. Five mL of RPMI+10% FBS was added to each sample to deactivate the collagenase and maintain viability of the immune cells. Samples were passed through a 70 μM cell strainer and placed into 50 mL conical tubes. An aliquot of each sample was removed for counting. The remaining amount sample was pelleted in a centrifuge at 330×g and resuspended in FACS buffer (PBS+2% FBS) at a concentration of $1\times10^7$ cells per mL.

11.1.7 Flow Cytometry Analysis 11.1.7.1 Analysis of Tissues from Non-tumor-bearing Mice Single-cell suspensions of blood or spleen cells were pelleted (300×g, 5 min), resuspended in 50 μL of Fc Block solution (1:50), diluted in eBiosciences Flow Buffer and incubated for 10 min on ice. Fifty microliters of fluorescently labelled antibodies (2× stock solution) were added to each sample (final volume 100 μL). Single antibody staining solutions (extracellular) were added at 1 μL per well and cell/antibody mixtures were incubated for 30 min on ice. Cells were pelleted (300×g, 5 min), washed twice (200 μL Flow Buffer per well, 300×g, 5 min), resuspended in 50 μL Fix/Penn buffer (one part concentrate to three part diluent) and then incubated overnight at 4° C. in the dark.

Treated cells were washed twice in 1× Permeabilization Buffer (diluted in water). Intracellular labelling antibodies were diluted into Permeabilization Buffer (100 μL per well) and added to the cells, which were then incubated at room temperature in the dark for 30 minutes. Antibodies for single marker staining (intracellular) were added to cells at 1 μL per well into 100 jut Permeabilization Buffer and incubated for 30 min on ice in the dark. Cells were washed once in Permeabilization Buffer and resuspended in 3.7% formaldehyde solution (100 μL) before being analyzed on a Canto II flow cytometer (BD Biosciences, San Jose, Calif.).

11.1.7.2 Analysis of Tissues from Tumor-bearing Mice 11.1.7.2.1 Cell Surface Staining Each sample of pelleted cells was resuspended in FACS Buffer. Fluorescent antibody mixtures in FACS Buffer were added to appropriate wells and incubated for 20-30 minutes at 4° C. in the dark. Cells were washed twice with FACS Buffer, resuspended in FACS Buffer and analyzed on a LSRII flow cytometer (BD Biosciences, San Jose, Calif.).

11.1.7.2.2 Intracellular Staining (Fixed and Permeabilized Cells)

Each sample of pelleted cells was resuspended in 50 μL of a 1:500 dilution of a fluorescence fixable blue dye for live/non-viable cell discrimination, and incubated for 15 minutes at 4° C. in the dark. Cells were washed once with FACS Buffer, resuspended in 30 μL PBS+4% normal mouse serum containing Fc Block, and incubated for 15 minutes at room temperature. Fluorescent antibody mixtures in FACS Buffer were added to appropriate wells, and incubated for 20-30 minutes at 4° C. in the dark. Cells were washed twice with FACS Buffer, resuspended in 150 μL freshly prepared FoxP3 Fix/Penn working solution and incubated at room temperature for 30 minutes in the dark. Cells were washed twice with 1× Permeabilization Buffer, resuspended in 100 μL 1× Permeabilization Buffer containing antibodies to stain intracellular antigens, and incubated at room temperature for 30 minutes in the dark. Cells were washed once with 1× Permeabilization Buffer, resuspended in FACS Buffer and analyzed on a LSRII flow cytometer.

11.1.8 Statistical Methods

One-way ANOVA was used to determine mean tumor volume differences and mean percentage of Ki67+ or ICOS+ cells. In the event of a significant F test, a Dunnett's or Sidak's multiple comparison test was utilized (where appropriate). Where applicable, a log 10 transformation was applied to mean values to account for heteroscedasticity. A p value<0.05 was considered significant. GraphPad Prism 6.0 was employed for linear regression analysis which generated the best fit line that best predicted Y from X, the level of statistical significance of the line and the goodness of fit ($r^2$) of the determined best fit line.

11.1.9 Materials

Materials used in this study, and their source, are listed in Table 11-4 and Table 11-5.

TABLE 11-4

Materials

| Item | Source |
|---|---|
| 0.25% Trypsin-EDTA (1X) | Life Technologies, Carlsbad, CA |
| 10 x Permeabilization Buffer | eBioscience, UK |
| 3.7% Formaldehyde solution | Sigma-Aldrich, UK |
| 40 and 70 μm cell strainers | Corning Life Sciences, Tewksbury, MA |
| Collagenase type 3 | Worthington Biochem Corp., Lakewood, NJ |
| Fc Block | eBioscience, UK |
| Fetal bovine serum, heat inactivated | Life Technologies, Carlsbad, CA |
| Fixation/Permeabilization Concentrate | eBioscience, UK |
| Fixation/Permeabilization Diluent | eBioscience, UK |
| Flow Buffer | eBioscience, UK |
| FoxP3 Fix/Perm Kit | eBioscience, UK |
| Hanks buffered salt solution | Life Technologies USA |
| Heat Inactivated Gamma Irradiated FBS for RBCL Buffer neutralization | SASC Biosciences, KS, USA |
| LSRII and Canto II Flow Cytometers | BD Biosciences, San Jose, CA |
| Normal mouse serum | Jackson Labs, Bar harbor, MA |
| Pen/Strep solution | Life Technologies UK |
| Permeabilization Buffer | eBiosciences, USA |
| Phosphate buffered saline, pH 7.2 | Life Technologies, Carlsbad, CA |
| Red Blood Cell Lysis Buffer | Sigma, UK |
| Roswell Park Memorial Institute 1640 medium | Life Technologies, Carlsbad, CA |

TABLE 11-5

| Fluorescent Antibodies for Flow Cytometry Studies | |
|---|---|
| Item | Source |
| APC conjugated Rat IgG2a anti-CD4 | eBiosciences, UK |
| FITC conjugated mIgG2a anti-MHC2 | eBiosciences USA |
| APC-H7 conjugated Rat IgG2a anti-CD8 | BD Biosciences, UK |
| EFluor 480 conjugated Rat IgG2a anti-Ki67 | eBioscience, UK |
| APC conjugated isotype control Rat IgG2a | eBioscience, UK |
| APC-H7 conjugated isotype control Rat IgGa | BD Biosciences, UK |
| eFluor conjugated isotype control Rat IgG2a | eBioscience, UK |
| PE conjugated isotype control Rat IgG2b | eBioscience, UK |
| PECy7 conjugated rlgG2a Ki67 | eBioscience, USA |
| BV605 conjugated rlgG2a anti CD4 | Biolegend USA |
| BV711 conjugated rlgG2a anti CD8 | Biolegend USA |
| Fixable Blue | Life Technologies, USA |
| PeCy7 conjugated Isotype control rlgG2a | Biolegend USA |

11.2 Results

Intraperitoneal treatment of naïve mice with the anti-OX40 antibody OX86 mouse IgG2a (OX86 mIgG2a) resulted in a significant, dose-dependent and transient increase in the percentage of Ki67+CD4+ and ICOS+CD4+ T cells in the blood over time, compared to mice treated with control articles (FIGS. 33A and C). The largest percentage of Ki67+CD4+ and ICOS+CD4+ T cells was detected on Day 10. A significant increase in the percentage of Ki67+CD4+ and ICOS+CD4+ T cells was measured in the spleens of mice on Day 10 following the administration of OX86 mIgG2a, compared to mice treated with control articles (FIGS. 33B and D). A statistically significant and strong correlation between the percentage of Ki67+CD4+ T cells and ICOS+CD4+ T cells in the blood and spleen on Day 10 was identified (FIGS. 34A and 34B).

Treatment of naïve mice with the OX86 mIgG2a also resulted in a significant, transient increase in the percentage of Ki67+CD8+ T cells in the blood over time, when compared to mice treated with control articles (FIG. 35A). Increases in the percentage of ICOS+CD8+ T cells in the blood over time (FIG. 35C), and the percentage of Ki67+CD8+ T cells in the spleen on Day 10 (FIG. 35B), were detected following treatment with OX86 mIgG2a, but were not statistically significant when compared to treatment with control articles. Treatment of naïve mice with OX86 mIgG2a did induce a significant, dose-dependent increase in the percentage of ICOS+CD8+ T cells in the spleen on Day 10, compared to mice treated with control articles (FIG. 35D). Moderate but significant correlations between the percentage of Ki67+CD8+ T cells and ICOS+CD8+ T cells in the blood and spleen was determined (FIGS. 36A and 36B).

Single-agent treatment of tumor-bearing wild-type mice with OX86 mIgG2a results in an antitumor activity that reduces growth of two histologically different tumors as compared to untreated and isotype control treated groups (See Example 9). Treatment with OX86 mIGg2a resulted in significantly reduced growth of MCA205 tumors on Day 20 (FIG. 38A, Table 11-7) when compared to treatment with control articles in C57BL/6 mice that were genetically engineered to lack expression of the inhibitory Fcγ receptor IIB (Fcgr2b$^{-/-}$ mice). Identical treatment of mice with CT26 tumors resulted in a reduced growth of tumors that did not reach statistical significance on Day 18 (FIG. 37A, Table 11-6) when compared to treatment with control articles in Fcgr2b$^{-/-}$BALB/c mice. No inhibition of growth, by any agent, was observed in tumor bearing Balb/c and C57BL/6 mice genetically engineered to lack expression of the activating Fcγ receptors (Fcer1g$^{-/-}$ mice; FIG. 37C; FIG. 38C). Mixed response is often observed in syngeneic models. However, the anti-tumor response following treatment with OX86 mIgG2a in the two different strains of Fcγ receptor knock-out mice can also be discerned from the individual animal tumor growth graphs (FIGS. 37B and D; FIGS. 38B and D); treatment with OX86 mIgG2a resulted in the inhibition of CT26 and MCA205 tumor growth and in some cases induced complete responses in Fcgr2b$^{-/-}$ mice (FIG. 37B; FIG. 38B).

TABLE 11-6

Treatment Groups and Percent TGI and Number of Complete Responders in CT26 Syngeneic Mouse Model

| Group [a] | Test/Control Article | Dose [b] (mg/kg) | Mouse Strain | % TGI [c] | Number of Complete Responders out of 8 mice [d] |
|---|---|---|---|---|---|
| 1 | None | NA | Balb/c | NA | 0 |
| 2 | Isotype control | 2.5 mg/kg | Fcgr2b$^{-/-}$ | NA | 0 |
| 3 | OX86 mIgG2a | 2.5 mg/kg | | 15 | 0 |
| 4 | None | NA | Balb/c | NA | 0 |
| 5 | Isotype control | 2.5 mg/kg | Fcer1g$^{-/-}$ | NA | 0 |
| 6 | OX86 mIgG2a | 2.5 mg/kg | | <0 | 0 |

TGI = tumor growth inhibition;

NA = not applicable;

IP = intraperitoneal;

V = volume

[a] Number of animals per group: 8.

[b] All animals received 200 μL of test article IP on Days 4 and 7.

[c] % TGI = [1 − (mean tumor V of treatment group) ÷ (mean tumor V of control group)] × 100; calculated on Day 18 for Fcgr2b$^{-/-}$ mice and Day 16 for Fcer1g$^{-/-}$ mice

[d] Number of animals in a group with a tumor volume measurement recorded as zero at the end of the study.

TABLE 11-7

Treatment Groups and Percent TGI on Day 20 and Number of Complete Responders in MCA205 Syngeneic Mouse Model

| Group [a] | Test/Control Article | Dose [b] (mg/kg) | Mouse Strain | % TGI [c] | Number of Complete Responders out of 8 mice [d] |
|---|---|---|---|---|---|
| 1 | None | NA | C57BL/6 | NA | 0 |
| 2 | Isotype control | 7.5 mg/kg | Fcgr2b$^{-/-}$ | NA | 0 |
| 3 | OX86 mIgG2a | 7.5 mg/kg | | 95 | 8 |
| 4 | None | NA | C57BL/6 | NA | 0 |
| 5 | Isotype control | 7.5 mg/kg | Fcer1g$^{-/-}$ | NA | 0 |
| 6 | OX86 mIgG2a | 7.5 mg/kg | | 35 | 1 |

TGI = tumor growth inhibition;
NA = not applicable;
IP = intraperitoneal;
V = volume
[a] Number of animals per group: 8.
[b] All animals received 200 μL of test article IP on Days 4 and 7.
[c] % TGI = [1 − (mean tumor V of treatment group) ÷ (mean tumor V of control group)] × 100
[d] Number of animals in a group with a tumor volume measurement recorded as zero at the end of the study.

In parallel pharmacodynamics studies, treatment with OX86 mIgG2a compared to control articles caused a significant increase in the percentage of Ki67+CD4+ T cells in the spleen (FIG. 39A) and Ki67+CD8+ T cells in the peripheral blood and the spleen, but not in the tumor (FIG. 40A), of CT26 tumor bearing Fcgr2b$^{-/-}$Balb/c mice. No increase in Ki67+CD4+ or CD8+ T cells was detected in the blood, spleen or tumor of CT26 tumor bearing Fcer1g$^{-/-}$ Balb/c mice following treatment with OX86 mIgG2a, as compared to control articles (FIG. 39B; FIG. 40B).

Additionally, in parallel studies, treatment with OX86 mIgG2a compared to control articles resulted in a significant increase in the percentage of Ki67+CD4+ T cells in the draining lymph node, spleen and tumor (FIG. 41A) and Ki67+CD8+ T cells in the draining lymph node and the spleen (FIG. 42A) of MCA205 tumor bearing Fcgr2b$^{-/-}$ C57BL/6 mice. Increases in the percentage of Ki67+CD8+ T cells in the tumor of MCA205 tumor bearing Fcgr2b$^{-/-}$ C57BL/6 mice were not statistically significant (FIG. 42A). Treatment with OX86 mIgG2a as compared to control articles also induced a significant increase in the percentage of Ki67+CD4+ T cells in the draining lymph node and spleen of MCA205 tumor bearing Fcer1g$^{-/-}$C57BL/6 mice (FIG. 41B). A significant increase in the percentage of Ki67+CD8+ T cells in the spleen of these mice was also observed (FIG. 42B). No significant increases in the percentage of Ki67+CD4+ T cells in the tumor (FIG. 42B) or Ki67+CD8+ T cells in the draining lymph node or tumor of MCA205 tumor bearing Fcgr2b$^{-/-}$C57BL/6 mice were detected (FIG. 42B).

11.3 Conclusions

A single dose of OX86 mIgG2a in naïve mice induced a transient increase in T-cell activation and proliferation as measured by increased expression of ICOS and Ki67, respectively. A significant linear correlation of the percentage of ICOS and Ki67 on CD4+ and CD8+ T cells was found. Antitumor activity of OX86 mIgG2a, measured as inhibition of the growth of CT26 and MCA205 tumors, was dependent on the expression of activating Fcγ receptors I, III and IV, but not the inhibitory Fcγ receptor IIB. Increases in peripheral blood, draining lymph node and/or spleen T-cell proliferation (Ki67) were observed in parallel pharmacodynamic experiments in tumor-bearing mice that expressed the activating Fcγ receptors; some T-cell proliferation was observed in mice that expressed only the inhibitory Fcγ receptor. Together with the pharmacodynamic results from naïve mice and while not wishing to be bound by theory, a potential mechanism for OX86 mIgG2a antitumor activity is increased peripheral and intratumoral T-cell proliferation (Ki67). Moreover, OX86 mIgG2a in vivo antitumor activity occurs upon expression of activating Fcγ receptors.

Example 12

T Cell Pharmacodynamic Changes in Response to OX40mAb24 Therapy in Immunocompromised Mice Engrafted with Human Hematopoietic Stem Cells This example investigates whether OX40mAb24 can activate and expand human CD4+ and CD8+ memory T cells or reduce human Tregs in immunocompromised mice with a reconstituted human immune system. OX40mAb24 was tested in an in vivo mouse model system reconstituted with human immune cells to determine if the drug has immunomodulatory effects on human T cells.

12.1 Materials and Methods 12.1.1 Test Animals

Nod.Cg-Prkdc$^{scid}$Il2rg$^{tm1Wy}$/SzJ (NSG) Mice (n=14 ages 23-26 weeks) were obtained from the Jackson Laboratory. The animals were humanely treated and housed according to Institutional Animal Care and Use Committee approved protocols in the Laboratory Animal Resources facility at MedImmune, an Association for Animal Accreditation of Laboratory Animal Care and United States Department of Agriculture-licensed facility. The animals were kept in sterile micro-isolator units, provided with sterile bedding and food, and acidified drinking water ad libitum. Environmental conditions were standardized (room temperature: 20° C.±1° C.; relative humidity: 50%±10%; 12-hour light-dark cycle). The animals were monitored daily for adverse clinical signs during the course of the study.

12.1.2 Pharmacodynamics of OX40mAb24 in HSC Engrafted (Humanized) Mice 12.1.2.1 Establishment of Human HSC Engrafted Mice Human CD34+HSC engrafted mice were purchased from the Jackson Laboratory. Mice were generated as follows: pooled human CD34+ cells from multiple umbilical cord blood donors were isolated and injected intravenously into the tail vein of Nod.Cg-Prkdc$^{scid}$112 re$^{tm1Wy}$/SzJ (NSG)

mice. At 12 weeks after engraftment, mouse peripheral blood was sampled and lysed with Pharm Lyse red blood cell lysis buffer and then analyzed by flow cytometry for human CD45, CD19 and CD3 positive cells to determine the degree of human immune cell engraftment in mice. Mice successfully engrafted with 25% or more CD45+ human immune cells of total viable blood cells were subsequently shipped to MedImmune.

12.1.2.2 Antigen Challenge and OX40mAb24 Treatment of Human HSC Engrafted Mice

The sustained engraftment of human immune cells into NSG mice was confirmed by flow cytometry at 22 weeks post injection of human CD34 cells, and at 23 weeks mice were placed into 3 groups that were left untouched or received treatment (Table 12-1). There were no statistically significant differences in the mean percentage of human CD45+ cell engraftment between eventual treatment groups at week 22 prior to the start of the experiment. Group 1 consisted of 4 mice and did not receive subcutaneous (SC) keyhole limpet hemocyanin (KLH) immunization or antibody administration. Group 2 consisted of 5 mice and received 300 μg/50 μL of KLH and 50 μL of complete Freund's adjuvant (CFA) at two independent injection SC sites. This group of mice also received 2 mg/kg of hIgG1 isotype control antibody, administered intraperitoneally (IP), one day after KLH immunization. Group 3 consisted of 5 mice and received KLH/CFA SC immunization as described above. In addition, mice were also administered one day later a single IP dose of 2 mg/kg OX40mAb24. On the day of KLH/CFA SC immunization, prior to immunization (pre-treatment), and seven days later (post-treatment), whole blood was obtained through retro-orbital bleed and cells were immunophenotyped and counted by flow cytometry.

TABLE 12-1

Experimental Groups, Human CD45+ Cell Engraftment, and Treatment

| Group | Mouse Number | Human CD45+ Cells as a Percentage of Total Viable Human Plus Mouse CD45 Cells[a] - Week 22 post HSC engraftment | Treatment[b] - Week 23 post HSC engraftment |
|---|---|---|---|
| 1 | 1-1 4575 | 39.5 | None |
| 1 | 1-2 4576 | 68.3 | None |
| 1 | 1-3 4577 | 20.9 | None |
| 1 | 1-4 4578 | 23.8 | None |
| 2 | 2-1 4579 | 29.6 | KLH immunization + NIP228 huIgG1 |
| 2 | 2-2 4580 | 21.7 | KLH immunization + NIP228 huIgG1 |
| 2 | 2-3 4581 | 27.8 | KLH immunization + NIP228 huIgG1 |
| 2 | 2-4 4582 | 50.3 | KLH immunization + NIP228 huIgG1 |
| 2 | 2-5 4583 | 32.5 | KLH immunization + NIP228 huIgG1 |

TABLE 12-1-continued

Experimental Groups, Human CD45+ Cell Engraftment, and Treatment

| Group | Mouse Number | Human CD45+ Cells as a Percentage of Total Viable Human Plus Mouse CD45 Cells[a] - Week 22 post HSC engraftment | Treatment[b] - Week 23 post HSC engraftment |
|---|---|---|---|
| 3 | 3-1 4584 | 15.4 | KLH immunization + OX40mAb24 |
| 3 | 3-2 4585 | 44.3 | KLH immunization + OX40mAb24 |
| 3 | 3-3 4586 | 20.3 | KLH immunization + OX40mAb24 |
| 3 | 3-4 4587 | 16.3 | KLH immunization + OX40mAb24 |
| 3 | 3-5 4588 | 25.6 | KLH immunization + OX40mAb24 |

Hu = human; KLH = keyhole limpet hemocyanin; HSC = hematopoietic stem cells.
[a]Human CD45+ cells determined by flow cytometry;
[b]KLH immunization, keyhole limpet hemocyanin plus complete Freund's adjuvant.

12.1.2.3 Immune Cell Analysis by Flow Cytometry

Cells were immunophenotyped by flow cytometry using a whole blood antibody binding protocol. Briefly, EDTA anti-coagulated whole blood at a constant volume was added to wells of a deep well plate and a T cell staining master mix added to cells to bind cell surface antigens. After washes in FACS buffer (PBS, pH 7.2 plus 2% heat-inactivated new-born calf serum), red blood cells (RBC) were lysed using 1×RBC lysis buffer, and cells fixed and permeabilized using EBiosciences Fix and Perm kit according to the manufacturer's protocol. Subsequently, anti-FoxP3 and anti-Ki67 mAbs were bound to cells. Cells were washed using 1× fix and perm buffer, re-suspended in FACS buffer and events analyzed using an LSRII flow cytometer. Raw flow cytometry standard (FCS) data was analyzed using FlowJo software, and cell populations identified after live/dead cell discrimination and removal of doublets and cell debris. After gating for CD4+ and CD8+ T cell populations, memory T cells were determined by CD45RA and CCR7 expression profile, with naïve T cells defined as CD45RA+/CCR7+, effector T cells (Teff) as CD45RA+/CCR7−, effector memory T cells (Tem) as CD4SRA−/CCR7−, and central memory T cells (Tcm) as CD45RA−/CCR7+. Tregs were defined as CD4+/FoxP3+ cells.

12.1.2.4 Statistical Methods

GraphPad Prism software for Windows (version 6.03) was used for graphing and statistical analysis of data.

One-way ANOVA multiple comparisons test with Turkey's post-test analysis was used to compare differences between experimental group means. In the event of a significant F test, a Sidak's multiple comparisons test was utilized. A p value of less than 0.05 was considered significant.

12.1.3 Materials

Materials used in this study, and their source, are listed in Table 12-2.

TABLE 12-2

Materials

| Item | Source |
|---|---|
| Anti-human CCR7 APC clone 150503 | R&D Systems, Minneapolis, MN |
| Anti-human CD14 APC clone M5E2 | Biolegend, San Diego, CA |
| Anti-human CD16 PE clone 1243 | Biolegend, San Diego, CA |
| Anti-human CD25 FITC clone M-A251 | Biolegend, San Diego, CA |

TABLE 12-2-continued

| Materials | |
|---|---|
| Item | Source |
| Anti-human CD3 FITC clone UCHT1 | Biolegend, San Diego, CA |
| Anti-human CD4 BV605 clone RPA-T4 | Becton Dickinson, San Jose, CA |
| Anti-human CD56 FITC clone HCD56 | Biolegend, San Diego, CA |
| Anti-human CD8 PE-CF594 clone RPA-T8 | Becton Dickinson, San Jose, CA |
| Anti-human CD19 APC clone HIB19 | Biolegend, San Diego, CA |
| Anti-human CD19 PE-CF594 clone HIB19 | Becton Dickinson, San Jose, CA |
| Anti-human CD45 PE clone HI30 | Biolegend, San Diego, CA |
| Anti-human CD45 PE clone HI30 | Biolegend, San Diego, CA |
| Anti-human FoxP3 PE clone PHC101 | eBioscience, San Diego, CA |
| Anti-human HLA-DR BV421 clone 3G8 | Biolegend, San Diego, CA |
| Anti-human Ki67 FITC clone B56 | Becton Dickinson, San Jose, CA |
| Anti-mouse CD16/32 PE-Cy7 | Biolegend, San Diego, CA |
| Anti-mouse CD45 PE-Cy7 clone 30F11 | Biolegend, San Diego, CA |
| Complete Freund's adjuvant (CFA) Difco ™ | Becton Dickinson, San Jose, CA |
| EBiosciences Fix and Perm Kit | EBioscience, San Diego, CA |
| FlowJo Software | FlowJo, Ashland, OR |
| FoxP3/Transcription Factor Fixation/Permeabilization Concentrate and Diluent | eBioscience, San Diego, CA |
| Graphpad Prism software, v 6.03 | Graphpad Software, San Diego, CA |
| Heat-inactivated newborn calf serum | Life Technologies, Frederick, MD |
| Keyhole limpet hemocyanin | Thermo Fisher Scientific, Waltham, MA |
| Live/Dead ® Fixable Blue Dye | Life Technologies, Frederick, MD |
| LSR II flow cytometer | BD Biosciences, San Jose, CA |
| Mouse IgG2a APC isotype control | eBioscience, San Diego, CA |
| Mouse IgG2b BV421 isotype control | Biolegend, San Diego, CA |
| Mouse IgG1 FITC isotype control | Biolegend, San Diego, CA |
| Phosphate-buffered saline (PBS), pH 7.2 | Life Technologies, Frederick, MD |
| Rat IgG1 PE-CF594 isotype control | Becton Dickinson, San Jose, CA |
| Rat IgG2a PE isotype control | eBioscience, San Diego, CA |
| Rat IgG2a PE-Cy7 isotype control | Biolegend, San Diego, CA |

12.2 Results

OX40mAb24 or huIgG1 control antibody was administered one day after immunization with KLH. OX40mAb24 resulted in a statistically significant reduction in the percentage of Treg in peripheral blood after six days relative to the group administered a huIgG1 isotype control antibody (p=0.019, one-way ANOVA; FIGS. 43A and 43B). No differences in the percentages of Tregs between treatment groups were observed prior to immunization and antibody administration.

In addition to a significant decrease in the percentage of peripheral blood Tregs, there was a statistically significant increase in the CD4+ Tem:Treg ratio following treatment with OX40mAb24 relative to huIgG1 isotype matched control (p=0.042), and trends towards significant increases for total CD4+:Treg (p=0.051), CD4+ Teff:Treg (p=0.10), and CD4+ Tem:Treg (p=0.069) ratios (FIGS. 44A-D) Likewise, a trend towards significance was observed for an increase in the CD8+ Teff:Treg ratio (p=0.064) in peripheral blood of mice treated with OX40mAb24 relative to that of mice treated with huIgG1 isotype control (FIGS. 45A-B).

CD25 (IL-2 receptor) is up-regulated on T cells following activation, and is considered a marker of recently activated T cells. Increases in the percentage of CD25 positive CD8+ T cells were observed for the OX40mAb24 treatment group relative to the huIgG1 treatment group for total CD8+ (p=0.038) effector CD8+ (p=0.076), and for effector memory CD8+ (p=0.040) T cells (FIGS. 46A-C). Therefore, agonism of OX40 by OX40mAb24 activated CD8+ T cells relative to the control antibody.

12.3 Conclusions

In mice engrafted with human immune cells, treatment with OX40mAb24 after antigen immunization resulted in decreased peripheral Treg cells relative to mice receiving a human IgG1 control antibody. Likewise, the ratio of total, effector, and memory CD4+ T cells, and effector CD8+ T cells, relative to Treg cells were also increased in the peripheral blood of mice receiving OX40mAb24 compared with those receiving huIgG1 control antibody. Finally, the percentage of CD8+ T cells expressing CD25 on the cell surface was increased after OX40mAb24 treatment, indicating an OX40 induction of peripheral CD8+ T-cell activation.

TABLE OF SEQUENCES

| SEQ ID NO | Description | Sequence |
|---|---|---|
| 1 | 9B12 VL | DIQMTQTTSSLSASLGDRVTISCRASQDISNYLNWYQQKPDGTVKLLIYYTSKLHSGVPSRFSGSGSR TDYSLTITDLDQEDIATYFCQQGSALPWTFGQGTKVEIK |
| 2 | LCDR1 | RASQDISNYLN |
| 3 | LCDR2 | YTSKLHS |
| 4 | LCDR3 | QQGSALPWT |

-continued

TABLE OF SEQUENCES

| SEQ ID NO | Description | Sequence |
|---|---|---|
| 5 | 9B12 VH | EVQLQESGPSLVKPSQTLSLTCSVTGDSFTSGYWNWIRKFPGNRLEYMGYISYNGITYHNPSLKSRIS<br>ITRDTSKNHYYLQLNSVTTEDTATYFCARYRYDYDGGHAMDYWGQGTLVTVSS |
| 6 | HFW1 | QVQLQESGPGLVKPSQTLSLTCAVYGGSFS |
| 7 | HFW1-variant | QVQLQESGPGLVKPSQTLSLTCAVYGDSFS |
| 8 | HCDR1 | SGYWN |
| 9 | HFW2-XXX | WIRX$_{39}$HPGKGLEX$_{47}$X$_{48}$G; where X$_{39}$ is Q or K, X$_{47}$ is W or Y, and X$_{48}$ is I or M |
| 10 | HFW2-variant | WIRQHPGKGLEWIG |
| 11 | HFW2-variant | WIRKHPGKGLEYMG |
| 12 | HFW2-variant | WIRKHPGKGLEWIG |
| 13 | HFW2-variant | WIRKHPGKGLEYIG |
| 14 | HCDR2 | YISYNGITYHNPSLKS |
| 15 | HCDR2-variant | YISYNAITYHNPSLKS |
| 16 | HCDR2-variant | YISYSGITYHNPSLKS |
| 17 | HFW3-XXX | RITINX$_{71}$DTSKNQX$_{78}$SLQLNSVTPEDTAVYX$_{91}$CAR;, where X$_{71}$ is P or R, X$_{78}$ is F or Y, and X$_{91}$ is Y or F |
| 18 | HFW3-variant | RITINPDTSKNQFSLQLNSVTPEDTAVYYCAR |
| 19 | HFW3-variant | RITINRDTSKNQYSLQLNSVTPEDTAVYFCAR |
| 20 | HFW3-variant | RITINRDTSKNQFSLQLNSVTPEDTAVYYCAR |
| 21 | HFW3-variant | RITINRDTSKNQFSLQLNSVTPEDTAVYFCAR |
| 22 | HFW3-variant | RITINRDTSKNQYSLQLNSVTPEDTAVYYCAR |
| 23 | HFW3-variant | RITINPDTSKNQYSLQLNSVTPEDTAVYFCAR |
| 24 | HFW3-variant | RITINPDTSKNQYSLQLNSVTPEDTAVYYCAR |
| 25 | HCDR3 | YRYDYDGGHAMDY |
| 26 | HCDR3-variant | YKYDYDAGHAMDY |
| 27 | HCDR3-variant | YKYDYDGGHAMDY |
| 28 | HFW4 | WGQGTLVTVSS |
| 29 | OX40mAb VL | DIQMTQSPSSLSASVGDRVTITCRASQDISNYLNWYQQKPGKAPKLLIYYTSKLHSGVPSRFSGSGS<br>GTDYTLTISSLQPEDFATYYCQQGSALPWTFGQGTKVEIK |
| 30 | OX40mAb light chain | DIQMTQSPSSLSASVGDRVTITCRASQDISNYLNWYQQKPGKAPKLLIYYTSKLHSGVPSRFSGSGS<br>GTDYTLTISSLQPEDFATYYCQQGSALPWTFGQGTKVEIKRTVAAPSVFIFPPSDEQLKSGTASVVCL<br>LNNFYPREAKVQWKVDNALQSGNSQESVTEQDSKDSTYSLSSTLTLSKADYEKHKVYACEVTHQGL<br>SSPVTKSFNRGEC |
| 31 | OX40Mab light chain DNA | GACATCCAGATGACCCAGAGCCCCAGCAGCCTGAGCGCCAGCGTGGGCGACAGAGTGACCAT<br>CACCTGTCGGGCCAGCCAGGACATCAGCAACTACCTGAACTGGTATCAGCAGAAGCCCGGCAA<br>GGCCCCCAAGCTGCTGATCTACTACACCAGCAAGCTGCACAGCGGCGTGCCCAGCAGATTCAG<br>CGGCAGCGGCTCCGGCACCGACTACACCCTGACCATCAGCAGCCTGCAGCCCGAGGACTTCGC<br>CACCTACTACTGCCAGCAGGGCTCCGCCCTGCCCTGGACCTTTGGCCAGGGCACCAAGGTGGA<br>AATCAAGCGTACGGTGGCTGCACCATCTGTCTTCATCTTCCCGCCATCTGATGAGCAGTTGAAA<br>TCTGGAACTGCCTCTGTTGTGTGCCTGCTGAATAACTTCTATCCCAGAGAGGCCAAAGTACAGT<br>GGAAGGTGGATAACGCCCTCCAATCGGGTAACTCCCAGGAGAGTGTCACAGAGCAGGACAGC<br>AAGGACAGCACCTACAGCCTCAGCAGCACCCTGACGCTGAGCAAAGCAGACTACGAGAAACA<br>CAAAGTCTACGCCTGCGAAGTCACCCATCAGGGCCTGAGCTCGCCCGTCACAAAGAGCTTCAA<br>CAGGGGAGAGTGT |
| 32 | OX40mAb VL-hu2 | DIQMTQSPSSLSASVGDRVTITCRASQDISNYLNWYQQKPGKAVKLLIYYTSKLHSGVPSRFSGSGS<br>RTDYTLTISSLQPEDFATYYCQQGSALPWTFGQGTKVEIK |

-continued

TABLE OF SEQUENCES

| SEQ ID NO | Description | Sequence |
|---|---|---|
| 33 | OX40mAb5 VH | QVQLQESGPGLVKPSQTLSLTCAVYGGSFSSGYWNWIRQHPGKGLEWIGYISYNGITYHNPSLKSRI TINPDTSKNQFSLQLNSVTPEDTAVYYCARYRYDYDGGHAMDYWGQGTLVTVSS |
| 34 | OX40mAb5 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGCAGCACCCCGG CAAGGGCCTGGAATGGATCGGCTACATCAGCTACAACGGCATCACCTACCACAACCCCAGCCT GAAGTCCCGGATCACCATCAACCCCGACACCAGCAAGAACCAGTTCTCCCTGCAGCTGAACAG CGTGACCCCCGAGGACACCGCCGTGTACTACTGCGCCCGGTACAGATACGACTACGACGGCGG CCACGCCATGGACTACTGGGGCCAGGGCACCCTGGTCACCGTGTCCTCT |
| 35 | OX40mAb8 VH | QVQLQESGPGLVKPSQTLSLTCAVYGGSFSSGYWNWIRKHPGKGLEWIGYISYNGITYHNPSLKSRI TINRDTSKNQFSLQLNSVTPEDTAVYYCARYRYDYDGGHAMDYWGQGTLVTVSS |
| 36 | OX40mAb8VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATGGATCGGCTACATCAGCTACAACGGCATCACCTACCACAACCCCAGCC TGAAGTCCCGGATCACCATCAACCGGGACACCAGCAAGAACCAGTTCTCCCTGCAGCTGAACA GCGTGACCCCCGAGGACACCGCCGTGTACTACTGCGCCCGGTACAGATACGACTACGACGGCG GCCACGCCATGGACTACTGGGGCCAGGGCACCCTGGTCACCGTGTCCTCT |
| 37 | OX40mAb13 VH | QVQLQESGPGLVKPSQTLSLTCAVYGDSFSSGYWNWIRKHPGKGLEYMGYISYNGITYHNPSLKSRI TINRDTSKNQYSLQLNSVTPEDTAVYFCARYRYDYDGGHAMDYWGQGTLVTVSS |
| 38 | OX40mAb13 VH DNA | CAGGTGCAGCTGCAGGAAAGCGGCCCTGGCCTGGTCAAGCCCAGCCAGACCCTGAGCCTGAC CTGTGCCGTGTACGGCGACAGCTTCAGCAGCGGCTACTGGAACTGGATCCGGAAGCACCCCGG CAAGGGCCTGGAATACATGGGCTACATCAGCTACAACGGCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTTCTGCGCCCGGTACAGATACGACTACGACGGCGG CCACGCCATGGACTACTGGGGCCAGGGCACCCTGGTCACCGTGTCCTCT |
| 39 | OX40mAb14 VH | QVQLQESGPGLVKPSQTLSLTCAVYGDSFSSGYWNWIRKHPGKGLEYIGYISYNGITYHNPSLKSRIT INRDTSKNQYSLQLNSVTPEDTAVYFCARYRYDYDGGHAMDYWGQGTLVTVSS |
| 40 | OX40mAb14 VH DNA | CAGGTGCAGCTGCAGGAAAGCGGCCCTGGCCTGGTCAAGCCCAGCCAGACCCTGAGCCTGAC CTGTGCCGTGTACGGCGACAGCTTCAGCAGCGGCTACTGGAACTGGATCCGGAAGCACCCCGG CAAGGGCCTGGAATACATCGGCTACATCAGCTACAACGGCATCACCTACCACAACCCCAGCCTG AAGTCCCGGATCACCATCAACCGGGACACCAGCAAGAACCAGTACTCCCTGCAGCTGAACAGC GTGACCCCCGAGGACACCGCCGTGTACTTCTGCGCCCGGTACAGATACGACTACGACGGCGGC CACGCCATGGACTACTGGGGCCAGGGCACCCTGGTCACCGTGTCCTCT |
| 41 | OX40mAb15 VH | QVQLQESGPGLVKPSQTLSLTCAVYGDSFSSGYWNWIRKHPGKGLEYIGYISYNGITYHNPSLKSRIT INRDTSKNQFSLQLNSVTPEDTAVYFCARYRYDYDGGHAMDYWGQGTLVTVSS |
| 42 | OX40mAb15 VH DNA | CAGGTGCAGCTGCAGGAAAGCGGCCCTGGCCTGGTCAAGCCCAGCCAGACCCTGAGCCTGAC CTGTGCCGTGTACGGCGACAGCTTCAGCAGCGGCTACTGGAACTGGATCCGGAAGCACCCCGG CAAGGGCCTGGAATACATCGGCTACATCAGCTACAACGGCATCACCTACCACAACCCCAGCCTG AAGTCCCGGATCACCATCAACCGGGACACCAGCAAGAACCAGTTCTCCCTGCAGCTGAACAGC GTGACCCCCGAGGACACCGCCGTGTACTTCTGCGCCCGGTACAGATACGACTACGACGGCGGC CACGCCATGGACTACTGGGGCCAGGGCACCCTGGTCACCGTGTCCTCT |
| 43 | OX40mAb16 VH | QVQLQESGPGLVKPSQTLSLTCAVYGDSFSSGYWNWIRKHPGKGLEYIGYISYNGITYHNPSLKSRIT INRDTSKNQYSLQLNSVTPEDTAVYYCARYRYDYDGGHAMDYWGQGTLVTVSS |
| 44 | OX40mAb16 VH DNA | CAGGTGCAGCTGCAGGAAAGCGGCCCTGGCCTGGTCAAGCCCAGCCAGACCCTGAGCCTGAC CTGTGCCGTGTACGGCGACAGCTTCAGCAGCGGCTACTGGAACTGGATCCGGAAGCACCCCGG CAAGGGCCTGGAATACATCGGCTACATCAGCTACAACGGCATCACCTACCACAACCCCAGCCTG AAGTCCCGGATCACCATCAACCGGGACACCAGCAAGAACCAGTACTCCCTGCAGCTGAACAGC GTGACCCCCGAGGACACCGCCGTGTACTACTGCGCCCGGTACAGATACGACTACGACGGCGGC CACGCCATGGACTACTGGGGCCAGGGCACCCTGGTCACCGTGTCCTCT |
| 45 | OX40mAb17 VH | QVQLQESGPGLVKPSQTLSLTCAVYGDSFSSGYWNWIRKHPGKGLEYIGYISYNGITYHNPSLKSRIT INRDTSKNQFSLQLNSVTPEDTAVYYCARYRYDYDGGHAMDYWGQGTLVTVSS |
| 46 | OX40mAb VH17 DNA | CAGGTGCAGCTGCAGGAAAGCGGCCCTGGCCTGGTCAAGCCCAGCCAGACCCTGAGCCTGAC CTGTGCCGTGTACGGCGACAGCTTCAGCAGCGGCTACTGGAACTGGATCCGGAAGCACCCCGG CAAGGGCCTGGAATACATCGGCTACATCAGCTACAACGGCATCACCTACCACAACCCCAGCCTG AAGTCCCGGATCACCATCAACCGGGACACCAGCAAGAACCAGTTCTCCCTGCAGCTGAACAGC GTGACCCCCGAGGACACCGCCGTGTACTACTGCGCCCGGTACAGATACGACTACGACGGCGGC CACGCCATGGACTACTGGGGCCAGGGCACCCTGGTCACCGTGTCCTCT |
| 47 | OX40mAb18 VH | QVQLQESGPGLVKPSQTLSLTCAVYGGSFSSGYWNWIRKHPGKGLEYIGYISYNGITYHNPSLKSRIT INPDTSKNQYSLQLNSVTPEDTAVYFCARYRYDYDGGHAMDYWGQGTLVTVSS |

-continued

TABLE OF SEQUENCES

| SEQ ID NO | Description | Sequence |
|---|---|---|
| 48 | OX40mAb18 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGGCATCACCTACCACAACCCCAGCCT GAAGTCCCGGATCACCATCAACCCCGACACCAGCAAGAACCAGTACTCCCTGCAGCTGAACAG CGTGACCCCCGAGGACACCGCCGTGTACTTCTGCGCCCGGTACAGATACGACTACGACGGCGG CCACGCCATGGACTACTGGGGCCAGGGCACCCTGGTCACCGTGTCCTCT |
| 49 | OX40mAb19 VH | QVQLQESGPGLVKPSQTLSLTCAVYGGSFSSGYWNWIRKHPGKGLEYIGYISYNGITYHNPSLKSRIT INRDTSKNQYSLQLNSVTPEDTAVYFCARYRYDYDGGHAMDYWGQGTLVTVSS |
| 50 | OX40mAb19 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGGCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTTCTGCGCCCGGTACAGATACGACTACGACGGCGG CCACGCCATGGACTACTGGGGCCAGGGCACCCTGGTCACCGTGTCCTCT |
| 51 | OX40mAb20 VH | QVQLQESGPGLVKPSQTLSLTCAVYGGSFSSGYWNWIRKHPGKGLEYIGYISYNGITYHNPSLKSRIT INRDTSKNQYSLQLNSVTPEDTAVYYCARYRYDYDGGHAMDYWGQGTLVTVSS |
| 52 | OX40mAb20 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGGCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTACTGCGCCCGGTACAGATACGACTACGACGGCGG CCACGCCATGGACTACTGGGGCCAGGGCACCCTGGTCACCGTGTCCTCT |
| 53 | OX40mAb21 VH | QVQLQESGPGLVKPSQTLSLTCAVYGGSFSSGYWNWIRKHPGKGLEYIGYISYNGITYHNPSLKSRIT INPDTSKNQYSLQLNSVTPEDTAVYYCARYRYDYDGGHAMDYWGQGTLVTVSS |
| 54 | OX40mAb21 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGGCATCACCTACCACAACCCCAGCCT GAAGTCCCGGATCACCATCAACCCCGACACCAGCAAGAACCAGTACTCCCTGCAGCTGAACAG CGTGACCCCCGAGGACACCGCCGTGTACTACTGCGCCCGGTACAGATACGACTACGACGGCGG CCACGCCATGGACTACTGGGGCCAGGGCACCCTGGTCACCGTGTCCTCT |
| 55 | OX40mAb22 VH | QVQLQESGPGLVKPSQTLSLTCAVYGGSFSSGYWNWIRKHPGKGLEYIGYISYNAITYHNPSLKSRIT INRDTSKNQYSLQLNSVTPEDTAVYYCARYKYDYDAGHAMDYWGQGTLVTVSS |
| 56 | OX40mAb22 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGCCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTACTGCGCCCGGTACAAATACGACTACGACGCCGG CCACGCCATGGACTACTGGGGCCAGGGCACCCTGGTCACCGTGTCCTCT |
| 57 | OX40mAb23 VH | QVQLQESGPGLVKPSQTLSLTCAVYGGSFSSGYWNWIRKHPGKGLEYIGYISYNAITYHNPSLKSRIT INRDTSKNQYSLQLNSVTPEDTAVYYCARYRYDYDGGHAMDYWGQGTLVTVSS |
| 58 | OX40mAb23 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGCCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTACTGCGCCCGGTACAGATACGACTACGACGGCGG CCACGCCATGGACTACTGGGGCCAGGGCACCCTGGTCACCGTGTCCTCT |
| 59 | OX40mAb24 VH | QVQLQESGPGLVKPSQTLSLTCAVYGGSFSSGYWNWIRKHPGKGLEYIGYISYNGITYHNPSLKSRIT INRDTSKNQYSLQLNSVTPEDTAVYYCARYKYDYDGGHAMDYWGQGTLVTVSS |
| 60 | OX40mAb24 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGGCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTACTGCGCCCGGTACAAATACGACTACGACGGCGG CCACGCCATGGACTACTGGGGCCAGGGCACCCTGGTCACCGTGTCCTCT |
| 61 | OX40mAb25 VH | QVQLQESGPGLVKPSQTLSLTCAVYGGSFSSGYWNWIRKHPGKGLEYIGYISYSGITYHNPSLKSRITI NRDTSKNQYSLQLNSVTPEDTAVYYCARYRYDYDGGHAMDYWGQGTLVTVSS |

-continued

TABLE OF SEQUENCES

| SEQ ID NO | Description | Sequence |
|---|---|---|
| 62 | OX40mAb25 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAGCGGCATCACCTACCACAACCCCAGCC TGAAGTCCCGGATCACCATCAACCGGGACACCAGCAAGAACCAGTACTCCCTGCAGCTGAACA GCGTGACCCCCGAGGACACCGCCGTGTACTACTGCGCCCGGTACAGATACGACTACGACGGCG GCCACGCCATGGACTACTGGGGCCAGGGCACCCTGGTCACCGTGTCCTCT |
| 63 | OX40mAb25a VH | QVQLQESGPGLVKPSQTLSLTCAVYGGSFSSGYWNWIRKHPGKGLEYIGYISYSGITYHNPSLKSRITI NRDTSKNQYSLQLNSVTPEDTAVYYCARYKYDYDGGHAMDYWGQGTLVTVSS |
| 64 | OX40mAb25a VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAGCGGCATCACCTACCACAACCCCAGCC TGAAGTCCCGGATCACCATCAACCGGGACACCAGCAAGAACCAGTACTCCCTGCAGCTGAACA GCGTGACCCCCGAGGACACCGCCGTGTACTACTGCGCCCGGTACAAATACGACTACGACGGCG GCCACGCCATGGACTACTGGGGCCAGGGCACCCTGGTCACCGTGTCCTCT |
| 65 | OX40mAb26 VH | EVQLQESGPSLVKPSQTLSLTCSVTGDSFTSGYWNWIRKFPGNRLEYMGYISYNAITYHNPSLKSRIS ITRDTSKNHYYLQLNSVTTEDTATYFCARYRYDYDGGHAMDYWGQGTLVTVSS |
| 66 | OX40mAb26 VH DNA | GAGGTGCAGCTGCAGGAAAGCGGCCCCAGCCTGGTCAAGCCCAGCCAGACCCTGAGCCTGAC CTGCAGCGTGACCGGCGACAGCTTCACCAGCGGCTACTGGAACTGGATCCGGAAGTTCCCCGG CAACCGGCTCGAGTACATGGGCTACATCAGCTACAACGCCATCACCTACCACAACCCCAGCCTG AAGTCCCGGATCAGCATCACCCGGGACACCAGCAAGAACCACTACTACCTGCAGCTGAACAGC GTGACCACCGAGGACACCGCCACCTACTTTTGCGCCCGGTACAGATACGACTACGACGGCGGC CACGCCATGGACTACTGGGGCCAGGGCACCCTGGTCACCGTGTCCTCT |
| 67 | OX40mAb27 VH | QVQLQESGPGLVKPSQTLSLTCAVYGGSFSSGYWNWIRKHPGKGLEYIGYISYNAITYHNPSLKSRIT INRDTSKNQYSLQLNSVTPEDTAVYYCARYKYDYDGGHAMDYWGQGTLVTVSS |
| 68 | OX40mA27 VH DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGCCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTACTGCGCCCGGTACAAATACGACTACGACGGCGG CCACGCCATGGACTACTGGGGCCAGGGCACCCTGGTCACCGTGTCCTCT |
| 69 | HumanIgG1 CH chain | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKRVEPKSCDKTHTCPPCPAPELLGGPSVFLFPPKPKDTLMI SRTPEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHNHYTQKSLSLSPGK |
| 70 | HumanIgG1 CH chain DNA | GCgTCgACCAAGGGCCCATCcGTCTTCCCCCTGGCACCCTCCTCCAAGAGCACCTCTGGGGGCA CAGCGGCCCTGGGCTGCCTGGTCAAGGACTACTTCCCCGAACCGGTGACGGTGTCcTGGAACT CAGGCGCtCTGACCAGCGGCGTGCACACCTTCCCGGCTGTCCTACAGTCCTCAGGACTCTACTC CCTCAGCAGCGTGGTGACCGTGCCCTCCAGCAGCTTGGGCACCCAGACCTACATCTGCAACGT GAATCACAAGCCCAGCAACACCAAGGTGGACAAGAGAGTTGAGCCCAAATCTTGTGACAAAAC TCACACATGCCCACCGTGCCCAGCACCTGAACTCCTGGGGGGACCGTCAGTCTTCCTCTTCCCC CCAAAACCCAAGGACACCCTCATGATCTCCCGGACCCCTGAGGTCACATGCGTGGTGGTGGAC GTGAGCCACGAAGACCCTGAGGTCAAGTTCAACTGGTACGTGGACGGCGTGGAGGTGCATAA TGCCAAGACAAAGCCGCGGGAGGAGCAGTACAACAGCACGTACCGTGTGGTCAGCGTCCTCA CCGTCCTGCACCAGGACTGGCTGAATGGCAAGGAGTACAAGTGCAAGGTCTCCAACAAAGCCC TCCCAGCCCCCATCGAGAAAACCATCTCCAAAGCCAAAGGGCAGCCCCGAGAACCACAGGTcT ACACCCTGCCCCCATCCCGGGAGGAGATGACCAAGAACCAGGTCAGCCTGACCTGCCTGGTCA AAGGCTTCTATCCCAGCGACATCGCCGTGGAGTGGGAGAGCAATGGGCAGCCGGAGAACAAC TACAAGACCACGCCTCCCGTGCTGGACTCCGACGGCTCCTTCTTCCTCTATAGCAAGCTCACCGT GGACAAGAGCAGGTGGCAGCAGGGGAACGTCTTCTCATGCTCCGTGATGCATGAGGCTCTGC ACAACCACTACACGCAGAAGAGCttaagCCTGTCTCCGGGTAAA |
| 71 | OX40mAb24 heavy chain | QVQLQESGPGLVKPSQTLSLTCAVYGGSFSSGYWNWIRKHPGKGLEYIGYISYNGITYHNPSLKSRIT INRDTSKNQYSLQLNSVTPEDTAVYYCARYKYDYDGGHAMDYWGQGTLVTVSSASTKGPSVFPLA PSSKSTSGGTAALGCLVKDYFPEPVTVSWNSGALTSGVHTFPAVLQSSGLYSLSSVVTVPSSSLGTQT YICNVNHKPSNTKVDKRVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGKEYKCKVSNKAL PAPIEKTISKAKGQPREPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSPGK |
| 72 | OX40mAb24 heavy chain DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGGCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTACTGCGCCCGGTACAAATACGACTACGACGGCGG |

-continued

TABLE OF SEQUENCES

| SEQ ID NO | Description | Sequence |
|---|---|---|
| | | CCACGCCATGGACTACTGGGGCCAGGGCACCCTGGTCACCGTGTCCTCTGCgTCgACCAAGGG<br>CCCATCcGTCTTCCCCCTGGCACCCTCCTCCAAGAGCACCTCTGGGGGCACAGCGGCCCTGGGC<br>TGCCTGGTCAAGGACTACTTCCCCGAACCGGTGACGGTGTCcTGGAACTCAGGCGCtCTGACCA<br>GCGGCGTGCACACCTTCCCGGCTGTCCTACAGTCCTCAGGACTCTACTCCCTCAGCAGCGTGGT<br>GACCGTGCCCTCCAGCAGCTTGGGCACCCAGACCTACATCTGCAACGTGAATCACAAGCCCAG<br>CAACACCAAGGTGGACAAGAGAGTTGAGCCCAAATCTTGTGACAAAACTCACACATGCCCACC<br>GTGCCCAGCACCTGAACTCCTGGGGGGACCGTCAGTCTTCCTCTTCCCCCCAAAACCCAAGGAC<br>ACCCTCATGATCTCCCGGACCCCTGAGGTCACATGCGTGGTGGTGGACGTGAGCCACGAAGAC<br>CCTGAGGTCAAGTTCAACTGGTACGTGGACGGCGTGGAGGTGCATAATGCCAAGACAAAGCC<br>GCGGGAGGAGCAGTACAACAGCACGTACCGTGTGGTCAGCGTCCTCACCGTCCTGCACCAGG<br>ACTGGCTGAATGGCAAGGAGTACAAGTGCAAGGTCTCCAACAAAGCCCTCCCAGCCCCCATCG<br>AGAAAACCATCTCCAAAGCCAAAGGGCAGCCCCGAGAACCACAGGTcTACACCCTGCCCCCAT<br>CCCGGGAGGAGATGACCAAGAACCAGGTCAGCCTGACCTGCCTGGTCAAAGGCTTCTATCCCA<br>GCGACATCGCCGTGGAGTGGGAGAGCAATGGGCAGCCGGAGAACAACTACAAGACCACGCCT<br>CCCGTGCTGGACTCCGACGGCTCCTTCTTCCTCTATAGCAAGCTCACCGTGGACAAGAGCAGGT<br>GGCAGCAGGGGAACGTCTTCTCATGCTCCGTGATGCATGAGGCTCTGCACAACCACTACACGC<br>AGAAGAGCttaagCCTGTCTCCGGGTAAA |
| 73 | OX40mAb28 heavy chain | QVQLQESGPGLVKPSQTLSLTCAVYGGSFSSGYWNWIRKHPGKGLEYIGYISYNGITYHNPSLKSRIT<br>INRDTSKNQYSLQLNSVTPEDTAVYYCARYKYDYDGGHAMDYWGQGTLVTVSSASTKGPSVFPLA<br>PCSRSTSESTAALGCLVKDYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLFPPKPKDTLMISRTPEVTCVVVDVS<br>QEDPEVQFNWYVDGVEVHNAKTKPREEQFNSTYRVVSVLTVLHQDWLNGKEYKCKVSNKGLPSSI<br>EKTISKAKGQPREPQVYTLPPSQEEMTKNQVSLTCLVKGFYPSDIAVEWESNGQPENNYKTTPPVL<br>DSDGSFFLYSRLTVDKSRWQEGNVFSCSVMHEALHNHYTQKSLSLSLGK |
| 74 | OX40mAb28 heavy chain DNA | CAGGTGCAGCTGCAGGAAAGCGGCCCTGGCCTGGTCAAGCCCAGCCAGACCCTGAGCCTGAC<br>CTGTGCCGTGTACGGCGGCAGCTTCAGCAGCGGCTACTGGAACTGGATCCGGAAGCACCCCG<br>GCAAGGGCCTGGAATACATCGGCTACATCAGCTACAACGGCATCACCTACCACAACCCCAGCCT<br>GAAGTCCCGGATCACCATCAACCGGGACACCAGCAAGAACCAGTACTCCCTGCAGCTGAACAG<br>CGTGACCCCCGAGGACACCGCCGTGTACTACTGCGCCCGGTACAAATACGACTACGACGGCGG<br>CCACGCCATGGACTACTGGGGCCAGGGCACCCTGGTCACCGTGTCCTCTGCGTCGACCAAGGG<br>CCCCAGCGTGTTCCCCCTGGCCCCTTGCAGCAGAAGCACCAGCGAGAGCACAGCCGCCCTGGG<br>CTGCCTGGTGAAGGACTACTTCCCCGAGCCCGTGACCGTGTCCTGGAACAGCGGCGCTCTGAC<br>CAGCGGCGTGCATACCTTCCCCGCCGTGCTCCAGAGCAGCGGACTGTACTCCCTGAGCAGCGT<br>GGTGACCGTGCCTTCCAGCAGCCTGGGCACCAAGACCTACACCTGCAACGTGGACCACAAGCC<br>CAGCAACACCAAGGTGGACAAGAGAGTGGAGAGCAAGTACGGCCCTCCCTGCCCCCCTTGCCC<br>TGCCCCCGAGTTCCTGGGCGGACCTAGCGTGTTCCTGTTCCCCCCCAAGCCCAAGGACACCCTG<br>ATGATCAGCAGAACCCCCGAGGTGACCTGCGTGGTGGTGGACGTGTCCCAGGAGGACCCCGA<br>GGTCCAGTTTAATTGGTACGTGGACGGCGTGGAAGTGCATAACGCCAAGACCAAGCCCAGAG<br>AGGAGCAGTTCAACAGCACCTACAGAGTGGTGTCCGTGCTGACCGTGCTGCACCAGGACTGGC<br>TGAACGGCAAGGAATACAAGTGCAAGGTCTCCAACAAGGGCCTGCCTAGCAGCATCGAGAAG<br>ACCATCAGCAAGGCCAAGGGCCAGCCACGGGAGCCCCAGGTCTACACCCTGCCACCTAGCCAA<br>GAGGAGATGACCAAGAACCAGGTGTCCCTGACCTGTCTGGTGAAAGGCTTCTATCCCAGCGAT<br>ATCGCCGTGGAGTGGGAGAGCAACGGCCAGCCCGAGAACAACTACAAGACCACCCCCCCTGT<br>GCTGGACAGCGACGGCAGCTTCTTCCTGTACTCCAGACTGACCGTGGACAAGTCCAGATGGCA<br>GGAGGGCAACGTCTTCAGCTGCTCCGTGATGCACGAGGCCCTGCACAACCACTACACCCAGAA<br>GTCCCTGAGCCTGAGCCTGGGCAAG |
| 75 | OX40mAb29 heavy chain | QVQLQESGPGLVKPSQTLSLTCAVYGGSFSSGYWNWIRKHPGKGLEYIGYISYNGITYHNPSLKSRIT<br>INRDTSKNQYSLQLNSVTPEDTAVYYCARYKYDYDGGHAMDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQT<br>YICNVNHKPSNTKVDKRVEPKSCDKTHTCPPCPAPEFEGGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKAL<br>PASIEKTISKAKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 76 | OX40mAb29 heavy chain DNA | CAGGTGCAGCTGCAGGAAAGCGGCCCTGGCCTGGTCAAGCCCAGCCAGACCCTGAGCCTGAC<br>CTGTGCCGTGTACGGCGGCAGCTTCAGCAGCGGCTACTGGAACTGGATCCGGAAGCACCCCG<br>GCAAGGGCCTGGAATACATCGGCTACATCAGCTACAACGGCATCACCTACCACAACCCCAGCCT<br>GAAGTCCCGGATCACCATCAACCGGGACACCAGCAAGAACCAGTACTCCCTGCAGCTGAACAG<br>CGTGACCCCCGAGGACACCGCCGTGTACTACTGCGCCCGGTACAAATACGACTACGACGGCGG<br>CCACGCCATGGACTACTGGGGCCAGGGCACCCTGGTCACCGTGTCCTCTGCGTCGACCAAGGG<br>CCCATCCGTCTTCCCCCTGGCACCCTCCTCCAAGAGCACCTCTGGGGGCACAGCGGCCCTGGGC<br>TGCCTGGTCAAGGACTACTTCCCCGAACCGGTGACGGTGTCcTGGAACTCAGGCGCtCTGACCA<br>GCGGCGTGCACACCTTCCCGGCTGTCCTACAGTCCTCAGGACTCTACTCCCTCAGCAGCGTGGT<br>GACCGTGCCCTCCAGCAGCTTGGGCACCCAGACCTACATCTGCAACGTGAATCACAAGCCCAG<br>CAACACCAAGGTGGACAAGAGAGTTGAGCCCAAATCTTGTGACAAAACTCACACATgcCCacCG<br>TGCCCAGCACCTGAATTCGAGGGGGGAcCGTCAGTCTTCCTCTTCCCCCCAAAACCCaaGgACAC<br>CCTCATGATCTCCCGGACCCCTGAGGTCACATGCGTGGTGGTGGACGTGAGCCACGAAGACCC<br>TGAGGTCAAGTTCAACTGGTACGTGGACGGCGTGGAGGTGCATAATGCCAAGACAAAGCCGC<br>GGGAGGAGCAGTACAACAGCACGTACCGTGTGGTCAGCGTCCTCACCGTCCTGCACCAGGACT<br>GGCTGAATGGCAAGGAGTACAAGTGCAAGGTCTCCAACAAAGCCCTCCCAGCCTCCATCGAGA |

-continued

TABLE OF SEQUENCES

| SEQ ID NO | Description | Sequence |
|---|---|---|
| | | AAACCATCTCCAAAGCCAAAGGGCAGCCCCGAGAACCACAGGTcTACACCCTGCCCCCATCCCG<br>GGAGGAGATGACCAAGAACCAGGTCAGCCTGACCTGCCTGGTCAAAGGCTTCTATCCCAGCGA<br>CATCGCCGTGGAGTGGGAGAGCAATGGGCAGCCGGAGAACAACTACAAGACCACGCCTCCCG<br>TGCTGGACTCCGACGGCTCCTTCTTCCTCTATAGCAAGCTCACCGTGGACAAGAGCAGGTGGCA<br>GCAGGGGAACGTCTTCTCATGCTCCGTGATGCATGAGGCTCTGCACAACCACTACACGCAGAA<br>GAGCCTCTCCCTGTCTCCGGGTAAA |
| 77 | OX40mAb31 heavy chain | QVQLQESGPGLVKPSQTLSLTCAVYGGSFSSGYWNWIRKHPGKGLEYIGYISYNAITYHNPSLKSRIT<br>INRDTSKNQYSLQLNSVTPEDTAVYYCARYKYDYDGGHAMDYWGQGTLVTVSSASTKGPSVFPLA<br>PCSRSTSESTAALGCLVKDYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLFPPKPKDTLMISRTPEVTCVVVDVS<br>QEDPEVQFNWYVDGVEVHNAKTKPREEQFNSTYRVVSVLTVLHQDWLNGKEYKCKVSNKGLPSSI<br>EKTISKAKGQPREPQVYTLPPSQEEMTKNQVSLTCLVKGFYPSDIAVEWESNGQPENNYKTTPPVL<br>DSDGSFFLYSRLTVDKSRWQEGNVFSCSVMHEALHNHYTQKSLSLSLGK |
| 78 | OX40mAb31 heavy chain DNA | CAGGTGCAGCTGCAGGAAAGCGGCCCTGGCCTGGTCAAGCCCAGCCAGACCCTGAGCCTGAC<br>CTGTGCCGTGTACGGCGGCAGCTTCAGCAGCGGCTACTGGAACTGGATCCGGAAGCACCCCG<br>GCAAGGGCCTGGAATACATCGGCTACATCAGCTACAACGCCATCACCTACCACAACCCCAGCCT<br>GAAGTCCCGGATCACCATCAACCGGGACACCAGCAAGAACCAGTACTCCCTGCAGCTGAACAG<br>CGTGACCCCCGAGGACACCGCCGTGTACTACTGCGCCCGGTACAAATACGACTACGACGGCGG<br>CCACGCCATGGACTACTGGGGCCAGGGCACCCTGGTCACCGTGTCCTCTGCGTCGACCAAGGG<br>CCCCAGCGTGTTCCCCCTGGCCCCTTGCAGCAGAAGCACCAGCGAGAGCACAGCCGCCCTGGG<br>CTGCCTGGTGAAGGACTACTTCCCCGAGCCCGTGACCGTGTCCTGGAACAGCGGCGCTCTGAC<br>CAGCGGCGTGCATACCTTCCCCGCCGTGCTCCAGAGCAGCGGACTGTACTCCCTGAGCAGCGT<br>GGTGACCGTGCCTTCCAGCAGCCTGGGCACCAAGACCTACACCTGCAACGTGGACCACAAGCC<br>CAGCAACACCAAGGTGGACAAGAGAGTGGAGAGCAAGTACGGCCCTCCCTGCCCCCCTTGCCC<br>TGCCCCCGAGTTCCTGGGCGGACCTAGCGTGTTCCTGTTCCCCCCCAAGCCCAAGGACACCCTG<br>ATGATCAGCAGAACCCCCGAGGTGACCTGCGTGGTGGTGGACGTGTCCCAGGAGGACCCCGA<br>GGTCCAGTTTAATTGGTACGTGGACGGCGTGGAAGTGCATAACGCCAAGACCAAGCCCAGAG<br>AGGAGCAGTTCAACAGCACCTACAGAGTGGTGTCCGTGCTGACCGTGCTGCACCAGGACTGGC<br>TGAACGGCAAGGAATACAAGTGCAAGGTCTCCAACAAGGGCCTGCCTAGCAGCATCGAGAAG<br>ACCATCAGCAAGGCCAAGGGCCAGCCACGGGAGCCCCAGGTCTACACCCTGCCACCTAGCCAA<br>GAGGAGATGACCAAGAACCAGGTGTCCCTGACCTGTCTGGTGAAAGGCTTCTATCCCAGCGAT<br>ATCGCCGTGGAGTGGGAGAGCAACGGCCAGCCCGAGAACAACTACAAGACCACCCCCCCTGT<br>GCTGGACAGCGACGGCAGCTTCTTCCTGTACTCCAGACTGACCGTGGACAAGTCCAGATGGCA<br>GGAGGGCAACGTCTTCAGCTGCTCCGTGATGCACGAGGCCCTGCACAACCACTACACCCAGAA<br>GTCCCTGAGCCTGAGCCTGGGCAAG |
| 79 | OX40mAb32 heavy chain | QVQLQESGPGLVKPSQTLSLTCAVYGGSFSSGYWNWIRKHPGKGLEYIGYISYNAITYHNPSLKSRIT<br>INRDTSKNQYSLQLNSVTPEDTAVYYCARYKYDYDGGHAMDYWGQGTLVTVSSASTKGPSVFPLA<br>PSSKSTSGGTAALGCLVKDYFPEPVTVSWNSGALTSGVHTFPAVLQSSGLYSLSSVVTVPSSSLGTQT<br>YICNVNHKPSNTKVDKRVEPKSCDKTHTCPPCPAPEFEGGPSVFLFPPKPKDTLMISRTPEVTCVVV<br>DVSHEDPEVKFNWYVDGVEVHNAKTKPREEQYNSTYRVVSVLTVLHQDWLNGKEYKCKVSNKAL<br>PASIEKTISKAKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 80 | OX40mAb32 heavy chain DNA | CAGGTGCAGCTGCAGGAAAGCGGCCCTGGCCTGGTCAAGCCCAGCCAGACCCTGAGCCTGAC<br>CTGTGCCGTGTACGGCGGCAGCTTCAGCAGCGGCTACTGGAACTGGATCCGGAAGCACCCCG<br>GCAAGGGCCTGGAATACATCGGCTACATCAGCTACAACGCCATCACCTACCACAACCCCAGCCT<br>GAAGTCCCGGATCACCATCAACCGGGACACCAGCAAGAACCAGTACTCCCTGCAGCTGAACAG<br>CGTGACCCCCGAGGACACCGCCGTGTACTACTGCGCCCGGTACAAATACGACTACGACGGCGG<br>CCACGCCATGGACTACTGGGGCCAGGGCACCCTGGTCACCGTGTCCTCTGCGTCGACCAAGGG<br>CCCATCCGTCTTCCCCCTGGCACCCTCCTCCAAGAGCACCTCTGGGGGCACAGCGGCCCTGGGC<br>TGCCTGGTCAAGGACTACTTCCCCGAACCGGTGACGGTGTCcTGGAACTCAGGCGCtCTGACCA<br>GCGGCGTGCACACCTTCCCGGCTGTCCTACAGTCCTCAGGACTCTACTCCCTCAGCAGCGTGGT<br>GACCGTGCCCTCCAGCAGCTTGGGCACCCAGACCTACATCTGCAACGTGAATCACAAGCCCAG<br>CAACACCAAGGTGGACAAGAGAGTTGAGCCCAAATCTTGTGACAAAACTCACACATgcCCacCG<br>TGCCCAGCACCTGAATTCGAGGGGGGAcCGTCAGTCTTCCTCTTCCCCCCAAAACCCaaGgACAC<br>CCTCATGATCTCCCGGACCCCTGAGGTCACATGCGTGGTGGTGGACGTGAGCCACGAAGACCC<br>TGAGGTCAAGTTCAACTGGTACGTGGACGGCGTGGAGGTGCATAATGCCAAGACAAAGCCGC<br>GGGAGGAGCAGTACAACAGCACGTACCGTGTGGTCAGCGTCCTCACCGTCCTGCACCAGGACT<br>GGCTGAATGGCAAGGAGTACAAGTGCAAGGTCTCCAACAAAGCCCTCCCAGCCTCCATCGAGA<br>AAACCATCTCCAAAGCCAAAGGGCAGCCCCGAGAACCACAGGTcTACACCCTGCCCCCATCCCG<br>GGAGGAGATGACCAAGAACCAGGTCAGCCTGACCTGCCTGGTCAAAGGCTTCTATCCCAGCGA<br>CATCGCCGTGGAGTGGGAGAGCAATGGGCAGCCGGAGAACAACTACAAGACCACGCCTCCCG<br>TGCTGGACTCCGACGGCTCCTTCTTCCTCTATAGCAAGCTCACCGTGGACAAGAGCAGGTGGCA<br>GCAGGGGAACGTCTTCTCATGCTCCGTGATGCATGAGGCTCTGCACAACCACTACACGCAGAA<br>GAGCCTCTCCCTGTCTCCGGGTAAA |
| 81 | OX40mAb37 heavy chain | QVQLQESGPGLVKPSQTLSLTCAVYGGSFSSGYWNWIRKHPGKGLEYIGYISYNGITYHNPSLKSRIT<br>INRDTSKNQYSLQLNSVTPEDTAVYYCARYKYDYDGGHAMDYWGQGTLVTVSSAKTTPPSVYPLA<br>PGSAAQTNSMVTLGCLVKGYFPEPVTVTWNSGSLSSGVHTFPAVLQSDLYTLSSSVTVPSSTWPSE<br>TVTCNVAHPASSTKVDKKIVPRDCGCKPCICTVPEVSSVFIFPPKPKDVLTITLTPKVTCVVVDISKDD |

-continued

TABLE OF SEQUENCES

| SEQ ID NO | Description | Sequence |
|---|---|---|
| | | PEVQFSWFVDDVEVHTAQTQPREEQFNSTFRSVSELPIMHQDWLNGKEFKCRVNSAAFPAPIEKTI SKTKGRPKAPQVYTIPPPKEQMAKDKVSLTCMITDFFPEDITVEWQWNGQPAENYKNTQPIMDT DGSYFVYSKLNVQKSNWEAGNTFTCSVLHEGLHNHHTEKSLSHSPGK |
| 82 | OX40mAb37 heavy chain DNA | CAGGTGCAGCTGCAGGAAAGCGGCCCTGGCCTGGTCAAGCCCAGCCAGACCCTGAGCCTGAC CTGTGCCGTGTACGGCGGCAGCTTCAGCAGCGGCTACTGGAACTGGATCCGGAAGCACCCCG GCAAGGGCCTGGAATACATCGGCTACATCAGCTACAACGGCATCACCTACCACAACCCCAGCCT GAAGTCCCGGATCACCATCAACCGGGACACCAGCAAGAACCAGTACTCCCTGCAGCTGAACAG CGTGACCCCCGAGGACACCGCCGTGTACTACTGCGCCCGGTACAAATACGACTACGACGGCGG CCACGCCATGGACTACTGGGGCCAGGGCACCCTGGTCACCGTGTCCTCTGCGaaGACGACACC CCCATCTGTCTATCCACTGGCCCCTGGATCTGCTGCCCAAACTAACTCCATGGTGACCCTGGGAT GCCTGGTCAAGGGCTATTTCCCTGAGCCAGTGACAGTGACCTGGAACTCTGGATCCCTGTCCAG CGGTGTGCACACCTTCCCAGCTGTCCTGCAGTCTGACCTCTACACTCTGAGCAGCTCAGTGACT GTCCCCTCCAGCACCTGGCCCAGCGAGACCGTCACCTGCAACGTTGCCCACCCGGCCAGCAGC ACCAAGGTGGACAAGAAAATTGTGCCCAGGGATTGTGGTTGTAAGCCTTGCATATGTACcGTC CCAGAAGTATCATCTGTCTTCATCTTCCCCCCAAAGCCCAAGGATGTGCTCACCATTACTCTGAC TCCTAAGGTCACGTGTGTTGTGGTAGACATCAGCAAGGATGATCCCGAGGTCCAGTTCAGCTG GTTTGTAGATGATGTGGAGGTGCACACAGCTCAGACGCAACCCCGGGAGGAGCAGTTCAACA GCACTTTCCGCTCAGTCAGTGAACTTCCCATCATGCACCAGGACTGGCTCAATGGCAAGGAGTT CAAATGCAGGGTCAACAGTGCAGCTTTCCCTGCCCCCATCGAGAAAACCATCTCCAAAACCAAA GGCAGACCGAAGGCTCCACAGGTGTATtACCATTCCACCTCCCAAGGAGCAGATGGCCAAGGAT AAAGTCAGTCTGACCTGCATGATAACAGACTTCTTCCCTGAAGACATTACTGTGGAGTGGCAGT GGAATGGGCAGCCAGCGGAGAACTACAAGAACACTCAGCCCATCATGGACACAGATGGCTCTT ACTTCGTCTACAGCAAGCTCAATGTGCAGAAGAGCAACTGGGAGGCAGGAAATACTTTCACCT GCTCTGTGTTACATGAGGGCCTGCACAACCACCATACTGAGAAGAGCCTCTCCCACTCTCCTGG TAAA |
| 83 | OX40mAb37 light chain | DIQMTQSPSSLSASVGDRVTITCRASQDISNYLNWYQQKPGKAPKLLIYYTSKLHSGVPSRFSGSGS GTDYTLTISSLQPEDFATYYCQQGSALPWTFGQGTKVEIKRADAAPTVSIFPPSSEQLTSGGASVVCF LNNFYPKDINVKWKIDGSERQNGVLNSWTDQDSKDSTYSMSSTLTLTKDEYERHNSYTCEATHKTS TSPIVKSFNRNEC |
| 84 | OX40mAb37 light chain DNA | GACATCCAGATGACCCAGAGCCCCAGCAGCCTGAGCGCCAGCGTGGGCGACAGAGTGACCAT CACCTGTCGGGCCAGCCAGGACATCAGCAACTACCTGAACTGGTATCAGCAGAAGCCCGGCAA GGCCCCCAAGCTGCTGATCTACTACACCAGCAAGCTGCACAGCGGCGTGCCCAGCAGATTCAG CGGCAGCGGCTCCGGCACCGACTACACCCTGACCATCAGCAGCCTGCAGCCCGAGGACTTCGC CACCTACTACTGCCAGCAGGGCTCCGCCCTGCCCTGGACCTTTGGCCAGGGCACCAAGGTGGA AATCAAGCGGGCTGATGCGGCGCCAACTGTATCCATCTTCCCACCATCCAGTGAGCAGTTAACA TCTGGAGGTGCCTCAGTCGTGTGCTTCTTGAACAACTTCTACCCCAAAGACATCAATGTCAAGT GGAAGATTGATGGCAGTGAACGACAAAATGGCGTCCTGAACAGTTGGACTGATCAGGACAGC AAAGACAGCACCTACAGCATGAGCAGCACCCTCACGTTGACCAAGGACGAGTATGAACGACAT AACAGCTATACCTGTGAGGCCACTCACAAGACATCAACTTCACCCATTGTCAAGAGCTTCAACA GGAATGAGTGT |
| 85 | OX86 VH | QVQLKESGPGLVQPSQTLSLTCTVSGFSLTGYNLHWVRQPPGKGLEWMGRMRYDGDTYYNSVLK SRLSISRDTSKNQVFLKMNSLQTDDTAIYYCTRDGRGDSFDYWGQGVMVTVSS |
| 86 | OX86 heavy chain | QVQLKESGPGLVQPSQTLSLTCTVSGFSLTGYNLHWVRQPPGKGLEWMGRMRYDGDIYYNSVLK SRLSISRDTSKNQVFLKMNSLQTDDTAIYYCTRDGRGDSFDYWGQGVMVTVSSASTTPPSVYPLAP GSAAQTNSMVTLGCLVKGYFPEPVTVTWNSGSLSSGVHTFPAVLQSDLYTLSSSVTVPSSTWPSET VTCNVAHPASSTKVDKKIVPRDCGCKPCICTVPEVSSVFIFPPKPKDVLTITLTPKVTCVVVDISKDDP EVQFSWFVDDVEVHTAQTQPREEQFNSTFRSVSELPIMHQDWLNGKEFKCRVNSAAFPAPIEKTIS KTKGRPKAPQVYTIPPPKEQMAKDKVSLTCMITDFFPEDITVEWQWNGQPAENYKNTQPIMDTD GSYFVYSKLNVQKSNWEAGNTFTCSVLHEGLHNHHTEKSLSHSPGK |
| 87 | OX86 heavy chain DNA | CAGGTGCAGCTGAAGGAGTCAGGACCTGGTCTGGTGCAGCCCTCACAGACCCTGTCCCTCACC TGCACTGTCTCTGGGTTCTCACTAACCGGTTACAATTTACACTGGGTTCGCCAGCCTCCAGGAA AGGGTCTGGAGTGGATGGGAAGAATGAGGTATGATGGAGACACATATTATAATTCAGTTCTCA AATCCCGACTGAGCATCAGCAGGGACACCTCCAAGAACCAAGTTTTCTTGAAAATGAACAGTCT GCAAACGGATGACACAGCCATTTACTATTGTACCAGAGACGGGCGTGGTGACTCCTTTGATTAC TGGGGCCAAGGAGTCATGGTCACAGTCTCCTCCGCGTCGACGACACCCCCATCTGTCTATCCAC TGGCCCCTGGATCTGCTGCCCAAACTAACTCCATGGTGACCCTGGGATGCCTGGTCAAGGGCT ATTTCCCTGAGCCAGTGACAGTGACCTGGAACTCTGGATCCCTGTCCAGCGGTGTGCACACCTT CCCAGCTGTCCTGCAGTCTGACCTCTACACTCTGAGCAGCTCAGTGACTGTCCCCTCCAGCACCT GGCCCAGCGAGACCGTCACCTGCAACGTTGCCCACCCGGCCAGCAGCACCAAGGTGGACAAG AAAATTGTGCCCAGGGATTGTGGTTGTAAGCCTTGCATATGTACCGTCCCAGAAGTATCATCTG TCTTCATCTTCCCCCCAAAGCCCAAGGATGTGCTCACCATTACTCTGACTCCTAAGGTCACGTGT GTTGTGGTAGACATCAGCAAGGATGATCCCGAGGTCCAGTTCAGCTGGTTTGTAGATGATGTG GAGGTGCACACAGCTCAGACGCAACCCCGGGAGGAGCAGTTCAACAGCACTTTCCGCTCAGTC AGTGAACTTCCCATCATGCACCAGGACTGGCTCAATGGCAAGGAGTTCAAATGCAGGGTCAAC AGTGCAGCTTTCCCTGCCCCCATCGAGAAAACCATCTCCAAAACCAAAGGCAGACCGAAGGCT CCACAGGTGTATACCATTCCACCTCCCAAGGAGCAGATGGCCAAGGATAAAGTCAGTCTGACC TGCATGATAACAGACTTCTTCCCTGAAGACATTACTGTGGAGTGGCAGTGGAATGGGCAGCCA |

-continued

TABLE OF SEQUENCES

| SEQ ID NO | Description | Sequence |
|---|---|---|
| | | GCGGAGAACTACAAGAACACTCAGCCCATCATGGACACAGATGGCTCTTACTTCGTCTACAGC AAGCTCAATGTGCAGAAGAGCAACTGGGAGGCAGGAAATACTTTCACCTGCTCTGTGTTACAT GAGGGCCTGCACAACCACCATACTGAGAAGAGCCTCTCCCACTCTCCTGGTAAA |
| 88 | OX86 VL | DIVMTQGALPNPVPSGESASITCRSSQSLVYKDGQTYLNWFLQRPGQSPQLLTYWMSTRASGVSD RFSGSGSGTYFTLKISRVRAEDAGVYYCQQVREYPFTFGSGTKLEIK |
| 89 | OX86 light chain | DIVMTQGALPNPVPSGESASITCRSSQSLVYKDGQTYLNWFLQRPGQSPQLLTYWMSTRASGVSD RFSGSGSGTYFTLKISRVRAEDAGVYYCQQVREYPFTFGSGTKLEIKRADAAPTVSIFPPSSEQLTSGG ASVVCFLNNFYPKDINVKWKIDGSERQNGVLNSWTDQDSKDSTYSMSSTLTLTKDEYERHNSYTCE ATHKTSTSPIVKSFNRNEC |
| 90 | OX86 light chain DNA | GATATTGTGATGACCCAGGGTGCACTCCCCAATCCTGTCCCTTCTGGAGAGTCAGCTTCCATCA CCTGCAGGTCTAGTCAGAGTCTGGTATACAAAGACGGCCAGACATACTTGAATTGGTTTCTGCA GAGGCCAGGACAGTCTCCTCAGCTTCTGACCTATTGGATGTCTACCCGTGCATCAGGAGTCTCA GACAGGTTCAGTGGCAGTGGGTCAGGAACATATTTCACACTGAAAATCAGTAGAGTGAGGGC TGAGGATGCGGGTGTGTATTACTGTCAGCAAGTTCGAGAGTATCCTTTCACTTTCGGCTCAGGG ACGAAGTTGGAAATAAAACGGGCTGATGCGGCGCCAACTGTATCCATCTTCCCACCATCCAGT GAGCAGTTAACATCTGGAGGTGCCTCAGTCGTGTGCTTCTTGAACAACTTCTACCCCAAAGACA TCAATGTCAAGTGGAAGATTGATGGCAGTGAACGACAAAATGGCGTCCTGAACAGTTGGACTG ATCAGGACAGCAAAGACAGCACCTACAGCATGAGCAGCACCCTCACGTTGACCAAGGACGAGT ATGAACGACATAACAGCTATACCTGTGAGGCCACTCACAAGACATCAACTTCACCCATTGTCAA GAGCTTCAACAGGAATGAGTGT |
| 91 | Human OX40 | MCVGARRLGRGPCAALLLLGLGLSTVTGLHCVGDTYPSNDRCCHECRPGNGMVSRCSRSQNTVC RPCGPGFYNDVVSSKPCKPCTWCNLRSGSERKQLCTATQDTVCRCRAGTQPLDSYKPGVDCAPCP PGHFSPGDNQACKPWTNCTLAGKHTLQPASNSSDAICEDRDPPATQPQETQGPPARPITVQPTEA WPRTSQGPSTRPVEVPGGRAVAAILGLGLVLGLLGPLAILLALYLLRRDQRLPPDHKPPGGGSFRT PIQEEQADAHSTLAKI |
| 92 | Mouse OX40 | MYVWVQQPTALLLLGLTLGVTARRLNCVKHTYPSGHKCCRECQPGHGMVSRCDHTRDTLCHPCE TGFYNEAVNYDTCKQCTQCNHRSGSELKQNCTPTQDTVCRCRPGTQPRQDSGYKLGVDCVPCPP GHFSPGNNQACKPWTNCTLSGKQTRHPASDSLDAVCEDRSLLATLLWETQRPTFRPTTVQSTTVW PRTSELPSPPTLVTPEGPAFAVLLGLGLGLLAPLTVLLALYLLRKAWRLPNTPKPCWGNSFRTPIQEE HTDAHFTLAKI |

What is claimed is:

1. An isolated antibody or fragment thereof comprising a humanized heavy chain variable region (VH) and a humanized light chain variable region (VL);

wherein the VH comprises:

(a) a CDR1 comprising the amino acid sequence of SEQ ID NO: 8, (b) a CDR2 comprising the amino acid sequence of SEQ ID NO: 14, and (c) a CDR1 comprising the amino acid sequence of SEQ ID NO: 27, and wherein the VL comprises:

(d) a CDR1 comprising the amino acid sequence of residues 24-34 of SEQ ID NO: 29, (e) a CDR2 comprising the amino acid sequence of residues 50-56 of SEQ ID NO: 29, and (f) a CDR3 comprising the amino acid sequence of residues 89-97 of SEQ ID NO: 29, wherein the antibody or fragment thereof can specifically bind to human OX40.

2. The antibody or fragment of claim 1, wherein the antigen-binding fragment is an Fv fragment, an Fab fragment, an F(ab')2 fragment, an Fab' fragment, a dsFv fragment, an scFv fragment, or an sc(Fv)2 fragment, or any combination thereof.

3. The antibody or fragment thereof of claim 1, which can induce dose-dependent proliferation of activated $CD4^+$ T cells and dose-dependent cytokine release in primary activated human $CD4^+$ T cells in a plate-based assay.

4. The antibody or fragment thereof of claim 3, wherein a 20% maximal proliferation response ($EC_{20}$) can be achieved in primary activated human $CD4^+$ T cells at an antibody concentration of about 14 pM to about 28 pM, a 50% maximal proliferation response ($EC_{50}$) can be achieved in primary activated human $CD4^+$ T cells at an antibody concentration of about 0.3 pM to about 130 pM, and a 90% maximal proliferation response ($EC_{90}$) can be achieved in primary activated human $CD4^+$ T cells at an antibody concentration of about 50 pM to about 90 pM, all as measured by flow cytometry.

5. The antibody or fragment thereof of claim 4, wherein $EC_{20}$ is about 21 pM, $EC_{50}$ is about 28 pM, and $EC_{90}$ is about 72 pM.

6. The antibody or fragment thereof of claim 3, wherein the cytokine is IFNγ, TNFα, IL-5, IL-10, IL-2, IL-4, IL-13, IL-8, IL-12 p70, IL-1β, or any combination thereof.

7. The antibody or fragment thereof of claim 6 wherein the cytokine is IFNγ, TNFα, IL-5, IL-10, IL-13, or any combination thereof.

8. The antibody or fragment thereof of claim 1, which can achieve $CD4^+$ T cell proliferation and cytokine release in primary activated cynomolgus monkey $CD4^+$ T cells and in primary activated rhesus monkey $CD4^+$ T cells.

9. The antibody or fragment thereof of claim 1, which can activate the NFκB pathway in OX40 expressing T cells in the presence of FcγR-expressing cells.

10. The antibody or fragment thereof of claim 9, wherein the OX40-expressing T cells are OX40-expressing Jurkat NFκB-luciferase reporter cells that produce luciferase in response to stimulation of the NFκB signaling pathway.

11. The antibody or fragment thereof of claim 1, which can trigger complement-dependent or antibody-dependent cellular cytotoxicity against OX40-expressing cells.

12. The antibody or fragment thereof of claim 11, which can bind to C1q and trigger NK-mediated antibody-dependent cellular cytotoxicity against the OX40-expressing cells.

13. The antibody or fragment thereof of claim 1, wherein administration of an effective dose to a subject in need of cancer treatment can inhibit tumor growth in the subject.

14. The antibody or fragment thereof of claim 13, wherein the tumor growth inhibition is achieved in the presence of T cells.

15. The antibody or fragment thereof of claim 13, wherein tumor growth is inhibited by at least 10%, at least 20%, at least 30%, at least 40%, and least 50%, at least 60%, or at least 70% compared to administration of an isotype-matched control antibody or fragment thereof.

16. A composition comprising the antibody or fragment thereof of claim 1, and a carrier.

17. An antibody or antigen-binding fragment thereof comprising a humanized heavy chain variable region (VH) and a humanized light chain variable region (VL), wherein the VH comprises the amino acid sequence SEQ ID NO: 59, wherein the VL comprises the amino acid sequence SEQ ID NO: 29, and wherein the antibody or fragment thereof can specifically bind to human OX40.

18. The antibody or fragment thereof of claim 17 comprising the heavy chain amino acid sequence SEQ ID NO: 71 and the light chain amino acid sequence SEQ ID NO: 30.

19. A polynucleotide comprising a nucleic acid that encodes the antibody or fragment thereof, of claim 17.

20. The polynucleotide of claim 19, comprising the nucleic acid of SEQ ID NO: 60, the nucleic acid of SEQ ID NO: 31, the nucleic acid of SEQ ID NO: 72, or any combination thereof.

21. A vector comprising the polynucleotide of claim 19.

22. A host cell comprising the polynucleotide of claim 19.

23. A method of producing an antibody or fragment thereof, comprising culturing the host cell of claim 22 under conditions in which the antibody or fragment thereof encoded by the polynucleotide is expressed, and recovering the antibody or fragment thereof.

24. A host cell comprising the vector of claim 21.

* * * * *

UNITED STATES PATENT AND TRADEMARK OFFICE

CERTIFICATE OF CORRECTION

PATENT NO. : 9,738,723 B2
APPLICATION NO. : 14/877547
DATED : August 22, 2017
INVENTOR(S) : Scott A. Hammond et al.

It is certified that error appears in the above-identified patent and that said Letters Patent is hereby corrected as shown below:

In the Claims

Column 209, Line 55, Claim 1, "(c) a CDR1 comprising the amino acid sequence of" should read --(c) a CDR3 comprising the amino acid sequence of--

Signed and Sealed this
Second Day of January, 2018

Joseph Matal

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 98

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Arg Thr Asp Tyr Ser Leu Thr Ile Thr Asp Leu Asp Gln
65                  70                  75                  80

Glu Asp Ile Ala Thr Tyr Phe Cys Gln Gln Gly Ser Ala Leu Pro Trp
                85                  90                  95

Thr Phe Gly Gln Gly Thr Lys Val Glu Ile Lys
```

```
            100                 105


<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ala Ser Gln Asp Ile Ser Asn Tyr Leu Asn
1               5                   10


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Thr Ser Lys Leu His Ser
1               5


<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln Gly Ser Ala Leu Pro Trp Thr
1               5


<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Phe Thr Ser Gly
            20                  25                  30

Tyr Trp Asn Trp Ile Arg Lys Phe Pro Gly Asn Arg Leu Glu Tyr Met
        35                  40                  45

Gly Tyr Ile Ser Tyr Asn Gly Ile Thr Tyr His Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Asn Ser Val Thr Thr Glu Asp Thr Ala Thr Tyr Phe Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120
```

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser
            20                  25                  30
```

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Asp Ser Phe Ser
            20                  25                  30
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

```
Ser Gly Tyr Trp Asn
1               5
```

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Gln or Lys
<220> FEATURE:
<221> NAME/KEY: MOD_RES
<222> LOCATION: (12)..(12)
<223> OTHER INFORMATION: Trp or Tyr
<220> FEATURE:
<221> NAME/KEY: MOD_RES
<222> LOCATION: (13)..(13)
<223> OTHER INFORMATION: Ile or Met

<400> SEQUENCE: 9

```
Trp Ile Arg Xaa His Pro Gly Lys Gly Leu Glu Xaa Xaa Gly
1               5                   10
```

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Trp Ile Arg Gln His Pro Gly Lys Gly Leu Glu Trp Ile Gly
1 5 10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Trp Ile Arg Lys His Pro Gly Lys Gly Leu Glu Tyr Met Gly
1 5 10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Trp Ile Arg Lys His Pro Gly Lys Gly Leu Glu Trp Ile Gly
1 5 10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Trp Ile Arg Lys His Pro Gly Lys Gly Leu Glu Tyr Ile Gly
1 5 10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Tyr Ile Ser Tyr Asn Gly Ile Thr Tyr His Asn Pro Ser Leu Lys Ser
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Tyr Ile Ser Tyr Asn Ala Ile Thr Tyr His Asn Pro Ser Leu Lys Ser
1 5 10 15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Tyr Ile Ser Tyr Ser Gly Ile Thr Tyr His Asn Pro Ser Leu Lys Ser
1 5 10 15

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (6)..(6)
<223> OTHER INFORMATION: Pro or Arg
<220> FEATURE:
<221> NAME/KEY: MOD_RES
<222> LOCATION: (13)..(13)
<223> OTHER INFORMATION: Phe or Tyr
<220> FEATURE:
<221> NAME/KEY: MOD_RES
<222> LOCATION: (29)..(29)
<223> OTHER INFORMATION: Tyr or Phe

<400> SEQUENCE: 17

Arg Ile Thr Ile Asn Xaa Asp Thr Ser Lys Asn Gln Xaa Ser Leu Gln
1 5 10 15

Leu Asn Ser Val Thr Pro Glu Asp Thr Ala Val Tyr Xaa Cys Ala Arg
20 25 30

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Arg Ile Thr Ile Asn Pro Asp Thr Ser Lys Asn Gln Phe Ser Leu Gln
1 5 10 15

Leu Asn Ser Val Thr Pro Glu Asp Thr Ala Val Tyr Tyr Cys Ala Arg
20 25 30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 19

Arg Ile Thr Ile Asn Arg Asp Thr Ser Lys Asn Gln Tyr Ser Leu Gln
1 5 10 15

Leu Asn Ser Val Thr Pro Glu Asp Thr Ala Val Tyr Phe Cys Ala Arg
20 25 30

<210> SEQ ID NO 20

<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Arg Ile Thr Ile Asn Arg Asp Thr Ser Lys Asn Gln Phe Ser Leu Gln
1               5                   10                  15

Leu Asn Ser Val Thr Pro Glu Asp Thr Ala Val Tyr Tyr Cys Ala Arg
            20                  25                  30
```

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Arg Ile Thr Ile Asn Arg Asp Thr Ser Lys Asn Gln Phe Ser Leu Gln
1               5                   10                  15

Leu Asn Ser Val Thr Pro Glu Asp Thr Ala Val Tyr Phe Cys Ala Arg
            20                  25                  30
```

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Arg Ile Thr Ile Asn Arg Asp Thr Ser Lys Asn Gln Tyr Ser Leu Gln
1               5                   10                  15

Leu Asn Ser Val Thr Pro Glu Asp Thr Ala Val Tyr Tyr Cys Ala Arg
            20                  25                  30
```

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Arg Ile Thr Ile Asn Pro Asp Thr Ser Lys Asn Gln Tyr Ser Leu Gln
1               5                   10                  15

Leu Asn Ser Val Thr Pro Glu Asp Thr Ala Val Tyr Phe Cys Ala Arg
            20                  25                  30
```

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Arg Ile Thr Ile Asn Pro Asp Thr Ser Lys Asn Gln Tyr Ser Leu Gln
1               5                   10                  15
```

Leu Asn Ser Val Thr Pro Glu Asp Thr Ala Val Tyr Tyr Cys Ala Arg
20 25 30

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Tyr Arg Tyr Asp Tyr Asp Gly Gly His Ala Met Asp Tyr
1 5 10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Tyr Lys Tyr Asp Tyr Asp Ala Gly His Ala Met Asp Tyr
1 5 10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Tyr Lys Tyr Asp Tyr Asp Gly Gly His Ala Met Asp Tyr
1 5 10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Trp Gly Gln Gly Thr Leu Val Thr Val Ser Ser
1 5 10

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Asn Tyr
20 25 30

Leu Asn Trp Tyr Gln Gln Lys Pro Gly Lys Ala Pro Lys Leu Leu Ile
35 40 45

```
Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys
            100                 105


<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 31
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

gacatccaga tgacccagag ccccagcagc ctgagcgcca gcgtgggcga cagagtgacc     60
```

-continued

```
atcacctgtc gggccagcca ggacatcagc aactacctga actggtatca gcagaagccc    120

ggcaaggccc ccaagctgct gatctactac accagcaagc tgcacagcgg cgtgcccagc    180

agattcagcg gcagcggctc cggcaccgac tacaccctga ccatcagcag cctgcagccc    240

gaggacttcg ccacctacta ctgccagcag ggctccgccc tgccctggac ctttggccag    300

ggcaccaagg tggaaatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Arg Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys
            100                 105


<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Gln His Pro Gly Lys Gly Leu Glu Trp Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Pro Asp Thr Ser Lys Asn Gln Phe Ser Leu
65                  70                  75                  80

Gln Leu Asn Ser Val Thr Pro Glu Asp Thr Ala Val Tyr Tyr Cys Ala
```

-continued 85 90 95

Arg Tyr Arg Tyr Asp Tyr Asp Gly Gly His Ala Met Asp Tyr Trp Gly
100 105 110

Gln Gly Thr Leu Val Thr Val Ser Ser
115 120

<210> SEQ ID NO 34
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
caggtgcagc tgcaggaaag cggccctggc ctggtcaagc ccagccagac cctgagcctg 60
acctgtgccg tgtacggcgg cagcttcagc agcggctact ggaactggat ccggcagcac 120
cccggcaagg gcctggaatg gatcggctac atcagctaca acggcatcac ctaccacaac 180
cccagcctga agtcccggat caccatcaac cccgacacca gcaagaacca gttctccctg 240
cagctgaaca gcgtgacccc cgaggacacc gccgtgtact actgcgcccg gtacagatac 300
gactacgacg gcggccacgc catggactac tggggccagg gcaccctggt caccgtgtcc 360
tct 363

<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

Tyr Trp Asn Trp Ile Arg Lys His Pro Gly Lys Gly Leu Glu Trp Ile
35 40 45

Gly Tyr Ile Ser Tyr Asn Gly Ile Thr Tyr His Asn Pro Ser Leu Lys
50 55 60

Ser Arg Ile Thr Ile Asn Arg Asp Thr Ser Lys Asn Gln Phe Ser Leu
65 70 75 80

Gln Leu Asn Ser Val Thr Pro Glu Asp Thr Ala Val Tyr Tyr Cys Ala
85 90 95

Arg Tyr Arg Tyr Asp Tyr Asp Gly Gly His Ala Met Asp Tyr Trp Gly
100 105 110

Gln Gly Thr Leu Val Thr Val Ser Ser
115 120

<210> SEQ ID NO 36
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

-continued

```
caggtgcagc tgcaggaaag cggccctggc ctggtcaagc ccagccagac cctgagcctg     60

acctgtgccg tgtacggcgg cagcttcagc agcggctact ggaactggat ccggaagcac    120

cccggcaagg gcctggaatg gatcggctac atcagctaca acggcatcac ctaccacaac    180

cccagcctga agtcccggat caccatcaac cgggacacca gcaagaacca gttctccctg    240

cagctgaaca gcgtgacccc cgaggacacc gccgtgtact actgcgcccg gtacagatac    300

gactacgacg gcggccacgc catggactac tggggccagg gcaccctggt caccgtgtcc    360

tct                                                                  363


<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Glu Ser Gly Pro Gly Leu Val Lys Pro Ser Gln
1               5                   10                  15

Thr Leu Ser Leu Thr Cys Ala Val Tyr Gly Asp Ser Phe Ser Ser Gly
            20                  25                  30

Tyr Trp Asn Trp Ile Arg Lys His Pro Gly Lys Gly Leu Glu Tyr Met
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Phe Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120


<210> SEQ ID NO 38
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

caggtgcagc tgcaggaaag cggccctggc ctggtcaagc ccagccagac cctgagcctg     60

acctgtgccg tgtacggcga cagcttcagc agcggctact ggaactggat ccggaagcac    120

cccggcaagg gcctggaata catgggctac atcagctaca acggcatcac ctaccacaac    180

cccagcctga agtcccggat caccatcaac cgggacacca gcaagaacca gtactccctg    240

cagctgaaca gcgtgacccc cgaggacacc gccgtgtact tctgcgcccg gtacagatac    300

gactacgacg gcggccacgc catggactac tggggccagg gcaccctggt caccgtgtcc    360

tct                                                                  363


<210> SEQ ID NO 39
<211> LENGTH: 121
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 39

Gln Val Gln Leu Gln Glu Ser Gly Pro Gly Leu Val Lys Pro Ser Gln
1 5 10 15

Thr Leu Ser Leu Thr Cys Ala Val Tyr Gly Asp Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Asn Gly Ile Thr Tyr His Asn Pro Ser Leu Lys
50 55 60

Ser Arg Ile Thr Ile Asn Arg Asp Thr Ser Lys Asn Gln Tyr Ser Leu
65 70 75 80

Gln Leu Asn Ser Val Thr Pro Glu Asp Thr Ala Val Tyr Phe Cys Ala
85 90 95

Arg Tyr Arg Tyr Asp Tyr Asp Gly Gly His Ala Met Asp Tyr Trp Gly
100 105 110

Gln Gly Thr Leu Val Thr Val Ser Ser
115 120

<210> SEQ ID NO 40
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40
caggtgcagc tgcaggaaag cggccctggc ctggtcaagc ccagccagac cctgagcctg 60
acctgtgccg tgtacggcga cagcttcagc agcggctact ggaactggat ccggaagcac 120
cccggcaagg gcctggaata catcggctac atcagctaca acggcatcac ctaccacaac 180
cccagcctga agtcccggat caccatcaac cgggacacca gcaagaacca gtactccctg 240
cagctgaaca gcgtgacccc cgaggacacc gccgtgtact tctgcgcccg gtacagatac 300
gactacgacg gcggccacgc catggactac tggggccagg gcaccctggt caccgtgtcc 360
tct 363

<210> SEQ ID NO 41
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Gln Val Gln Leu Gln Glu Ser Gly Pro Gly Leu Val Lys Pro Ser Gln
1 5 10 15

Thr Leu Ser Leu Thr Cys Ala Val Tyr Gly Asp Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Asn Gly Ile Thr Tyr His Asn Pro Ser Leu Lys
50 55 60

Ser Arg Ile Thr Ile Asn Arg Asp Thr Ser Lys Asn Gln Phe Ser Leu

```
65                  70                  75                  80

Gln Leu Asn Ser Val Thr Pro Glu Asp Thr Ala Val Tyr Phe Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120


<210> SEQ ID NO 42
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

caggtgcagc tgcaggaaag cggccctggc ctggtcaagc ccagccagac cctgagcctg     60

acctgtgccg tgtacggcga cagcttcagc agcggctact ggaactggat ccggaagcac    120

cccggcaagg gcctggaata catcggctac atcagctaca acggcatcac ctaccacaac    180

cccagcctga agtcccggat caccatcaac cgggacacca gcaagaacca gttctccctg    240

cagctgaaca gcgtgacccc cgaggacacc gccgtgtact tctgcgcccg gtacagatac    300

gactacgacg gcggccacgc catggactac tggggccagg gcaccctggt caccgtgtcc    360

tct                                                                  363


<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Ala Val Tyr Gly Asp Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120


<210> SEQ ID NO 44
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 44
caggtgcagc tgcaggaaag cggccctggc ctggtcaagc ccagccagac cctgagcctg 60
acctgtgccg tgtacggcga cagcttcagc agcggctact ggaactggat ccggaagcac 120
cccggcaagg gcctggaata catcggctac atcagctaca acggcatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacagatac 300
gactacgacg gcggccacgc catggactac tggggccagg gcaccctggt caccgtgtcc 360
tct 363

<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Gln Val Gln Leu Gln Glu Ser Gly Pro Gly Leu Val Lys Pro Ser Gln
1 5 10 15

Thr Leu Ser Leu Thr Cys Ala Val Tyr Gly Asp Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Asn Gly Ile Thr Tyr His Asn Pro Ser Leu Lys
50 55 60

Ser Arg Ile Thr Ile Asn Arg Asp Thr Ser Lys Asn Gln Phe Ser Leu
65 70 75 80

Gln Leu Asn Ser Val Thr Pro Glu Asp Thr Ala Val Tyr Tyr Cys Ala
85 90 95

Arg Tyr Arg Tyr Asp Tyr Asp Gly Gly His Ala Met Asp Tyr Trp Gly
100 105 110

Gln Gly Thr Leu Val Thr Val Ser Ser
115 120

<210> SEQ ID NO 46
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46
caggtgcagc tgcaggaaag cggccctggc ctggtcaagc ccagccagac cctgagcctg 60
acctgtgccg tgtacggcga cagcttcagc agcggctact ggaactggat ccggaagcac 120
cccggcaagg gcctggaata catcggctac atcagctaca acggcatcac ctaccacaac 180
cccagcctga agtcccggat caccatcaac cgggacacca gcaagaacca gttctccctg 240
cagctgaaca gcgtgacccc cgaggacacc gccgtgtact actgcgcccg gtacagatac 300
gactacgacg gcggccacgc catggactac tggggccagg gcaccctggt caccgtgtcc 360
tct 363

<210> SEQ ID NO 47

<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Asn Gly Ile Thr Tyr His Asn Pro Ser Leu Lys
50 55 60

Ser Arg Ile Thr Ile Asn Pro Asp Thr Ser Lys Asn Gln Tyr Ser Leu
65 70 75 80

Gln Leu Asn Ser Val Thr Pro Glu Asp Thr Ala Val Tyr Phe Cys Ala
85 90 95

Arg Tyr Arg Tyr Asp Tyr Asp Gly Gly His Ala Met Asp Tyr Trp Gly
100 105 110

Gln Gly Thr Leu Val Thr Val Ser Ser
115 120

<210> SEQ ID NO 48
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca acggcatcac ctaccacaac 180
cccagcctga agtcccggat caccatcaac cccgacacca gcaagaacca gtactccctg 240
cagctgaaca gcgtgacccc cgaggacacc gccgtgtact tctgcgcccg gtacagatac 300
gactacgacg gcggccacgc catggactac tggggccagg gcaccctggt caccgtgtcc 360
tct 363

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Asn Gly Ile Thr Tyr His Asn Pro Ser Leu Lys

```
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Phe Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120
```

<210> SEQ ID NO 50
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

```
caggtgcagc tgcaggaaag cggccctggc ctggtcaagc ccagccagac cctgagcctg     60

acctgtgccg tgtacggcgg cagcttcagc agcggctact ggaactggat ccggaagcac    120

cccggcaagg gcctggaata catcggctac atcagctaca acggcatcac ctaccacaac    180

cccagcctga agtcccggat caccatcaac cgggacacca gcaagaacca gtactccctg    240

cagctgaaca gcgtgacccc cgaggacacc gccgtgtact tctgcgcccg gtacagatac    300

gactacgacg gcggccacgc catggactac tggggccagg gcaccctggt caccgtgtcc    360

tct                                                                  363
```

<210> SEQ ID NO 51
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120
```

<210> SEQ ID NO 52
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca acggcatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacagatac 300
gactacgacg gcggccacgc catggactac tggggccagg gcaccctggt caccgtgtcc 360
tct 363

<210> SEQ ID NO 53
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Asn Gly Ile Thr Tyr His Asn Pro Ser Leu Lys
50 55 60

Ser Arg Ile Thr Ile Asn Pro Asp Thr Ser Lys Asn Gln Tyr Ser Leu
65 70 75 80

Gln Leu Asn Ser Val Thr Pro Glu Asp Thr Ala Val Tyr Tyr Cys Ala
85 90 95

Arg Tyr Arg Tyr Asp Tyr Asp Gly Gly His Ala Met Asp Tyr Trp Gly
100 105 110

Gln Gly Thr Leu Val Thr Val Ser Ser
115 120

<210> SEQ ID NO 54
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca acggcatcac ctaccacaac 180
cccagcctga agtcccggat caccatcaac cccgacacca gcaagaacca gtactccctg 240
cagctgaaca gcgtgacccc cgaggacacc gccgtgtact actgcgcccg gtacagatac 300
gactacgacg gcggccacgc catggactac tggggccagg gcaccctggt caccgtgtcc 360
tct 363

<210> SEQ ID NO 55
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Ala Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Ala Gly His Ala Met Asp Tyr Trp Gly
            100                 105                 110

Gln Gly Thr Leu Val Thr Val Ser Ser
        115                 120
```

<210> SEQ ID NO 56
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56

```
caggtgcagc tgcaggaaag cggccctggc ctggtcaagc ccagccagac cctgagcctg     60

acctgtgccg tgtacggcgg cagcttcagc agcggctact ggaactggat ccggaagcac    120

cccggcaagg gcctggaata catcggctac atcagctaca acgccatcac ctaccacaac    180

cccagcctga agtcccggat caccatcaac cgggacacca gcaagaacca gtactccctg    240

cagctgaaca gcgtgacccc cgaggacacc gccgtgtact actgcgcccg gtacaaatac    300

gactacgacg ccggccacgc catggactac tggggccagg gcaccctggt caccgtgtcc    360

tct                                                                  363
```

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
```

```
        35                  40                  45

Gly Tyr Ile Ser Tyr Asn Ala Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120


<210> SEQ ID NO 58
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

caggtgcagc tgcaggaaag cggccctggc ctggtcaagc ccagccagac cctgagcctg      60

acctgtgccg tgtacggcgg cagcttcagc agcggctact ggaactggat ccggaagcac     120

cccggcaagg gcctggaata catcggctac atcagctaca acgccatcac ctaccacaac     180

cccagcctga agtcccggat caccatcaac cgggacacca gcaagaacca gtactccctg     240

cagctgaaca gcgtgacccc cgaggacacc gccgtgtact actgcgcccg gtacagatac     300

gactacgacg gcggccacgc catggactac tggggccagg gcaccctggt caccgtgtcc     360

tct                                                                   363


<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser
        115                 120


<210> SEQ ID NO 60
```

<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca acggcatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacaaatac 300
gactacgacg gcggccacgc catggactac tggggccagg gcaccctggt caccgtgtcc 360
tct 363

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Ser Gly Ile Thr Tyr His Asn Pro Ser Leu Lys
50 55 60

Ser Arg Ile Thr Ile Asn Arg Asp Thr Ser Lys Asn Gln Tyr Ser Leu
65 70 75 80

Gln Leu Asn Ser Val Thr Pro Glu Asp Thr Ala Val Tyr Tyr Cys Ala
85 90 95

Arg Tyr Arg Tyr Asp Tyr Asp Gly Gly His Ala Met Asp Tyr Trp Gly
100 105 110

Gln Gly Thr Leu Val Thr Val Ser Ser
115 120

<210> SEQ ID NO 62
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca gcggcatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacagatac 300
gactacgacg gcggccacgc catggactac tggggccagg gcaccctggt caccgtgtcc 360
tct 363

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Ser Gly Ile Thr Tyr His Asn Pro Ser Leu Lys
50 55 60

Ser Arg Ile Thr Ile Asn Arg Asp Thr Ser Lys Asn Gln Tyr Ser Leu
65 70 75 80

Gln Leu Asn Ser Val Thr Pro Glu Asp Thr Ala Val Tyr Tyr Cys Ala
85 90 95

Arg Tyr Lys Tyr Asp Tyr Asp Gly Gly His Ala Met Asp Tyr Trp Gly
100 105 110

Gln Gly Thr Leu Val Thr Val Ser Ser
115 120

<210> SEQ ID NO 64
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca gcggcatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacaaatac 300
gactacgacg gcggccacgc catggactac tggggccagg gcaccctggt caccgtgtcc 360
tct 363

<210> SEQ ID NO 65
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Glu Val Gln Leu Gln Glu Ser Gly Pro Ser Leu Val Lys Pro Ser Gln
1 5 10 15

Thr Leu Ser Leu Thr Cys Ser Val Thr Gly Asp Ser Phe Thr Ser Gly

```
            20                  25                  30

Tyr Trp Asn Trp Ile Arg Lys Phe Pro Gly Asn Arg Leu Glu Tyr Met
        35                  40                  45

Gly Tyr Ile Ser Tyr Asn Ala Ile Thr Tyr His Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Asn Ser Val Thr Thr Glu Asp Thr Ala Thr Tyr Phe Cys Ala
                85                  90                  95

Arg Tyr Arg Tyr Asp Tyr Asp Gly Gly His Ala Met Asp Tyr Trp Gly
            100                 105                 110

Gln Gly Thr Leu Val Thr Val Ser Ser
        115                 120


<210> SEQ ID NO 66
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

gaggtgcagc tgcaggaaag cggccccagc ctggtcaagc ccagccagac cctgagcctg     60

acctgcagcg tgaccggcga cagcttcacc agcggctact ggaactggat ccggaagttc    120

cccggcaacc ggctcgagta catgggctac atcagctaca acgccatcac ctaccacaac    180

cccagcctga agtcccggat cagcatcacc cgggacacca gcaagaacca ctactacctg    240

cagctgaaca gcgtgaccac cgaggacacc gccacctact tttgcgcccg gtacagatac    300

gactacgacg gcggccacgc catggactac tggggccagg gcaccctggt caccgtgtcc    360

tct                                                                  363


<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Ala Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser
        115                 120
```

<210> SEQ ID NO 68
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca acgccatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacaaatac 300
gactacgacg gcggccacgc catggactac tggggccagg gcaccctggt caccgtgtcc 360
tct 363

<210> SEQ ID NO 69
<211> LENGTH: 330
<212> TYPE: PRT
<213> ORGANISM: Homo sapiens

<400> SEQUENCE: 69

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 70
<211> LENGTH: 990
<212> TYPE: DNA
<213> ORGANISM: Homo sapiens

<400> SEQUENCE: 70

gcgtcgacca agggcccatc cgtcttcccc ctggcaccct cctccaagag cacctctggg      60

ggcacagcgg ccctgggctg cctggtcaag gactacttcc ccgaaccggt gacggtgtcc     120

tggaactcag gcgctctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagag agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtctacaccc tgcccccatc ccgggaggag     720

atgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctat agcaagctca ccgtggacaa gagcaggtgg     900

cagcagggga acgtcttctc atgctccgtg atgcatgagg ctctgcacaa ccactacacg     960

cagaagagct taagcctgtc tccgggtaaa                                      990


<210> SEQ ID NO 71
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45
```

```
Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 72
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
caggtgcagc tgcaggaaag cggccctggc ctggtcaagc ccagccagac cctgagcctg     60

acctgtgccg tgtacggcgg cagcttcagc agcggctact ggaactggat ccggaagcac    120

cccggcaagg gcctggaata catcggctac atcagctaca acggcatcac ctaccacaac    180

cccagcctga agtcccggat caccatcaac cgggacacca gcaagaacca gtactccctg    240

cagctgaaca gcgtgacccc cgaggacacc gccgtgtact actgcgcccg gtacaaatac    300

gactacgacg gcggccacgc catggactac tggggccagg gcaccctggt caccgtgtcc    360

tctgcgtcga ccaagggccc atccgtcttc cccctggcac cctcctccaa gagcacctct    420

gggggcacag cggccctggg ctgcctggtc aaggactact tccccgaacc ggtgacggtg    480

tcctggaact caggcgctct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gagagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtctaca ccctgccccc atcccgggag   1080

gagatgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tatagcaagc tcaccgtgga caagagcagg   1260

tggcagcagg ggaacgtctt ctcatgctcc gtgatgcatg aggctctgca caaccactac   1320

acgcagaaga gcttaagcct gtctccgggt aaa                                1353
```

<210> SEQ ID NO 73
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60
```

```
Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 74
<211> LENGTH: 1344
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 74
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca acggcatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacaaatac 300
gactacgacg gcggccacgc catggactac tggggccagg gcaccctggt caccgtgtcc 360
tctgcgtcga ccaagggccc cagcgtgttc cccctggccc cttgcagcag aagcaccagc 420
gagagcacag ccgccctggg ctgcctggtg aaggactact tccccgagcc cgtgaccgtg 480
tcctggaaca gcggcgctct gaccagcggc gtgcatacct tccccgccgt gctccagagc 540
agcggactgt actccctgag cagcgtggtg accgtgcctt ccagcagcct gggcaccaag 600
acctacacct gcaacgtgga ccacaagccc agcaacacca aggtggacaa gagagtggag 660
agcaagtacg gccctccctg ccccccttgc cctgccccccg agttcctggg cggacctagc 720
gtgttcctgt tcccccccaa gcccaaggac accctgatga tcagcagaac ccccgaggtg 780
acctgcgtgg tggtggacgt gtcccaggag gaccccgagg tccagtttaa ttggtacgtg 840
gacggcgtgg aagtgcataa cgccaagacc aagcccagag aggagcagtt caacagcacc 900
tacagagtgg tgtccgtgct gaccgtgctg caccaggact ggctgaacgg caaggaatac 960
aagtgcaagg tctccaacaa gggcctgcct agcagcatcg agaagaccat cagcaaggcc 1020
aagggccagc cacgggagcc ccaggtctac accctgccac ctagccaaga ggagatgacc 1080
aagaaccagg tgtccctgac ctgtctggtg aaaggcttct atcccagcga tatcgccgtg 1140
gagtgggaga gcaacggcca gcccgagaac aactacaaga ccaccccccc tgtgctggac 1200
agcgacggca gcttcttcct gtactccaga ctgaccgtgg acaagtccag atggcaggag 1260
ggcaacgtct tcagctgctc cgtgatgcac gaggccctgc acaaccacta cacccagaag 1320
tccctgagcc tgagcctggg caag 1344

<210> SEQ ID NO 75
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

```
Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 76
<211> LENGTH: 1353
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 76
caggtgcagc tgcaggaaag cggccctggc ctggtcaagc ccagccagac cctgagcctg 60
acctgtgccg tgtacggcgg cagcttcagc agcggctact ggaactggat ccggaagcac 120
cccggcaagg gcctggaata catcggctac atcagctaca acggcatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacaaatac 300
gactacgacg gcggccacgc catggactac tggggccagg gcaccctggt caccgtgtcc 360
tctgcgtcga ccaagggccc atccgtcttc cccctggcac cctcctccaa gagcacctct 420
gggggcacag cggccctggg ctgcctggtc aaggactact tccccgaacc ggtgacggtg 480
tcctggaact caggcgctct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacaa gagagttgag 660
cccaaatctt gtgacaaaac tcacacatgc ccaccgtgcc cagcacctga attcgagggg 720
ggaccgtcag tcttcctctt ccccccaaaa cccaaggaca ccctcatgat ctcccggacc 780
cctgaggtca catgcgtggt ggtggacgtg agccacgaag accctgaggt caagttcaac 840
tggtacgtgg acggcgtgga ggtgcataat gccaagacaa agccgcggga ggagcagtac 900
aacagcacgt accgtgtggt cagcgtcctc accgtcctgc accaggactg gctgaatggc 960
aaggagtaca agtgcaaggt ctccaacaaa gccctcccag cctccatcga gaaaaccatc 1020
tccaaagcca aagggcagcc ccgagaacca caggtctaca ccctgccccc atcccgggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tatagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaa 1353

<210> SEQ ID NO 77
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Ala Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

```
Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 78
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
caggtgcagc tgcaggaaag cggccctggc ctggtcaagc ccagccagac cctgagcctg      60

acctgtgccg tgtacggcgg cagcttcagc agcggctact ggaactggat ccggaagcac     120
```

cccggcaagg gcctggaata catcggctac atcagctaca acgccatcac ctaccacaac 180
cccagcctga agtcccggat caccatcaac cgggacacca gcaagaacca gtactccctg 240
cagctgaaca gcgtgacccc cgaggacacc gccgtgtact actgcgcccg gtacaaatac 300
gactacgacg gcggccacgc catggactac tggggccagg gcaccctggt caccgtgtcc 360
tctgcgtcga ccaagggccc cagcgtgttc cccctggccc cttgcagcag aagcaccagc 420
gagagcacag ccgccctggg ctgcctggtg aaggactact tccccgagcc cgtgaccgtg 480
tcctggaaca gcggcgctct gaccagcggc gtgcatacct tccccgccgt gctccagagc 540
agcggactgt actccctgag cagcgtggtg accgtgcctt ccagcagcct gggcaccaag 600
acctacacct gcaacgtgga ccacaagccc agcaacacca aggtggacaa gagagtggag 660
agcaagtacg gccctccctg ccccccttgc cctgcccccg agttcctggg cggacctagc 720
gtgttcctgt tccccccaa gcccaaggac accctgatga tcagcagaac ccccgaggtg 780
acctgcgtgg tggtggacgt gtcccaggag gaccccgagg tccagtttaa ttggtacgtg 840
gacggcgtgg aagtgcataa cgccaagacc aagcccagag aggagcagtt caacagcacc 900
tacagagtgg tgtccgtgct gaccgtgctg caccaggact ggctgaacgg caaggaatac 960
aagtgcaagg tctccaacaa gggcctgcct agcagcatcg agaagaccat cagcaaggcc 1020
aagggccagc cacgggagcc ccaggtctac accctgccac ctagccaaga ggagatgacc 1080
aagaaccagg tgtccctgac ctgtctggtg aaaggcttct atcccagcga tatcgccgtg 1140
gagtgggaga gcaacggcca gcccgagaac aactacaaga ccacccccc tgtgctggac 1200 agcgacggca gcttcttcct gtactccaga ctgaccgtgg acaagtccag atggcaggag 1260
ggcaacgtct tcagctgctc cgtgatgcac gaggccctgc acaaccacta cacccagaag 1320
tccctgagcc tgagcctggg caag 1344

<210> SEQ ID NO 79
<211> LENGTH: 451
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

Tyr Trp Asn Trp Ile Arg Lys His Pro Gly Lys Gly Leu Glu Tyr Ile
35 40 45

Gly Tyr Ile Ser Tyr Asn Ala Ile Thr Tyr His Asn Pro Ser Leu Lys
50 55 60

Ser Arg Ile Thr Ile Asn Arg Asp Thr Ser Lys Asn Gln Tyr Ser Leu
65 70 75 80

Gln Leu Asn Ser Val Thr Pro Glu Asp Thr Ala Val Tyr Tyr Cys Ala
85 90 95

Arg Tyr Lys Tyr Asp Tyr Asp Gly Gly His Ala Met Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 80
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

caggtgcagc tgcaggaaag cggccctggc ctggtcaagc ccagccagac cctgagcctg      60

acctgtgccg tgtacggcgg cagcttcagc agcggctact ggaactggat ccggaagcac     120

cccggcaagg gcctggaata catcggctac atcagctaca acgccatcac ctaccacaac     180

cccagcctga agtcccggat caccatcaac cgggacacca gcaagaacca gtactccctg     240
```

```
cagctgaaca gcgtgacccc cgaggacacc gccgtgtact actgcgcccg gtacaaatac    300

gactacgacg gcggccacgc catggactac tggggccagg gcaccctggt caccgtgtcc    360

tctgcgtcga ccaagggccc atccgtcttc cccctggcac cctcctccaa gagcacctct    420

gggggcacag cggccctggg ctgcctggtc aaggactact tccccgaacc ggtgacggtg    480

tcctggaact caggcgctct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gagagttgag    660

cccaaatctt gtgacaaaac tcacacatgc ccaccgtgcc cagcacctga attcgagggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcccag cctccatcga gaaaaccatc   1020

tccaaagcca aagggcagcc ccgagaacca caggtctaca ccctgccccc atcccgggag   1080

gagatgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tatagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353
```

<210> SEQ ID NO 81
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160
```

```
Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445
```

```
<210> SEQ ID NO 82
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

caggtgcagc tgcaggaaag cggccctggc ctggtcaagc ccagccagac cctgagcctg      60

acctgtgccg tgtacggcgg cagcttcagc agcggctact ggaactggat ccggaagcac     120

cccggcaagg gcctggaata catcggctac atcagctaca acggcatcac ctaccacaac     180

cccagcctga agtcccggat caccatcaac cgggacacca gcaagaacca gtactccctg     240

cagctgaaca gcgtgacccc cgaggacacc gccgtgtact actgcgcccg gtacaaatac     300

gactacgacg gcggccacgc catggactac tggggccagg gcaccctggt caccgtgtcc     360

tctgcgaaga cgacaccccc atctgtctat ccactggccc ctggatctgc tgcccaaact     420
```

```
aactccatgg tgaccctggg atgcctggtc aagggctatt tccctgagcc agtgacagtg    480

acctggaact ctggatccct gtccagcggt gtgcacacct tcccagctgt cctgcagtct    540

gacctctaca ctctgagcag ctcagtgact gtcccctcca gcacctggcc cagcgagacc    600

gtcacctgca acgttgccca cccggccagc agcaccaagg tggacaagaa aattgtgccc    660

agggattgtg gttgtaagcc ttgcatatgt accgtcccag aagtatcatc tgtcttcatc    720

ttccccccaa agcccaagga tgtgctcacc attactctga ctcctaaggt cacgtgtgtt    780

gtggtagaca tcagcaagga tgatcccgag gtccagttca gctggtttgt agatgatgtg    840

gaggtgcaca cagctcagac gcaaccccgg gaggagcagt tcaacagcac tttccgctca    900

gtcagtgaac ttcccatcat gcaccaggac tggctcaatg gcaaggagtt caaatgcagg    960

gtcaacagtg cagctttccc tgcccccatc gagaaaacca tctccaaaac caaaggcaga   1020

ccgaaggctc cacaggtgta taccattcca cctcccaagg agcagatggc caaggataaa   1080

gtcagtctga cctgcatgat aacagacttc ttccctgaag acattactgt ggagtggcag   1140

tggaatgggc agccagcgga gaactacaag aacactcagc ccatcatgga cacagatggc   1200

tcttacttcg tctacagcaa gctcaatgtg cagaagagca actgggaggc aggaaatact   1260

ttcacctgct ctgtgttaca tgagggcctg cacaaccacc atactgagaa gagcctctcc   1320

cactctcctg gtaaa                                                    1335
```

```
<210> SEQ ID NO 83
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190
```

Thr Cys Glu Ala Thr His Lys Thr Ser Thr Ser Pro Ile Val Lys Ser
195 200 205

Phe Asn Arg Asn Glu Cys
210

<210> SEQ ID NO 84
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84
gacatccaga tgacccagag ccccagcagc ctgagcgcca gcgtgggcga cagagtgacc 60
atcacctgtc gggccagcca ggacatcagc aactacctga actggtatca gcagaagccc 120
ggcaaggccc ccaagctgct gatctactac accagcaagc tgcacagcgg cgtgcccagc 180
agattcagcg gcagcggctc cggcaccgac tacaccctga ccatcagcag cctgcagccc 240
gaggacttcg ccacctacta ctgccagcag ggctccgccc tgccctggac ctttggccag 300
ggcaccaagg tggaaatcaa gcgggctgat gcggcgccaa ctgtatccat cttcccacca 360
tccagtgagc agttaacatc tggaggtgcc tcagtcgtgt gcttcttgaa caacttctac 420
cccaaagaca tcaatgtcaa gtggaagatt gatggcagtg aacgacaaaa tggcgtcctg 480
aacagttgga ctgatcagga cagcaaagac agcacctaca gcatgagcag caccctcacg 540
ttgaccaagg acgagtatga acgacataac agctatacct gtgaggccac tcacaagaca 600
tcaacttcac ccattgtcaa gagcttcaac aggaatgagt gt 642

<210> SEQ ID NO 85
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Gln Val Gln Leu Lys Glu Ser Gly Pro Gly Leu Val Gln Pro Ser Gln
1 5 10 15

Thr Leu Ser Leu Thr Cys Thr Val Ser Gly Phe Ser Leu Thr Gly Tyr
20 25 30

Asn Leu His Trp Val Arg Gln Pro Pro Gly Lys Gly Leu Glu Trp Met
35 40 45

Gly Arg Met Arg Tyr Asp Gly Asp Thr Tyr Tyr Asn Ser Val Leu Lys
50 55 60

Ser Arg Leu Ser Ile Ser Arg Asp Thr Ser Lys Asn Gln Val Phe Leu
65 70 75 80

Lys Met Asn Ser Leu Gln Thr Asp Asp Thr Ala Ile Tyr Tyr Cys Thr
85 90 95

Arg Asp Gly Arg Gly Asp Ser Phe Asp Tyr Trp Gly Gln Gly Val Met
100 105 110

Val Thr Val Ser Ser
115

<210> SEQ ID NO 86
<211> LENGTH: 441
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 86

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Gly Tyr
            20                  25                  30

Asn Leu His Trp Val Arg Gln Pro Pro Gly Lys Gly Leu Glu Trp Met
        35                  40                  45

Gly Arg Met Arg Tyr Asp Gly Asp Thr Tyr Tyr Asn Ser Val Leu Lys
    50                  55                  60

Ser Arg Leu Ser Ile Ser Arg Asp Thr Ser Lys Asn Gln Val Phe Leu
65                  70                  75                  80

Lys Met Asn Ser Leu Gln Thr Asp Asp Thr Ala Ile Tyr Tyr Cys Thr
                85                  90                  95

Arg Asp Gly Arg Gly Asp Ser Phe Asp Tyr Trp Gly Gln Gly Val Met
            100                 105                 110

Val Thr Val Ser Ser Ala Ser Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380
```

```
Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440
```

<210> SEQ ID NO 87
<211> LENGTH: 1323
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
caggtgcagc tgaaggagtc aggacctggt ctggtgcagc cctcacagac cctgtccctc     60

acctgcactg tctctgggtt ctcactaacc ggttacaatt tacactgggt tcgccagcct    120

ccaggaaagg gtctggagtg gatgggaaga atgaggtatg atggagacac atattataat    180

tcagttctca aatcccgact gagcatcagc agggacacct ccaagaacca agttttcttg    240

aaaatgaaca gtctgcaaac ggatgacaca gccatttact attgtaccag agacgggcgt    300

ggtgactcct ttgattactg gggccaagga gtcatggtca cagtctcctc cgcgtcgacg    360

acacccccat ctgtctatcc actggcccct ggatctgctg cccaaactaa ctccatggtg    420

accctgggat gcctggtcaa gggctatttc cctgagccag tgacagtgac ctggaactct    480

ggatccctgt ccagcggtgt gcacaccttc ccagctgtcc tgcagtctga cctctacact    540

ctgagcagct cagtgactgt cccctccagc acctggccca gcgagaccgt cacctgcaac    600

gttgcccacc cggccagcag caccaaggtg gacaagaaaa ttgtgcccag ggattgtggt    660

tgtaagcctt gcatatgtac cgtcccagaa gtatcatctg tcttcatctt ccccccaaag    720

cccaaggatg tgctcaccat tactctgact cctaaggtca cgtgtgttgt ggtagacatc    780

agcaaggatg atcccgaggt ccagttcagc tggtttgtag atgatgtgga ggtgcacaca    840

gctcagacgc aaccccggga ggagcagttc aacagcactt tccgctcagt cagtgaactt    900

cccatcatgc accaggactg gctcaatggc aaggagttca aatgcagggt caacagtgca    960

gctttccctg cccccatcga gaaaaccatc tccaaaacca aaggcagacc gaaggctcca   1020

caggtgtata ccattccacc tcccaaggag cagatggcca aggataaagt cagtctgacc   1080

tgcatgataa cagacttctt ccctgaagac attactgtgg agtggcagtg gaatgggcag   1140

ccagcggaga actacaagaa cactcagccc atcatggaca cagatggctc ttacttcgtc   1200

tacagcaagc tcaatgtgca gaagagcaac tgggaggcag gaaatacttt cacctgctct   1260

gtgttacatg agggcctgca caaccaccat actgagaaga gcctctccca ctctcctggt   1320

aaa                                                                 1323
```

<210> SEQ ID NO 88
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Asp Ile Val Met Thr Gln Gly Ala Leu Pro Asn Pro Val Pro Ser Gly
1               5                   10                  15

Glu Ser Ala Ser Ile Thr Cys Arg Ser Ser Gln Ser Leu Val Tyr Lys
            20                  25                  30

Asp Gly Gln Thr Tyr Leu Asn Trp Phe Leu Gln Arg Pro Gly Gln Ser
        35                  40                  45

Pro Gln Leu Leu Thr Tyr Trp Met Ser Thr Arg Ala Ser Gly Val Ser
    50                  55                  60

Asp Arg Phe Ser Gly Ser Gly Ser Gly Thr Tyr Phe Thr Leu Lys Ile
65                  70                  75                  80

Ser Arg Val Arg Ala Glu Asp Ala Gly Val Tyr Tyr Cys Gln Gln Val
                85                  90                  95

Arg Glu Tyr Pro Phe Thr Phe Gly Ser Gly Thr Lys Leu Glu Ile Lys
            100                 105                 110


<210> SEQ ID NO 89
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Val Met Thr Gln Gly Ala Leu Pro Asn Pro Val Pro Ser Gly
1               5                   10                  15

Glu Ser Ala Ser Ile Thr Cys Arg Ser Ser Gln Ser Leu Val Tyr Lys
            20                  25                  30

Asp Gly Gln Thr Tyr Leu Asn Trp Phe Leu Gln Arg Pro Gly Gln Ser
        35                  40                  45

Pro Gln Leu Leu Thr Tyr Trp Met Ser Thr Arg Ala Ser Gly Val Ser
    50                  55                  60

Asp Arg Phe Ser Gly Ser Gly Ser Gly Thr Tyr Phe Thr Leu Lys Ile
65                  70                  75                  80

Ser Arg Val Arg Ala Glu Asp Ala Gly Val Tyr Tyr Cys Gln Gln Val
                85                  90                  95

Arg Glu Tyr Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 90
<211> LENGTH: 657
<212> TYPE: DNA
```

<213> ORGANISM: Artificial Sequence
<220> FEATURE:
<223> OTHER INFORMATION: Description of Artificial Sequence: Synthetic
polynucleotide

<400> SEQUENCE: 90
gatattgtga tgacccaggg tgcactcccc aatcctgtcc cttctggaga gtcagcttcc 60
atcacctgca ggtctagtca gagtctggta tacaaagacg gccagacata cttgaattgg 120
tttctgcaga ggccaggaca gtctcctcag cttctgacct attggatgtc tacccgtgca 180
tcaggagtct cagacaggtt cagtggcagt gggtcaggaa catatttcac actgaaaatc 240
agtagagtga gggctgagga tgcgggtgtg tattactgtc agcaagttcg agagtatcct 300
ttcactttcg gctcagggac gaagttggaa ataaaacggg ctgatgcggc gccaactgta 360
tccatcttcc caccatccag tgagcagtta acatctggag gtgcctcagt cgtgtgcttc 420
ttgaacaact tctaccccaa agacatcaat gtcaagtgga agattgatgg cagtgaacga 480
caaaatggcg tcctgaacag ttggactgat caggacagca aagacagcac ctacagcatg 540
agcagcaccc tcacgttgac caaggacgag tatgaacgac ataacagcta tacctgtgag 600
gccactcaca agacatcaac ttcacccatt gtcaagagct tcaacaggaa tgagtgt 657

<210> SEQ ID NO 91
<211> LENGTH: 277
<212> TYPE: PRT
<213> ORGANISM: Homo sapiens

<400> SEQUENCE: 91

Met Cys Val Gly Ala Arg Arg Leu Gly Arg Gly Pro Cys Ala Ala Leu
1 5 10 15

Leu Leu Leu Gly Leu Gly Leu Ser Thr Val Thr Gly Leu His Cys Val
20 25 30

Gly Asp Thr Tyr Pro Ser Asn Asp Arg Cys Cys His Glu Cys Arg Pro
35 40 45

Gly Asn Gly Met Val Ser Arg Cys Ser Arg Ser Gln Asn Thr Val Cys
50 55 60

Arg Pro Cys Gly Pro Gly Phe Tyr Asn Asp Val Val Ser Ser Lys Pro
65 70 75 80

Cys Lys Pro Cys Thr Trp Cys Asn Leu Arg Ser Gly Ser Glu Arg Lys
85 90 95

Gln Leu Cys Thr Ala Thr Gln Asp Thr Val Cys Arg Cys Arg Ala Gly
100 105 110

Thr Gln Pro Leu Asp Ser Tyr Lys Pro Gly Val Asp Cys Ala Pro Cys
115 120 125

Pro Pro Gly His Phe Ser Pro Gly Asp Asn Gln Ala Cys Lys Pro Trp
130 135 140

Thr Asn Cys Thr Leu Ala Gly Lys His Thr Leu Gln Pro Ala Ser Asn
145 150 155 160

Ser Ser Asp Ala Ile Cys Glu Asp Arg Asp Pro Pro Ala Thr Gln Pro
165 170 175

Gln Glu Thr Gln Gly Pro Pro Ala Arg Pro Ile Thr Val Gln Pro Thr
180 185 190

Glu Ala Trp Pro Arg Thr Ser Gln Gly Pro Ser Thr Arg Pro Val Glu
195 200 205

Val Pro Gly Gly Arg Ala Val Ala Ala Ile Leu Gly Leu Gly Leu Val
210 215 220

-continued

```
Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 92
<211> LENGTH: 272
<212> TYPE: PRT
<213> ORGANISM: Mus musculus

<400> SEQUENCE: 92

```
Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Pro Thr Leu Val Thr Pro
        195                 200                 205

Glu Gly Pro Ala Phe Ala Val Leu Leu Gly Leu Gly Leu Gly Leu Leu
    210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270
```

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Tyr Asp Tyr Asp Gly
1 5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Lys Tyr Asp Tyr Asp Ala
1 5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Lys Tyr Asp Tyr Asp Gly
1 5

<210> SEQ ID NO 96
<211> LENGTH: 177
<212> TYPE: PRT
<213> ORGANISM: Homo sapiens

<400> SEQUENCE: 96

Met Cys Val Gly Ala Arg Arg Leu Gly Arg Gly Pro Cys Ala Ala Leu
1 5 10 15

Leu Leu Leu Gly Leu Gly Leu Ser Thr Val Thr Gly Leu His Cys Val
20 25 30

Gly Asp Thr Tyr Pro Ser Asn Asp Arg Cys Cys His Glu Cys Arg Pro
35 40 45

Gly Asn Gly Met Val Ser Arg Cys Ser Arg Ser Gln Asn Thr Val Cys
50 55 60

Arg Pro Cys Gly Pro Gly Phe Tyr Asn Asp Val Val Ser Ser Lys Pro
65 70 75 80

Cys Lys Pro Cys Thr Trp Cys Asn Leu Arg Ser Gly Ser Glu Arg Lys
85 90 95

Gln Leu Cys Thr Ala Thr Gln Asp Thr Val Cys Arg Cys Arg Ala Gly
100 105 110

Thr Gln Pro Leu Asp Ser Tyr Lys Pro Gly Val Asp Cys Ala Pro Cys
115 120 125

Pro Pro Gly His Phe Ser Pro Gly Asp Asn Gln Ala Cys Lys Pro Trp
130 135 140

Thr Asn Cys Thr Leu Ala Gly Lys His Thr Leu Gln Pro Ala Ser Asn
145 150 155 160

Ser Ser Asp Ala Ile Cys Glu Asp Arg Asp Pro Pro Ala Thr Gln Pro
165 170 175

Gln

<210> SEQ ID NO 97

-continued

```
<211> LENGTH: 175
<212> TYPE: PRT
<213> ORGANISM: Mus musculus

<400> SEQUENCE: 97

Met Tyr Val Trp Val Gln Gln Pro Thr Ala Leu Leu Leu Leu Ala Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp
                165                 170                 175


<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 98

His His His His His His
1               5
```